United States Patent
Bhattacharya et al.

(10) Patent No.: US 11,203,594 B2
(45) Date of Patent: Dec. 21, 2021

(54) ANTI-PROLIFERATIVE AGENTS FOR TREATING PAH

(71) Applicant: Pfizer Inc., New York, NY (US)

(72) Inventors: Samit Kumar Bhattacharya, Waltham, MA (US); Douglas Carl Behenna, San Juan Capistrano, CA (US); Kimberly O. Cameron, Cambridge, MA (US); Ping Chen, San Diego, CA (US); John M. Curto, Mystic, CT (US); Kevin Daniel Freeman-Cook, Carlsbad, CA (US); Mehran Jalaie, San Diego, CA (US); Robert Steven Kania, Del Mar, CA (US); Yajing Lian, Waterford, CT (US); Sajiv Krishnan Nair, San Diego, CA (US); Cynthia Louise Palmer, La Mesa, CA (US); Martin Youngjin Pettersson, Littleton, MA (US); Eugene Yuanjin Rui, San Diego, CA (US); Matthew Sammons, Quincy, MA (US); Qingyi Yang, Lexington, MA (US); Liying Zhang, Lexington, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/849,329

(22) Filed: Apr. 15, 2020

(65) Prior Publication Data

US 2020/0331909 A1 Oct. 22, 2020

Related U.S. Application Data

(60) Provisional application No. 62/981,620, filed on Feb. 26, 2020, provisional application No. 62/836,340, filed on Apr. 19, 2019.

(51) Int. Cl.
*C07D 471/04* (2006.01)
*A61P 9/12* (2006.01)

(52) U.S. Cl.
CPC .............. *C07D 471/04* (2013.01); *A61P 9/12* (2018.01)

(58) Field of Classification Search
CPC .................. C07D 471/04; A61P 9/12

USPC ...................................... 514/210.16
See application file for complete search history.

(56) References Cited

U.S. PATENT DOCUMENTS

2006/0047118 A1* 3/2006 Stadtmueller ........... A61P 13/12
544/184

FOREIGN PATENT DOCUMENTS

| WO | 2015/120049 | 8/2015 |
| WO | 2018/033815 | 2/2018 |

OTHER PUBLICATIONS

Sanchez-Martinez Concepcion et al., "Cyclin dependent kinase (CDK) inhibitors as anticancer drugs", Bioorganic & Medicinal Chemistry Letters, vol. 25(17), pp. 3420-3435 (2015).
International Search Report and the Written Opinion of the International Searching Authority for International Application No. PCT/IB2020/053550, dated Jun. 12, 2020.

* cited by examiner

*Primary Examiner* — Niloofar Rahmani
(74) *Attorney, Agent, or Firm* — Richard V. Zanzalari

(57) ABSTRACT

This invention relates to compounds of general Formula I

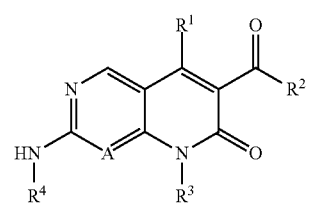

in which A, $R^1$, $R^2$, $R^3$ and $R^4$ are as defined herein, and the pharmaceutically acceptable salts thereof; to pharmaceutical compositions comprising such compounds and salts; to methods of using such compounds, salts and compositions for treating pulmonary hypertension and related diseases, like pulmonary arterial hypertension; to methods of using such compounds, salts and compositions for treating abnormal cell growth, such as cancer; and to processes to make such compounds, salts and compositions.

30 Claims, 1 Drawing Sheet

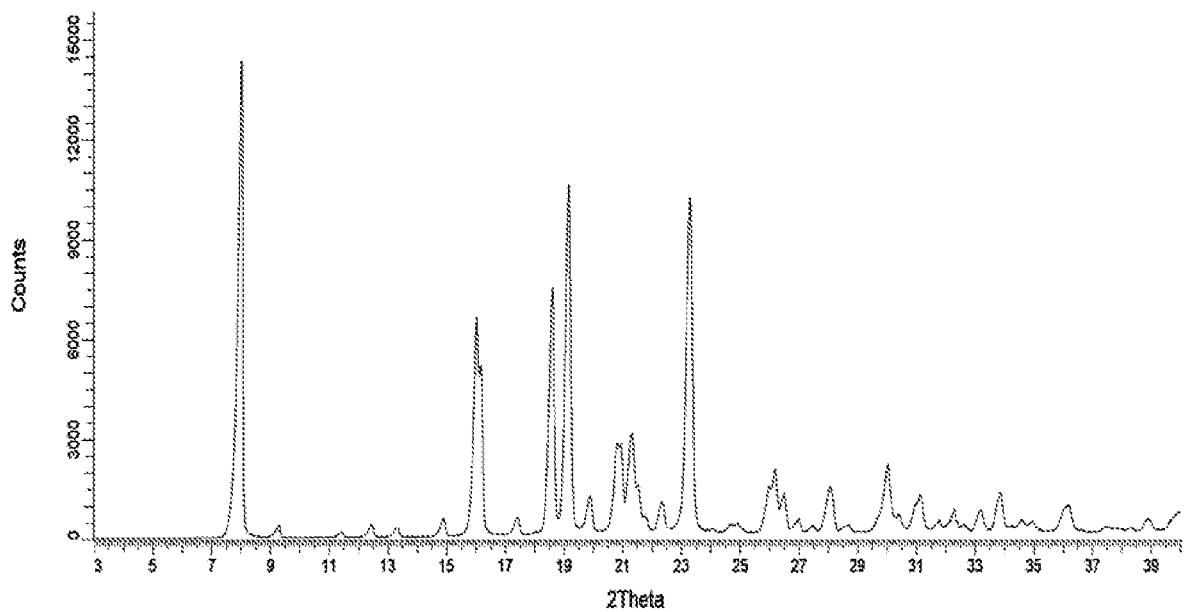

ANTI-PROLIFERATIVE AGENTS FOR TREATING PAH

This application claims the benefit of priority to U.S. Provisional Patent Application Ser. No. 62/836,340 filed Apr. 19, 2019, and to U.S. Provisional Patent Application Ser. No. 62/981,620 filed Feb. 26, 2020, the disclosure of each of which is hereby incorporated by reference in its entirety.

FIELD OF INVENTION

Provided herein are 1,6-naphthyridinyl and pyrido[2,3-d]pyrimidinyl compounds useful for treating pulmonary hypertension and related diseases and useful for treating abnormal cell growth, such as cancer; processes to make such compounds; and methods of use of such compounds for treatment of pulmonary hypertension and related diseases, like pulmonary arterial hypertension, and for treatment of abnormal cell growth, such as cancer.

BACKGROUND OF THE INVENTION

Pulmonary hypertension (PH) has been previously classified as primary (idiopathic) or secondary. Recently, the World Health Organization (WHO) has classified pulmonary hypertension into five groups: Group 1: pulmonary arterial hypertension (PAH); Group 2: PH with left heart disease; Group 3: PH with lung disease and/or hypoxemia; Group 4: PH due to chronic thrombotic and/or embolic disease; and Group 5: miscellaneous conditions (e.g., sarcoidosis, histiocytosis X, lymphangiomatosis and compression of pulmonary vessels).

Pulmonary arterial hypertension is a serious, complex, progressive and life-threatening disease of the pulmonary vasculature, characterized by profound vasoconstriction and an abnormal proliferation of smooth muscle cells in the walls of the pulmonary arteries. Severe narrowing of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in pulmonary vascular resistance (PVR) and sustained elevations in pulmonary artery pressure (PAP), which ultimately lead to right ventricular failure and death. Patients diagnosed with PAH have a poor prognosis and equally compromised quality of life, with a mean life expectancy of 2 to 5 years from the time of diagnosis if untreated.

There are currently 10 approved therapies for the treatment of PAH in the United States (US) and Europe. All of these therapies fall within one of 3 vasodilator classes including the prostacyclin analogs (epoprostenol, treprostinil, iloprost and selexipag), the endothelin receptor antagonists (ERA) (bosentan, ambrisentan, and macitentan), and agents affecting the Nitric Oxide signaling pathway including the soluble guanylate cyclase activator riociguat and the phosphodiesterase type-5 inhibitors sildenafil and tadalafil. These interventions address predominantly the endothelial and vascular hemodynamic dysfunction associated with the condition, and although it has been demonstrated that these therapies delay progression of the disease, morbidity and mortality remain high in this patient population. Despite the availability of these therapies, the five-year survival of patients with PAH remains as low at 57%. McGoon M D, Miller D P. REVEAL: A contemporary US pulmonary arterial hypertension registry. *Eur Respir Rev.* 2012; 21:8-18.

The pathophysiology driving the vascular remodeling characteristic of PAH is multifactorial and includes abnormal vascular cell proliferation, reduced apoptosis, inflammation, in situ thrombosis and vasoconstriction. PAH is recognized to share many characteristics of a malignant phenotype including abnormal proliferation, formation of plexiform lesions in the proximity of pulmonary vasculature, altered mitochondrial metabolism and a switch to anaerobic metabolic pathways despite adequate oxygen supply. Two key cell types involved in progression towards PAH are Pulmonary Arterial Smooth Muscle Cells (PASMCs) and Pulmonary Artery Adventitial Fibroblasts (PAAFs). In WO2018/073687, inhibitors of cyclin-dependent kinases (CDKs), like palbociclib, are identified as being useful for the treatment of PAH, by assessing the effects on human and rat PASMCs and human PAAFs. However, there remains a need for treatment of PAH.

Moreover, CDKs and related serine/threonine protein kinases are important cellular enzymes that perform essential functions in regulating cell division and proliferation. The CDK catalytic units are activated by regulatory subunits known as cyclins. At least sixteen mammalian cyclins have been identified (Johnson D G, Walker C L. Cyclins and Cell Cycle Checkpoints. Annu. Rev. Pharmacol. Toxicol. (1999) 39:295 312). Additional functions of Cyclin/CDK heterodynes include regulation of transcription, DNA repair, differentiation and apoptosis (Morgan D O. Cyclin dependent kinases: engines, clocks, and microprocessors. Annu. Rev. Cell. Dev. Biol. (1997) 13:261 291).

CDK inhibitors have been demonstrated to be useful in treating cancer. Increased activity or temporally abnormal activation of CDKs has been shown to result in the development of human tumors, and human tumor development is commonly associated with alterations in either the CDK proteins themselves or their regulators (Cordon Cardo C. Mutations of cell cycle regulators: biological and clinical implications for human neoplasia. Am. J. Pathol. (1995) 147:545 560; Karp J E, Broder S. Molecular foundations of cancer: new targets for intervention. Nat. Med. (1995) 1:309 320; Hall M, Peters G. Genetic alterations of cyclins, cyclin dependent kinases, and CDK inhibitors in human cancer. Adv. Cancer Res. (1996) 68:67 108).

CDK4 and CDK6 are important regulators of cell cycle progression at the G1-S checkpoint, which are controlled by D-type cyclins and INK4 endogenous CDK inhibitors, such as p16INK4a (CDKN2A). Dysregulation of the cyclin D-CDK4/6-INK4-retinoblastoma (Rb) pathway has been reported to be associated with development of endocrine therapy resistance.

Mutations of CDK4 and CDK6 have been described in subgroups of melanoma and other tumors (Zuo L, et al., Germline mutations in the p16INK4a binding domain of CDK4 in familial melanoma. *Nature Genet.* (1996) 12, 97-99; Ortega S, et al. Cyclin D dependent kinases, INK4 inhibitors and cancer. *Biochim. Biophys. Acta* (2002) 1602: 73 87; Smalley K S M et al. Identification of a novel subgroup of melanomas with KIT/cyclin dependent kinase 4 overexpression. *Cancer Res* (2008) 68: 5743 52). Amplifications of the regulatory subunits of CDKs and cyclins, and mutation, gene deletion, or transcriptional silencing of endogenous INK4 CDK inhibitors have also been reported as mechanism by which the pathway can be activated (Smalley KSM (2008)).

The development of CDK inhibitors has been reviewed in the literature. For example, see Sánchez-Martinez et al. Cyclin dependent kinase (CDK) inhibitors as anticancer drugs, *Bioorg. Med. Chem. Lett.* (2015) 25: 3420-3435 (and references cited therein). The use of CDK4/6 inhibitors in combination with endocrine therapy has demonstrated significant efficacy in the treatment of hormone receptor (HR)-positive, human epidermal growth factor 2 (HER2)-negative advanced or metastatic breast cancers, and CDK4/6 inhibitors, including palbociclib, ribociclib and abemaciclib, have been approved in combination with endocrine therapy in a first- or second-line setting.

Nevertheless, due to the potential for development of acquired resistance and other bypass mechanisms to CDK4/6 inhibitors, there remains a need to identify novel CDK4/6 inhibitors having an appropriate pharmacological profile, for example in terms of potency, selectivity, pharmacokinetics, and duration of action.

SUMMARY OF THE INVENTION

In one aspect, the invention provides a compound of Formula I:

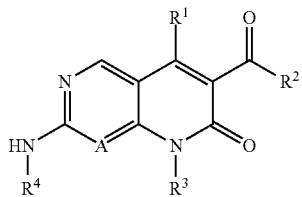

or a pharmaceutically acceptable salt thereof, wherein:
A is CH or N;
$R^1$ is $C_1$-$C_2$ alkyl or $C_1$-$C_2$ fluoroalkyl;
$R^2$ is $C_1$-$C_4$ alkyl optionally substituted with 1, 2, or 3 substituents each independently selected from the group consisting of —OH, $C_1$-$C_2$ alkoxy, and F;
$R^3$ is 4- to 8-membered heterocyclyl, $C_3$-$C_8$ cycloalkyl, (4- to 8-membered heterocyclyl)-$C_1$-$C_4$ alkyl-, or ($C_3$-$C_8$ cycloalkyl)-$C_1$-$C_4$ alkyl-,
 wherein each of the 4- to 8-membered heterocyclyl and the 4- to 8-membered heterocyclyl moiety in (4- to 8-membered heterocyclyl)-$C_1$-$C_4$ alkyl- is optionally substituted with 1 or 2 $R^5$,
 wherein each of the $C_3$-$C_8$ cycloalkyl and the $C_3$-$C_8$ cycloalkyl moiety in ($C_3$-$C_8$ cycloalkyl)-$C_1$-$C_4$ alkyl- is optionally substituted with 1 or 2 $R^5$ and further optionally substituted with 1-$N(R^6)_2$, and
 wherein each of the $C_1$-$C_4$ alkyl moieties in (4- to 8-membered heterocyclyl)-$C_1$-$C_4$ alkyl- and ($C_3$-$C_8$ cycloalkyl)-$C_1$-$C_4$ alkyl- is optionally substituted with 1, 2, or 3 $R^5$; $R^4$ is a moiety having the structure of

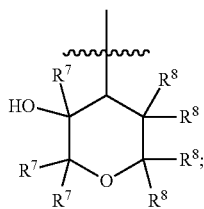

each $R^5$ is independently selected from the group consisting of —F, —OH, —CN, $C_1$-$C_4$ alkyl, $C_1$-$C_4$ fluoroalkyl, $C_1$-$C_4$ alkoxy, $C_1$-$C_4$ fluoroalkoxy, $C_1$-$C_4$ alkoxy-$C_1$-$C_4$ alkyl-, $C_1$-$C_4$ fluoroalkoxy-$C_1$-$C_4$ alkyl-, $C_1$-$C_4$ alkoxy-$C_1$-$C_4$ fluoroalkyl, and $C_1$-$C_4$ fluoroalkoxy-$C_1$-$C_4$ fluoroalkyl-;
each $R^6$ is independently selected from the group consisting of H and $C_1$-$C_2$ alkyl;
each $R^7$ is independently H or $C_1$-$C_2$ alkyl; and
each $R^8$ is independently H, F, or $C_1$-$C_2$ alkyl.

The present invention also provides a pharmaceutical composition that includes a compound of Formula I, or a pharmaceutically acceptable salt thereof, and a pharmaceutically acceptable excipient or carrier.

The present invention also provides a method for treating a disease or disorder in a subject, which method includes administering to the subject in need thereof a therapeutically effective amount of a compound of Formula I or a pharmaceutically acceptable salt thereof, wherein the disease or disorder is selected from the group consisting of pulmonary hypertension, pulmonary arterial hypertension, pulmonary hypertension with left heart disease, pulmonary hypertension with lung disease and/or hypoxemia, pulmonary hypertension due to chronic thrombotic and/or embolic disease, and diseases associated with pulmonary hypertension including sarcoidosis, histiocytosis X, lymphangiomatosis and compression of pulmonary vessels.

The present invention also provides a method for treating abnormal cell growth (such as cancer) in a subject, which method includes administering to the subject in need thereof a therapeutically effective amount of a compound of Formula I or a pharmaceutically acceptable salt thereof.

The present invention also provides use of a compound of Formula I, or a pharmaceutically acceptable salt thereof, for treating a disease or disorder, or in preparation a medicament for treating a disease or disorder, wherein the disease or disorder is selected from the group consisting of pulmonary hypertension, pulmonary arterial hypertension, pulmonary hypertension with left heart disease, pulmonary hypertension with lung disease and/or hypoxemia, pulmonary hypertension due to chronic thrombotic and/or embolic disease, and diseases associated with pulmonary hypertension including sarcoidosis, histiocytosis X, lymphangiomatosis and compression of pulmonary vessels.

The present invention also provides use of a compound of Formula I or a pharmaceutically acceptable salt thereof, for treating abnormal cell growth (such as cancer), or in preparation a medicament for treating abnormal cell growth (such as cancer).

The present invention also provides a method for inhibiting CDK (e.g. CDK4 and/or CDK6), which method including contacting the CDK with a compound of Formula I or a pharmaceutically acceptable salt thereof.

It is to be understood that both the foregoing general description and the following detailed description are exemplary and explanatory only and are not restrictive of the invention, as claimed.

BRIEF DESCRIPTION OF FIGURES

FIG. 1 represents an observed powder X-ray diffraction pattern for an anhydrous (anhydrate) crystalline form (designated as Form 1) of compound 5.

DETAILED DESCRIPTION OF THE INVENTION

The present invention may be understood more readily by reference to the following Detailed Description and the Examples and schemes provided herein. It is to be understood that the terminology used herein is for the purpose of describing specific embodiments only and is not intended to be limiting.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

As used herein, the term "alkyl" is defined to include any acyclic, saturated aliphatic hydrocarbons including straight chains and branched chains. In some embodiments, the alkyl group 1 to 4 carbon atoms, 1 to 3 carbon atoms, 1 to 2 carbon atoms, or only one carbon atom. For example, the term "$C_{1-6}$ alkyl" refers to linear or branched aliphatic hydrocarbon chains of 1 to 6 carbon atoms, inclusive (e.g., methyl, ethyl, n-propyl, isopropyl, n-butyl, isobutyl, sec-butyl, tert-butyl, n-pentyl, or n-hexyl); the term "$C_{1-4}$ alkyl" refers to linear or branched aliphatic hydrocarbon chains of 1 to 4 carbon atoms, inclusive (e.g., methyl, ethyl, n-propyl, isopropyl, n-butyl, isobutyl, sec-butyl, or tert-butyl); the term "$C_{1-2}$ alkyl" refers to aliphatic hydrocarbon chains of 1 to 2 carbon atoms, inclusive; and the term "$C_1$ alkyl" refers to methyl and the term "$C_2$ alkyl" refers to ethyl. An alkyl group optionally can be substituted by one or more (e.g. 1 to 5) suitable substituents if and when so specified.

As used herein, the term "alkoxy" or "alkyloxy" refers to an —O-alkyl group. For example, the term "$C_1$-$C_4$ alkoxy" or "$C_1$-$C_4$ alkyloxy" refers to an —O—($C_1$-$C_4$ alkyl) group; and the term "$C_1$-$C_2$ alkoxy" or "$C_1$-$C_2$ alkyloxy" refers to an —O—($C_1$-$C_2$ alkyl) group. Examples of alkoxy include methoxy, ethoxy, propoxy (e.g., n-propoxy and isopropoxy), tert-butoxy, and the like. $C_1$-$C_2$ alkoxy include methoxy and ethoxy. The alkoxy or alkyloxy group optionally can be substituted by 1 or more (e.g., 1 to 5) suitable substituents if and when so specified. As used herein, the term "cycloalkyl" refers to saturated or unsaturated, non-aromatic, monocyclic or polycyclic (such as bicyclic) hydrocarbon rings [e.g., monocyclics such as cyclopropyl, cyclobutyl, cyclopentyl, cyclopentenyl, cyclohexyl, cyclohexenyl, cyclohexadienyl, cycloheptyl, cycloheptatrienyl, or bicyclics including spiro, fused, or bridged systems (such as bicyclo[1.1.1]pentanyl, bicyclo[2.2.1]heptanyl, bicyclo[3.1.0]hexanyl, or bicyclo[3.2.1]octanyl, etc.)]. In some embodiments the cycloalkyl may optionally contain one, two or more non-aromatic double or triple bonds in the ring structure and/or may optionally be substituted with one or more (e.g. one to three) oxo groups. In some embodiments, the bicycloalkyl group has 3 to 8 carbon atoms. For example, the term "$C_{3-8}$ cycloalkyl" refers to saturated or unsaturated, non-aromatic, monocyclic or polycyclic (such as bicyclic) hydrocarbon rings of 3 to 8 ring-forming carbon atoms (e.g., cyclopropyl, cyclobutyl, cyclopentyl, cyclopentenyl cyclohexyl, bicyclo[3.1.0]hexanyl, bicyclo[1.1.1]pentanyl, or bicyclo[3.2.1]octanyl); and the term "Cm cycloalkyl" refers to saturated or unsaturated, non-aromatic, monocyclic or polycyclic (such as bicyclic) hydrocarbon rings of 3 to 6 ring-forming carbon atoms (e.g., cyclopropyl, cyclobutyl, cyclopentyl, cyclohexyl, bicyclo[3.1.0]hexanyl, bicyclo[1.1.1]pentan-1-yl, or bicyclo[1.1.1]pentan-2-yl). For yet another example, the term "$C_{3-4}$ cycloalkyl" refers to saturated or unsaturated, non-aromatic, monocyclic hydrocarbon rings of 3 to 4 ring-forming carbon atoms (e.g. cyclopropyl or cyclobutyl). In some embodiments, a $C_{3-8}$ cycloalkyl group includes saturated monocyclic or polycyclic (such as bicyclic) hydrocarbon rings of 3 to 8 ring-forming carbon atoms and unsaturated monocyclic or polycyclic (such as bicyclic) hydrocarbon rings of 3 to 8 ring-forming carbon atoms with one ring double bond. In some embodiments, a $C_{3-8}$ cycloalkyl group includes saturated monocyclic or polycyclic (such as bicyclic) hydrocarbon rings of 3 to 8 ring-forming carbon atoms. The cycloalkyl group optionally can be substituted by 1 or more (e.g., 1 to 5) suitable substituents if and when so specified.

The term "heterocyclyl" means a saturated or partially unsaturated, nonaromatic ring system containing one or more (e.g. one, two, three, or four) ring-forming carbon atoms and one or more (e.g. one, two, three, or four) ring-forming heteroatoms each independently selected from the group consisting of oxygen, nitrogen and sulfur. The ring system of the heterocyclyl can be monocyclic or polycyclic (including 2 or more rings, for example, a bicyclic ring system), including spiro, fused, and/or bridged systems, wherein each of the individual ring within the ring system contains 1 or more ring-forming carbon atoms and 0, 1, or more (e.g. 0, 1, 2, or 3) ring-forming heteroatoms (each of which is independently selected from oxygen, nitrogen and sulfur). In some embodiments, a heterocyclyl group includes a saturated ring system containing one or more (e.g. one, two, three, or four) ring-forming carbon atoms and one or more (e.g. one, two, three, or four) ring-forming heteroatoms each independently selected from the group consisting of oxygen, nitrogen and sulfur. Some examples of "heterocyclyl" include lactones, lactams, cyclic ethers and cyclic amines. Certain nonlimiting examples of "heterocyclyl" include pyrrolidinonyl, 2,5-dihydro-1H-pyrrolyl, piperidinonyl, morpholinonyl, piperazinonyl, oxazolidinonyl, imidazolidinonyl, 1,3-oxazinan-2-onyl, tetrahydropyrimidin-2(1H)-onyl, epoxidyl, tetrahydrofuranyl, tetrahydropyranyl, dioxanyl, aziridinyl, azetidinyl, oxetanyl, pyrrolidinyl, oxazolidinyl, thiazolidinyl, piperidinyl, morpholinyl, piperazinyl, thiomorpholinyl, 1,3-oxazinanyl, 1,3-thiazinanyl, 2-azaspiro[3.3]heptanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl and 2-oxa-6-azaspiro[3.3]heptanyl. In some embodiments, a ring-forming S atom in the heterocyclyl may be optionally substituted by one or two oxo groups if and when so specified, and/or a ring-forming carbon atom in the heterocyclyl may be optionally substituted by one oxo group if and when so specified. The heterocyclyl group optionally can be substituted by 1 or more (e.g., 1 to 5) suitable substituents if and when so specified.

As used herein, the term "halo" or "halogen" group is defined to include fluorine (F), chlorine (Cl), bromine (Br) or iodine (I).

As used herein, the term "fluoroalkyl" refers to an alkyl group having one or more halogen substituents (up to perfluoroalkyl, i.e., every hydrogen atom of the alkyl group has been replaced by a fluorine atom, for example, 1 to 5 hydrogen atoms of the alkyl group have been replaced by fluorine atoms). For example, as used herein, the term "$C_1$-$C_4$ fluoroalkyl" means, a $C_1$-$C_4$ alkyl, as defined herein, having one or more fluorine (F) substituents (up to perfluoroalkyl, i.e., every hydrogen atom of the $C_1$-$C_4$ alkyl group has been replaced by a fluorine atom, for example, 1 to 5 hydrogen atoms of the alkyl group have been replaced by fluorine atoms; and the term "$C_1$-$C_2$ fluoroalkyl" means, a $C_1$-$C_2$ alkyl, as defined herein, having one or more fluorine (F) substituents (up to perfluoroalkyl, i.e., every hydrogen atom of the $C_1$-$C_2$ alkyl group has been replaced by a fluorine atom). For another example, the term "$C_1$ fluoroalkyl" means methyl having one or more fluorine (F) substituents (up to perfluoroalkyl, i.e., every hydrogen atom of the methyl group has been replaced by a fluorine atom). Examples of $C_1$-$C_4$ fluoroalkyl include $CF_3$, $CHF_2$, $CH_2F$, $CH_2CF_3$, $CH_2CHF_2$, $C_2F_5$, $CH_2C_2F_5$, $CH_2CH_2CH_2CF_3$, and the like; $C_1$-$C_2$ fluoroalkyl includes $CF_3$, $CHF_2$, $CH_2F$, $CH_2CF_3$, $CH_2CHF_2$, $CH_2CH_2F$; $CHFCF_3$, $CHFCHF_2$, $CHFCH_2F$, $CHFCH_3$, $CF_2CF_3$, $CF_2CHF_2$, $CF_2CH_2F$, and $CF_2CH_3$; and $C_1$ fluoroalkyl includes $CF_3$, $CHF_2$, and $CH_2F$.

As used herein, the term "fluoroalkoxy" or "fluoroalkyloxy" refers to an —O-fluoroalkyl group. For example, the term "$C_1$-$C_6$ fluoroalkoxy" or "$C_1$-$C_6$ fluoroalkyloxy" refers to an —O—($C_1$-$C_6$ fluoroalkyl) group; the term "$C_1$-$C_4$ fluoroalkoxy" or "$C_1$-$C_4$ fluoroalkyloxy" refers to an —O—($C_1$-$C_4$ fluoroalkyl) group; and the term "$C_1$-$C_2$ fluoroalkoxy" or "$C_1$-$C_2$ fluoroalkyloxy" refers to an —O—($C_1$-$C_2$ fluoroalkyl) group. Examples of fluoroalkoxy include monofluoromethoxy (—$OCH_2F$), difluoromethoxy (—$OCHF_2$), trifluromethoxy (—$OCF_3$), —$OCH_2CF_3$, —$OC_2F_5$, and the like.

A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is substituted, then up to 3 hydrogen atoms on the carbon atom can be replaced with substituent groups. For another example, if a piperdin-4-yl is substituted with a substituent group, then any hydrogen atom on the ring-forming carbon atom or the ring-forming nitrogen atom can be replaced with the substituent group. Some examples of substituent groups for alkyl include halogen (e.g. F), OH, and —O—$C_1$-$C_4$ alkyl (i.e. $C_1$-$C_4$ alkoxy). Some examples of substituent groups for cycloalkyl or heterocyclyl include halogen, OH, —$NH_2$, —$NH(C_1$-$C_4$ alkyl), $N(C_1$-$C_4$ alkyl)$_2$, $C_1$-$C_4$ alkyl (which further can be substituted with 0, 1 or more substituents each independently selected from halogen, OH, $C_1$-$C_4$ alkoxy, and $C_1$-$C_4$ haloalkoxy) and $C_1$-$C_4$ alkoxy (which further can be substituted with 0, 1 or more substituents each independently selected from halogen, OH, $C_1$-$C_4$ alkoxy and $C_1$-$C_4$ fluoroalkoxy).

As used herein, the term "optionally substituted" means that substitution is optional and therefore includes both unsubstituted and substituted atoms and moieties.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

As used herein, the term "n-membered" where n is an integer typically describes the number of ring-forming atoms in a ring moiety where the number of ring-forming atoms is n. For example, piperidinyl is an example of a 6-membered heterocyclyl ring and tetrahydropyranyl is an example of a 5-membered heterocyclyl group. Relatedly, the term "n- to m-membered" heterocyclyl (wherein the integer "n" describes the lower number of ring-forming atoms in the heterocyclyl and the integer "m" describes the upper number of ring-forming atoms) is specifically intended to include any of n-membered, (n+1)-membered, ... and up to m-membered heterocyclyl group; for example, the term "4- to 8-membered heterocyclyl" is specifically intended to include any 4-, 5-, 6-, 7-, or 8-membered heterocyclyl group, inclusive.

At various places in the present specification, substituents of compounds of the invention are disclosed in groups or in ranges. It is specifically intended that the invention include each and every individual sub-combination of the members of such groups and ranges (including the end points). For example, the carbon atom content of alkyl and various other hydrocarbon-containing moieties can be indicated by a prefix designating the number of carbon atoms in the moiety, that is, the prefix $C_i$ indicates a moiety of the integer "i" carbon atoms. For one example, $C_3$ alkyl indicates any alkyl with 3 carbon atoms, including propan-1-yl and propan-2-yl. For another example, the carbon atom content of alkyl and various other hydrocarbon-containing moieties is indicated by a prefix designating a lower and upper number of carbon atoms in the moiety, that is, the prefix indicates a moiety of the integer "i" to the integer "j" carbon atoms, inclusive. For one example, the term "$C_1$-$C_6$ alkyl" is specifically intended to include $C_1$ alkyl (methyl), $C_2$ alkyl (ethyl), $C_3$ alkyl (i.e., propan-1-yl or propan-2-yl), $C_4$ alkyl (e.g. n-butyl, iso-butyl, or tert-butyl), $C_5$ alkyl (e.g. pentan-1-yl or 3-methylbutan-1-yl), and $C_6$ alkyl (e.g. hexan-1-yl or 3-methylpentan-1-yl). For another example, the term "$C_3$-$C_6$ cycloalkyl" is specifically intended to include any $C_3$ cycloalkyl (cyclopropyl), $C_4$ cycloalkyl (e.g. cyclobutyl), $C_5$ cycloalkyl (e.g. cyclocpentyl), or $C_6$ cycloalkyl (e.g. cyclohexyl).

At various places in the present specification, the chemical terms such as alkyl, alkoxy, fluoroalkoxy (e.g. $C_1$-$C_2$ alkyl, $C_1$-$C_4$ alkyl, $C_1$-$C_4$ fluoroalkyl, $C_1$-$C_2$ alkoxy, $C_1$-$C_2$ fluoroalkoxy) can be used in combination with one or more other chemical terms, for example, "$C_1$-$C_2$ alkoxy-$C_1$-$C_2$ fluoroalkyl-", "—$C_1$-$C_4$ alkyl-(4- to 8-membered heterocyclyl)", or "—$C_1$-$C_4$ alkyl-($C_3$-$C_8$ cycloalkyl)". In such situation, those skilled in the art would readily recognize the indicated point of attachment for the combination [e.g., the indicated point attachment for the "—$C_1$-$C_4$ alkyl-($C_3$-$C_8$ cycloalkyl)" is through the "$C_1$-$C_4$ alkyl" moiety] and that each moiety of the combination fulfills the normal valency rule [e.g. the "$C_1$-$C_4$ alkyl" moiety of "—$C_1$-$C_4$ alkyl-($C_3$-$C_8$ cycloalkyl)" is bivalent, i.e., linking to the "$C_3$-$C_8$ cycloalkyl" moiety and attaching to the base molecular moiety through the indicated point of attachment; and for another example, the "$C_1$-$C_2$ fluoroalkyl" moiety of the "$C_1$-$C_2$ alkoxy-$C_1$-$C_2$ fluoroalkyl-" is bivalent, linking to the "$C_1$-$C_2$ alkoxy" moiety and attaching to the base molecular moiety through the indicated point of attachment].

An embodiment of the invention is a compound of Formula I, or a pharmaceutically acceptable salt thereof, wherein $R^2$ is $C_1$-$C_4$ alkyl optionally substituted with 1, 2, or 3 F and further optionally substituted with 1 OH or $C_1$-$C_2$ alkoxy. In a further embodiment, $R^2$ is $C_1$-$C_4$ alkyl optionally substituted with 1, 2, or 3 F and further optionally substituted with 1 $C_1$-$C_2$ alkoxy. In a yet further embodiment, $R^2$ is $C_1$-$C_2$ alkyl optionally substituted with 1, 2, or 3 F and further optionally substituted with 1 $C_1$-$C_2$ alkoxy.

An embodiment of the invention is a compound of Formula I, or a pharmaceutically acceptable salt thereof, wherein $R^2$ is $C_1$-$C_2$ alkyl optionally substituted with 1, 2, or 3 F. In a further embodiment, $R^2$ is $C_1$-$C_2$ alkyl. In a yet further embodiment, $R^2$ is methyl.

An embodiment of the invention is a compound of Formula I, or a pharmaceutically acceptable salt thereof, wherein $R^3$ is 4- to 8-membered heterocyclyl or $C_3$-$C_8$ cycloalkyl, wherein the 4- to 8-membered heterocyclyl is optionally substituted with 1 or 2 $R^5$, and wherein the $C_3$-$C_8$ cycloalkyl is optionally substituted with 1 or 2 $R^5$ and further optionally substituted with 1-$N(R^6)_2$. In a further embodiment, $R^3$ is 5- to 7-membered heterocyclyl or $C_3$-$C_6$ cycloalkyl, wherein the 5- to 7-membered heterocyclyl is optionally substituted with 1 or 2 $R^5$, and wherein the $C_3$-$C_6$ cycloalkyl is optionally substituted with 1 or 2 $R^5$ and further optionally substituted with 1-$N(R^6)_2$.

An embodiment of the invention is a compound of Formula I, or a pharmaceutically acceptable salt thereof, wherein $R^3$ is 4- to 8-membered heterocyclyl optionally substituted with 1 or 2 $R^5$.

An embodiment of the invention is a compound of Formula I, or a pharmaceutically acceptable salt thereof, wherein $R^3$ is $C_3$-$C_8$ cycloalkyl optionally substituted with 1 or 2 $R^5$ and further optionally substituted with 1-$N(R^6)_2$. In a further embodiment, $R^3$ is $C_3$-$C_8$ cycloalkyl. In a yet further embodiment, $R^3$ is cyclopropyl, cyclobutyl, cyclopentyl, cyclohexyl or bicyclo[3.1.0]hexanyl.

An embodiment of the invention is a compound of Formula I, or a pharmaceutically acceptable salt thereof, wherein:

A is CH or N;

$R^1$ is $CH_3$ or $C_1$ fluoroalkyl;

$R^2$ is $CH_3$;

$R^3$ is 5- to 7-membered heterocyclyl, $C_3$-$C_6$ cycloalkyl, (5- to 7-membered heterocyclyl)-$C_1$-$C_4$ alkyl-, or ($C_3$-$C_6$ cycloalkyl)-$C_1$-$C_4$ alkyl-, wherein each of the 5- to 7-membered heterocyclyl and the 5- to 7-membered heterocyclyl moiety in (5- to 7-membered heterocyclyl)-$C_1$-$C_4$ alkyl- is optionally substituted with 1 $R^5$, wherein each of the $C_3$-$C_6$ cycloalkyl and the $C_3$-$C_6$ cycloalkyl moiety in ($C_3$-$C_6$ cycloalkyl)-$C_1$-$C_4$ alkyl- is optionally substituted with 1 or 2 $R^5$ and further optionally substituted with 1-$N(R^6)_2$, and wherein each of the $C_1$-$C_4$ alkyl moieties in (5- to 7-membered heterocyclyl)-$C_1$-$C_4$ alkyl- and ($C_3$-$C_6$ cycloalkyl)-$C_1$-$C_4$ alkyl- is optionally substituted with 1, 2, or 3 $R^5$; $R^4$ is a moiety having the structure of

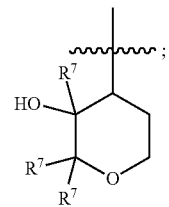

each $R^5$ is independently selected from the group consisting of —F, —OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-;

each $R^6$ is independently selected from the group consisting of H and $C_1$-$C_2$ alkyl; and each $R^7$ is independently H or $CH_3$, provided that no more than two $R^7$ are $CH_3$.

An embodiment of the compound of Formula I of the present invention, or a pharmaceutically acceptable salt thereof, is a compound of Formula II:

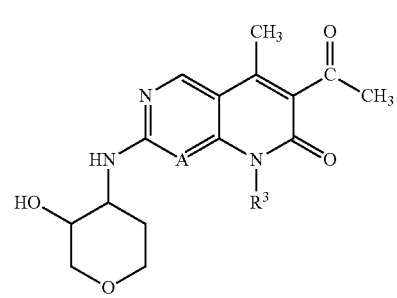

or a pharmaceutically acceptable salt thereof (wherein A and $R^3$ are as defined in any of the embodiment described herein). In a further embodiment, the two substituents on the tetrahydropyran ring of Formula II are trans to each other (i.e., the two substituents on the tetrahydropyran ring are on the opposite sides of the tetrahydropyran ring).

An embodiment of the compound of Formula I or II, or a pharmaceutically acceptable salt thereof, is a compound of Formula III:

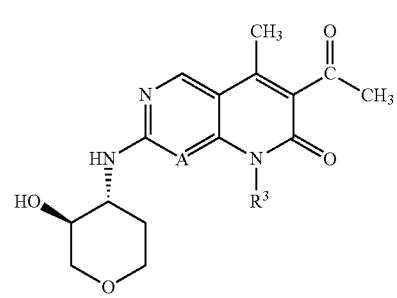

or a pharmaceutically acceptable salt thereof (wherein A and $R^3$ are as defined in any of the embodiment described herein).

An embodiment of the compound of Formula I, or a pharmaceutically acceptable salt thereof, of the invention, is a compound of Formula II:

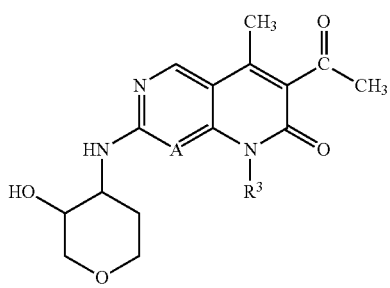

II or a pharmaceutically acceptable salt thereof, wherein:
A is CH or N;
$R^3$ is 5- to 7-membered heterocyclyl optionally substituted with 1 $R^5$; and
$R^5$ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-.

In a further embodiment of the compound of Formula II, $R^3$ is 5- to 7-membered heterocyclyl optionally substituted with 1 $R^5$ (and $R^5$ is as defined in any of the embodiments described herein), and the two substituents on the tetrahydropyran ring of Formula II are trans to each other (i.e., the two substituents on the tetrahydropyran ring are on the opposite sides of the tetrahydropyran ring).

An embodiment of the compound of Formula I or II, or a pharmaceutically acceptable salt thereof, of the invention, is a compound of Formula III:

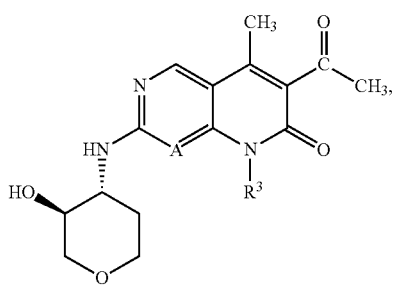

III or a pharmaceutically acceptable salt thereof, wherein $R^3$ is 5- to 7-membered heterocyclyl optionally substituted with 1 $R^5$ (and $R^5$ is as defined in any of the embodiments described herein).

Another embodiment of the invention includes a compound of any one of Formulas I, II, and III, or a pharmaceutically acceptable salt thereof, wherein the 4- to 8-membered heterocyclyl or 5- to 7-membered heterocyclyl of $R^3$ comprises one ring-forming heteroatom selected from nitrogen or oxygen, and wherein the heterocyclyl is optionally substituted with 1 $R^5$, and wherein $R^5$ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-.

Another embodiment of the invention includes a compound of any one of Formulas I, II, and III, or a pharmaceutically acceptable salt thereof, wherein the 4- to 8-membered heterocyclyl or 5- to 7-membered heterocyclyl of $R^3$ is selected from the group consisting of 2-azaspiro[3.3]heptanyl, tetrahydrofuranyl, pyrrolidinyl, and piperidinyl, wherein each of the heterocyclyl selections is optionally optionally substituted with 1 $R^5$, and wherein $R^5$ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-. One skilled in the art would appreciate that the 4- to 8-membered heterocyclyl or 5- to 7-membered heterocyclyl of $R^3$ can be attached to the base molecular moiety through a ring-forming carbon or ring-forming nitrogen atom of the heterocyclyl. In addition, one skilled in the art would appreciate that a $R^5$ substituent can attach to a ring-forming carbon or ring-forming nitrogen atom of the heterocyclyl.

Another embodiment of the invention includes a compound of any one of Formula I, II, or III, or a pharmaceutically acceptable salt thereof, wherein the 4- to 8-membered heterocyclyl or 5- to 7-membered heterocyclyl of $R^3$ is selected from the group consisting of 2-azaspiro[3.3]heptan-6-yl, pyrrolidin-3-yl, piperidin-4-yl, and tetrahydrofuran-3-yl, each is optionally substituted with 1 $R^5$, and $R^5$ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-. In a yet further embodiment, the 4- to 8-membered heterocyclyl or 5- to 7-membered heterocyclyl of $R^3$ is selected from the group consisting of 2-azaspiro[3.3]heptan-6-yl, pyrrolidin-3-yl, 1-methylpyrrolidin-3-yl, 2-(2-methoxyethyl)-2-azaspiro[3.3]heptan-6-yl, 2-(2,2-difluoroethyl)-2-azaspiro[3.3]heptan-6-yl, and piperidin-4-yl.

Another embodiment of the invention includes a compound of any one of Formula I, II, or III, or a pharmaceutically acceptable salt thereof, wherein $R^3$ is 2-azaspiro[3.3]heptan-6-yl optionally substituted with 1 $R^5$ that is selected from the group consisting of $C_1$-$C_2$ alkyl, $C_1$-$C_2$ fluoroalkyl, $C_1$-$C_2$ alkoxy-$C_1$-$C_2$ alkyl-, and $C_1$-$C_2$ fluoroalkoxy-$C_1$-$C_2$ alkyl-.

An embodiment of the invention is a compound of Formula I, or a pharmaceutically acceptable salt thereof, wherein A is N, and $R^3$ is 4- to 8-membered heterocyclyl optionally substituted with 1 $R^5$ (and $R^5$ is as defined in any of the embodiments described herein). In a further embodiment, the compound or a pharmaceutically acceptable salt thereof is a compound of Formula II or III, wherein $R^3$ is 5- to 7-membered heterocyclyl optionally substituted with 1 $R^5$.

An embodiment of the invention is a compound of Formula I, or a pharmaceutically acceptable salt thereof, wherein A is CH, and $R^3$ is 4- to 8-membered heterocyclyl optionally substituted with 1 $R^5$ (and $R^5$ is as defined in any of the embodiments described herein). In a further embodiment, the compound or a pharmaceutically acceptable salt thereof is a compound of Formula II or III, wherein $R^3$ is 5- to 7-membered heterocyclyl optionally substituted with 1 $R^5$ (and $R^5$ is as defined in any of the embodiments described herein).

An embodiment of the invention is a compound of Formula I, or a pharmaceutically acceptable salt thereof, wherein $R^3$ is $C_3$-$C_6$ cycloalkyl optionally substituted with 1 or 2 $R^5$ and further optionally substituted with 1-$N(R^6)_2$, wherein each of $R^5$ and $R^6$ is as defined in any of the embodiments described herein. In a further embodiment, $R^3$ is selected from the group consisting of cyclopropyl, cyclobutyl, cyclopentyl, cyclopentenyl, cyclohexanyl, and bicyclo[3.1.0]hexanyl, wherein each of the cycloalkyl selections is optionally substituted with 1 or 2 $R^5$, and further optionally substituted with 1-$N(R^6)_2$; each $R^5$ is independently selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-; and each $R^6$ is independently selected from the group consisting of H and $C_1$-$C_2$ alkyl.

An embodiment of the invention is a compound of Formula I, or a pharmaceutically acceptable salt thereof, wherein $R^3$ is cyclobutyl or cyclopentyl, each optionally substituted with 1 or 2 $R^5$; and each $R^5$ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-.

An embodiment of the compound of Formula I, or a pharmaceutically acceptable salt thereof, of the invention, is a compound of Formula II:

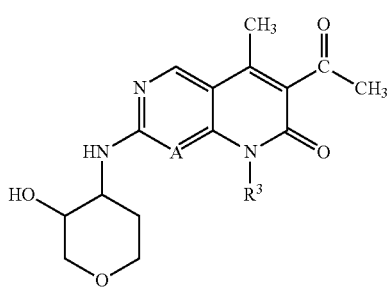

or a pharmaceutically acceptable salt thereof, wherein:

A is CH or N;

$R^3$ is $C_3$-$C_6$ cycloalkyl optionally substituted with 1 or 2 $R^5$ and further optionally substituted with 1-$N(R^6)_2$;

each $R^5$ is independently selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-; and each $R^6$ is independently selected from the group consisting of H and $C_1$-$C_2$ alkyl.

In a further embodiment of the compound of Formula II wherein $R^3$ is $C_3$-$C_6$ cycloalkyl optionally substituted with 1 or 2 $R^5$ and further optionally substituted with 1 —$N(R^6)_2$ (wherein each of $R^5$ and $R^6$ is as defined in any of the embodiments described herein), and the two substituents on the tetrahydropyran ring of Formula II are trans to each other (i.e., the two substituents on the tetrahydropyran ring are on the opposite side of the tetrahydropyran ring).

An embodiment of the compound of Formula I or II, or a pharmaceutically acceptable salt thereof, of the invention, is a compound of Formula III:

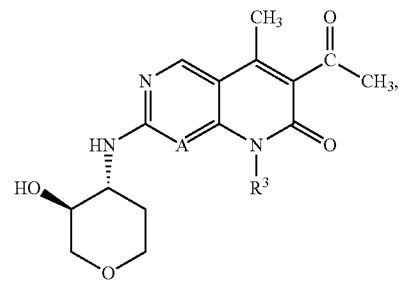

or a pharmaceutically acceptable salt thereof, wherein $R^3$ is $C_3$-$C_6$ cycloalkyl optionally substituted with 1 or 2 $R^5$ and further optionally substituted with 1 —$N(R^6)_2$ (wherein each of $R^5$ and $R^6$ is as defined in any of the embodiments described herein).

An embodiment of the invention includes a compound of any one of Formulas I, II, or III, wherein the $C_3$-$C_8$ cycloalkyl or $C_3$-$C_6$ cycloalkyl of $R^3$ is selected from the group consisting of cyclopropyl, cyclobutyl, cyclopentyl, cyclopentenyl, cyclohexanyl, and bicyclo[3.1.0]hexanyl, wherein each of the cycloalkyl selections is optionally substituted with 1 or 2 $R^5$, and further optionally substituted with 1 —$N(R^6)_2$; each $R^5$ is independently selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-; and each $R^6$ is independently selected from the group consisting of H and $C_1$-$C_2$ alkyl.

An embodiment of the invention includes a compound of any one of Formulas I, II, and III, wherein the $C_3$-$C_8$ cycloalkyl or $C_3$-$C_6$ cycloalkyl of $R^3$ is selected from the group consisting of cyclopropyl, cyclobutyl, cyclopentyl, cyclohexyl, and bicyclo[3.1.0]hexanyl, wherein each of the cycloalkyl selections is optionally substituted with 1 or 2 $R^5$ and further optionally substituted with 1 —$N(R^6)_2$; each $R^5$ is independently selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-; and each $R^6$ is independently selected from the group consisting of H and $C_1$-$C_2$ alkyl. In a further embodiment, the $C_3$-$C_8$ cycloalkyl or $C_3$-$C_6$ cycloalkyl of $R^3$ is selected from the group consisting of cyclopropyl, cyclobutyl, cyclopentyl, cyclohexyl, and bicyclo[3.1.0]hexan-2-yl, wherein each of the cycloalkyl selections is optionally substituted with 1 or 2 $R^5$ and further optionally substituted with 1 —$N(R^6)_2$. In a yet further embodiment, each $R^5$ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-. In a still further embodiment, each $R^5$ is independently selected from the group consisting of F, OH, $C_1$-$C_2$ alkyl, $C_1$-$C_2$ fluoroalkyl, and $C_1$-$C_2$ alkoxy-$C_1$-$C_2$ alkyl-. In a yet still further embodiment, each $R^5$ is independently selected from the group consisting of F, OH, $CH_3$, and $CH_2CH_3$; and each $R^6$ is independently selected from the group consisting of H and $CH_3$.

An embodiment of the invention includes a compound of any one of Formulas I, II, or III, or a pharmaceutically acceptable salt thereof, wherein $R^3$ is bicyclo[3.1.0]hexan- 2-yl, optionally substituted with 1 or 2 $R^5$; and each $R^5$ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-.

An embodiment of the invention includes a compound of any one of Formulas I, II, or III, or a pharmaceutically acceptable salt thereof, wherein the $C_3$-$C_8$ cycloalkyl or $C_3$-$C_6$ cycloalkyl of $R^3$ is cyclohexyl (also known as cyclohexanyl) optionally substituted with 1 or 2 $R^5$ and further optionally substituted with 1 —$N(R^6)_2$ (wherein each of $R^5$ and $R^6$ is as defined in any of the embodiments described herein). In a further embodiment, $R^3$ is cyclohexyl substituted with 1-$N(R^6)_2$ (wherein each of $R^6$ is as defined in any of the embodiments described herein). In a yet further embodiment, each $R^6$ is independently selected from the group consisting of H and $CH_3$.

An embodiment of the invention includes a compound of any one of Formulas I, II, or III, or a pharmaceutically acceptable salt thereof, wherein the $C_3$-$C_8$ cycloalkyl or $C_3$-$C_6$ cycloalkyl of $R^3$ is cyclobutyl optionally substituted with 1 or 2 $R^5$ (wherein each of $R^5$ is as defined in any of the embodiments described herein). In a further embodiment, each $R^5$ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-.

An embodiment of the invention includes a compound of any one of Formulas I, II, or III, or a pharmaceutically acceptable salt thereof, wherein the $C_3$-$C_8$ cycloalkyl or $C_3$-$C_6$ cycloalkyl of $R^3$ is cyclopentyl optionally substituted with 1 or 2 $R^5$ and further optionally substituted with 1 —$N(R^6)_2$ (wherein each of $R^5$ and $R^6$ is as defined in any of the embodiments described herein). In a further embodiment, $R^3$ is cyclopentyl optionally substituted with 1 or 2 $R^5$ (wherein each of $R^5$ is as defined in any of the embodiments described herein). In a yet further embodiment, $R^3$ is cyclopentyl optionally substituted with 1 or 2 $R^5$; and each $R^5$ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-. In a still further embodiment, $R^3$ is cyclopentyl.

An embodiment of the invention includes a compound of any one of Formulas I, II, or III, or a pharmaceutically acceptable salt thereof, wherein A is CH (and the other variables, such as $R^1$, $R^2$, $R^3$, $R^4$, when present, are as defined in any of the embodiments described herein).

An embodiment of the invention includes a compound of any one of Formulas I, II, or III, or a pharmaceutically acceptable salt thereof, wherein A is N (and the other variables, such as $R^1$, $R^2$, $R^3$, $R^4$, when present, are as defined in any of the embodiments described herein).

An embodiment of the invention is a compound of Formula I, II, or III, wherein $R^3$ is (5- to 7-membered heterocyclyl)-$C_1$-$C_4$ alkyl- or ($C_3$-$C_6$ cycloalkyl)-$C_1$-$C_4$ alkyl-, wherein each of the 5- to 7-membered heterocyclyl moiety in (5- to 7-membered heterocyclyl)-$C_1$-$C_4$ alkyl- is optionally substituted with 1 or 2 $R^5$, and wherein the $C_3$-$C_6$ cycloalkyl moiety in ($C_3$-$C_6$ cycloalkyl)-$C_1$-$C_4$ alkyl- is optionally substituted with 1 or 2 $R^5$ and further optionally substituted with 1 —$N(R^6)_2$ (wherein each of $R^5$ and $R^6$ is as defined in any of the embodiments described herein). Some examples of the 5- to 7-membered heterocyclyl moiety include 2-azaspiro[3.3]heptanyl, tetrahydrofuranyl, pyrrolidinyl, or piperidinyl, each of which is optionally substituted with 1 $R^5$, and $R^5$ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-. Some examples of the $C_3$-$C_6$ cycloalkyl moiety include cyclopropyl, cyclobutyl, cyclopentyl, cyclohexanyl, or bicyclo[3.1.0]hexanyl, each of which is optionally substituted with 1 or 2 $R^5$ and further optionally substituted with 1 —$N(R^6)_2$; wherein each $R^5$ is independently selected from the group consisting of F, OH, $CH_3$, and $CH_2CH_3$; and each $R^6$ is independently selected from H and $CH_3$.

An embodiment of the invention includes a compound of Formula II or III, or a pharmaceutically acceptable salt thereof, wherein A is N; $R^3$ is cyclobutyl, cyclopentyl, or bicyclo[3.1.0]hexanyl, each is optionally substituted with 1 or 2 $R^5$; and each $R^5$ is independently selected from the group consisting of F, OH, $CH_3$, or $CH_2CH_3$. In a further embodiment, $R^3$ is cyclobutyl, cyclopentyl, or bicyclo[3.1.0]hexan-2-yl, each is optionally substituted with 1 or 2 $R^5$; and each $R^5$ is independently selected from the group consisting of F and $CH_3$. In a yet further embodiment, the compound or a pharmaceutically acceptable salt thereof is a compound of Formula III or a pharmaceutically acceptable salt thereof.

An embodiment of the invention includes a compound of Formula II or III, or a pharmaceutically acceptable salt thereof, wherein A is CH; $R^3$ is cyclobutyl, cyclopentyl, or bicyclo[3.1.0]hexanyl, each is optionally substituted with 1 or 2 $R^5$; and each $R^5$ is independently selected from the group consisting of F, OH, $CH_3$, or $CH_2CH_3$. In a further embodiment, $R^3$ is cyclobutyl, cyclopentyl, or bicyclo[3.1.0]hexan-2-yl, each is optionally substituted with 1 or 2 $R^5$; and each $R^5$ is independently selected from the group consisting of F and $CH_3$. In a yet further embodiment, the compound or a pharmaceutically acceptable salt thereof is a compound of Formula III or a pharmaceutically acceptable salt thereof.

An embodiment of the invention includes a compound of Formula II or III, or a pharmaceutically acceptable salt thereof, wherein A is N; $R^3$ is cyclopentyl optionally substituted with 1 or 2 $R^5$; and each $R^5$ is independently selected from the group consisting of F, OH, $CH_3$, or $CH_2CH_3$. In a further embodiment, $R^3$ is cyclopentyl optionally substituted with 1 or 2 $R^5$; and each $R^5$ is independently selected from the group consisting of F and $CH_3$. In a yet further embodiment, the compound or a pharmaceutically acceptable salt thereof is a compound of Formula III or a pharmaceutically acceptable salt thereof.

An embodiment of the invention includes a compound of Formula II or III, or a pharmaceutically acceptable salt thereof, wherein A is CH; $R^3$ is cyclopentyl optionally substituted with 1 or 2 $R^5$; and each $R^5$ is independently selected from the group consisting of F, OH, $CH_3$, or $CH_2CH_3$. In a further embodiment, $R^3$ is cyclopentyl optionally substituted with 1 or 2 $R^5$; and each $R^5$ is independently selected from the group consisting of F and $CH_3$. In a yet further embodiment, the compound or a pharmaceutically acceptable salt thereof is a compound of Formula III or a pharmaceutically acceptable salt thereof.

An embodiment of the invention includes a compound of Formula II or III, or a pharmaceutically acceptable salt thereof, wherein A is N; $R^3$ is pyrrolidinyl, piperidinyl, or 2-azaspiro[3.3]heptanyl, each is optionally substituted with 1 $R^5$, and wherein $R^5$ is selected from the group consisting of $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-. In a further embodiment, $R^3$ is pyrrolidine-3-yl, piperidin-4-yl, or 2-azaspiro[3.3]heptan-6-yl, each is optionally substituted with 1 $R^5$, and wherein $R^5$ is selected from the group consisting of $C_1$-$C_2$ alkyl, $C_1$-$C_2$ fluoroalkyl, $C_1$-$C_2$ alkoxy-$C_1$-$C_2$ alkyl-, and $C_1$-$C_2$ fluoroalkoxy-$C_1$-$C_2$ alkyl-. In a yet further embodiment, $R^3$ is 2-azaspiro[3.3]heptan-6-yl optionally substituted with 1 $R^5$ that is selected from the group consisting of $C_1$-$C_2$ alkyl, $C_1$-$C_2$ fluoroalkyl, $C_1$-$C_2$ alkoxy-$C_1$-$C_2$ alkyl-, and $C_1$-$C_2$ fluoroalkoxy-$C_1$-$C_2$ alkyl-. In a still further embodiment, the compound or a pharmaceutically acceptable salt thereof is a compound of Formula III or a pharmaceutically acceptable salt thereof.

An embodiment of the invention includes a compound of Formula II or III, or a pharmaceutically acceptable salt thereof, wherein A is CH; $R^3$ is pyrrolidinyl, piperidinyl, or 2-azaspiro[3.3]heptanyl, each is optionally substituted with 1 $R^5$, and wherein $R^5$ is selected from the group consisting of $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-. In a further embodiment, $R^3$ is pyrrolidine-3-yl, piperidin-4-yl, or 2-azaspiro[3.3]heptan-6-yl, each is optionally substituted with 1 $R^5$, and wherein $R^5$ is selected from the group consisting of $C_1$-$C_2$ alkyl, $C_1$-$C_2$ fluoroalkyl, $C_1$-$C_2$ alkoxy-$C_1$-$C_2$ alkyl-, and $C_1$-$C_2$ fluoroalkoxy-$C_1$-$C_2$ alkyl-. In a yet further embodiment, $R^3$ is 2-azaspiro[3.3]heptan-6-yl optionally substituted with 1 $R^5$ that is selected from the group consisting of $C_1$-$C_2$ alkyl, $C_1$-$C_2$ fluoroalkyl, $C_1$-$C_2$ alkoxy-$C_1$-$C_2$ alkyl-, and $C_1$-$C_2$ fluoroalkoxy-$C_1$-$C_2$ alkyl-. In a still further embodiment, the compound or a pharmaceutically acceptable salt thereof is a compound of Formula III or a pharmaceutically acceptable salt thereof.

In one embodiment, the present invention provides a compound selected from Examples 1 to 34 in the EXAMPLES section or a pharmaceutically acceptable salt thereof (or the parent/basic compound thereof where the exemplary compound, for example, is a salt) herein below.

One embodiment includes a compound selected from:
6-acetyl-8-cyclobutyl-2-{[3-hydroxytetrahydro-2H-pyran-4-yl]amino}-5-methylpyrido[2,3-d]pyrimidin-7(8H)-one;
6-acetyl-8-cyclopentyl-2-{[3-hydroxytetrahydro-2H-pyran-4-yl]amino}-5-methylpyrido[2,3-d]pyrimidin-7(8H)-one;
6-acetyl-8-(2-azaspiro[3.3]heptan-6-yl)-2-{[3-hydroxytetrahydro-2H-pyran-4-yl]amino}-5-methylpyrido[2,3-d]pyrimidin-7(8H)-one;
6-acetyl-2-{[3-hydroxytetrahydro-2H-pyran-4-yl]amino}-5-methyl-8-[2-methylcyclopentyl]pyrido[2,3-d]pyrimidin-7(8H)-one;
3-acetyl-1-cyclopentyl-7-{[3-hydroxytetrahydro-2H-pyran-4-yl]amino}-4-methyl-1,6-naphthyridin-2(1H)-one;
6-acetyl-8-[bicyclo[3.1.0]hexan-2-yl]-2-{[3-hydroxytetrahydro-2H-pyran-4-yl]amino}-5-methylpyrido[2,3-d]pyrimidin-7(8H)-one;
6-acetyl-8-[2-fluoro-2-methylcyclopentyl]-2-{[3-hydroxytetrahydro-2H-pyran-4-yl]amino}-5-methylpyrido[2,3-d]pyrimidin-7(8H)-one; and
6-acetyl-8-[2-(2,2-difluoroethyl)-2-azaspiro[3.3]heptan-6-yl]-2-{[3-hydroxytetrahydro-2H-pyran-4-yl]amino}-5-methylpyrido[2,3-d]pyrimidin-7(8H)-one,
or a pharmaceutically acceptable salt thereof.

One embodiment includes a compound selected from:
6-acetyl-8-cyclobutyl-2-{[(3S,4R)-3-hydroxytetrahydro-2H-pyran-4-yl]amino}-5-methylpyrido[2,3-d]pyrimidin-7(8H)-one;
6-acetyl-8-cyclopentyl-2-{[(3S,4R)-3-hydroxytetrahydro-2H-pyran-4-yl]amino}-5-methylpyrido[2,3-d]pyrimidin-7(8H)-one;
6-acetyl-8-(2-azaspiro[3.3]heptan-6-yl)-2-{[(3S,4R)-3-hydroxytetrahydro-2H-pyran-4-yl]amino}-5-methylpyrido[2,3-d]pyrimidin-7(8H)-one;
6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one;
3-acetyl-1-cyclopentyl-7-{[(3S,4R)-3-hydroxytetrahydro-2H-pyran-4-yl]amino}-4-methyl-1,6-naphthyridin-2(1H)-one;
6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one;
6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one;
6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one;
6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one; and
6-acetyl-8-[2-(2,2-difluoroethyl)-2-azaspiro[3.3]heptan-6-yl]-2-{[(3S,4R)-3-hydroxytetrahydro-2H-pyran-4-yl]amino}-5-methylpyrido[2,3-d]pyrimidin-7(8H)-one,
or a pharmaceutically acceptable salt thereof.

One embodiment includes a compound selected from:
6-acetyl-8-cyclobutyl-2-{[(3S,4R)-3-hydroxytetrahydro-2H-pyran-4-yl]amino}-5-methylpyrido[2,3-d]pyrimidin-7(8H)-one;
6-acetyl-8-cyclopentyl-2-{[(3S,4R)-3-hydroxytetrahydro-2H-pyran-4-yl]amino}-5-methylpyrido[2,3-d]pyrimidin-7(8H)-one;
6-acetyl-8-(2-azaspiro[3.3]heptan-6-yl)-2-{[(3S,4R)-3-hydroxytetrahydro-2H-pyran-4-yl]amino}-5-methylpyrido[2,3-d]pyrimidin-7(8H)-one;
6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one;
3-acetyl-1-cyclopentyl-7-{[(3S,4R)-3-hydroxytetrahydro-2H-pyran-4-yl]amino}-4-methyl-1,6-naphthyridin-2(1H)-one;
6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one, or 6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one, or a mixture thereof;
6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one, or 6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one, or a mixture thereof; and
6-acetyl-8-[2-(2,2-difluoroethyl)-2-azaspiro[3.3]heptan-6-yl]-2-{[(3S,4R)-3-hydroxytetrahydro-2H-pyran-4-yl]amino}-5-methylpyrido[2,3-d]pyrimidin-7(8H)-one,
or a pharmaceutically acceptable salt thereof.

One embodiment includes a compound selected from:
6-acetyl-8-cyclobutyl-2-{[(3S,4R)-3-hydroxytetrahydro-2H-pyran-4-yl]amino}-5-methylpyrido[2,3-d]pyrimidin-7(8H)-one;

6-acetyl-8-cyclopentyl-2-{[(3S,4R)-3-hydroxytetrahydro-2H-pyran-4-yl]amino}-5-methylpyrido[2,3-d]pyrimidin-7(8H)-one;

6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one;

6-acetyl-8-[(1S,2S)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one, or 6-acetyl-8-[(1R,2R)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one, or a mixture thereof;

6-acetyl-8-[(1R,2S)-2-ethylcyclopentyl]-2-{[(3S,4R)-3-hydroxytetrahydro-2H-pyran-4-yl]amino}-5-methylpyrido[2,3-d]pyrimidin-7(8H)-one;

6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one, or 6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one, or a mixture thereof;

6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one, or 6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one, or a mixture thereof;

6-acetyl-8-(3,3-dimethylcyclobutyl)-2-{[(3S,4R)-3-hydroxytetrahydro-2H-pyran-4-yl]amino}-5-methylpyrido[2,3-d]pyrimidin-7(8H)-one;

3-acetyl-1-(3-hydroxycyclopentyl)-7-{[(3S,4R)-3-hydroxytetrahydro-2H-pyran-4-yl]amino}-4-methyl-1,6-naphthyridin-2(1H)-one, including resolved diastereomers or as a mixture;

6-acetyl-8-(cis-4-hydroxycyclohexyl)-2-{[(3S,4R)-3-hydroxytetrahydro-2H-pyran-4-yl]amino}-5-methylpyrido[2,3-d]pyrimidin-7(8H)-one; and 6-acetyl-8-(trans-3-hydroxycyclobutyl)-2-{[(3S,4R)-3-hydroxytetrahydro-2H-pyran-4-yl]amino}-5-methylpyrido[2,3-d]pyrimidin-7(8H)-one, or a pharmaceutically acceptable salt thereof.

In some embodiments, the present invention provides a crystalline form of 3-acetyl-1-cyclopentyl-7-{[(3S,4R)-3-hydroxytetrahydro-2H-pyran-4-yl]amino}-4-methyl-1,6-naphthyridin-2(1H)-one (e.g. the crystalline form as in Example 5). In some further embodiments, the crystalline form of 3-acetyl-1-cyclopentyl-7-{[(3S,4R)-3-hydroxytetrahydro-2H-pyran-4-yl]amino}-4-methyl-1,6-naphthyridin-2 (1H)-one is anhydrous. In some further embodiments, the crystalline form of anhydrous (anhydrate) 3-acetyl-1-cyclopentyl-7-{[(3S,4R)-3-hydroxytetrahydro-2H-pyran-4-yl]amino}-4-methyl-1,6-naphthyridin-2(1H)-one is designated as "Form I" that is characterized according to its unique solid state signatures with respect to, for example, powder X-ray diffraction (PXRD), described herein (such as substantially as depicted in FIG. 1). A list of diffraction peaks expressed in terms of the degree 2θ and relative intensities with a relative intensity of 3.0% (as depicted FIG. 1) is provided in Table X1 herein. As is well known in the art of powder diffraction, the relative intensities of the peaks (reflections) can vary, depending upon the sample preparation technique, the sample mounting procedure and the particular instrument employed. Moreover, instrument variation and other factors can affect the 2-theta values. Therefore, the XRPD peak assignments can vary by plus or minus about 0.2°.

In some embodiments, Form I exhibits a powder X-ray diffraction pattern comprising at least two characteristic peaks, in terms of 2θ, selected from at 8.0±0.2°; 18.6±0.2°; 19.1±0.2°; and 21.3±0.2°. In some embodiments, Form I exhibits a powder X-ray diffraction pattern comprising at least three characteristic peaks, in terms of 2θ, selected from at 8.0±0.2°; 18.6±0.2°; 19.1±0.2°; and 21.3±0.2°. In some embodiments, Form I exhibits a powder X-ray diffraction pattern comprising all four characteristic peaks, in terms of 2θ, selected from at 8.0±0.2°; 18.6±0.2°; 19.1±0.2°; and 21.3±0.2°.

In some embodiments, Form I exhibits a powder X-ray diffraction pattern comprising characteristic peaks, in terms of 2θ, at 8.0±0.2° and 18.6±0.2°.

In some embodiments, Form I exhibits a powder X-ray diffraction pattern comprising characteristic peaks, in terms of 2θ, at 8.0±0.2° and 19.1±0.2°.

In some embodiments, Form I exhibits a powder X-ray diffraction pattern comprising characteristic peaks, in terms of 2θ, at 18.6±0.2° and 19.1±0.2°.

In some embodiments, Form I exhibits a powder X-ray diffraction pattern comprising all three characteristic peaks, in terms of 2θ, selected from at 8.0±0.2°; 18.6±0.2°; and 19.1±0.2°.

In some embodiments, Form I exhibits a powder X-ray diffraction pattern comprising at least two characteristic peaks, in terms of 2θ, as those listed in Table X1.

In some embodiments, Form I exhibits a powder X-ray diffraction pattern comprising at least three characteristic peaks, in terms of 2θ, as those listed in Table X1.

In some embodiments, Form I exhibits a powder X-ray diffraction pattern comprising at least four (e.g. 4, 5, 6, 7, 8, 9, or 10) characteristic peaks, in terms of 2θ, as those listed in Table X1.

In some embodiments, Form I exhibits a powder X-ray diffraction pattern comprising at least two characteristic peaks, in terms of 2θ, selected from at 8.0±0.2°; 18.6±0.2°; 19.1±0.2°; and 21.3±0.2°; and at least one additional characteristic peaks, in terms of 2θ, as those listed in Table X1 (e.g. peak at 23.3).

In some embodiments, Form I exhibits a powder X-ray diffraction pattern substantially as shown in FIG. 1.

The present invention includes any subset of any embodiment described herein.

The present invention includes combinations of two or more embodiments described hereinabove, or any subset thereof.

In another embodiment, the invention provides a pharmaceutical composition comprising a compound of the invention described herein, and at least one pharmaceutically acceptable excipient or carrier.

The present invention further provides use of a compound of the invention described herein in treating a disease or disorder described herein (i.e. method of treatment).

The compound of the present invention is a CDK inhibitor (e.g. a CDK4 and/or CDK6 inhibitor). Thus, the present invention further provides a method for inhibiting CDK (i.e., an activity of CDK either in vitro or in vivo), comprising contacting (including incubating) the CDK with the compound of the invention described herein.

As used herein, the compounds of invention in the pharmaceutical compositions (including formulations), uses, methods, and/or kits of the present invention described herein include compounds of Formula I or pharmaceutically acceptable salts thereof (including a compound of Formula II or III, or a pharmaceutically acceptable salt thereof, and including all embodiments and combinations of two or more embodiments described herein or any subcombination thereof, for example, any one of the compounds selected from Examples 1 to 34, or a pharmaceutically acceptable salt thereof).

As used herein, the term "contacting" refers to the bringing together of indicated moieties in an in vitro system or an in vivo system. For example, "contacting" CDK with a compound of the invention includes the administration of a compound of the present invention to an individual or patient, such as a human, having the CDK, as well as, for example, introducing a compound of the invention into a sample containing a cellular or purified preparation containing the CDK.

The present invention further provides a method for treating a disease or disorder in a patient, which method including administering to the patient in need thereof a therapeutic effective amount of a compound or a pharmaceutically acceptable salt of the invention, wherein the disease or disorder is selected from the group consisting of pulmonary hypertension, pulmonary arterial hypertension, pulmonary hypertension with left heart disease, pulmonary hypertension with lung disease and/or hypoxemia, pulmonary hypertension due to chronic thrombotic and/or embolic disease, and diseases associated with pulmonary hypertension including sarcoidosis, histiocytosis X, lymphangiomatosis and compression of pulmonary vessels.

The present invention further provides a method for treating pulmonary hypertension in a patient, which method includes administering to the patient in need thereof an effective amount of a compound of the present invention, or a pharmaceutically acceptable salt thereof. In some embodiments, the compound administered is in the form of a pharmaceutically acceptable salt. In other embodiments, the compound administered is not in the form of a pharmaceutically acceptable salt (e.g., the base/parent compound is administered).

When discussing treatment of pulmonary hypertension, any one or more of these related diseases are included within that treatment as they fall within the WHO categorization of pulmonary hypertension: Group 1: pulmonary arterial hypertension (PAH); Group 2: PH with left heart disease; Group 3: PH with lung disease and/or hypoxemia; Group 4: PH due to chronic thrombotic and/or embolic disease; and Group 5: miscellaneous conditions (e.g., sarcoidosis, histiocytosis X, lymphangiomatosis and compression of pulmonary vessels).

Another embodiment of the invention includes a method for treating pulmonary arterial hypertension in a patient, which method includes administering to the patent in need thereof an effective amount of a compound or a pharmaceutically acceptable salt of the invention.

In an embodiment, the present invention further provides a method for treating abnormal cell growth in a subject, which method includes administering to the subject in need thereof a therapeutically effective amount of a compound or a pharmaceutically acceptable salt of the invention. In a further embodiment, the abnormal cell growth is cancer. Compounds or salts of the invention may be administered as single agent, or may be administered in combination with one or more other anti cancer therapeutic agents, in particular standard of care agents appropriate for the particular cancer. In a yet further embodiment, the cancer is selected from breast cancer, ovarian cancer, bladder cancer, uterine cancer, prostate cancer, lung cancer [including non-small cell lung cancer (NSCLC), small cell lung cancer (SCLC), squamous cell carcinoma or adenocarcinoma], esophageal cancer, head and neck cancer, colorectal cancer, kidney cancer (including renal cell carcinoma or RCC), liver cancer (including hepatocellular carcinoma or HCC), pancreatic cancer, stomach (i.e., gastric) cancer, and thyroid cancer. In further embodiments of the methods provided herein, the cancer is breast cancer, ovarian cancer, bladder cancer, uterine cancer, prostate cancer, lung cancer, esophageal cancer, liver cancer, pancreatic cancer, or stomach cancer.

In an embodiment, the present invention further provides a method for treating cancer in a subject, which method includes administering to the subject in need thereof a therapeutic effective amount of a compound or a pharmaceutically acceptable salt of the invention. In a further embodiment, the cancer is breast cancer, including, e.g., ER-positive/HR-positive, HER2-negative breast cancer; ER-positive/HR-positive, HER2-positive breast cancer; triple negative breast cancer (TNBC); or inflammatory breast cancer. In another embodiment, the breast cancer is endocrine resistant breast cancer, trastuzumab resistant breast cancer, or breast cancer demonstrating primary or acquired resistance to CDK4/CDK6 inhibition. In yet another embodiment, the breast cancer is advanced or metastatic breast cancer.

In a further aspect, the invention provides a method for the treatment of abnormal cell growth, in particular cancer, in a subject in need thereof, which method includes administering to the subject an amount of a compound of the invention, in combination with an amount of an additional anti cancer therapeutic agent, which amounts are together effective in treating said abnormal cell growth.

The present invention further provides use of a compound of the present invention, for treating a disease or disorder described herein (e.g. those described in the method of treatment herein).

The present invention further provides use of a compound of the present invention, in manufacturing a medicament for treating a disease or disorder described herein (e.g. those described in the method of treatment herein).

The invention also includes the following embodiments:

a compound of the present invention, including in any of the embodiments described herein, for use as a medicament;

a compound of the present invention, including any of the embodiments described herein, for use in the manufacture of a medicament;

use of a compound of the present invention, including any of the embodiments described herein, for treating abnormal cell growth such as cancer;

use of a compound of the present invention, including any of the embodiments described herein, in the manufacture of a medicament for treating abnormal cell growth such as cancer;

use of a compound of the present invention, including any of the embodiments described herein, in the manufacture of a medicament for treating pulmonary arterial hypertension;

use of a compound of the present invention, including any of the embodiments described herein, in the manufacture of a medicament for treating pulmonary hypertension (PH), or any of the diseases within the WHO categorization of PH;

a compound of the present invention, including any of the embodiments described herein, for use in the treatment of abnormal cell growth such as cancer;

a compound of the present invention, including any of the embodiments described herein, for use in the treatment of pulmonary arterial hypertension; and a compound of the present invention, including any of the embodiments described herein, for use in the treatment of pulmonary hypertension (PH), or any of the diseases within the WHO categorization of PH.

Every Example or a pharmaceutically acceptable salt thereof may be claimed individually or grouped together in any combination with any number of each and every embodiment described herein.

The invention also relates to a pharmaceutical composition comprising a compound of the present invention, including any of the embodiments described herein, for use in the treatment of a disease or disorder described herein, for example, one selected from: pulmonary hypertension, pulmonary arterial hypertension, pulmonary hypertension with left heart disease, pulmonary hypertension with lung disease and/or hypoxemia, pulmonary hypertension due to chronic thrombotic and/or embolic disease, and diseases associated with pulmonary hypertension including sarcoidosis, histiocytosis X, lymphangiomatosis and compression of pulmonary vessels.

In another embodiment of the invention, a compound of the present invention is administered to a subject diagnosed with or at risk of developing pulmonary hypertension or PAH including, but are not limited to, idiopathic PAH, hereditary or familial PAH, and secondary pulmonary hypertension (e.g. hypertension resulting from pulmonary emboli, emphysema, pulmonary fibrosis, and congenital heart disease). In one embodiment, the subject is diagnosed with idiopathic PAH or hereditary PAH. In some embodiments, the subject at risk of developing PAH has a mutation in the gene encoding the bone morphogenetic protein type-2 receptor.

The present invention also includes a kit for the treatment or prevention of pulmonary arterial hypertension. In one embodiment, the kit comprises a compound of the present invention and an administration device. The administration device can be designed for pulmonary delivery, such as inhalers, nebulizers, insufflators, droppers, and aerosolizers. In other embodiments, the administration device can be designed for intravenous or intra-arterial delivery, such as a catheter. The compound or the pharmaceutically acceptable salt of the present invention may be optionally formulated to be stored in the administration device. The kit may further comprise instructions for administering the compound or the pharmaceutically acceptable salt of the present invention, to a subject (e.g., human) for treating or preventing PAH or other diseases discussed herein. In one embodiment, the instructions elaborate and qualify the mode of administration, for example, by specifying the days of administration for the compound or the pharmaceutically acceptable salt of the present invention during a 28-day cycle.

The invention includes a method of treating a disorder disclosed herein (e.g. PAH or cancer), where the method includes using a compound of the present invention either as monotherapy or in a combination therapy in which a subject or patient in need of treatment is administered the compound or salt of the invention in combination with one or more drugs (referred to also as active agent) approved for the treatment of the disease or disorder disclosed herein (e.g. PAH or cancer). For example, an additional active agent may include but is not limited to a prostaglandin (e.g., epoprostenol, treprostinil, iloprost, selexipag), an endothelin receptor antagonist (e.g., bosentan, ambrisentan, macitentan), a guanylate cyclase inhibitor (e.g., riociguat), vasodilators (e.g., prostacyclin and sildenafil), calcium channel blockers (e.g., amlodipine, diltiazem, and nifedipine); anticoagulants (e.g., warfarin), and diuretics. Reference to a drug, e.g., sildenafil, includes sildenafil and all pharmaceutically acceptable salts, e.g., sildenafil citrate. For another example, an additional active agent may include an anti-cancer agent such as one of the standard of care agents appropriate for the cancer to be treated.

In another aspect, a compound of the present invention is used in the manufacture of a medicament for the treatment or prevention of PAH. Yet in another aspect, a compound of the present invention is used in the manufacture of a medicament for the treatment or prevention of related diseases as discussed herein. In various embodiments, the medicament is formulated for oral administration, including both immediate release and sustained (modified) release pharmaceutical formulations. In other embodiments the medicament is formulated for administration by inhalation. In all of these embodiments, the invention provides unit dose forms of the medicament.

The invention also provides a combination that includes a compound of the present invention and another therapeutic agent. Such combination can be used in the uses and methods of the invention described herein.

The present invention also includes isotopically labelled compounds, which are identical to a compound of the present invention (e.g. a compound of Formula I, II, or III, or a pharmaceutically acceptable salt thereof), but for the fact that one or more atoms are replaced by atoms having the same atomic number, but an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, and pharmaceutically acceptable salts of said compounds, which contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14 i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I, II, or III, or a pharmaceutically acceptable salt thereof, can generally be prepared by carrying out the procedures disclosed in the Schemes and/or in the Examples and Preparations below, by substituting a readily available isotopically labelled reagent for a non-isotopically labelled reagent.

The compounds of the invention may exhibit the phenomena of tautomerism and structural isomerism. For example, the compounds of the invention may exist in several tautomeric forms. All such tautomeric forms are included within the scope of the compounds of the invention. Tautomers may exist as mixtures of a tautomeric set in solution. In solid form, usually one tautomer predominates. Even though one tautomer may be described, the present invention includes all tautomers of the compounds of the invention.

The invention also relates to prodrugs of the compounds of the present invention. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains an alcohol functionality (—OH), an ether thereof, for example, replacement of the hydrogen with ($C_1$-$C_6$)alkanoyloxymethyl, or with a phosphate ether group; and (ii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

The term "subject" or "patient", as used herein, refers to a mammal such as a human, a primate, cow, sheep, or a companion animal (including cat or dog).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

For the purposes of this invention, beneficial or desired clinical results in the treatment of cancer include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in a number of ways (see, for example, W. A. Weber, Assessing tumor response to therapy, J. Nucl. Med. 50 Suppl. 1:1S-10S (2009). For example, with respect to tumor growth inhibition (T/C), according to the National Cancer Institute (NCI) standards, a T/C less than or equal to 42% is the minimum level of anti-tumor activity. A T/C <10% is considered a high anti-tumor activity level, with T/C (%)=median tumor volume of the treated/median tumor volume of the control×100.

The phrase "therapeutically effective amount" means an amount of a compound of the invention that (i) treats or prevents the particular disease, (ii) attenuates, ameliorates, or eliminates one or more symptoms of the particular disease, or (iii) prevents or delays the onset of one or more symptoms of the particular disease described herein.

The phrase "pharmaceutically acceptable" indicates that the substance or composition must be compatible chemically and toxicologically, with the other ingredients comprising a formulation, and for the mammal being treated therewith.

Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphthalenedisulfonic acid and xinafoate salts.

Suitable base salts are formed from bases which form non-toxic salts. Examples include the aluminium, arginine, benzathine, calcium, choline, diethylamine, bis(2-hydroxyethyl)amine (diolamine), glycine, lysine, magnesium, meglumine, 2-aminoethanol (olamine), potassium, sodium, 2-Amino-2-(hydroxymethyl)propane-1,3-diol (tris or tromethamine) and zinc salts.

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

Abnormal cell growth includes the abnormal growth of: (1) tumor cells (tumors) that show increased expression of CDK4 and/or CDK6; (2) tumors that proliferate by aberrant CDK4 and or CDK6 activation; and (3) tumors that are resistant to endocrine therapy, HER2 antagonists or CDK4/6 inhibition.

The term "additional anticancer therapeutic agent" as used herein means any one or more therapeutic agent, other than a compound of the invention, that is or can be used in the treatment of cancer. In some embodiments, such additional anticancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like.

In some embodiments, the additional anticancer agent is an endocrine agent, such as an aromatase inhibitor, a SERD or a SERM.

In other embodiments, a compound of the invention may be administered in combination with a standard of care agent, such as tamoxifen, docetaxel, paclitaxel, cisplatin, capecitabine, gemcitabine, vinorelbine, exemestane, letrozole, fulvestrant, anastrozole or trastuzumab.

In some embodiments, the additional anticancer agent is an anti-angiogenesis agent, including for example VEGF inhibitors, VEGFR inhibitors, TIE-2 inhibitors, PDGFR inhibitors, angiopoetin inhibitors, PKCβ inhibitors, COX-2

(cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (AG 13736), SU 14813 (Pfizer), and AG 13958 (Pfizer). Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™) valdecoxib (Bextra™), rofecoxib (Vioxx™) iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™ Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Procyon). Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In other embodiments, the additional anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors. Additional examples of signal transduction inhibitors which may be used in conjunction with a compound of the invention and pharmaceutical compositions described herein include BMS 214662 (Bristol-Myers Squibb), Ionafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples of signal transduction inhibitors include gefitinib (Iressa™), cetuximab (Erbitux™), erlotinib (Tarceva™), trastuzumab (Herceptin™), sunitinib (Sutent™), imatinib (Gleevec™), crizotinib (Pfizer), dacomitinib (Pfizer), bosutinib (Pfizer), canertinib (CI 1033), pertuzumab (Omnitarg™) lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), ARRY 142886 (Array Biopharm), everolimus (Certican™), zotarolimus (Endeavor™), temsirolimus (Torisel™), AP 23573 (ARIAD), and VX 680 (Vertex), XL 647 (Exelixis), sorafenib (Nexavar™), LE-AON (Georgetown University), and GI-4000 (GlobeImmune). Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), palbociclib (Pfizer), and AG 024322 (Pfizer).

In other embodiments, the additional anti-cancer agent is a so called classical antineoplastic agent. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib, olapariv, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi), Selective Estrogen-Receptor Down-regulators (SERD's; such as fulvestrant), exemestane (Aromasin), anastrozole (Arimidex), atamestane, fadrozole, letrozole (Femara), formestane; gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide; antiandrogen agents, such as enzalutamide, abiraterone acetate, bicalutamide (Casodex); and combinations thereof. Other examples of classical antineoplastic agents used in combination with a compound of the invention include but are not limited to PARP inhibitors, such as talazoparib, olapariv, rucaparib, niraparib, iniparib, veliparib; suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In still other embodiments, the additional anti-cancer agent is a so called dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™) cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof. Further examples of classical antineoplastic agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

In other embodiments, the additional anti-cancer agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In further embodiments, the additional anti-cancer agent is an immunomodulatory agent, such as an inhibitor of CTLA-4, PD-1 or PD-L1 (e.g., pembrolizumab, nivolumab or avelumab), LAG-3, TIM-3, TIGIT, 4-1BB, OX40, GITR, CD40, or a CAR-T-cell therapy.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments of the methods provided herein, the cancer is selected from the group consisting of breast cancer, ovarian cancer, bladder cancer, uterine cancer, prostate cancer, lung cancer (including NSCLC), esophageal cancer, liver cancer, pancreatic cancer and stomach cancer.

This invention also comprises a pharmaceutical formulation comprising a therapeutically effective amount of a compound of the invention, together with a pharmaceutically acceptable carrier. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material. For tablet dosage forms, depending on dose, a compound or a pharmaceutically acceptable salt of the invention, may make up from 1 wt % to 80 wt % of the dosage form, typically from 5 wt % to 60 wt %, more typically from about 10 wt % to about 35 wt %, or even more typically from about 15 wt % to about 25 wt % of the dosage form. In specific embodiments, a compound or a pharmaceutically acceptable salt of the invention, comprises about 20 wt % of the dosage form by weight.

In the solid dosage forms of the invention, the carrier may comprise a variety of pharmaceutically acceptable excipients, including, for example, diluents, disintegrants, binders, lubricants, glidants and surface-active agents. Formulations may also include excipients such as preservatives, antioxidants, flavors and colorants, as well as other excipients known in the art.

Solid dosage forms, such as tablets, typically contain diluents, e.g., lactose (monohydrate, spray-dried monohydrate, anhydrous and the like), mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers, polyethylene oxide, hydroxypropyl methyl cellulose and mixtures thereof. Different types of microcrystalline cellulose may be suitable for use in the formulations described herein. Examples of microcrystalline cellulose include Avicel® types: PH101, PH102, PH103, PH105, PH 112, PH113, PH200, PH301, and other types of microcrystalline cellulose, such as silicified microcrystalline cellulose (SMCC). In some embodiments, the diluent is selected from the group consisting of microcrystalline cellulose, lactose monohydrate, mannitol, sorbitol, xylitol, magnesium carbonate, dibasic calcium phosphate, tribasic calcium phosphate, or mixtures thereof. In certain embodiments, the diluent comprises microcrystalline cellulose. In some embodiments, the diluent comprises one or more types of microcrystalline cellulose, for example Avicel® PH105, Avicel® PH200 or mixtures thereof. In some such embodiments, the diluent excludes lactose monohydrate. In other such embodiments, the diluent comprises microcrystalline cellulose and further comprises lactose monohydrate. Diluents frequently comprise from about 25 wt % to about 75 wt % of the solid dosage form, and preferably from about 50 wt % to about 75 wt % of the dosage form.

Solid dosage forms frequently contain disintegrants. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch, and sodium alginate. In some embodiments, the disintegrant is crospovidone. Any grade of crospovidone can be used; for example CL, CL-SF and XL grades of crospovidone are suitable for use in the formulations described herein. Specific examples include Kollidon, Kollidon CL®, Kollidon CL-M®, Polyplasdone XL®, Polyplasdone XL-100, and Polyplasdone INF-100. In some embodiments, the carrier comprises at least one disintegrant selected from the group consisting of crospovidone, croscarmellose sodium and sodium starch glycolate. In specific embodiments, the disintegrant is crospovidone. Disintegrants frequently comprise from about 1 wt % to about 25 wt %, preferably from about 5 wt % to about 20 wt %, more preferably from about 5 wt % to about 10 wt % of the dosage form.

Binders may be used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose, and hydroxypropyl methylcellulose. In some embodiments, the binder is selected from the group consisting of microcrystalline cellulose, hydroxypropyl cellulose and hydroxypropyl methylcellulose. In specific embodiments, the binder is microcrystalline cellulose, e.g. Avicel® PH105. When present, binders may comprise from about 0 wt % to about 15 wt %, or from about 0.2 wt % to about 10 wt % of the dosage form. In some embodiments, the binder comprises about 5 wt % to about 10 wt % of the dosage form. In particular embodiments, the binder comprises about 10 wt % of the dosage form.

Solid dosage forms frequently contain one or more lubricants. Examples of lubricants include magnesium stearate, calcium stearate, zinc stearate, sodium stearyl fumarate, mixtures of magnesium stearate with sodium lauryl sulfate, or mixtures of two or more of these. In some embodiments, the lubricant is magnesium stearate and/or sodium stearyl fumarate. In some embodiments, the lubricant is magnesium stearate. In some such embodiments, the solid dosage form is a tablet comprising intragranular and extragranular magnesium stearate. In other embodiments, the solid dosage form is a tablet comprising intragranular magnesium stearate and extragranular sodium stearyl fumarate. When present, lubricants frequently comprise from about 0.25 wt % to about 10 wt %, preferably from about 0.5 wt % to about 6 wt % of the dosage form.

Tablets may also compromise glidants, for example silicon dioxide, colloidal silicon dioxide, magnesium silicate, magnesium trisilicate, talc, and other forms of silicon dioxide, such as aggregated silicates and hydrated silica. In some embodiments, the glidant is silicon dioxide. When present, glidants may comprise from about 0 wt % to about 10 wt %, preferably from about 0.2 wt % to about 5 wt %, or from about 0.5 wt % to about 2 wt % of the tablet.

Tablets may optionally include surface-active agents, such as sodium lauryl sulfate and polysorbate 80. When present, surface-active agents may comprise from 0 wt % to 10 wt %, or preferably 0.2 wt % to 5 wt % of the tablet.

In general, the solid dosage forms of the invention are prepared according to methods usual in pharmaceutical chemistry. Selected carrier (or excipients) may be incorporated along with the active pharmaceutical ingredient into either or both of the extragranular or intragranular compartments.

The therapeutically effective dose of a compound or a pharmaceutically acceptable salt of the invention, will vary from approximately 0.01 mg/kg to approximately 100 mg/kg of body weight per day. Typical adult doses will be approximately 0.1 mg to approximately 3000 mg per day. More typically, the therapeutically effective adult dose of a compound or a pharmaceutically acceptable salt of the invention, is 50 mg, 75 mg, 100 mg, 125 mg, 175 mg, or 200 mg per day. The quantity of active component in a unit dose preparation may be varied or adjusted from approximately 0.1 mg to approximately 500 mg, preferably about 25 mg to about 200 mg according to the particular application. The composition can, if desired, also contain other compatible therapeutic agents. A subject in need of treatment with a compound or a pharmaceutically acceptable salt of the invention, is administered a dosage of about 0.6 to about 500 mg per day, and preferably about 25 mg to about 200 mg per day, either singly or in multiple doses over a 24-hour period. Such treatment may be repeated at successive intervals for as long as necessary.

The compounds of the present invention (including compounds of Formula I, II, or III, or salts thereof) may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Exemplary embodiments include the following groups of diastereomers or enantiomers wherein the diastereomers or enantiomers in each group may be separated or prepared as described herein and by using techniques well-known in the art:

(1) 6-acetyl-8-cyclobutyl-2-{[(3S,4R)-3-hydroxytetrahydro-2H-pyran-4-yl]amino}-5-methylpyrido[2,3-d]pyrimidin-7(8H)-one, 6-acetyl-8-cyclobutyl-2-{[(3S,4S)-3-hydroxytetrahydro-2H-pyran-4-yl]amino}-5-methylpyrido[2,3-d]pyrimidin-7(8H)-one, 6-acetyl-8-cyclobutyl-2-{[(3R,4S)-3-hydroxytetrahydro-2H-pyran-4-yl]amino}-5-methylpyrido[2,3-d]pyrimidin-7(8H)-one, and 6-acetyl-8-cyclobutyl-2-{[(3R,4R)-3-hydroxytetrahydro-2H-pyran-4-yl]amino}-5-methylpyrido[2,3-d]pyrimidin-7(8H)-one;

(2) 6-acetyl-8-cyclopentyl-2-{[(3S,4R)-3-hydroxytetrahydro-2H-pyran-4-yl]amino}-5-methylpyrido[2,3-d]pyrimidin-7(8H)-one, 6-acetyl-8-cyclopentyl-2-{[(3S,4S)-3-hydroxytetrahydro-2H-pyran-4-yl]amino}-5-methylpyrido[2,3-d]pyrimidin-7(8H)-one, 6-acetyl-8-cyclopentyl-2-{[(3R,4S)-3-hydroxytetrahydro-2H-pyran-4-yl]amino}-5-methylpyrido[2,3-d]pyrimidin-7(8H)-one, and 6-acetyl-8-cyclopentyl-2-{[(3R,4R)-3-hydroxytetrahydro-2H-pyran-4-yl]amino}-5-methylpyrido[2,3-d]pyrimidin-7(8H)-one;

(3) 6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one, 6-acetyl-2-{[(3S,4S)-3-hydroxytetrahydro-2H-pyran-4-yl]amino}-5-methyl-8-[(1R,2S)-2-methylcyclopentyl]pyrido[2,3-d]pyrimidin-7(8H)-one, 6-acetyl-2-{[(3R,4S)-3-hydroxytetrahydro-2H-pyran-4-yl]amino}-5-methyl-8-[(1R,2S)-2-methylcyclopentyl]pyrido[2,3-d]pyrimidin-7(8H)-one, 6-acetyl-2-{[(3R,4R)-3-hydroxytetrahydro-2H-pyran-4-yl]amino}-5-methyl-8-[(1R,2S)-2-methylcyclopentyl]pyrido[2,3-d]pyrimidin-7(8H)-one, 6-acetyl-2-{[(3S,4R)-3-hydroxytetrahydro-2H-pyran-4-yl]amino}-5-methyl-8-[(1S,2S)-2-methylcyclopentyl]pyrido[2,3-d]pyrimidin-7(8H)-one, 6-acetyl-2-{[(3S,4S)-3-hydroxytetrahydro-2H-pyran-4-yl]amino}-5-methyl-8-[(1S,2S)-2-methylcyclopentyl]pyrido[2,3-d]pyrimidin-7(8H)-one, 6-acetyl-2-{[(3R,4S)-3-hydroxytetrahydro-2H-pyran-4-yl]amino}-5-methyl-8-[(1S,2S)-2-methylcyclopentyl]pyrido[2,3-d]pyrimidin-7(8H)-one, 6-acetyl-2-{[(3R,4R)-3-hydroxytetrahydro-2H-pyran-4-yl]amino}-5-methyl-8-[(1S,2S)-2-methylcyclopentyl]pyrido[2,3-d]pyrimidin-7(8H)-one, 6-acetyl-2-{[(3S,4R)-3-hydroxytetrahydro-2H-pyran-4-yl]amino}-5-methyl-8-[(1R,2R)-2-methylcyclopentyl]pyrido[2,3-d]pyrimidin-7(8H)-one, 6-acetyl-2-{[(3S,4S)-3-hydroxytetrahydro-2H-pyran-4-yl]amino}-5-methyl-8-[(1R,2R)-2-methylcyclopentyl]pyrido[2,3-d]pyrimidin-7(8H)-one, 6-acetyl-2-{[(3R,4S)-3-hydroxytetrahydro-2H-pyran-4-yl]amino}-5-methyl-8-[(1R,2R)-2-methylcyclopentyl]pyrido[2,3-d]pyrimidin-7(8H)-one, 6-acetyl-2-{[(3R,4R)-3-hydroxytetrahydro-2H-pyran-4-yl]amino}-5-methyl-8-[(1R,2R)-2-methylcyclopentyl]pyrido[2,3-d]pyrimidin-7(8H)-one, 6-acetyl-2-{[(3S,4R)-3-hydroxytetrahydro-2H-pyran-4-yl]amino}-5-methyl-8-[(1S,2R)-2-methylcyclopentyl]pyrido[2,3-d]pyrimidin-7(8H)-one, 6-acetyl-2-{[(3S,4S)-3-hydroxytetrahydro-2H-pyran-4-yl]amino}-5-methyl-8-[(1S,2R)-2-methylcyclopentyl]pyrido[2,3-d]pyrimidin-7(8H)-one, 6-acetyl-2-{[(3R,4S)-3-hydroxytetrahydro-2H-pyran-4-yl]amino}-5-methyl-8-[(1S,2R)-2-methylcyclopentyl]pyrido[2,3-d]pyrimidin-7(8H)-one, 6-acetyl-2-{[(3R,4R)-3-hydroxytetrahydro-2H-pyran-4-yl]amino}-5-methyl-8-[(1S,2R)-2-methylcyclopentyl]pyrido[2,3-d]pyrimidin-7(8H)-one;

(4) 3-acetyl-1-cyclopentyl-7-{[(3S,4R)-3-hydroxytetrahydro-2H-pyran-4-yl]amino}-4-methyl-1,6-naphthyridin-2(1H)-one; 3-acetyl-1-cyclopentyl-7-{[(3S,4S)-3-hydroxytetrahydro-2H-pyran-4-yl]amino}-4-methyl-1,6-naphthyridin-2(1H)-one; 3-acetyl-1-cyclopentyl-7-{[(3R,4S)-3-hydroxytetrahydro-2H-pyran-4-yl]amino}-4-methyl-1,6-naphthyridin-2(1H)-one, and 3-acetyl-1-cyclopentyl-7-{[(3R,4R)-3-hydroxytetrahydro-2H-pyran-4-yl]amino}-4-methyl-1,6-naphthyridin-2(1H)-one;

(5) 6-acetyl-8-[2-(2,2-difluoroethyl)-2-azaspiro[3.3]heptan-6-yl]-2-{[(3S,4R)-3-hydroxytetrahydro-2H-pyran-4-yl]amino}-5-methylpyrido[2,3-d]pyrimidin-7(8H)-one, 6-acetyl-8-[2-(2,2-difluoroethyl)-2-azaspiro[3.3]heptan-6-yl]-2-{[(3S,4S)-3-hydroxytetrahydro-2H-pyran-4-yl]amino}-5-methylpyrido[2,3-d]pyrimidin-7(8H)-one, 6-acetyl-8-[2-(2,2-difluoroethyl)-2-azaspiro[3.3]heptan-6-yl]-2-{[(3R,4S)-3-hydroxytetrahydro-2H-pyran-4-yl]amino}-5-methylpyrido[2,3-d]pyrimidin-7(8H)-one, and 6-acetyl-8-[2-(2,2-difluoroethyl)-2-azaspiro[3.3]heptan-6-yl]-2-{[(3R,4R)-3-hydroxytetrahydro-2H-pyran-4-yl]amino}-5-methylpyrido[2,3-d]pyrimidin-7(8H)-one.

According to the methods of the invention, a compound of the present invention or a combination is preferably administered in the form of a pharmaceutical composition. Accordingly, a compound of the present invention or a combination thereof can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensu-rate with therapeutic needs.

The pharmaceutical composition comprises a compound of the invention or a combination thereof in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or nonaqueous solutions, dispersions, suspensions, or emulsions, and sterile powders for reconstitution into sterile injectable solutions or dis-persions. Examples of suitable aqueous and nonaqueous carriers or diluents (including solvents and vehicles) include water, ethanol, polyols (propylene glycol, polyeth-ylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or pro-pylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for exam-ple, aluminum monostearate and gelatin.

Solid dosage forms for oral administration include capsules, tablets, chews, loz-enges, pills, powders, and multiparticulate preparations (granules). In such solid dos-age forms, a compound of the present invention or a combination is admixed with at least one inert excipient, diluent or carrier. Suitable excipients, diluents or carriers in-clude materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calci-um hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellu-lose, polyvinyl alcohol, pullulan, pregelatinized starch, agar, tragacanth, alginates, gel-atin, polyvinylpyrrolidone, sucrose, acacia and the like); (c) one or more humectants (e.g., glycerol and the like); (d) one or more disintegrating agents (e.g., agar-agar, calci-um carbonate, potato or tapioca starch, alginic acid, certain complex silicates, sodium carbonate, sodium lauryl sulphate, sodium starch glycolate (available as Ex-plotab™ from Edward Mendell Co.), cross-linked polyvinyl pyrrolidone, croscarmel-lose sodium A-type (available as Ac-di-sol™), polyacrilin potassium (an ion ex-change resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, di-methylpolysiloxane, microcrystalline wax, yellow beeswax, white beeswax, solid poly-ethylene glycols, sodium lauryl sulfate and the like). In the case of capsules and tab-lets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharma-ceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubri-cants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for ex-ample about 1%.

Tablets may be manufactured by standard tabletting processes, for example, direct compression or a wet, dry or melt granulation, melt congealing process and extru-sion. The tablet cores may be mono or multi-layer(s) and can be coated with appropri-ate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dime-thylformamide, oils (e.g., cottonseed oil, groundnut oil, corn germ oil, olive oil, castor oil, sesame seed oil and the like), Miglyole® (available from CONDEA Vista Co., Cran-ford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and per-fuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyeth-ylene glycol, polypropylene glycol, edible oils and glyceryl- and glyceride-based sys-tems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Cap-mul™ MCM (medium chain mono- and diglycerides, fromAbitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycer-ides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usu-ally greater than about 80%, for example about 95% or 99%. Adjuvants and additives may also be included with the solvents principally as taste-mask agents, palatability and flavoring agents, antioxidants, stabilizers, texture and viscosity modifiers and solu-bilizers.

Suspensions, in addition to the compound of the present invention or the com-bination, may further comprise carriers such as suspending agents, e.g., ethoxylated isostearyl alcohols, polyoxyethylene sorbitol and sorbitan esters, microcrystalline cellu-lose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, poly-ethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1 µg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the in-vention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crys-talline" is meant that the compound exhibits long-range order in three dimensions of at least 100 repeat units in each dimension. Thus, the term amor-phous is intended to include not only material which has essentially no order, but also material which may have some small degree of order, but the order is in less than three dimensions and/or is only over short distances. Amorphous material may be character-ized by techniques known in the art such as powder x-ray diffraction (PXRD) crystal-lography, solid state NMR, or thermal techniques such as differential scanning calo-rimetry (DSC).

In some embodiments, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substan-tially homogeneous" means that the fraction of the compound that is present in relatively pure amorphous domains or re-gions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The pol-ymer can be neutral or ionizable, and should have an aqueous-solubility of at least 0.1 mg/mL over at least a portion of the pH range of 1-8.

Water-soluble polymers suitable for use with the present invention may be cellu-losic or non-cellulosic. The polymers may be neutral or ionizable in aqueous solution. Of these, ionizable and cellulosic polymers are preferred, with ionizable cellulosic pol-ymers being more preferred.

Exemplary water-soluble polymers include hydroxypropyl methyl cellulose acetate succinate (HPMCAS), hydroxypropyl methyl cellulose (HPMC), hydroxypropyl me-thyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of eth-ylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, sol-vent-modified fusion and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous disper-sions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup®-LF, Aqoat.sup®-MF and Aqoat.sup®-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a com-pound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination thereof) can also be added directly to the feed, as such, or in the form of an animal feed supplement, al-so referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of pre-mix with the feed to obtain a desired level of compound.

High potency concentrates may be blended by the feed manufacturer with pro-teinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination thereof) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a com-pound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Preparation

Compounds of the present invention may be synthesized by synthetic routes that include processes analogous to those well-known in the chemical arts, particularly in light of the description contained herein. The starting materials are generally availa-ble from commercial sources such as Aldrich Chemicals (Milwaukee, Wis.) or are readily prepared using methods well known to those skilled in the art (e.g., prepared by meth-ods generally described in Louis F. Fieser and Mary Fieser, Reagents for Organic Syn-thesis, v. 1-19, Wiley, New York (1967-1999 ed.), or Beilsteins Handbuch der organ-ischen Chemie, 4, Aufl. ed. Springer-Verlag, Berlin, including supplements (also avail-able via the Beilstein online database)). Many of the compounds used herein, are re-lated to, or are derived from compounds in which there is a large scientific interest and commercial need, and accordingly many such compounds are commercially avail-able or are reported in the literature or are easily prepared from other commonly available substances by methods which are reported in the literature.

For illustrative purposes, the reaction schemes depicted below provide potential routes for synthesizing the com-pounds of the present invention as well as key inter-mediates. For a more detailed description of the individual reaction steps, see the Examples section below. Those skilled in the art will appreciate that other synthetic routes may be used to synthesize the inventive compounds. Although specific starting materials and reagents are discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Unless stated otherwise, the variables in Schemes A-L have the same meanings as defined herein. The amines mentioned herein may constitute protected amines that are deprotected under standard conditions known to those skilled in the art. The need for such protection/deprotection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities that may interfere with reactions at other sites of the molecule if left unprotected. Accordingly, such functionalities may be protected by an appropriate protecting group, which may be removed in a subsequent step. Suitable protecting groups for amine and carboxylic acid protection include those protecting groups commonly used in peptide synthesis (such as N-tert-butoxy-carbonyl (Boc), benzyloxycarbonyl (Cbz), and 9-fluorenyl-methylenoxycarbonyl (Fmoc) for amines, and lower alkyl or benzyl esters for carboxylic acids), which are generally not chemically reactive under the reaction conditions described and can typically be removed without chemically altering other functionality in the compounds of the present invention.

The Reaction Schemes described below are intended to provide a general description of the methodology employed in the preparation of the compounds of the present invention. Some of the compounds of the present invention contain a single chiral center. In the following Schemes, the general methods for the preparation of the compounds are shown either in racemic or enantioenriched form. It will be apparent to one skilled in the art that all of the synthetic transforma-tions can be conducted in a precisely similar manner whether the materials are enantioenriched or racemic. Moreover, the resolution to the desired optically active material may take place at any desired point in the sequence, using well-known methods such as described herein and in the chemistry literature.

In the following Reaction Schemes, the variables $R^1$, $R^2$, $R^3$, and $R^4$ are as described in the Summary except where otherwise noted.

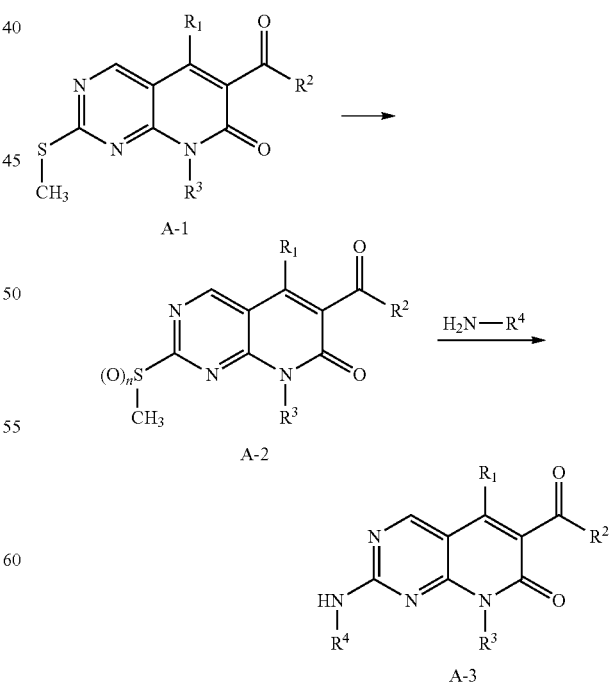

As illustrated in Scheme A, oxidation of A-1 to afford the mixture A-2 [sulfoxide (n=1) and/or sulfone (n=2)] can be carried out under appropriate conditions, such as with potassium peroxymonosulfate (Oxone®) in tetrahydrofuran (THF) and water as solvent (this oxidation can be used in e.g. Scheme D). A subsequent nucleophilic aromatic substitution ($S_NAr$ reaction) provides the 2-substituted pyrido[2,3-d]pyrimidin-7(8H)-ones A-3. The $S_NAr$ reactions are typically carried out in the presence of a suitable base such as N,N-diisopropylethylamine (DIPEA) in a suitable solvent such as dimethyl sulfoxide (DMSO) or tetrahydrofuran (THF).

similar to that described by Duan, S. et al., *Org. Process Res. Dev.* 2016, 20, 1191-1202) with a vinyl ether precursor such as tributyl(1-ethoxyethenyl)stannane or 1-(ethenyloxy)butane, under standard palladium-catalyzed cross-coupling conditions, affords the vinyl ether B-2 where R is H. Alternatively, substituted vinyl stannane or alkoxy vinyl ether reagents could be employed to afford B-2 intermediates wherein R is other than H, for example, wherein R is methyl optionally substituted with one or more fluorine atoms. $S_NAr$ reaction of B-2 with various substituted amines in the presence of a base such as DIPEA in a suitable solvent such as DMSO provides B-3. Hydrolysis of the vinyl ether under acidic conditions, such as aqueous HCl in THF, provides the 2-substituted pyrido[2,3-d]pyrimidin-7(8H)-ones B-4 (wherein $R^2$ is for example, $CH_2R$, and R is H or methyl optionally substituted with one or more fluorine atoms).

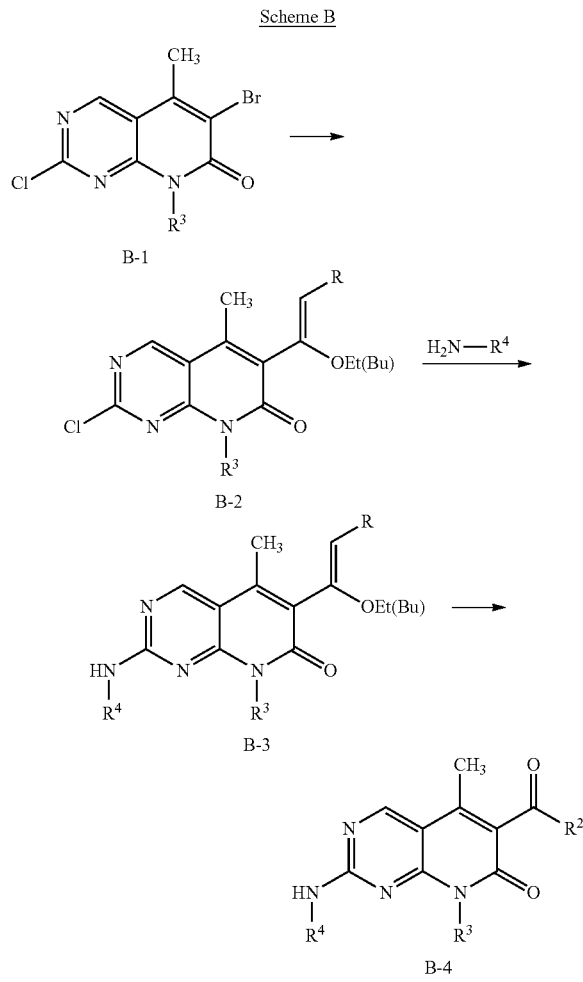

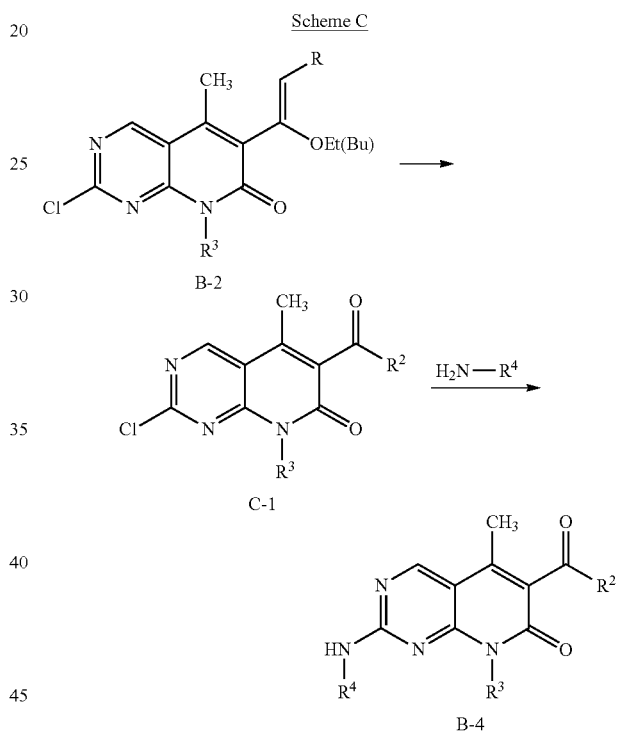

An alternative synthetic route to B-4 is depicted in Scheme C. Hydrolysis of vinyl ether B-2 in the presence of an acid, such as aqueous HCl in THF, affords C-1. $S_NAr$ reaction of C-1 with various substituted amines in the presence of a base, such as DIPEA, in a suitable solvent, such as DMSO, provides B-4.

As illustrated in Scheme B, treatment of B-1 such as 6-bromo-2-chloro-8-cyclopentyl-5-methylpyrido[2,3-d]pyrimidin-7(8H)-one (purchased or synthesized in a manner

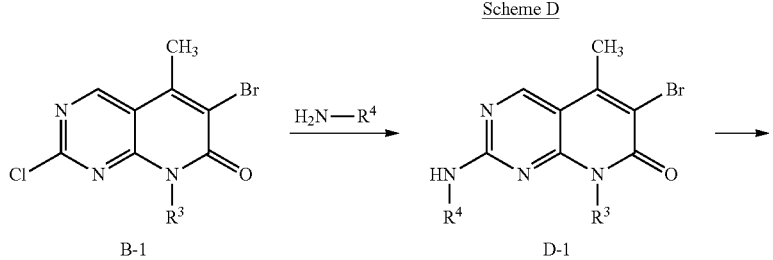

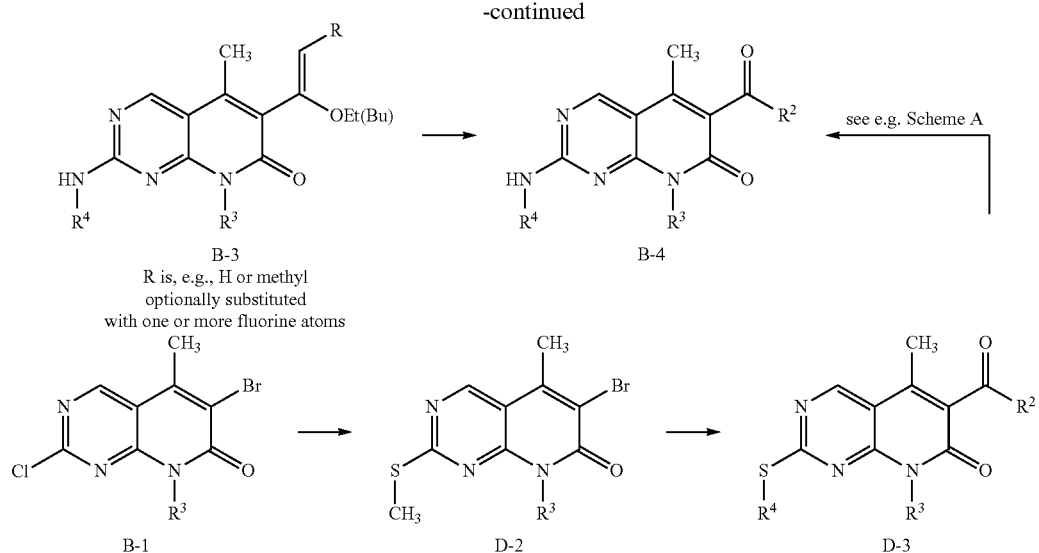

Scheme D illustrates an alternative $S_NAr$ reaction of B-1 with various substituted amines to provide pyrimidine D-1. Functionalization of D-1 at the C(6) position is achieved by treatment with a suitable substituted vinyl stannane or an alkoxy vinyl ether under standard cross-coupling conditions known to those skilled in the art, followed by the acid-mediated hydrolysis of the resulting vinyl ether, to afford the ketone intermediate B-4. Alternatively, an $S_NAr$ reaction of B-1 with sodium methanethiolate in a suitable solvent such as THF or DMSO generates methylthiopyrimidine D-2, which is followed by standard cross-coupling conditions and acid-mediated hydrolysis to afford ketone D-3. Following the procedure described in Scheme A would provide B-4.

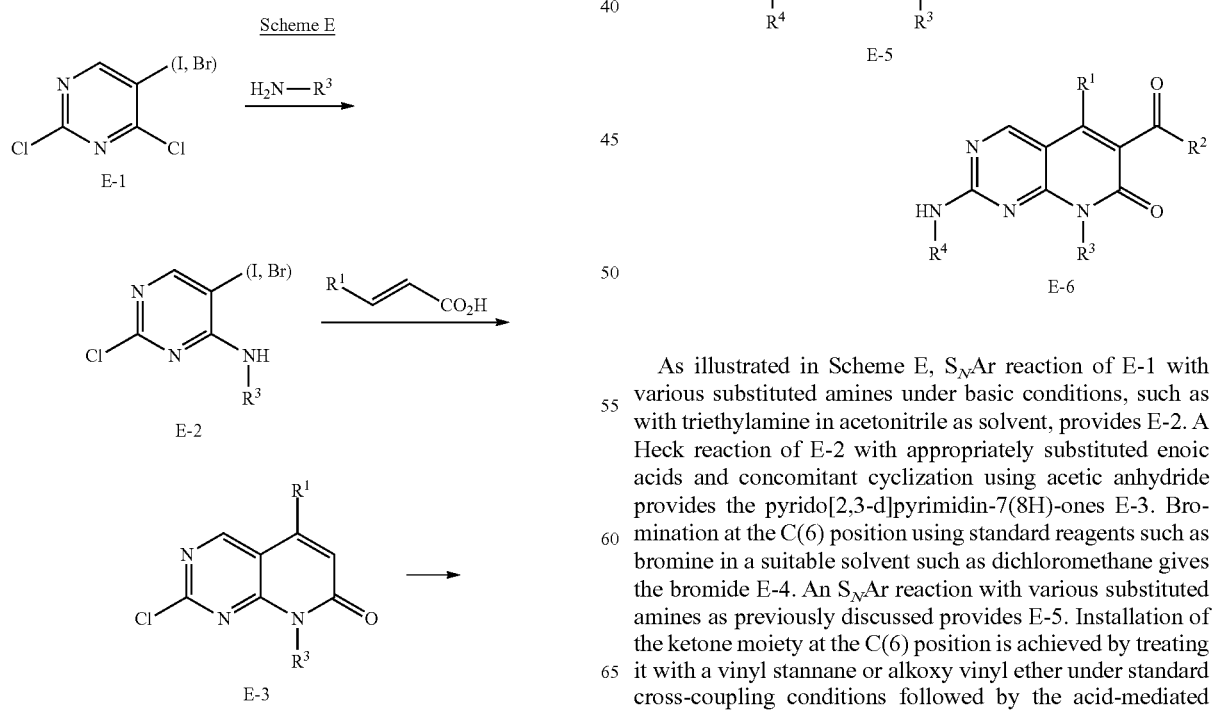

As illustrated in Scheme E, $S_NAr$ reaction of E-1 with various substituted amines under basic conditions, such as with triethylamine in acetonitrile as solvent, provides E-2. A Heck reaction of E-2 with appropriately substituted enoic acids and concomitant cyclization using acetic anhydride provides the pyrido[2,3-d]pyrimidin-7(8H)-ones E-3. Bromination at the C(6) position using standard reagents such as bromine in a suitable solvent such as dichloromethane gives the bromide E-4. An $S_NAr$ reaction with various substituted amines as previously discussed provides E-5. Installation of the ketone moiety at the C(6) position is achieved by treating it with a vinyl stannane or alkoxy vinyl ether under standard cross-coupling conditions followed by the acid-mediated hydrolysis of the corresponding vinyl ether to provide E-6.

Scheme F

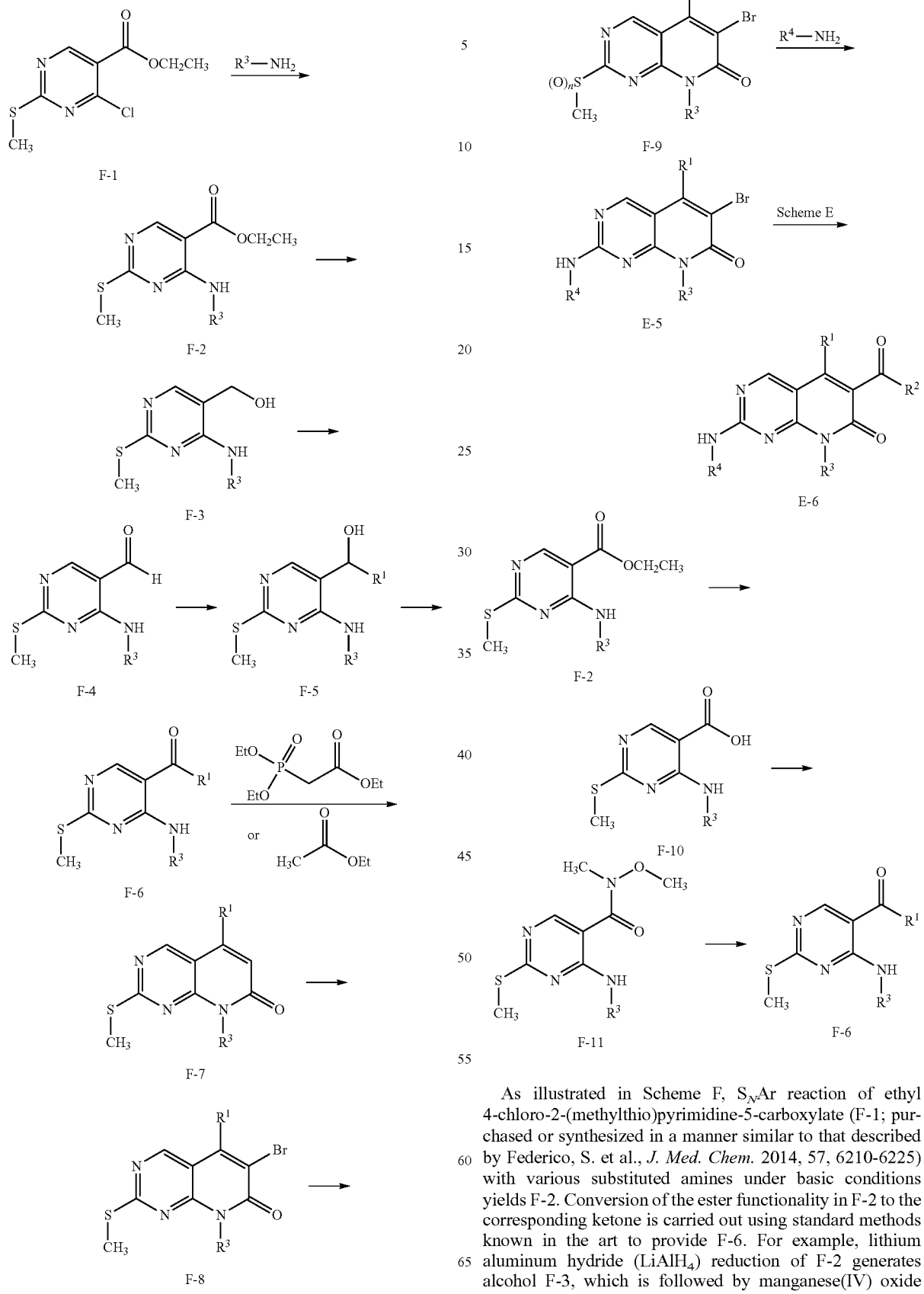

As illustrated in Scheme F, S$_N$Ar reaction of ethyl 4-chloro-2-(methylthio)pyrimidine-5-carboxylate (F-1; purchased or synthesized in a manner similar to that described by Federico, S. et al., *J. Med. Chem.* 2014, 57, 6210-6225) with various substituted amines under basic conditions yields F-2. Conversion of the ester functionality in F-2 to the corresponding ketone is carried out using standard methods known in the art to provide F-6. For example, lithium aluminum hydride (LiAlH$_4$) reduction of F-2 generates alcohol F-3, which is followed by manganese(IV) oxide oxidation to afford aldehyde F-4. Addition of a suitable Grignard reagent such as methylmagnesium chloride (where R¹=Me) to F-4 generates alcohol F-5, which is then converted to ketone F-6 through manganese(IV) oxide oxidation. The pyrido[2,3-d]pyrimidin-7(8H)-one F-7 is obtained through a cyclocondensation using either standard Horner-Wadsworth-Emmons reaction conditions or ethyl acetate and a suitable base such as sodium bis(trimethylsilyl)amide. Bromination at C(6), which provides F-8, is followed by oxidation of the thiomethyl group at C(2) under standard conditions described previously (Scheme A), yielding F-9. $S_NAr$ reaction with various substituted amines as previously discussed provides E-5. E-6 is then obtained from E-5 as described in Scheme E. Alternatively, introduction of the ketone moiety onto F-8 under similar conditions as described in Scheme D yields A-1, which is then used following the procedure as described in Scheme A to provide A-3. An alternative approach to convert F-2 to F-6 is the hydrolysis of ester F-2 to generate acid F-10, which is subsequently converted to the Weinreb amide F-11. Addition of a suitable Grignard reagent such as methylmagnesium chloride (in the case where R¹=Me) to F-11 in THF generates F-6.

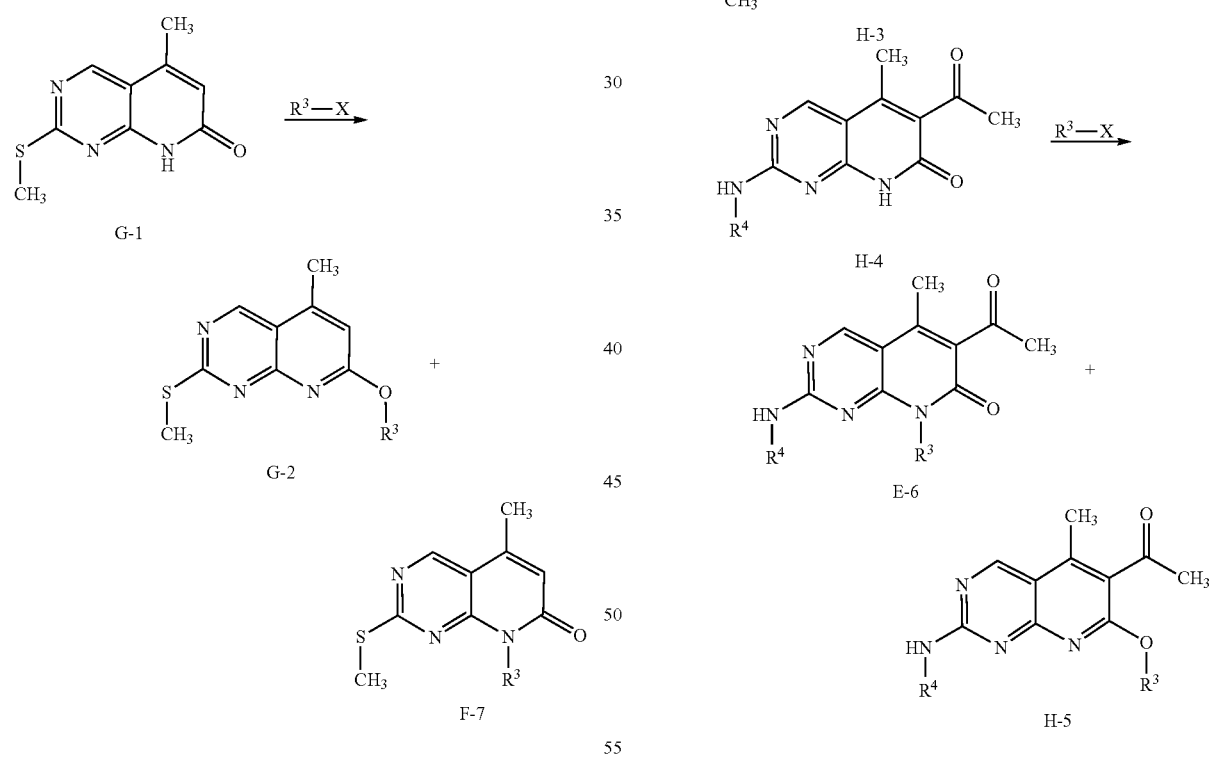

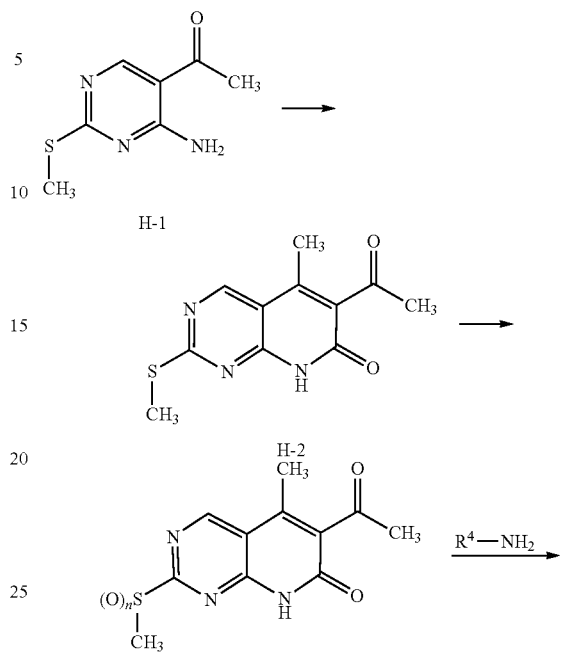

As illustrated in Scheme G, alkylation of 5-methyl-2-(methylthio)pyrido[2,3-d] pyrimidin-7(8H)-one G-1 (purchased or synthesized in a manner similar to that described by VanderWel, S. N. et al., *J. Med. Chem.* 2005, 48, 2371-2387) with a compound R³-X such as an alkyl halide or mesylate (i.e., methanesulfonate) in the presence of a base, such as 2-tert-butyl-1,1,3,3-tetramethylguanidine, yields a mixture of positional isomers 7-O— and 8-N-alkyl pyrido[2,3-d]pyrimidines G-2 and F-7, respectively, which are separated to provide F-7 that can be used as illustrated in Scheme F to obtain E-6.

As illustrated in Scheme H, amidation/cyclization of 1-[4-amino-2-(methylthio)pyrimidin-5-yl]ethan-1-one H-1 with a diketene precursor (i.e., 2,2,6-trimethyl-4H-1,3-dioxin-4-one) with or without solvents, such as toluene, yields methylthiopyrimidine H-2. Oxidation of the thiomethyl group of H-2 under standard conditions (vide supra), followed by $S_NAr$ reaction with various substituted amines R⁴—NH₂ under basic conditions, affords H-4. A standard $S_N2$ reaction between H-4 and R³—X (e.g. alkyl halides) under basic conditions, using a base such as NaH, affords a mixture of 7-O— and 8-N-alkyl pyrido[2,3-d]pyrimidines H-5 and E-6 (a compound of A-3 wherein $R^2$ is $CH_3$), respectively. Separation of these positional isomers provides E-6 that can be used as discussed herein.

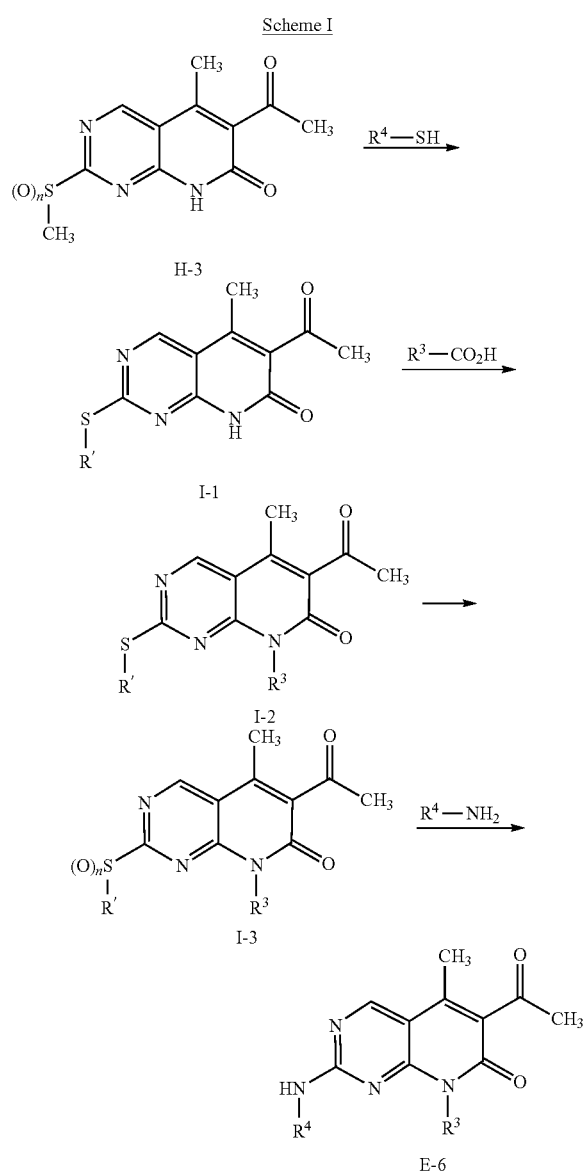

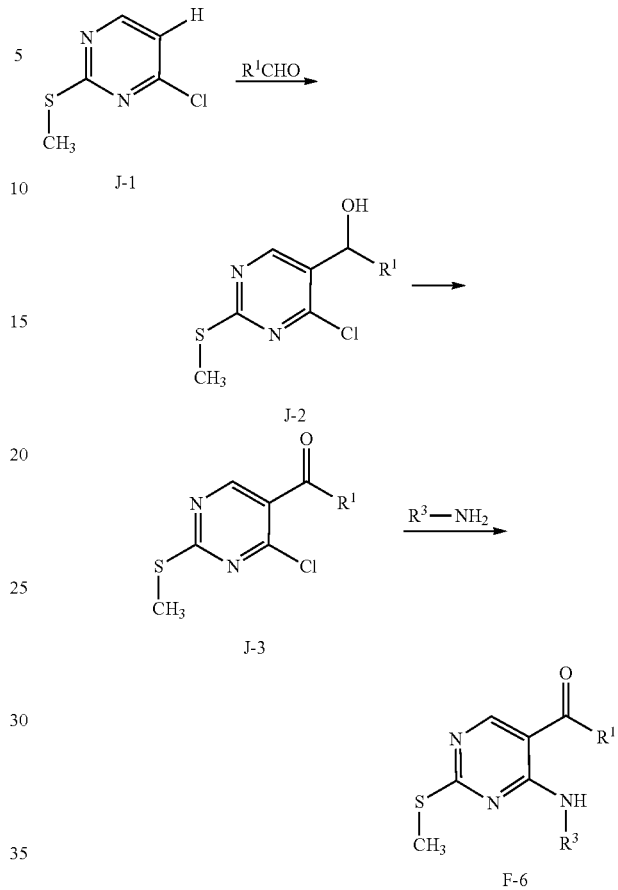

As illustrated in Scheme I, to improve the solubility and enable subsequent transformations, H-3 was subjected to an $S_NAr$ reaction with various alkyl thiols R'—SH wherein R' is an alkyl having at least 4 carbons (e.g., decylthiol) under basic conditions, such as with triethylamine and THF as solvent, to generate I-1. A photo-catalyzed regioselective N-alkylation of I-1, using various carboxylic acids $R^3$—$CO_2H$, yields the pyridopyrimidine I-2. This reaction may be carried out using bis(acetyloxy)(2,4,6-trimethylphenyl)-$\lambda^3$-iodane as oxidant and (2,2'-bipyridine-$\kappa^2N^1,N^1$){bis[3,5-difluoro-2-(5-fluoropyridin-2-yl)phenyl]}iridium hexafluorophosphate as catalyst in dichloromethane. Oxidation of the thiomethyl group at C(2) under the standard conditions described above generates I-3. $S_NAr$ reaction of I-3 with various substituted amines $R^4$—$NH_2$ under standard conditions yields E-6.

As illustrated in Scheme J, treatment of the commercially available 4-chloro-2-(methylthio)pyrimidine J-1 with a base, such as lithium diisopropylamide (LDA) in a suitable solvent such as THF, followed by the addition of a suitably substituted aldehyde $R^1CHO$, provides the alcohol J-2. Oxidation of the alcohol J-2 under standard conditions, such as with manganese(IV) oxide in chloroform, gives the ketone J-3. $S_NAr$ reaction of J-3 with various substituted amines $R^3$—$NH_2$ under basic conditions provides F-6, which can provide, e.g., E-6, as illustrated in Scheme F.

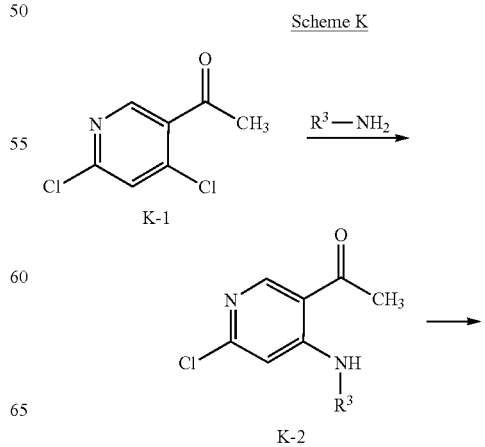

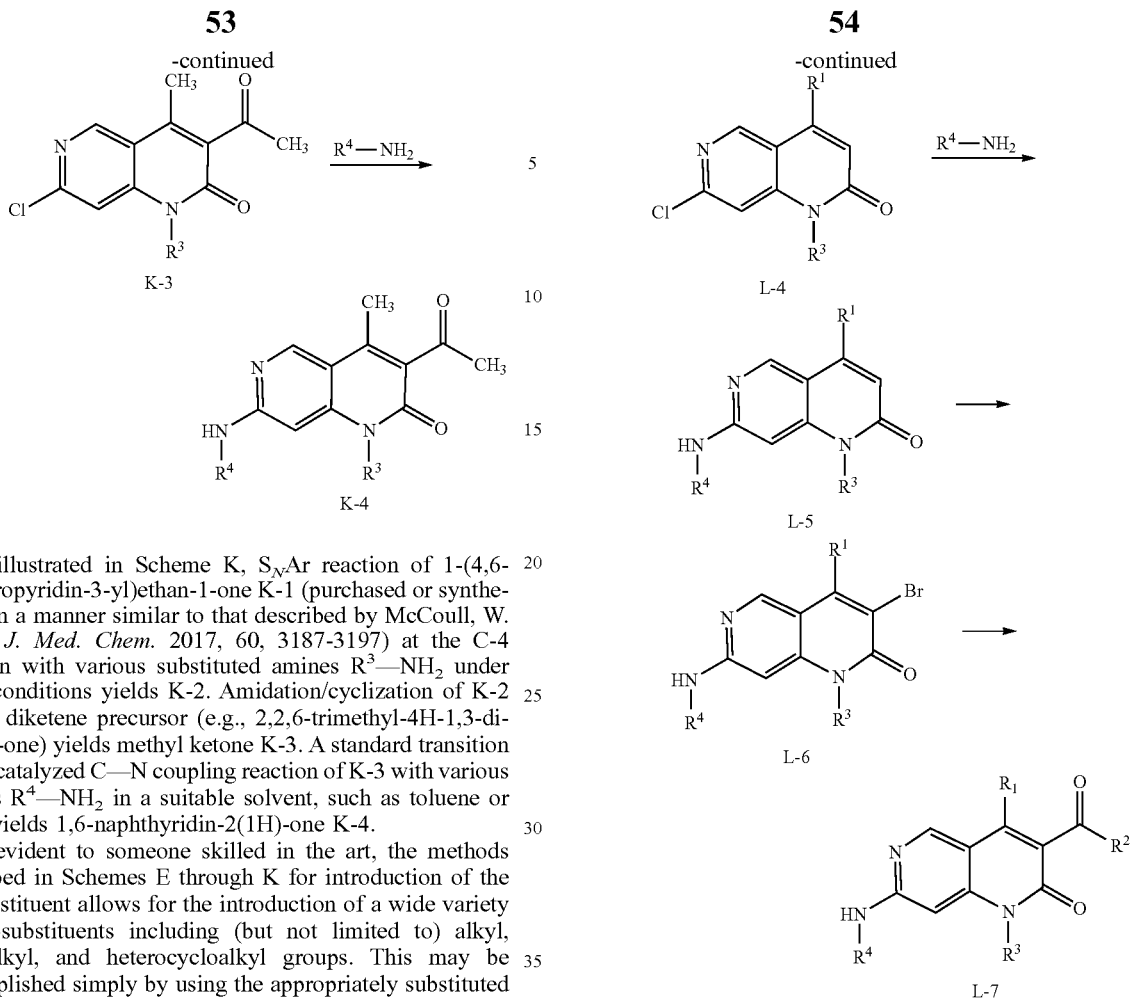

As illustrated in Scheme K, $S_NAr$ reaction of 1-(4,6-dichloropyridin-3-yl)ethan-1-one K-1 (purchased or synthesized in a manner similar to that described by McCoull, W. et al., *J. Med. Chem.* 2017, 60, 3187-3197) at the C-4 position with various substituted amines $R^3$—$NH_2$ under basic conditions yields K-2. Amidation/cyclization of K-2 with a diketene precursor (e.g., 2,2,6-trimethyl-4H-1,3-dioxin-4-one) yields methyl ketone K-3. A standard transition metal-catalyzed C—N coupling reaction of K-3 with various amines $R^4$—$NH_2$ in a suitable solvent, such as toluene or THF, yields 1,6-naphthyridin-2(1H)-one K-4.

As evident to someone skilled in the art, the methods described in Schemes E through K for introduction of the $R^3$-substituent allows for the introduction of a wide variety of $R^3$-substituents including (but not limited to) alkyl, cycloalkyl, and heterocycloalkyl groups. This may be accomplished simply by using the appropriately substituted amine reagent (Schemes E, F, J), halide reagent (Schemes G, H), or carboxylic acid reagent (Scheme I).

Scheme L

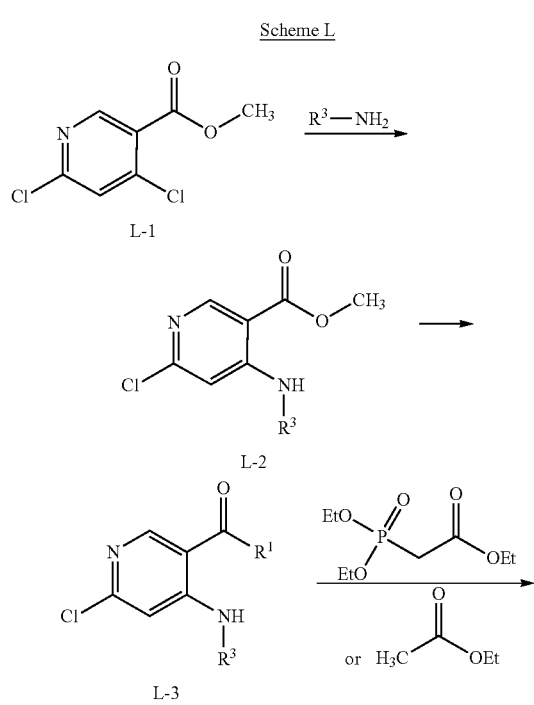

As illustrated in Scheme L, $S_NAr$ reaction of the commercially available methyl 4,6-dichloronicotinate L-1 with various substituted amines $R^3$—$NH_2$ under basic conditions yields L-2. The transformation of the ester functionality of L-2 to the corresponding ketone group was accomplished using standard methods known in the art (like those described in Scheme F) to afford ketone L-3. A cyclocondensation of L-3 using either standard Horner-Wadsworth-Emmons conditions or ethyl acetate and a suitable base such as sodium bis(trimethylsilyl)amide yields naphthyridin-2(1H)-one L-4. A standard transitional metal-catalyzed C—N coupling reaction of L-4 with various substituted amines $R^4$—$NH_2$ under basic conditions affords L-5. Following bromination of L-5 in at the C(6) position, the ketone moiety is introduced by treatment with an appropriately substituted vinyl stannane or alkoxy vinyl ether under standard cross-coupling reaction conditions followed by acid-mediated hydrolysis to yield aminopyridine L-7.

EXAMPLES

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Similarly, in some examples separations were carried out to separate diastereomers of certain compounds of the invention; in some examples, the separated diastereomers are designated as DIAST-1 and DIAST-2, according to their order of elution. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

The compounds and intermediates described below were named using the naming convention provided with ACD/ChemSketch 2017.2.1, File Version N40E41, Build 96719 (Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England) and Tyger Scientific (Princeton, N.J.). Certain common abbreviations and acronyms have been employed which may include: AcOH (acetic acid), DBU (1,8-diazabicyclo[5.4.0]undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N'-dimethylformamide), DMSO (dimethylsulfoxide), EDCl (N-(3-dimethylaminopropyl)-N'-ethylcarbodiimide), Et2O (diethyl ether), EtOAc (ethyl acetate), EtOH (ethanol), HATU (2-(1H-7-azabenzotriazol-1-yl)-1,1,3,3-tetramethyl uronium hexafluorophosphate methanaminium), HBTU (O-benzotriazol-1-yl-N,N,N',N'-tetramethyluronium hexafluoro phosphate), HOBT (1-hydroxybenzotriazole), IPA (isopropyl alcohol), KHMDS (potassium hexamethyldisilazane), MeOH (methanol), MTBE (tert-butyl methyl ether), NaBH(OAc)3 (sodium triacetoxyborohydride), NaHMDS (sodium hexamethyldisilazane), NMP (N-methylpyrrolidone), SEM ([2-(Trimethylsilyl)ethoxy]methyl), TEA (triethylamine), TFA (trifluoroacetic acid), THF (tetrahydrofuran), 5-FAM-Dyrktide (peptide RRRFR-PASPLRGPPK which is labeled with a trifluoro acetate salt at the 5' end of the peptid) and T3P (propane phosphonic acid anhydride).

The terms "concentrated", "evaporated", and "concentrated in vacuo" refer to the removal of solvent at reduced pressure on a rotary evaporator with a bath temperature less than 60□C. The abbreviation "min" and "h" stand for "minutes" and "hours" respectively. The term "TLC" refers to thin layer chromatography, "room temperature or ambient temperature" means a temperature between 18° C. to 25° C., "LCMS" refers to liquid chromatography-mass spectrometry, "UPLC" refers to ultra performance liquid chromatography and "HPLC" refers to high pressure liquid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.

HPLC, UPLC, LCMS, and SFC retention times were measured using the methods noted in the procedures.

Preparation P1

6-Bromo-2-chloro-8-cyclobutyl-5-methylpyrido[2,3-d]pyrimidin-7(8H)-one (P1)

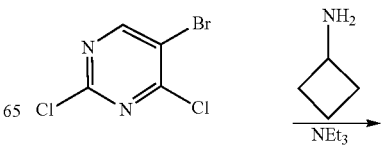

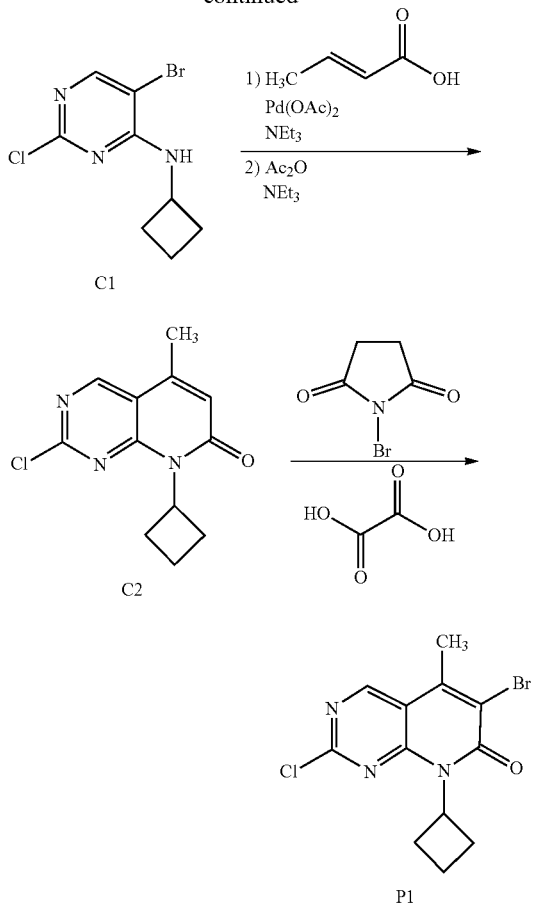

Step 1. Synthesis of 5-bromo-2-chloro-N-cyclobutylpyrimidin-4-amine (C1)

Cyclobutanamine (1.56 g, 21.9 mmol) was added to a 0° C. suspension of 5-bromo-2,4-dichloropyrimidine (5.00 g, 21.9 mmol) and triethylamine (9.51 mL, 68.2 mmol) in acetonitrile, and the reaction mixture was allowed to warm to room temperature as it stirred overnight. It was then concentrated in vacuo, and the residue was purified using silica gel chromatography (Gradient: 0% to 30% ethyl acetate in heptane) to provide $C_1$ as a solid. Yield: 4.67 g, 17.8 mmol, 81%. LCMS m/z 262.1 (bromine-chlorine isotope pattern observed) [M+H]$^+$. $^1$H NMR (400 MHz, chloroform-d) δ 8.10 (s, 1H), 5.61 (br s, 1H), 4.67-4.52 (m, 1H), 2.52-2.41 (m, 2H), 2.03-1.89 (m, 2H), 1.86-1.74 (m, 2H).

Step 2. Synthesis of 2-chloro-8-cyclobutyl-5-methylpyrido[2,3-c]pyrimidin-7(8H)-one (C2)

Triethylamine (16.6 mL, 119 mmol) and 1-methylpyrrolidin-2-one (70 mL) were added to a mixture of C1 (4.67 g, 17.8 mmol), (2E)-but-2-enoic acid (6.13 g, 71.2 mmol), and palladium(II) acetate (399 mg, 1.78 mmol), and the resulting mixture was sparged with nitrogen for 20 minutes. The reaction mixture was heated overnight at 65° C., whereupon it was treated with triethylamine (1.24 mL, 8.90 mmol) and acetic anhydride (3.36 mL, 35.5 mmol), and heated at 65° C. for an additional 2.5 hours. After it had been cooled to room temperature, the reaction mixture was poured into water (500 mL) and extracted with ethyl acetate (4×120 mL). LCMS analysis of the combined organic layers at this point indicated conversion to the product C2: LCMS m/z 250.1 (chlorine isotope pattern observed) [M+H]$^+$. The combined organic layers were washed sequentially with water and saturated aqueous sodium chloride solution, concentrated under reduced pressure, and purified via silica gel chromatography (Gradient: 0% to 45% ethyl acetate in heptane), affording C2 as a solid. Yield: 3.22 g, 12.9 mmol, 72%. $^1$H NMR (400 MHz, chloroform-d) δ 8.73 (s, 1H), 6.51 (q, J=1.3 Hz, 1H), 5.83-5.71 (m, 1H), 3.15-3.02 (m, 2H), 2.43 (d, J=1.3 Hz, 3H), 2.42-2.32 (m, 2H), 2.12-1.99 (m, 1H), 1.94-1.79 (m, 1H).

Step 3. Synthesis of 6-bromo-2-chloro-8-cyclobutyl-5-methylpyrido[2,3-c]pyrimidin-7(8H)-one (P1)

A mixture of C2 (2.00 g, 8.01 mmol), N-bromosuccinimide (2.49 g, 14.0 mmol), and oxalic acid (147 mg, 1.63 mmol) in acetonitrile (40 mL) was stirred at 55° C. for 5 hours, whereupon oxalic acid (50 mg, 0.55 mmol) and N-bromosuccinimide (800 mg, 4.49 mmol) were again added. After it had been heated for an additional 3.5 hours, the reaction mixture was cooled to room temperature, treated with a solution of sodium bisulfite (1.68 g, 16.1 mmol) in water (approximately 10 mL), and stirred for 10 minutes at room temperature. The resulting mixture was then diluted with water (150 mL); filtration provided P1 as a solid. Yield: 2.13 g, 6.48 mmol, 81%. LCMS m/z 328.0 (bromine-chlorine isotope pattern observed) [M+H]$^+$. $^1$H NMR (400 MHz, chloroform-d) δ 8.84 (s, 1H), 5.90-5.77 (m, 1H), 3.13-2.99 (m, 2H), 2.66 (s, 3H), 2.48-2.37 (m, 2H), 2.14-2.01 (m, 1H), 1.95-1.81 (m, 1H).

Preparation P2 tert-Butyl 6-[6-acetyl-5-methyl-2-(methylsulfinyl)-7-oxopyrido[2,3-c]pyrimidin-8(7H)-yl]-2-azaspiro[3.3]heptane-2-carboxylate (P2)

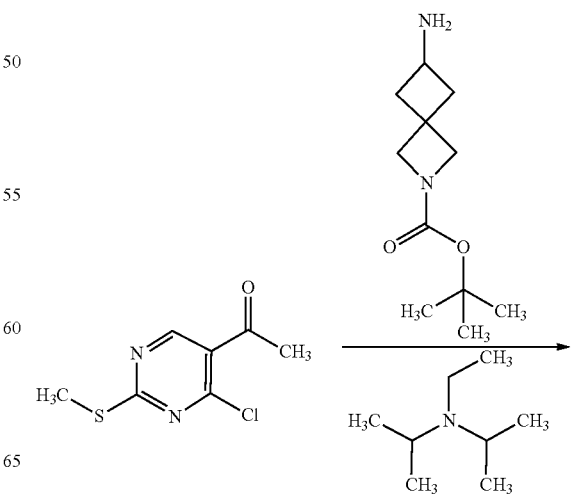

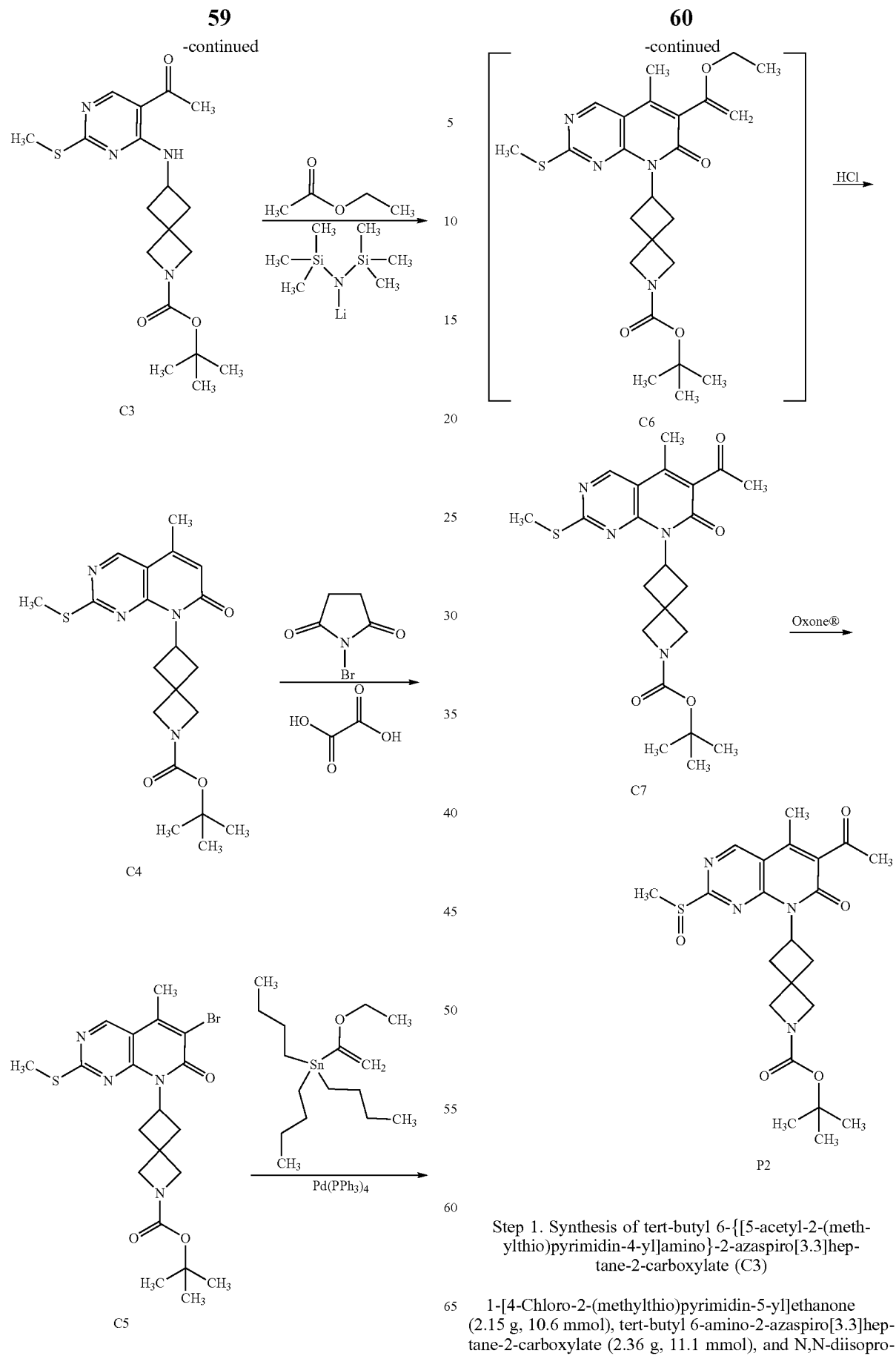
Step 1. Synthesis of tert-butyl 6-{[5-acetyl-2-(methylthio)pyrimidin-4-yl]amino}-2-azaspiro[3.3]heptane-2-carboxylate (C3)
1-[4-Chloro-2-(methylthio)pyrimidin-5-yl]ethanone (2.15 g, 10.6 mmol), tert-butyl 6-amino-2-azaspiro[3.3]heptane-2-carboxylate (2.36 g, 11.1 mmol), and N,N-diisopropylethylamine (5.54 mL, 31.8 mmol) were dissolved in a mixture of tetrahydrofuran (20 mL) and acetonitrile (5 mL). The reaction mixture was stirred at room temperature for 18 hours, whereupon it was concentrated to dryness, and the residue was subjected to silica gel chromatography (Gradient: 0% to 20% ethyl acetate in dichloromethane), affording C3 (4.18 g) as a light yellow gum. By $^1$H NMR analysis, this material contained some N,N-diisopropylethylamine hydrochloride. Corrected yield, taking the N,N-diisopropylethylamine hydrochloride into account: 3.90 g, 10.3 mmol, 97%. LCMS m/z 379.0 [M+H]$^+$. $^1$H NMR (400 MHz, chloroform-d) δ 9.26 (br d, J=6.3 Hz, 1H), 8.56 (s, 1H), 4.55-4.42 (m, 1H), 4.00 (s, 2H), 3.88 (s, 2H), 2.73-2.63 (m, 2H), 2.52 (s, 3H), 2.50 (s, 3H), 2.23-2.13 (m, 2H), 1.43 (s, 9H).

Step 2. Synthesis of tert-butyl 6-[5-methyl-2-(methylthio)-7-oxopyrido[2,3-c]pyrimidin-8(7H)-yl]-2-azaspiro[3.3]heptane-2-carboxylate (C4)

To an ice-cooled solution of C3 (1.70 g, 4.49 mmol) and ethyl acetate (1.39 g, 15.8 mmol) in tetrahydrofuran (20 mL) was added lithium bis(trimethylsilyl)amide (1 M solution; 13.5 mL, 13.5 mmol) in a portion-wise manner, at a rate of 0.5 mL every 10 seconds. The reaction mixture was stirred under ice-cooling for 30 minutes, and then at 40° C. for approximately 1 hour, whereupon it was diluted with aqueous ammonium chloride solution (5 mL), and combined with a similar reaction carried out using C3 (100 mg, 0.264 mmol). After the resulting mixture had been partitioned between ethyl acetate (30 mL) and saturated aqueous sodium chloride solution (20 mL), the aqueous layer was extracted with ethyl acetate (2×10 mL), and the combined organic layers were dried over sodium sulfate, filtered, and concentrated in vacuo. The residue was purified via chromatography on silica gel (Gradient: 0% to 30% ethyl acetate in dichloromethane) to provide C4 as a light yellow solid. Combined yield: 1.65 g, 4.10 mmol, 86%. LCMS m/z 402.9 [M+H]$^+$.

Step 3. Synthesis of tert-butyl 6-[6-bromo-5-methyl-2-(methylthio)-7-oxopyrido[2,3-c]pyrimidin-8(7H)-yl]-2-azaspiro[3.3]heptane-2-carboxylate (C5)

Oxalic acid (36.9 mg, 0.410 mmol) and N-bromosuccinimide (802 mg, 4.51 mmol) were added portion-wise to an ice-cooled solution of C4 (1.65 g, 4.10 mmol) in a mixture of acetonitrile (20 mL) and dichloromethane (10 mL). After the reaction mixture had been stirred for 45 minutes at 0° C., it was diluted with dichloromethane (50 mL) and saturated aqueous sodium chloride solution (10 mL), and then treated with aqueous sodium sulfite solution (5 mL). The resulting aqueous layer was extracted with dichloromethane (2×10 mL), and the combined organic layers were dried over sodium sulfate, filtered, and concentrated in vacuo. Silica gel chromatography (Gradient: 0% to 30% ethyl acetate in dichloromethane) provided C5 as a light yellow solid. Yield: 1.45 g, 3.01 mmol, 73%. LCMS m/z 481.1 (bromine isotope pattern observed) [M+H]$^+$. $^1$H NMR (400 MHz, chloroform-d) δ 8.79 (s, 1H), 6.03-5.84 (br m, 1H), 4.08 (s, 2H), 4.05 (s, 2H), 3.35-3.22 (m, 2H), 2.67-2.56 (m, 2H), 2.63 (s, 3H), 2.62 (s, 3H), 1.44 (s, 9H).

Step 4. Synthesis of tert-butyl 6-[6-acetyl-5-methyl-2-(methylthio)-7-oxopyrido[2,3-d]pyrimidin-8(7H)-yl]-2-azaspiro[3.3]heptane-2-carboxylate (C7)

Nitrogen was bubbled into a suspension of C5 (2.00 g, 4.15 mmol) in a mixture of toluene (30 mL) and 1,4-dioxane (15 mL), and then tributyl(1-ethoxyethenyl)stannane (7.50 g, 20.8 mmol) and tetrakis(triphenylphosphine)palladium(0) (480 mg, 0.415 mmol) were sequentially added. The reaction vial was capped, and the reaction mixture was heated at 110° C. for 6 hours. It was then filtered; after the filtrate had been concentrated in vacuo, the residue was dissolved in ethyl acetate (50 mL), treated with hydrochloric acid (1 M; 10 mL), and stirred for approximately 1 hour, until thin-layer chromatographic analysis (Eluent: 1:2 ethyl acetate/petroleum ether) indicated complete conversion of intermediate C6 {tert-butyl 6-[6-(1-ethoxyethenyl)-5-methyl-2-(methylthio)-7-oxopyrido[2,3-d]pyrimidin-8(7H)-yl]-2-azaspiro[3.3]heptane-2-carboxylate} to C7. The organic layer was dried over sodium sulfate, filtered, and concentrated under reduced pressure. Chromatography on silica gel (Gradient: 0% to 70% ethyl acetate in petroleum ether) afforded C7 as a light yellow solid. Yield: 1.30 g, 2.92 mmol, 70%. LCMS m/z 389.1 [(M−2-methylprop-1-ene)+H]$^+$. $^1$H NMR (400 MHz, chloroform-d) δ 8.79 (s, 1H), 5.87-5.71 (m, 1H), 4.05 (s, 2H), 4.05 (s, 2H), 3.36-3.23 (m, 2H), 2.66-2.57 (m, 2H), 2.62 (s, 3H), 2.53 (s, 3H), 2.36 (s, 3H), 1.44 (s, 9H).

Step 5. Synthesis of tert-butyl 6-[6-acetyl-5-methyl-2-(methylsulfinyl)-7-oxopyrido[2,3-c]pyrimidin-8(7H)-yl]-2-azaspiro[3.3]heptane-2-carboxylate (P2)

To a 0° C. solution of C7 (100 mg, 0.225 mmol) in tetrahydrofuran (8 mL) was added potassium peroxymonosulfate (Oxone®; 207 mg, 0.337 mmol), followed by water (4 mL). The reaction mixture was stirred at room temperature (10° C.) for 1 hour, whereupon it was partitioned between ethyl acetate (15 mL) and saturated aqueous sodium chloride solution (5 mL). The aqueous layer was extracted with ethyl acetate (2×5 mL), and the combined organic layers were dried over sodium sulfate, filtered, and concentrated in vacuo, providing P2 (120 mg) as a light yellow solid. This material was used directly in subsequent chemistry.

Preparation P3

6-Bromo-2-chloro-5-methyl-8-[(1R,2S)-2-methylcyclopentyl]pyrido[2,3-d]pyrimidin-7(8H)-one (P3)

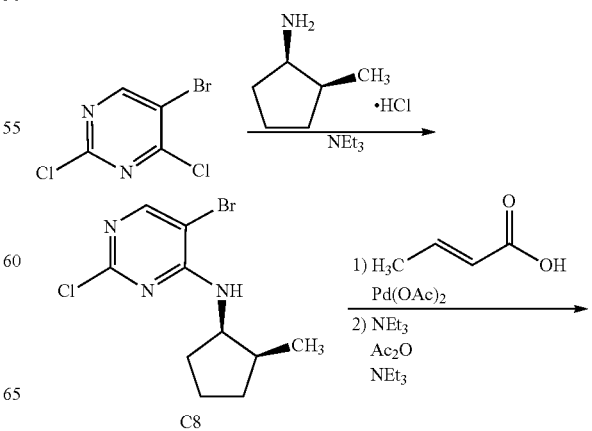

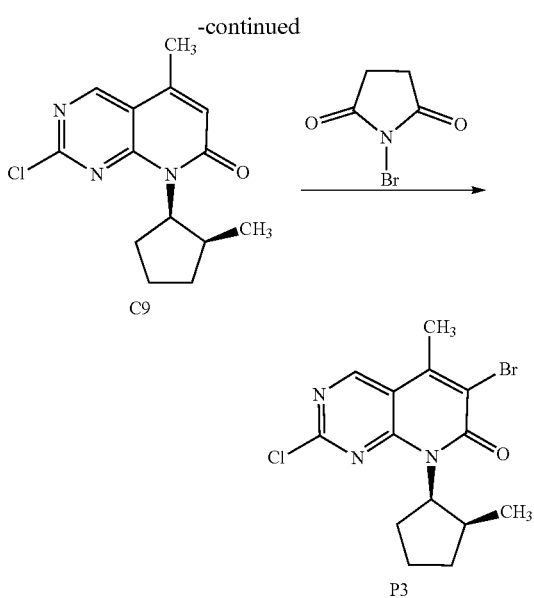

Step 1. Synthesis of 5-bromo-2-chloro-N-[(1R,2S)-2-methylcyclopentyl]pyrimidin-4-amine (C8)

A mixture of 5-bromo-2,4-dichloropyrimidine (21.5 g, 94.4 mmol) and (1R,2S)-2-methylcyclopentanamine hydrochloride (this material was prepared using the method described by W. Wiehl and A. W. Frahm, *Chemische Berichte* 1986, 119, 2668-2677; its absolute stereochemistry was further established by an X-ray crystal structure determination on the derived P3, see below) (12.8 g, 94.4 mmol) was degassed with nitrogen for 3 minutes, whereupon acetonitrile (500 mL) was added, and the mixture was cooled to 0° C. Triethylamine (38.2 g, 377 mmol) was added in a drop-wise manner, and the reaction mixture was stirred at 0° C. for 1 hour, and then stirred at 15° C. for 12 hours. The reaction mixture was then partitioned between saturated aqueous sodium bicarbonate solution (400 mL) and dichloromethane (400 mL). The aqueous layer was extracted with dichloromethane (4×200 mL), and the combined organic layers were dried over sodium sulfate, filtered, and concentrated in vacuo. Purification was carried out via silica gel chromatography (Gradient: 0% to 4% ethyl acetate in petroleum ether), affording C8 as an oil. Yield: 25.5 g, 87.8 mmol, 93%. $^1$H NMR (400 MHz, chloroform-d) δ 8.09 (s, 1H), 5.44 (br d, J=7.3 Hz, 1H), 4.55-4.43 (m, 1H), 2.35-2.23 (m, 1H), 2.16-2.03 (m, 1H), 1.98-1.87 (m, 1H), 1.84-1.71 (m, 1H), 1.70-1.51 (m, 2H), 1.42-1.31 (m, 1H), 0.90 (d, J=7.0 Hz, 3H).

Step 2. Synthesis of 2-chloro-5-methyl-8-[(1R,2S)-2-methylcyclopentyl]pyrido[2,3-d]pyrimidin-7(8H)-one (C9)

This reaction was carried out in three identical batches. Triethylamine (14.8 g, 146 mmol) and 1-methylpyrrolidin-2-one (100 mL) were added to a mixture of C8 (8.50 g, 29.2 mmol), (2E)-but-2-enoic acid (7.56 g, 87.8 mmol), and palladium(II) acetate (656 mg, 2.92 mmol). The reaction mixture was degassed with nitrogen for 15 minutes, and then stirred for 2 hours at 65° C. After cooling to room temperature (15° C.), the reaction mixture was treated with triethylamine (1.48 g, 14.6 mmol) and acetic anhydride (5.97 g, 58.5 mmol), and heated at 65° C. for 1 hour. The three batches were combined at this point, poured into ice water (1.2 L), and extracted with ethyl acetate (4×300 mL). The combined organic layers were washed sequentially with saturated aqueous potassium fluoride solution (300 mL), water (300 mL), and saturated aqueous sodium chloride solution (300 mL), dried over sodium sulfate, filtered, and concentrated in vacuo. Silica gel chromatography (Eluent: 15% ethyl acetate in petroleum ether) provided a yellow solid (17 g), which was heated in a 1:10 mixture of ethyl acetate and petroleum ether, cooled, and filtered to afford C9 (11.9 g) as a light yellow solid. The mother liquor was concentrated under reduced pressure and purified using silica gel chromatography, providing additional C9 (4.4 g) as a light yellow solid. Combined yield: 16.3 g, 58.7 mmol, 67%. LCMS m/z 277.9 (chlorine isotope pattern observed) [M+H]$^+$. $^1$H NMR (400 MHz, chloroform-d) δ 8.73 (s, 1H), 6.56-6.51 (m, 1H), 5.94 (ddd, J=9.9, 9.8, 6.7 Hz, 1H), 2.62-2.35 (m, 2H), 2.45 (d, J=1.3 Hz, 3H), 2.17-2.05 (m, 1H), 2.05-1.93 (m, 2H), 1.91-1.81 (m, 1H), 1.65-1.50 (m, 1H), 0.74 (d, J=7.1 Hz, 3H).

Step 3. Synthesis of 6-bromo-2-chloro-5-methyl-8-[(1R,2S)-2-methylcyclopentyl]pyrido[2,3-d]pyrimidin-7(8H)-one (P3)

A solution of C9 (11.9 g, 42.8 mmol) in N,N-dimethylformamide (120 mL) was divided into 6 reaction vessels, which were individually heated to 80° C. N-Bromosuccinimide (3.84 g, 21.6 mmol) was added to each reaction mixture in 8 portions; each portion was added over 2 minutes. The resulting reaction mixtures were stirred at 80° C. overnight, whereupon they were poured into ice water (1 L) and allowed to stand for 12 hours. The resulting solid was collected by filtration, and purified using chromatography on silica gel (Gradient: 10% to 20% ethyl acetate in petroleum ether) to afford P3 as a light yellow solid. Yield: 10.74 g, 30.1 mmol, 70%. LCMS m/z 356.1 (bromine isotope pattern observed) [M+H]$^+$. $^1$H NMR (400 MHz, DMSO-d$_6$) 9.21 (s, 1H), 5.91 (ddd, J=9.8, 9.7, 6.6 Hz, 1H), 2.66 (s, 3H), 2.45-2.31 (m, 2H), 2.06-1.86 (m, 3H), 1.86-1.77 (m, 1H), 1.65-1.49 (m, 1H), 0.67 (d, J=7.0 Hz, 3H).

A sample of P3 (30 mg) was dissolved in diethyl ether (2.0 mL) and treated with heptane (2.0 mL); the mixture was allowed to sit over a weekend in an unsealed vessel. One of the resulting crystals was used for X-ray structural determination (see below).

Single-Crystal X-Ray Structural Determination of P3

Single Crystal X-Ray Analysis

Data collection was performed on a Bruker D8 Quest diffractometer at room temperature. Data collection consisted of omega and phi scans.

The structure was solved by intrinsic phasing using SHELX software suite in the monoclinic space group P2$_1$. The structure was subsequently refined by the full-matrix least squares method. All non-hydrogen atoms were found and refined using anisotropic displacement parameters.

The hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correctly assigned is 100%. The Hooft parameter is reported as 0.018 with an esd of (8) and the Parsons parameter is reported as 0.024 with an esd of (9). The asymmetric unit contains two molecules of P3, and the absolute configuration was confirmed for both of these.

The final R-index was 2.8%. A final difference Fourier revealed no missing or misplaced electron density.

Pertinent crystal, data collection and refinement information is summarized in Table A. Atomic coordinates, bond lengths, bond angles, and displacement parameters are listed in Tables B-D.

Software and References

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE A

Crystal data and structure refinement for P3.

| | |
|---|---|
| Empirical formula | $C_{14}H_{15}Br\;ClN_3O$ |
| Formula weight | 356.65 |
| Temperature | 296(2) K |
| Wavelength | 1.54178 Å |
| Crystal system | Monoclinic |
| Space group | $P2_1$ |
| Unit cell dimensions | $a = 5.6861(2)$ Å   $\alpha = 90°$ |
| | $b = 20.2339(7)$ Å   $\beta = 101.0660(10)°$ |
| | $c = 13.3114(4)$ Å   $\gamma = 90°$ |
| Volume | 1503.03(9) Å$^3$ |
| Z | 4 |
| Density (calculated) | 1.576 Mg/m$^3$ |
| Absorption coefficient | 5.358 mm$^{-1}$ |
| F(000) | 720 |
| Crystal size | 0.200 × 0.080 × 0.040 mm$^3$ |
| Theta range for data collection | 3.383 to 72.473° |
| Index ranges | $-6 <= h <= 6, -24 <= k <= 20,$ |
| | $-16 <= l <= 16$ |
| Reflections collected | 19564 |
| Independent reflections | 5156 [$R_{int}$ = 0.0354] |
| Completeness to theta = 67.679° | 99.6% |
| Absorption correction | Empirical |
| Refinement method | Full-matrix least-squares on F$^2$ |
| Data/restraints/parameters | 5156/1/366 |
| Goodness-of-fit on F$^2$ | 1.044 |
| Final R indices [I > 2σ(I)] | R1 = 0.0281, wR2 = 0.0688 |
| R indices (all data) | R1 = 0.0300, wR2 = 0.0701 |
| Absolute structure parameter | 0.017(8) |
| Extinction coefficient | 0.0052(3) |
| Largest diff. peak and hole | 0.501 and −0.527 e.Å$^{-3}$ |

TABLE B

Atomic coordinates (×10$^4$) and equivalent isotropic displacement parameters (Å$^2$ × 10$^3$) for P3. U(eq) is defined as one-third of the trace of the orthogonalized U$^{ij}$ tensor.

| | x | y | z | U(eq) |
|---|---|---|---|---|
| Br(1) | 13936(1) | 5339(1) | 5089(1) | 58(1) |
| Br(2) | 13448(1) | 5072(1) | 15(1) | 62(1) |
| Cl(1) | 3798(2) | 3623(1) | 8132(1) | 65(1) |
| Cl(2) | 3620(2) | 6807(1) | 3210(1) | 62(1) |
| N(1) | 6549(7) | 4648(2) | 8161(3) | 58(1) |
| N(2) | 6790(6) | 3810(2) | 6928(2) | 41(1) |
| N(3) | 9393(6) | 3894(2) | 5775(2) | 39(1) |
| N(4) | 6774(8) | 5870(2) | 3336(3) | 55(1) |
| N(5) | 6228(6) | 6559(2) | 1858(2) | 45(1) |
| N(6) | 8391(5) | 6408(2) | 563(2) | 39(1) |
| O(1) | 11893(6) | 4004(2) | 4646(3) | 65(1) |
| O(2) | 10700(6) | 6284(2) | −638(2) | 58(1) |
| C(1) | 8179(8) | 4991(3) | 7785(3) | 55(1) |
| C(2) | 5966(7) | 4077(3) | 7685(3) | 47(1) |
| C(3) | 8448(7) | 4166(2) | 6566(2) | 37(1) |
| C(4) | 9197(7) | 4788(2) | 6970(3) | 40(1) |
| C(5) | 10923(8) | 5170(2) | 6553(3) | 46(1) |
| C(6) | 11664(11) | 5836(3) | 6997(4) | 70(2) |
| C(7) | 11754(7) | 4898(2) | 5767(3) | 43(1) |
| C(8) | 11081(7) | 4245(2) | 5344(3) | 44(1) |
| C(9) | 8789(7) | 3201(2) | 5447(3) | 44(1) |
| C(10) | 10970(10) | 2740(3) | 5679(4) | 60(1) |
| C(11) | 10595(10) | 2251(3) | 4794(4) | 66(1) |
| C(12) | 9406(10) | 2661(3) | 3887(4) | 64(1) |
| C(13) | 7615(8) | 3089(2) | 4304(3) | 49(1) |
| C(14) | 6724(9) | 3685(3) | 3661(4) | 61(1) |
| C(15) | 8377(8) | 5526(2) | 2955(3) | 53(1) |
| C(16) | 5801(7) | 6361(2) | 2751(3) | 46(1) |
| C(17) | 7886(6) | 6213(2) | 1489(3) | 38(1) |
| C(18) | 9050(7) | 5663(2) | 2018(3) | 41(1) |
| C(19) | 10778(7) | 5286(2) | 1596(3) | 45(1) |
| C(20) | 11922(12) | 4691(3) | 2144(4) | 71(2) |
| C(21) | 11254(7) | 5503(2) | 702(3) | 44(1) |
| C(22) | 10159(7) | 6090(2) | 155(3) | 43(1) |
| C(23) | 7006(7) | 6962(2) | −19(3) | 46(1) |
| C(24) | 5941(8) | 6783(3) | −1141(3) | 58(1) |
| C(25) | 6715(14) | 7306(4) | −1791(4) | 110(3) |
| C(26) | 8807(12) | 7652(3) | −1174(5) | 76(2) |
| C(27) | 8382(9) | 7608(3) | −68(4) | 59(1) |
| C(28) | 10582(12) | 7712(4) | 735(5) | 93(2) |

TABLE C

Bond lengths [Å] and angles [°] for P3.

| | |
|---|---|
| Br(1)—C(7) | 1.891(4) |
| Br(2)—C(21) | 1.895(4) |
| Cl(1)—C(2) | 1.731(5) |
| Cl(2)—C(16) | 1.737(5) |
| N(1)—C(2) | 1.329(7) |
| N(1)—C(1) | 1.330(7) |
| N(2)—C(2) | 1.306(5) |
| N(2)—C(3) | 1.347(5) |
| N(3)—C(3) | 1.385(4) |
| N(3)—C(8) | 1.402(5) |
| N(3)—C(9) | 1.490(5) |
| N(4)—C(16) | 1.317(6) |
| N(4)—C(15) | 1.322(6) |
| N(5)—C(16) | 1.320(5) |
| N(5)—C(17) | 1.342(5) |
| N(6)—C(17) | 1.377(4) |
| N(6)—C(22) | 1.388(5) |
| N(6)—C(23) | 1.497(5) |
| O(1)—C(8) | 1.216(5) |
| O(2)—C(22) | 1.220(5) |
| C(1)—C(4) | 1.386(6) |
| C(1)—H(1) | 0.9300 |
| C(3)—C(4) | 1.404(6) |
| C(4)—C(5) | 1.441(6) |
| C(5)—C(7) | 1.346(6) |
| C(5)—C(6) | 1.498(7) |
| C(6)—H(6A) | 0.9600 |
| C(6)—H(6B) | 0.9600 |
| C(6)—H(6C) | 0.9600 |
| C(7)—C(8) | 1.460(6) |
| C(9)—C(10) | 1.534(6) |

TABLE C-continued

Bond lengths [Å] and angles [°] for P3.

| | |
|---|---|
| C(9)—C(13) | 1.555(6) |
| C(9)—H(9) | 0.9800 |
| C(10)—C(11) | 1.521(7) |
| C(10)—H(10A) | 0.9700 |
| C(10)—H(10B) | 0.9700 |
| C(11)—C(12) | 1.512(7) |
| C(11)—H(11A) | 0.9700 |
| C(11)—H(11B) | 0.9700 |
| C(12)—C(13) | 1.522(6) |
| C(12)—H(12A) | 0.9700 |
| C(12)—H(12B) | 0.9700 |
| C(13)—C(14) | 1.509(7) |
| C(13)—H(13) | 0.9800 |
| C(14)—H(14A) | 0.9600 |
| C(14)—H(14B) | 0.9600 |
| C(14)—H(14C) | 0.9600 |
| C(15)—C(18) | 1.400(6) |
| C(15)—H(15) | 0.9300 |
| C(17)—C(18) | 1.412(6) |
| C(18)—C(19) | 1.440(6) |
| C(19)—C(21) | 1.344(5) |
| C(19)—C(20) | 1.492(7) |
| C(20)—H(20A) | 0.9600 |
| C(20)—H(20B) | 0.9600 |
| C(20)—H(20C) | 0.9600 |
| C(21)—C(22) | 1.469(6) |
| C(23)—C(27) | 1.532(7) |
| C(23)—C(24) | 1.543(6) |
| C(23)—H(23) | 0.9800 |
| C(24)—C(25) | 1.486(8) |
| C(24)—H(24A) | 0.9700 |
| C(24)—H(24B) | 0.9700 |
| C(25)—C(26) | 1.485(9) |
| C(25)—H(25A) | 0.9700 |
| C(25)—H(25B) | 0.9700 |
| C(26)—C(27) | 1.539(7) |
| C(26)—H(26A) | 0.9700 |
| C(26)—H(26B) | 0.9700 |
| C(27)—C(28) | 1.496(7) |
| C(27)—H(27) | 0.9800 |
| C(28)—H(28A) | 0.9600 |
| C(28)—H(28B) | 0.9600 |
| C(28)—H(28C) | 0.9600 |
| C(2)—N(1)—C(1) | 113.8(4) |
| C(2)—N(2)—C(3) | 115.8(4) |
| C(3)—N(3)—C(8) | 120.4(3) |
| C(3)—N(3)—C(9) | 119.7(3) |
| C(8)—N(3)—C(9) | 119.6(3) |
| C(16)—N(4)—C(15) | 114.3(4) |
| C(16)—N(5)—C(17) | 115.8(4) |
| C(17)—N(6)—C(22) | 120.6(3) |
| C(17)—N(6)—C(23) | 119.9(3) |
| C(22)—N(6)—C(23) | 119.5(3) |
| N(1)—C(1)—C(4) | 124.5(5) |
| N(1)—C(1)—H(1) | 117.8 |
| C(4)—C(1)—H(1) | 117.8 |
| N(2)—C(2)—N(1) | 129.3(4) |
| N(2)—C(2)—Cl(1) | 115.5(4) |
| N(1)—C(2)—Cl(1) | 115.2(3) |
| N(2)—C(3)—N(3) | 117.4(3) |
| N(2)—C(3)—C(4) | 121.6(3) |
| N(3)—C(3)—C(4) | 121.0(4) |
| C(1)—C(4)—C(3) | 115.1(4) |
| C(1)—C(4)—C(5) | 124.1(4) |
| C(3)—C(4)—C(5) | 120.8(3) |
| C(7)—C(5)—C(4) | 116.6(4) |
| C(7)—C(5)—C(6) | 124.0(4) |
| C(4)—C(5)—C(6) | 119.4(4) |
| C(5)—C(6)—H(6A) | 109.5 |
| C(5)—C(6)—H(6B) | 109.5 |
| H(6A)—C(6)—H(6B) | 109.5 |
| C(5)—C(6)—H(6C) | 109.5 |
| H(6A)—C(6)—H(6C) | 109.5 |
| H(66)—C(6)—H(6C) | 109.5 |
| C(5)—C(7)—C(8) | 124.4(4) |
| C(5)—C(7)—Br(1) | 122.6(3) |
| C(8)—C(7)—Br(1) | 113.0(3) |
| O(1)—C(8)—N(3) | 120.0(4) |
| O(1)—C(8)—C(7) | 123.2(4) |
| N(3)—C(8)—C(7) | 116.8(3) |
| N(3)—C(9)—C(10) | 112.4(4) |
| N(3)—C(9)—C(13) | 117.1(3) |
| C(10)—C(9)—C(13) | 106.7(3) |
| N(3)—C(9)—H(9) | 106.7 |
| C(10)—C(9)—H(9) | 106.7 |
| C(13)—C(9)—H(9) | 106.7 |
| C(11)—C(10)—C(9) | 104.6(4) |
| C(11)—C(10)—H(10A) | 110.8 |
| C(9)—C(10)—H(10A) | 110.8 |
| C(11)—C(10)—H(10B) | 110.8 |
| C(9)—C(10)—H(10B) | 110.8 |
| H(10A)—C(10)—H(10B) | 108.9 |
| C(12)—C(11)—C(10) | 103.7(4) |
| C(12)—C(11)—H(11A) | 111.0 |
| C(10)—C(11)—H(11A) | 111.0 |
| C(12)—C(11)—H(11B) | 111.0 |
| C(10)—C(11)—H(11B) | 111.0 |
| H(11A)—C(11)—H(11B) | 109.0 |
| C(11)—C(12)—C(13) | 104.4(4) |
| C(11)—C(12)—H(12A) | 110.9 |
| C(13)—C(12)—H(12A) | 110.9 |
| C(11)—C(12)—H(12B) | 110.9 |
| C(13)—C(12)—H(12B) | 110.9 |
| H(12A)—C(12)—H(12B) | 108.9 |
| C(14)—C(13)—C(12) | 115.0(4) |
| C(14)—C(13)—C(9) | 118.3(4) |
| C(12)—C(13)—C(9) | 104.3(4) |
| C(14)—C(13)—H(13) | 106.1 |
| C(12)—C(13)—H(13) | 106.1 |
| C(9)—C(13)—H(13) | 106.1 |
| C(13)—C(14)—H(14A) | 109.5 |
| C(13)—C(14)—H(14B) | 109.5 |
| H(14A)—C(14)—H(14B) | 109.5 |
| C(13)—C(14)—H(14C) | 109.5 |
| H(14A)—C(14)—H(14C) | 109.5 |
| H(14B)—C(14)—H(14C) | 109.5 |
| N(4)—C(15)—C(18) | 124.4(4) |
| N(4)—C(15)—H(15) | 117.8 |
| C(18)—C(15)—H(15) | 117.8 |
| N(4)—C(16)—N(5) | 129.3(4) |
| N(4)—C(16)—Cl(2) | 115.6(3) |
| N(5)—C(16)—Cl(2) | 115.2(4) |
| N(5)—C(17)—N(6) | 117.4(4) |
| N(5)—C(17)—C(18) | 121.6(3) |
| N(6)—C(17)—C(18) | 121.0(3) |
| C(15)—C(18)—C(17) | 114.7(4) |
| C(15)—C(18)—C(19) | 124.5(4) |
| C(17)—C(18)—C(19) | 120.8(3) |
| C(21)—C(19)—C(18) | 116.2(3) |
| C(21)—C(19)—C(20) | 123.6(4) |
| C(18)—C(19)—C(20) | 120.2(4) |
| C(19)—C(20)—H(20A) | 109.5 |
| C(19)—C(20)—H(20B) | 109.5 |
| H(20A)—C(20)—H(20B) | 109.5 |
| C(19)—C(20)—H(20C) | 109.5 |
| H(20A)—C(20)—H(20C) | 109.5 |
| H(20B)—C(20)—H(20C) | 109.5 |
| C(19)—C(21)—C(22) | 124.4(4) |
| C(19)—C(21)—Br(2) | 122.7(3) |
| C(22)—C(21)—Br(2) | 112.9(3) |
| O(2)—C(22)—N(6) | 120.8(4) |
| O(2)—C(22)—C(21) | 122.4(4) |
| N(6)—C(22)—C(21) | 116.8(3) |
| N(6)—C(23)—C(27) | 116.1(3) |
| N(6)—C(23)—C(24) | 113.3(4) |
| C(27)—C(23)—C(24) | 105.5(3) |
| N(6)—C(23)—H(23) | 107.2 |
| C(27)—C(23)—H(23) | 107.2 |
| C(24)—C(23)—H(23) | 107.2 |
| C(25)—C(24)—C(23) | 107.0(5) |
| C(25)—C(24)—H(24A) | 110.3 |
| C(23)—C(24)—H(24A) | 110.3 |
| C(25)—C(24)—H(24B) | 110.3 |

TABLE C-continued

Bond lengths [Å] and angles [°] for P3.

| | |
|---|---|
| C(23)—C(24)—H(24B) | 110.3 |
| H(24A)—C(24)—H(24B) | 108.6 |
| C(26)—C(25)—C(24) | 108.0(4) |
| C(26)—C(25)—H(25A) | 110.1 |
| C(24)—C(25)—H(25A) | 110.1 |
| C(26)—C(25)—H(25B) | 110.1 |
| C(24)—C(25)—H(25B) | 110.1 |
| H(25A)—C(25)—H(25B) | 108.4 |
| C(25)—C(26)—C(27) | 104.2(5) |
| C(25)—C(26)—H(26A) | 110.9 |
| C(27)—C(26)—H(26A) | 110.9 |
| C(25)—C(26)—H(26B) | 110.9 |
| C(27)—C(26)—H(26B) | 110.9 |
| H(26A)—C(26)—H(26B) | 108.9 |
| C(28)—C(27)—C(23) | 117.0(5) |
| C(28)—C(27)—C(26) | 114.3(6) |
| C(23)—C(27)—C(26) | 105.4(4) |
| C(28)—C(27)—H(27) | 106.5 |
| C(23)—C(27)—H(27) | 106.5 |
| C(26)—C(27)—H(27) | 106.5 |
| C(27)—C(28)—H(28A) | 109.5 |
| C(27)—C(28)—H(28B) | 109.5 |
| H(28A)—C(28)—H(28B) | 109.5 |
| C(27)—C(28)—H(28C) | 109.5 |
| H(28A)—C(28)—H(28C) | 109.5 |
| H(28B)—C(28)—H(28C) | 109.5 |

TABLE D

Anisotropic displacement parameters (Å² × 10³) for P3. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| Br(1) | 61(1) | 56(1) | 56(1) | 8(1) | 12(1) | −16(1) |
| Br(2) | 61(1) | 65(1) | 63(1) | −9(1) | 18(1) | 19(1) |
| Cl(1) | 56(1) | 90(1) | 55(1) | 6(1) | 27(1) | 2(1) |
| Cl(2) | 64(1) | 77(1) | 55(1) | −11(1) | 32(1) | −2(1) |
| N(1) | 62(2) | 69(3) | 47(2) | −12(2) | 19(2) | 7(2) |
| N(2) | 43(2) | 44(2) | 36(2) | 2(1) | 13(1) | 4(1) |
| N(3) | 48(2) | 37(2) | 34(1) | −7(1) | 15(1) | −1(1) |
| N(4) | 68(2) | 58(3) | 43(2) | 5(2) | 23(2) | −8(2) |
| N(5) | 46(2) | 53(2) | 38(2) | −3(2) | 14(1) | −4(2) |
| N(6) | 42(2) | 44(2) | 34(1) | 3(1) | 13(1) | 4(1) |
| O(1) | 74(2) | 66(2) | 67(2) | −23(2) | 42(2) | −24(2) |
| O(2) | 69(2) | 64(2) | 49(2) | 10(1) | 33(1) | 15(2) |
| C(1) | 66(3) | 51(3) | 47(2) | −14(2) | 10(2) | 5(2) |
| C(2) | 44(2) | 62(3) | 38(2) | 3(2) | 12(2) | 12(2) |
| C(3) | 42(2) | 37(2) | 31(2) | 2(2) | 6(1) | 8(2) |
| C(4) | 49(2) | 38(2) | 33(2) | −2(2) | 4(1) | 7(2) |
| C(5) | 58(2) | 36(3) | 40(2) | 1(2) | −2(2) | 1(2) |
| C(6) | 101(4) | 47(3) | 62(3) | −11(2) | 16(3) | −13(3) |
| C(7) | 47(2) | 44(3) | 37(2) | 6(2) | 5(1) | −6(2) |
| C(8) | 48(2) | 47(2) | 39(2) | −3(2) | 13(2) | −6(2) |
| C(9) | 55(2) | 37(2) | 42(2) | −7(2) | 21(2) | −7(2) |
| C(10) | 76(3) | 49(3) | 53(2) | −6(2) | 4(2) | 9(2) |
| C(11) | 78(3) | 50(3) | 72(3) | −10(2) | 16(2) | 13(2) |
| C(12) | 88(4) | 52(3) | 52(2) | −12(2) | 17(2) | 10(3) |
| C(13) | 50(2) | 44(2) | 53(2) | −10(2) | 12(2) | −7(2) |
| C(14) | 65(3) | 57(3) | 58(2) | −6(2) | 3(2) | 9(2) |
| C(15) | 66(3) | 52(3) | 42(2) | 7(2) | 12(2) | −6(2) |
| C(16) | 49(2) | 55(3) | 38(2) | −8(2) | 18(2) | −10(2) |
| C(17) | 38(2) | 44(2) | 32(2) | −2(2) | 9(1) | −5(2) |
| C(18) | 46(2) | 40(2) | 36(2) | −1(2) | 6(2) | −6(2) |
| C(19) | 50(2) | 40(2) | 43(2) | −1(2) | 5(2) | 2(2) |
| C(20) | 96(4) | 56(3) | 62(3) | 11(3) | 18(3) | 23(3) |
| C(21) | 44(2) | 45(3) | 42(2) | −6(2) | 10(2) | 3(2) |
| C(22) | 45(2) | 48(2) | 38(2) | −1(2) | 13(2) | 4(2) |
| C(23) | 42(2) | 60(3) | 38(2) | 8(2) | 15(2) | 14(2) |
| C(24) | 49(2) | 76(3) | 46(2) | 5(2) | 2(2) | 3(2) |
| C(25) | 143(6) | 126(6) | 53(3) | 31(4) | −1(3) | −39(5) |
| C(26) | 93(4) | 64(4) | 79(3) | 24(3) | 34(3) | 4(3) |
| C(27) | 65(3) | 50(3) | 63(3) | 0(2) | 12(2) | 10(2) |
| C(28) | 92(4) | 65(4) | 110(5) | −11(4) | −16(4) | −9(3) |

Preparation P4

3-Acetyl-7-chloro-1-cyclopentyl-4-methyl-1,6-naphthyridin-2(1H)-one (P4)

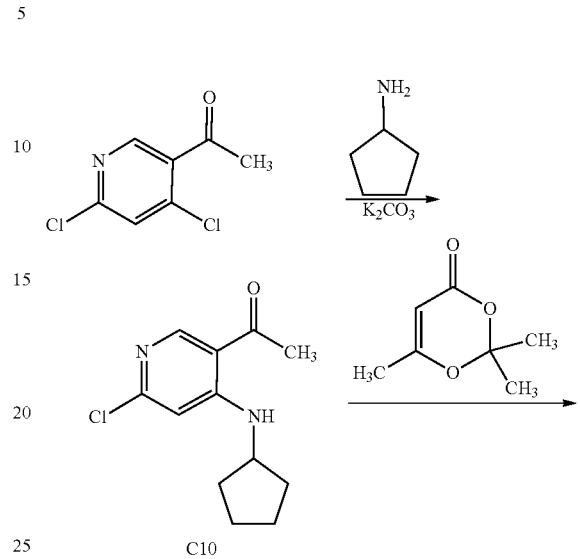

C10

Step 1. Synthesis of 1-[6-chloro-4-(cyclopentylamino)pyridin-3-yl]ethanone (C10)

A mixture of 1-(4,6-dichloropyridin-3-yl)ethanone (176 g, 926 mmol), cyclopentanamine (197 g, 2.31 mol), and potassium carbonate (448 g, 3.24 mol) in acetonitrile (1.76 L, 10 volumes; for units presented as 'volumes' in this experiment, 1 volume=0.176 L) was stirred at 15° C. to 30° C. for 30 hours, whereupon the reaction mixture was filtered, and the filter pad was washed with acetonitrile (3×5 volumes). The combined filtrates were concentrated in vacuo to approximately 2 to 3 volumes. tert-Butyl methyl ether (5 volumes) was then added, and concentration was carried out to 2 to 3 volumes, until the acetonitrile residue, as assessed by GC analysis, was ≥0.3%. tert-Butyl methyl ether (5 volumes) was again added, and the resulting solution was washed with purified water (2×5 volumes) and concentrated in vacuo to approximately 2 to 3 volumes. After addition of heptane (5 volumes), the mixture was concentrated in vacuo to approximately 2 to 3 volumes; this addition/concentration was repeated until the percentage of tert-butyl methyl ether remaining was ≥0.1% by GC analysis. The resulting mixture was stirred at −20° C. to −5° C. for 1 to 2 hours, whereupon the solid was collected via filtration to afford C10 as a solid. Yield: 204 g, 855 mmol, 92%. Representative $^1$H NMR (500 MHz, chloroform-d) δ 9.20 (br s, 1H), 8.56 (s, 1H), 6.58 (s, 1H), 3.87-3.77 (m, 1H), 2.55 (s, 3H), 2.10-1.98 (m, 2H), 1.83-1.72 (m, 2H), 1.72-1.61 (m, 2H), 1.61-1.52 (m, 2H).

Step 2. Synthesis of 3-acetyl-7-chloro-1-cyclopentyl-4-methyl-1,6-naphthyridin-2(1H)-one (P4)

A mixture of C10 (177 g, 741 mmol) and 2,2,6-trimethyl-4H-1,3-dioxin-4-one (316 g, 2.22 mol) was stirred at 75° C. to 85° C. for 72 hours, whereupon toluene (354 g, 2 volumes) was added, and the resulting mixture was cooled to 15° C. to 30° C. Dichloromethane (2 volumes) was added, and the mixture was stirred at 15° C. to 30° C. for 30 to 40 minutes, whereupon it was treated with silica gel (354 g) and stirring was continued at 15° C. to 30° C. for 20 to 30 minutes. After this mixture had been filtered through a pad of silica gel (177 g), the filter pad was further eluted with a 1:1 mixture of propan-2-yl acetate and heptane (approximately 45 volumes), and the eluent was monitored by thin-layer chromatography (Eluent: 3:1 petroleum ether/heptane) until no further product P4 was detected. The appropriate eluates were combined and concentrated in vacuo, to 2 to 3 volumes. 2-Propanol (5 volumes) was then added, and the mixture was concentrated to 2 to 3 volumes; this process was repeated until the residual propan-2-yl acetate was ≥0.2% by GC analysis. The resulting mixture was cooled to −5° C. to 5° C. and stirred for 1 to 2 hours, whereupon it was filtered to provide P4 as a solid. Yield: 69.0 g, 226 mmol, 30%. Representative $^1$H NMR (500 MHz, DMSO-$d_6$) δ 8.86 (s, 1H), 7.84 (s, 1H), 5.31-5.20 (m, 1H), 2.43 (s, 3H), 2.36 (s, 3H), 2.16-2.04 (m, 2H), 2.00-1.84 (m, 4H), 1.70-1.58 (m, 2H).

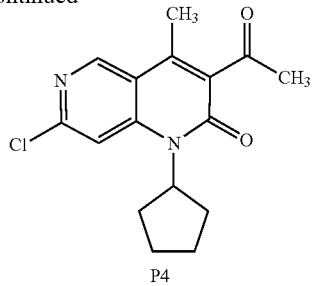

P4

Preparation P5 rac-(1S,2S)-2-[6-Bromo-5-methyl-2-(methylthio)-7-oxopyrido[2,3-d]pyrimidin-8(7H)-yl]-1-methylcyclopentyl acetate (P5)

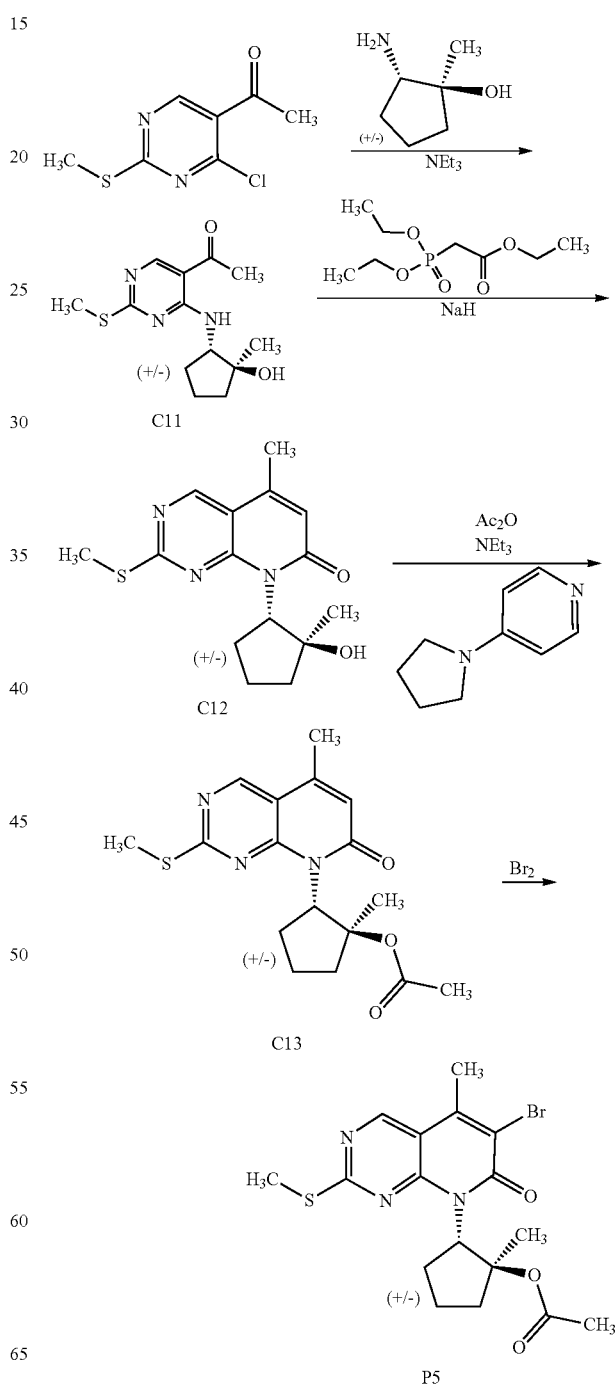

Step 1. Synthesis of rac-1-[4-{[(1S,2S)-2-hydroxy-2-methylcyclopentyl]amino}-2-(methylthio)pyrimidin-5-yl]ethanone (C11)

A mixture of 1-[4-chloro-2-(methylthio)pyrimidin-5-yl] ethanone (1.24 g, 6.12 mmol), triethylamine (2.56 mL, 18.4 mmol), and trans-2-amino-1-methylcyclopentanol (this reactant may be prepared using the method of A. Saeed et al., *J. Med. Chem.* 2016, 59, 750-755) (775 mg, 6.73 mmol) in ethanol (12 mL) was stirred at room temperature for 2 hours. After the reaction mixture had been concentrated in vacuo, the residue was diluted with water and extracted three times with ethyl acetate. The combined organic layers were dried over magnesium sulfate, filtered, concentrated under reduced pressure, and purified via chromatography on silica gel (Gradient: 20% to 60% ethyl acetate in heptane), affording C11 as a pale yellow solid. Yield: 1.52 g, 5.40 mmol, 88%. LCMS m/z 282.0 [M+H]$^+$. $^1$H NMR (400 MHz, chloroform-d) δ 9.29 (br s, 1H), 8.61 (s, 1H), 4.40-4.33 (m, 1H), 4.33 (s, 1H), 2.54 (s, 3H), 2.53 (s, 3H), 2.30-2.19 (m, 1H), 2.03-1.90 (m, 1H), 1.90-1.57 (m, 4H), 1.14 (s, 3H).

Step 2. Synthesis of rac-8-[(1S,2S)-2-hydroxy-2-methylcyclopentyl]-5-methyl-2-(methylthio)pyrido[2,3-d]pyrimidin-7(8H)-one (C12)

Ethyl (diethoxyphosphoryl)acetate (8.99 mL, 45.3 mmol) was slowly added to a 0° C. mixture of sodium hydride (60% in mineral oil; 1.73 g, 43.2 mmol) in tetrahydrofuran (60 mL), whereupon the cooling bath was removed and a solution of C11 (2.54 g, 9.03 mmol) in tetrahydrofuran (30 mL) was added. The reaction mixture was heated to 65° C. for 18 hours, then cooled to room temperature, diluted with water, and extracted twice with ethyl acetate. The combined organic layers were dried over magnesium sulfate, filtered, and concentrated in vacuo; silica gel chromatography (Gradient: 0% to 60% ethyl acetate in heptane) provided C12 as a pale yellow solid (2.52 g). By $^1$H NMR analysis, this material contained impurities; a portion of this material was progressed directly into the following step. LCMS m/z 306.1 [M+H]$^+$. $^1$H NMR (400 MHz, chloroform-d), characteristic peaks: δ 8.71 (s, 1H), 6.42 (br q, J=1.2 Hz, 1H), 5.81 (dd, J=9.0, 8.2 Hz, 1H), 2.88-2.75 (m, 1H), 2.64 (s, 3H), 2.43 (d, J=1.2 Hz, 3H), 2.30-2.19 (m, 1H), 1.14 (s, 3H).

Step 3. Synthesis of rac-(1S,2S)-1-methyl-2-[5-methyl-2-(methylthio)-7-oxopyrido[2,3-d]pyrimidin-8(7H)-yl]cyclopentyl acetate (C13)

4-(Pyrrolidin-1-yl)pyridine (124 mg, 0.837 mmol) was added to a mixture of C12 (from the previous step; 1.26 g, ≥4.13 mmol), triethylamine (1.73 mL, 12.4 mmol), and acetic anhydride (0.780 mL, 8.25 mmol) in chloroform (20 mL), and the reaction mixture was heated to 70° C. for 16 hours. It was then quenched with water and extracted twice with ethyl acetate. The combined organic layers were dried over magnesium sulfate, filtered, concentrated in vacuo, and purified via chromatography on silica gel (Gradient: 0% to 50% ethyl acetate in heptane) to afford C13 as a white solid. Yield: 793 mg, 2.28 mmol, 51% over 2 steps. $^1$H NMR (400 MHz, DMSO-d$_6$), characteristic peaks: δ 8.91 (s, 1H), 6.45-6.41 (m, 1H), 6.28-6.20 (m, 1H), 2.62 (s, 3H), 2.45 (d, J=1.2 Hz, 3H), 2.25 (ddd, J=13.3, 11.1, 7.3 Hz, 1H), 1.95 (s, 3H), 1.35 (s, 3H).

Step 4. Synthesis of rac-(1S,2S)-2-[6-bromo-5-methyl-2-(methylthio)-7-oxopyrido[2,3-d]pyrimidin-8(7H)-yl]-1-methylcyclopentyl acetate (P5)

A solution of bromine (0.16 mL, 3.1 mmol) in dichloromethane (10 mL) was added to a solution of C13 (715 mg, 2.06 mmol) in dichloromethane (10 mL), and the reaction mixture was stirred at room temperature for 1 hour. LCMS analysis at this point indicated the presence of product P5: LCMS m/z 426.0 (bromine isotope pattern observed) [M+H]$^+$. The reaction mixture was quenched by addition of 10% aqueous sodium thiosulfate solution, and then extracted with ethyl acetate. The organic layer was dried over magnesium sulfate, filtered, and concentrated in vacuo. After purification via silica gel chromatography (Gradient: 0% to 35% ethyl acetate in heptane), P5 was isolated as a white foam. Yield: 475 mg, 1.11 mmol, 54%. $^1$H NMR (400 MHz, chloroform-d), characteristic peaks: δ 8.81 (s, 1H), 6.52-6.34 (br m, 1H), 2.65 (s, 3H), 2.63 (s, 3H), 2.11-2.01 (m, 2H), 2.00 (s, 3H), 1.87-1.69 (m, 2H, assumed; partially obscured by water peak), 1.43 (s, 3H).

Preparation P6

6-Acetyl-2-chloro-8-cyclopentyl-5-methylpyrido[2,3-d]pyrimidin-7(8H)-one (P6)

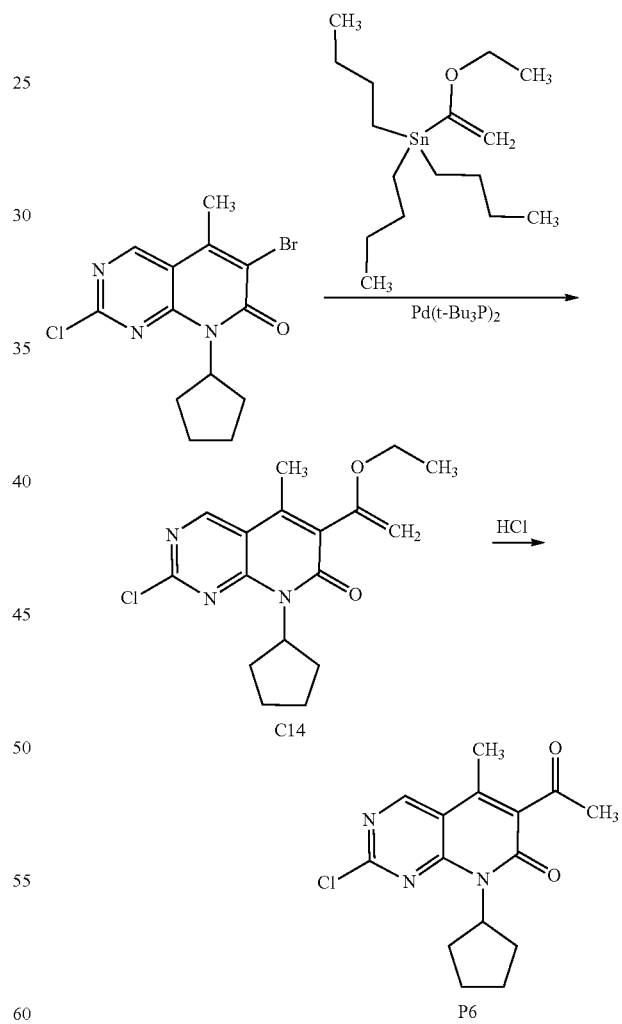

Step 1. Synthesis of 2-chloro-8-cyclopentyl-6-(1-ethoxyethenyl)-5-methylpyrido[2,3-c]pyrimidin-7(8H)-one (C14)

Bis(tri-tert-butylphosphine)palladium(0) (1.96 g, 3.84 mmol) and tributyl(1-ethoxyethenyl)stannane (36.0 g, 99.7 mmol) were added to a solution of 6-bromo-2-chloro-8-cyclopentyl-5-methylpyrido[2,3-d]pyrimidin-7(8H)-one (26.3 g, 76.8 mmol) in 1-methylpyrrolidin-2-one (400 mL). After the reaction mixture had been stirred at 45° C. for 48 hours, it was poured into a mixture of saturated aqueous sodium chloride solution (1 L) and ice (400 g), and then diluted with ethyl acetate (1 L). The aqueous layer was extracted with ethyl acetate (2×1 L), and the combined organic layers were washed with saturated aqueous sodium chloride solution (1 L), dried over magnesium sulfate (100 g), filtered, and concentrated in vacuo. Silica gel chromatography (Gradient: 5% to 9% ethyl acetate in petroleum ether) provided C14 as a light yellow gum. Yield: 23.0 g, 68.9 mmol, 90%. LCMS m/z 333.9 (chlorine isotope pattern observed) [M+H]⁺. ¹H NMR (400 MHz, chloroform-d) δ 8.78 (s, 1H), 5.93-5.81 (m, 1H), 4.54 (d, J=2.6 Hz, 1H), 4.18 (d, J=2.6 Hz, 1H), 3.93 (q, J=7.0 Hz, 2H), 2.46 (s, 3H), 2.27-2.15 (m, 2H), 2.15-2.04 (m, 2H), 1.94-1.83 (m, 2H), 1.70-1.58 (m, 2H), 1.35 (t, J=7.0 Hz, 3H).

Step 2. Synthesis of 6-acetyl-2-chloro-8-cyclopentyl-5-methylpyrido[2,3-c]pyrimidin-7(8H)-one (P6)

To a solution of C14 (14.3 g, 42.8 mmol) in tetrahydrofuran (200 mL) was added hydrochloric acid (1 M; 156 mL, 156 mmol). After the reaction mixture had been stirred at 25° C. for 30 minutes, it was partitioned between saturated aqueous sodium bicarbonate solution (200 mL) and ethyl acetate (400 mL). Upon cessation of carbon dioxide production, the aqueous layer was extracted with ethyl acetate (2×200 mL), and the combined organic layers were dried over magnesium sulfate (30 g), filtered, concentrated in vacuo, and purified by silica gel chromatography (Gradient: 9% to 25% ethyl acetate in petroleum ether), affording P6 as a light yellow solid. Yield: 9.1 g, 30 mmol, 70%. LCMS m/z 305.9 (chlorine isotope pattern observed) [M+H]⁺. ¹H NMR (400 MHz, chloroform-d) δ 8.85 (s, 1H), 5.91-5.78 (m, 1H), 2.53 (s, 3H), 2.39 (s, 3H), 2.27-2.16 (m, 2H), 2.16-2.04 (m, 2H), 1.97-1.86 (m, 2H), 1.74-1.61 (m, 2H).

Preparation P7

6-Bromo-2-chloro-8-[(1R,2S)-2-ethylcyclopentyl]-5-methylpyrido[2,3-d]pyrimidin-7(8H)-one (P7)

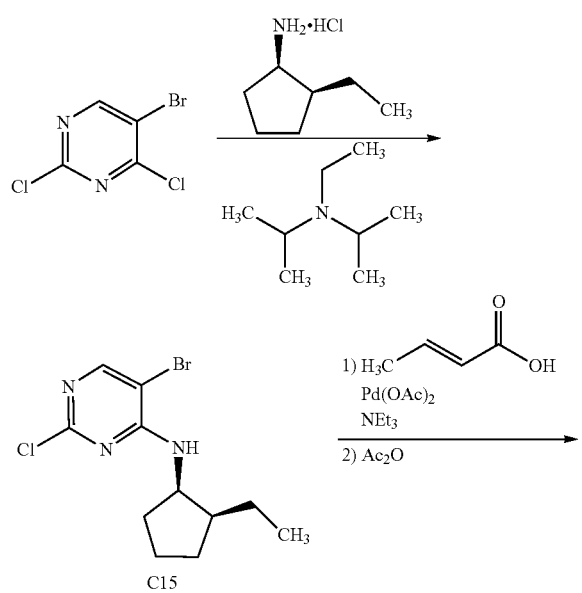

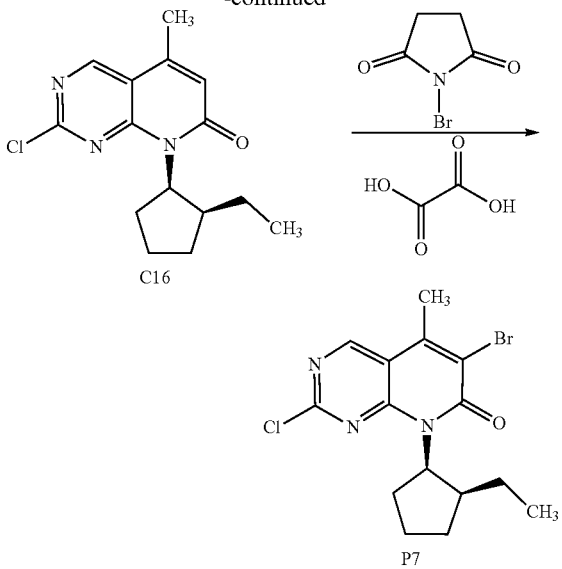

Step 1. Synthesis of 5-bromo-2-chloro-N-[(1R,2S)-2-ethylcyclopentyl]pyrimidin-4-amine (C15)

A solution of (1R,2S)-2-ethylcyclopentanamine hydrochloride (prepared using the method described by W. Wiehl and A. W. Frahm, Chemische Berichte 1986, 119, 2668-2677) (250 mg, 1.67 mmol), 5-bromo-2,4-dichloropyrimidine (381 mg, 1.67 mmol), and N,N-diisopropylethylamine (864 mg, 6.68 mmol) in dimethyl sulfoxide (40 mL) was stirred at room temperature for 20 hours. The reaction mixture was then diluted with water (20 mL) and extracted with ethyl acetate (3×50 mL); the combined organic layers were washed with water (3×50 mL) and with saturated aqueous sodium chloride solution (30 mL), dried over sodium sulfate, filtered, and concentrated in vacuo. Silica gel chromatography (Gradient: 0% to 20% ethyl acetate in heptane) provided C15 as a colorless oil. Yield: 162 mg, 0.532 mmol, 32%. LCMS m/z 303.8 (bromine-chlorine isotope pattern observed) [M+H]⁺. ¹H NMR (400 MHz, chloroform-d) δ 8.09 (s, 1H), 5.43 (br d, J=8.2 Hz, 1H), 4.63-4.51 (m, 1H), 2.12-1.87 (m, 3H), 1.82-1.56 (m, 3H), 1.45-1.29 (m, 2H), 1.28-1.15 (m, 1H), 0.91 (t, J=7.3 Hz, 3H). It is noted that the absolute stereochemistry of C15 was not confirmed. See Preparation P3 for the absolute stereochemistry determination of P3, derived from the corresponding methyl congener (1R,2S)-2-methylcyclopentanamine. (1R,2S)-2-Methylcyclopentanamine and (1R,2S)-2-ethylcyclopentanamine were synthesized via the same method of Wiehl and Frahm, and it has been assumed that (1R,2S)-2-ethylcyclopentanamine would therefore exhibit the same stereochemistry around the cyclopentane.

Step 2. Synthesis of 2-chloro-8-[(1R,2S)-2-ethylcyclopentyl]-5-methylpyrido[2,3-d]pyrimidin-7(8H)-one (C16)

A mixture of C15 (162 mg, 0.532 mmol), (2E)-but-2-enoic acid (137 mg, 1.59 mmol), palladium(II) acetate (11.9 mg, 53.0 µmol), and triethylamine (0.371 mL, 2.66 mmol) in 1-methylpyrrolidin-2-one (20 mL) was degassed with nitrogen for 10 minutes. The reaction vial was then capped and heated to 65° C. for 20 hours. (2E)-But-2-enoic acid (137 mg, 1.59 mmol), palladium(II) acetate (11.9 mg, 53.0 µmol), and triethylamine (0.371 mL, 2.66 mmol) were again added, followed by a similar degassing with nitrogen, whereupon the reaction mixture was heated to 65° C. for 16 hours. Palladium(II) acetate (11.9 mg, 53.0 µmol) was added once again, the nitrogen purge was repeated, and heating at 65° C. was continued for 3 hours. Acetic anhydride (0.100 mL, 1.06 mmol) was then added and the reaction mixture was heated to 65° C. for 16 hours, whereupon it was poured into water and neutralized by addition of saturated aqueous sodium bicarbonate solution. The resulting mixture was extracted with ethyl acetate (3×10 mL) and the combined organic layers were washed with saturated aqueous sodium chloride solution (3×10 mL), dried over sodium sulfate, filtered, and concentrated in vacuo. The residue was purified via silica gel chromatography (Gradient: 0% to 30% ethyl acetate in heptane) to provide a mixture of C16 and (2E)-but-2-enoic acid as a yellow oil (115 mg). LCMS m/z 291.8 (chlorine isotope pattern observed) [M+H]$^+$. $^1$H NMR (400 MHz, chloroform-d), characteristic peaks for C16: δ 8.72 (s, 1H), 6.51 (br s, 1H), 6.02-5.91 (m, 1H), 2.41 (d, J=1.3 Hz, 3H), 0.74 (t, J=7.4 Hz, 3H).

Step 3. Synthesis of 6-bromo-2-chloro-8-[(1R,2S)-2-ethylcyclopentyl]-5-methylpyrido[2,3-d]pyrimidin-7(8H)-one (P7)

N-Bromosuccinimide (105 mg, 0.590 mmol) and oxalic acid (9.9 mg, 0.11 mmol) were added to a solution of C16 (from the previous step; 115.0 mg, <0.394 mmol) in acetonitrile, and the reaction mixture was heated to 60° C. for 16 hours. It was then concentrated in vacuo, and the residue was purified using silica gel chromatography (Gradient: 0% to 50% ethyl acetate in heptane) to provide P7 as a clear yellow oil. By $^1$H NMR analysis, this material was not entirely pure. Yield: 80 mg, 0.22 mmol, 41% over 2 steps. LCMS m/z 369.7 (bromine-chlorine isotope pattern observed) [M+H]$^+$. $^1$H NMR (400 MHz, DMSO-$d_6$), product peaks only: δ 9.20 (s, 1H), 6.04-5.91 (m, 1H), 2.66 (s, 3H), 2.43-2.29 (m, 1H), 2.22-2.08 (m, 1H), 2.07-1.84 (m, 4H), 1.63-1.46 (m, 1H), 1.07-0.90 (m, 2H), 0.74 (t, J=7.3 Hz, 3H).

Preparation P8

7-Chloro-4-methyl-1-[(3S)-tetrahydrofuran-3-yl]-1,6-naphthyridin-2(1H)-one (P8)

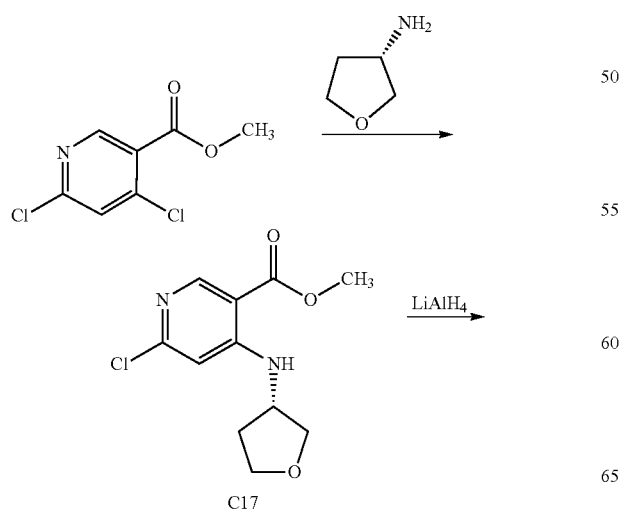

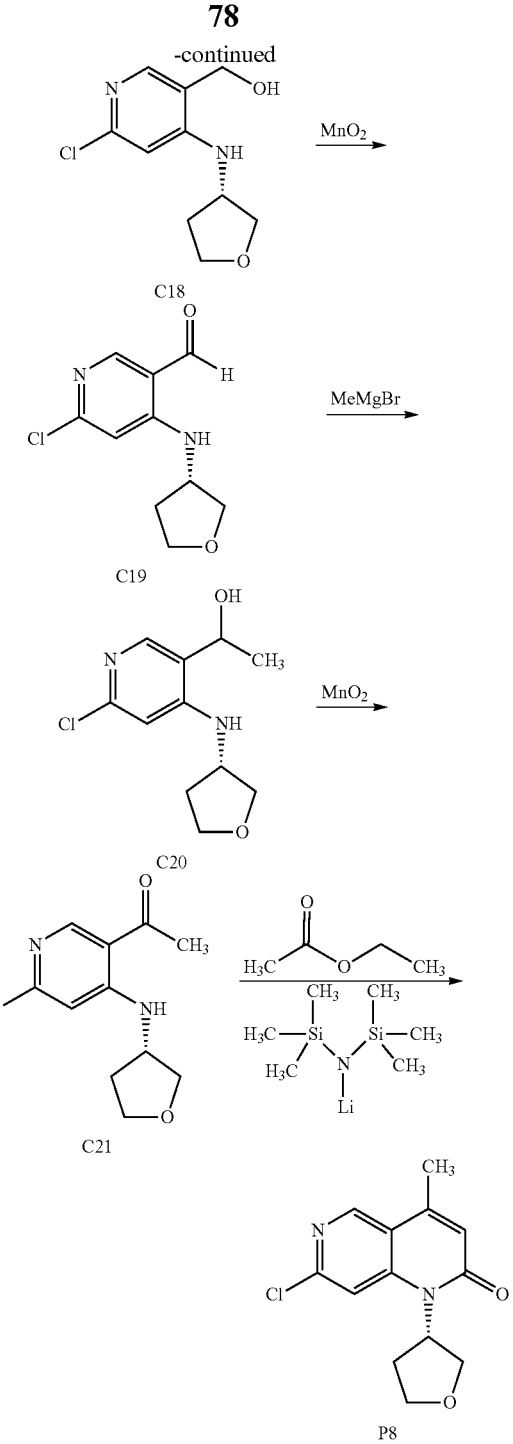

Step 1. Synthesis of methyl 6-chloro-4-[(3S)-tetrahydrofuran-3-ylamino]pyridine-3-carboxylate (C17)

(3S)-Tetrahydrofuran-3-amine (1.69 g, 19.4 mmol) was added portion-wise to a 0° C. solution of methyl 4,6-dichloropyridine-3-carboxylate (2.0 g, 9.7 mmol) in acetonitrile (50 mL). After the reaction mixture had been stirred at 40° C. for 44 hours, it was diluted with ethyl acetate (50 mL), washed sequentially with saturated aqueous ammonium chloride solution (20 mL) and saturated aqueous sodium chloride solution (20 mL), dried over sodium sulfate, filtered, and concentrated in vacuo. Purification via silica gel chromatography (Gradient: 0% to 30% ethyl acetate in petroleum ether) afforded C17 as a white solid. Yield: 1.70 g, 6.62 mmol, 68%. LCMS m/z 256.7 (chlorine isotope pattern observed) [M+H]$^+$. $^1$H NMR (400 MHz, methanol-d$_4$) δ 8.58 (s, 1H), 8.45 (br d, J=7 Hz, 1H), 6.84 (s, 1H), 4.33-4.25 (m, 1H), 4.01-3.93 (m, 2H), 3.92-3.84 (m, 1H), 3.89 (s, 3H), 3.74 (dd, J=9.4, 2.7 Hz, 1H), 2.44-2.33 (m, 1H), 1.96-1.87 (m, 1H).

Step 2. Synthesis of {6-chloro-4-[(3S)-tetrahydrofuran-3-ylamino]pyridin-3-yl}methanol (C18)

To a 0° C. solution of C17 (1.90 g, 7.40 mmol) in tetrahydrofuran (30 mL) was added lithium aluminum hydride (843 mg, 22.2 mmol) in a portion-wise manner. After the reaction mixture had been stirred at room temperature (15° C.) for 2 hours, it was quenched with sodium sulfate decahydrate and filtered. The filter cake was washed with ethyl acetate (5×50 mL), and the combined filtrates were concentrated in vacuo to provide C18 (1.96 g) as a pale yellow gum. By $^1$H NMR analysis, this material was not pure. LCMS m/z 270.8 (chlorine isotope pattern observed) [M+H]$^+$ for acetylated derivative. $^1$H NMR (400 MHz, chloroform-d), product peaks only: δ 7.76 (s, 1H), 6.46 (s, 1H), 5.82-5.70 (m, 1H), 4.62 (s, 2H), 4.13-4.03 (m, 1H), 4.02-3.94 (m, 2H), 3.93-3.85 (m, 1H), 3.74 (dd, J=9.3, 2.8 Hz, 1H), 2.38-2.27 (m, 1H), 1.96-1.86 (m, 1H).

Step 3. Synthesis of 6-chloro-4-[(3S)-tetrahydrofuran-3-ylamino]pyridine-3-carbaldehyde (C19)

To a solution of C18 (from the previous step; 1.96 g, 7.40 mmol) in chloroform (50 mL) was added manganese(IV) oxide (6.44 g, 74.1 mmol), and the reaction mixture was stirred at 50° C. for 6 hours. It was then filtered, and the filtrate was concentrated in vacuo; purification of the residue via silica gel chromatography (Gradient: 10% to 30% ethyl acetate in petroleum ether) afforded C19 as a yellow solid. Yield: 1.17 g, 5.16 mmol, 70% over 2 steps. LCMS m/z 227.0 (chlorine isotope pattern observed) [M+H]$^+$. $^1$H NMR (400 MHz, chloroform-d) δ 9.84 (d, J=0.7 Hz, 1H), 8.76 (br s, 1H), 8.33 (s, 1H), 6.57 (s, 1H), 4.19-4.10 (m, 1H), 4.06-3.97 (m, 2H), 3.91 (ddd, J=8.6, 8.5, 5.3 Hz, 1H), 3.77 (dd, J=9.4, 3.2 Hz, 1H), 2.46-2.30 (m, 1H), 2.01-1.90 (m, 1H).

Step 4. Synthesis of 1-{6-chloro-4-[13S)-tetrahydrofuran-3-ylamino]pyridin-3-yl}ethanol (C20).

To a 0° C. solution of C19 (1.17 g, 5.16 mmol) in tetrahydrofuran (30 mL) was added methylmagnesium bromide (3 M solution in diethyl ether; 5.16 mL, 15.5 mmol). The reaction mixture was stirred at 15° C. for 16 hours, whereupon it was treated with water (15 mL) and extracted with ethyl acetate (4×50 mL). The combined organic layers were filtered, and the filtrate was concentrated in vacuo to provide C20 as a white solid. Yield: 1.19 g, 4.90 mmol, 95%. LCMS m/z 243.0 (chlorine isotope pattern observed) [M+H]$^+$. $^1$H NMR (400 MHz, chloroform-d) δ 7.68 (s, 1H), 6.42 (s, 1H), 6.25 (br d, J=6.4 Hz, 1H), 4.88 (q, J=6.7 Hz, 1H), 4.09-4.01 (m, 1H), 4.01-3.85 (m, 3H), 3.76-3.68 (m, 1H), 2.86-2.69 (m, 1H), 2.37-2.24 (m, 1H), 1.97-1.82 (m, 1H), 1.55 (d, J=6.6 Hz, 3H).

Step 5. Synthesis of 1-{6-chloro-4-[(3S)-tetrahydrofuran-3-ylamino]pyridin-3-yl}ethanone (C21)

Manganese(IV) oxide (4.26 g, 49.0 mmol) was added to a solution of C20 (1.19 g, 4.90 mmol) in chloroform (70 mL), and the reaction mixture was stirred at 50° C. for 16 hours. It was then filtered; concentration of the filtrate in vacuo provided C21 as a white solid. Yield: 1.10 g, 4.57 mmol, 93%. $^1$H NMR (400 MHz, chloroform-d) δ 9.36 (br s, 1H), 8.61 (s, 1H), 6.55 (s, 1H), 4.15-4.07 (m, 1H), 4.06-3.95 (m, 2H), 3.90 (ddd, J=8.6, 8.4, 5.2 Hz, 1H), 3.75 (dd, J=9.3, 3.2 Hz, 1H), 2.58 (s, 3H), 2.41-2.29 (m, 1H), 1.98-1.89 (m, 1H).

Step 6. Synthesis of 7-chloro-4-methyl-1-[(3S)-tetrahydrofuran-3-yl]-1,6-naphthyridin-2(1H)-one (P8)

Ethyl acetate (1.13 mL, 11.6 mmol) was slowly added, in a drop-wise manner, to a −78° C. solution of lithium bis(trimethylsilyl)amide (1 M solution in tetrahydrofuran; 11.6 mL, 11.6 mmol) in tetrahydrofuran (10 mL). Stirring was continued at −78° C. for 30 minutes, whereupon a solution of C21 (929 mg, 3.86 mmol) in tetrahydrofuran (8 mL) was added in one portion. The reaction mixture was then removed from the cooling bath and allowed to warm to room temperature (15° C.); stirring was continued at room temperature for an additional 16 hours. After the reaction mixture had been quenched with water (30 mL), it was diluted with ethyl acetate (30 mL), and extracted with ethyl acetate (3×30 mL). The combined organic layers were washed sequentially with saturated aqueous ammonium chloride solution (20 mL) and saturated aqueous sodium chloride solution (25 mL), dried over magnesium sulfate, filtered, and concentrated in vacuo. The residue was combined with the crude product of a similar reaction carried out using C21 (250 mg, 1.04 mmol) and purified using silica gel chromatography (Gradient: 0% to 50% ethyl acetate in petroleum ether). This afforded P8 as a white solid. Combined yield: 1.20 g, 4.53 mmol, 92%. LCMS m/z 264.9 [M+H]$^+$. $^1$H NMR (400 MHz, methanol-d$_4$) δ 8.78 (s, 1H), 8.01 (s, 1H), 6.57 (q, J=1.3 Hz, 1H), 6.21-6.08 (m, 1H), 4.44 (ddd, J=8.6, 8.5, 3.1 Hz, 1H), 4.10 (dd, J=10.1, 4.4 Hz, 1H), 3.98 (dd, J=9.7, 9.6 Hz, 1H), 3.82 (ddd, J=9.3, 9.3, 6.8 Hz, 1H), 2.53 (d, J=1.2 Hz, 3H), 2.40-2.21 (m, 2H).

Preparation P9 rac-8-[(1S,2R,5R)-Bicyclo[3.1.0]hexan-2-yl]-2-chloro-5-methylpyrido[2,3-d]pyrimidin-7(8H)-one (P9)

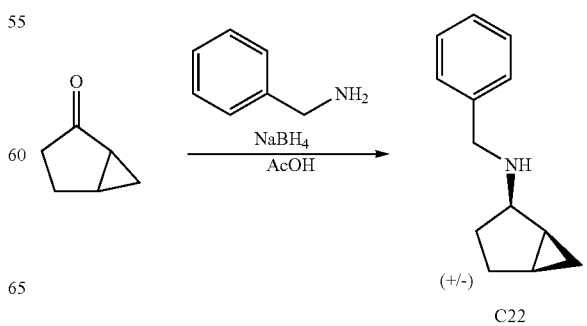

C22

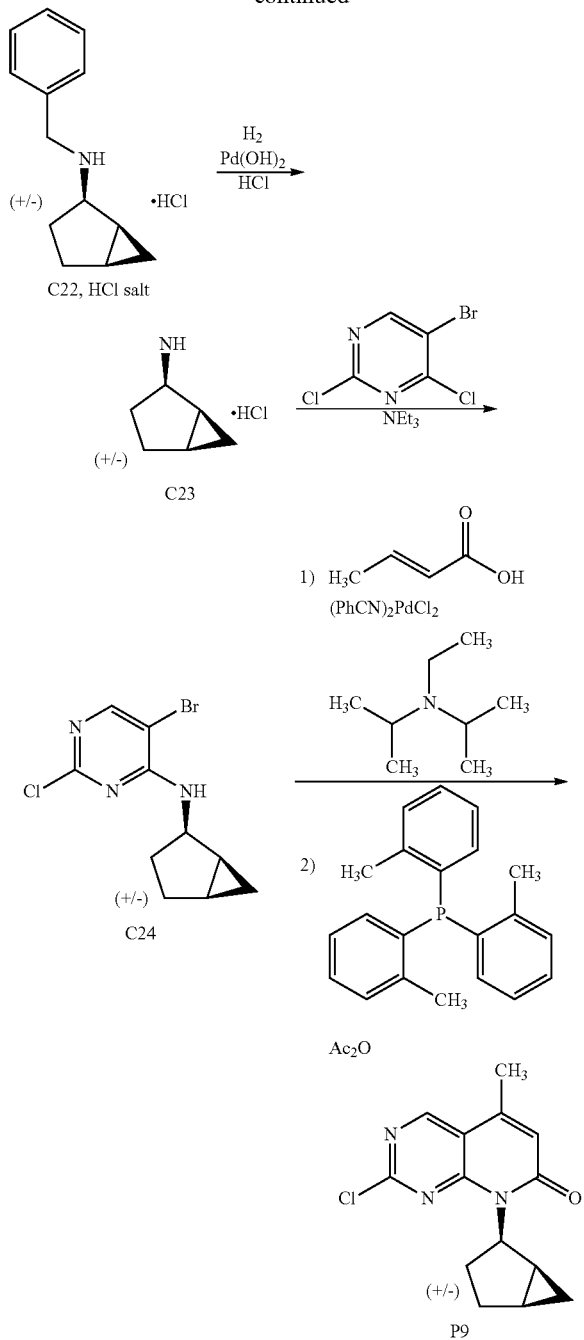

Step 1. Synthesis of rac-(1S,2R,5R)—N-benzylbicyclo[3.1.0]hexan-2-amine (C22)

A mixture of bicyclo[3.1.0]hexan-2-one (385 mg, 4.00 mmol), benzylamine (429 mg, 4.00 mmol), sodium borohydride (227 mg, 6.00 mmol), and acetic acid (240 mg, 4.0 mmol) in a mixture of dichloromethane (5 mL) and methanol (5 mL) was stirred at 18° C. for 10 hours. Concentration in vacuo provided C22 as a yellow gum. By $^1$H NMR analysis, this material was not pure, and was judged to contain residual benzylamine. Yield: 700 mg, <3.7 mmol, <92%. $^1$H NMR (400 MHz, chloroform-d), characteristic/ assumed peaks for C22: δ 7.40-7.21 (m, 5H), 3.93-3.78 (m, 2H), 3.48-3.38 (m, 1H), 0.40-0.34 (m, 1H), 0.33-0.25 (m, 1H).

Step 2. Synthesis of rac-(1S,2R,5R)-bicyclo[3.1.0]hexan-2-amine, hydrochloride salt (C23)

A mixture of C22, hydrochloride salt (800 mg, 3.58 mmol), palladium hydroxide on carbon (800 mg), and hydrogen chloride (4 M solution in ethyl acetate; 1.8 mL, 7.2 mmol) in methanol (15 mL) was degassed 3 times with hydrogen. The reaction mixture was then stirred under hydrogen (1 atmosphere) for 5 hours at 50° C., whereupon it was filtered; the filtrate was concentrated in vacuo to afford C23 as a white solid. Yield: 452 mg, 3.38 mmol, 94%.

Step 3. Synthesis of rac-N-[(1S,2R,5R)-bicyclo[3.1.0]hexan-2-yl]-5-bromo-2-chloropyrimidin-4-amine (C24)

Triethylamine (1.51 g, 14.9 mmol) was added drop-wise to a 0° C. solution of 5-bromo-2,4-dichloropyrimidine (850 mg, 3.73 mmol) and C23 (452 mg, 3.38 mmol) in acetonitrile (50 mL). The reaction mixture was allowed to warm to room temperature, and stirred at 20° C. for 18 hours, whereupon it was treated with aqueous ammonium chloride solution (30 mL) and extracted with ethyl acetate (2×50 mL). The combined organic layers were dried, filtered, concentrated in vacuo, and subjected to chromatography on silica gel (Gradient: 1% to 4% ethyl acetate in petroleum ether), providing C24 as a white solid. Yield: 790 mg, 2.74 mmol, 81%. LCMS m/z 289.6 (bromine-chlorine isotope pattern observed) [M+H]$^+$.

Step 4. Synthesis of rac-8-[(1S,2R,5R)-bicyclo[3.1.0]hexan-2-yl]-2-chloro-5-methylpyrido[2,3-d]pyrimidin-7(8H)-one (P9)

Argon was bubbled through a solution of C24 (395 mg, 1.37 mmol), (2E)-but-2-enoic acid (354 mg, 4.11 mmol), and N,N-diisopropylethylamine (1.77 g, 13.7 mmol) in tetrahydrofuran (20 mL), and then bis(benzonitrile)palladium(II) chloride (52.5 mg, 0.137 mmol) and tri-o-tolylphosphine (41.7 mg, 0.137 mmol) were added. The reaction vessel was sealed and heated at 70° C. for 18 hours, whereupon acetic anhydride (279 mg, 2.73 mmol) was added, and heating was continued for 3 hours at 70° C. After volatiles had been removed under reduced pressure, the residue was purified by silica gel chromatography (Gradient: 1% to 30% ethyl acetate in petroleum ether), affording P9 as a light yellow solid. Yield: 290 mg, 1.05 mmol, 77%. LCMS m/z 275.8 (chlorine isotope pattern observed) [M+H]$^+$.

Preparation P10 rac-6-Bromo-8-[(1R,2S)-2-fluoro-2-methylcyclopentyl]-5-methyl-2-(methylthio)pyrido[2,3-d]pyrimidin-7(8H)-one (P10)

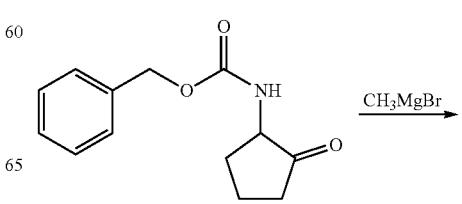

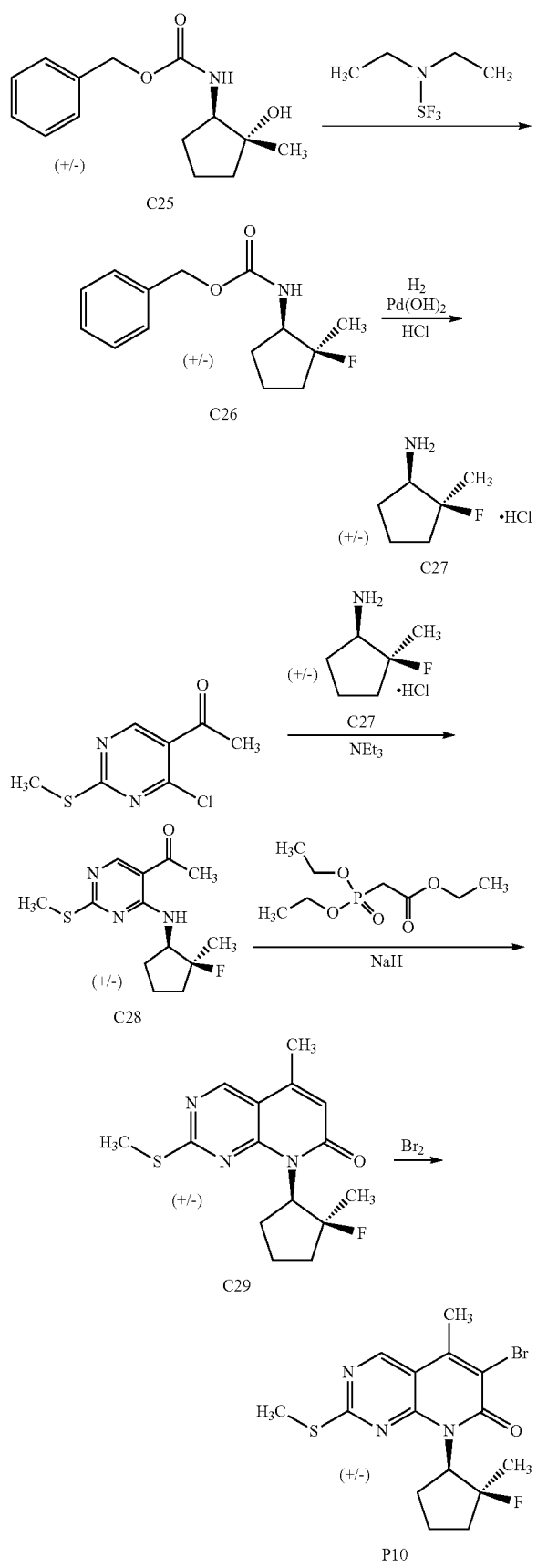

Step 1. Synthesis of rac-benzyl[(1R,2R)-2-hydroxy-2-methylcyclopentyl]carbamate (C25)

Methylmagnesium bromide (3.0 M; 11.4 mL, 34.2 mmol) was slowly added to a −78° C. solution of benzyl (2-oxo-cyclopentyl)carbamate (2.67 g, 11.4 mmol) in tetrahydrofuran (24 mL), and the reaction mixture was stirred at −78° C. for 4 hours; it was then allowed to warm to room temperature. Water was carefully added to the reaction mixture, followed by hydrochloric acid (1 M; 2 mL), and the aqueous layer was extracted twice with ethyl acetate. After the combined organic layers had been dried over sodium sulfate, filtered, and concentrated in vacuo, the residue was purified via silica gel chromatography (Gradient: 0% to 100% ethyl acetate in heptane) to provide C25 as a pale yellow solid. Starting material benzyl (2-oxocyclopentyl)carbamate (1.36 g, 5.83 mmol) was also recovered from the chromatographic purification. Yield of C25: 878 mg, 3.52 mmol, 31%; based on recovered starting material, the yield of C25 was 63%. $^1$H NMR (400 MHz, chloroform-d) δ 7.41-7.29 (m, 5H), 5.12 (s, 2H), 4.77 (br s, 1H), 3.87 (ddd, J=9.9, 8.2, 6.0 Hz, 1H), 2.19-2.08 (m, 1H), 1.94-1.82 (m, 1H), 1.81-1.68 (m, 2H), 1.68-1.57 (m, 1H), 1.40-1.28 (m, 1H), 1.16 (s, 3H).

Step 2. Synthesis of rac-benzyl [(1R,2S)-2-fluoro-2-methylcyclopentyl]carbamate (C26)

(Diethylamino)sulfur trifluoride (0.40 mL, 3.0 mmol) was added to a −78° C. solution of C25 (349 mg, 1.40 mmol) in dichloromethane (8 mL). The reaction mixture was stirred at −78° C. for 4 hours, whereupon it was diluted with 2-propanol at −78° C., and then warmed to room temperature. After the reaction mixture had been concentrated in vacuo, the residue was purified via silica gel chromatography (Gradient: 0% to 30% ethyl acetate in heptane), affording C26 as a white solid. The indicated relative stereochemistry of C26 was established on the basis of a single-crystal X-ray structural determination (see below). Yield: 281 mg, 1.12 mmol, 80%. $^1$H NMR (400 MHz, chloroform-d) δ 7.41-7.29 (m, 5H), 5.12 (s, 2H), 5.03-4.92 (m, 1H), 3.92-3.75 (m, 1H), 2.18-1.94 (m, 2H), 1.89-1.68 (m, 2H), 1.68-1.54 (m, 2H), 1.40 (d, $J_{HF}$=21.7 Hz, 3H).

Vapor diffusion of pentane into a dichloroethane solution of C26 provided crystals for the X-ray structure determination.

Single-Crystal X-Ray Structural Determination of C26

Single Crystal X-Ray Analysis

Data collection was performed on a Bruker Kappa APEX-II CCD diffractometer equipped with Mo K$_α$ radiation (λ=0.71073 Å). A 0.313×0.155×0.117 mm piece of a colorless block was mounted on a CryoLoop with Paratone oil. Data were collected in a nitrogen gas stream at 100(2) K using φ and ω scans. The crystal-to-detector distance was 40 mm and exposure time was 30 seconds per frame using a scan width of 1.0°. Data collection was 99.9% complete to 25.00° in e. A total of 9647 reflections were collected covering the indices, −21<=h<=25, −5<=k<=5, −15<=/<=13. 2400 reflections were found to be symmetry independent, with an $R_{int}$ of 0.0561. Indexing and unit cell refinement indicated a primitive, monoclinic lattice. The space group was found to be P2$_1$/c. The data were integrated using the Bruker SAINT software program and scaled using the SADABS software program. Solution by direct methods (SHELXT) produced a complete phasing model consistent with the proposed structure. All non-hydrogen atoms were refined anisotropically by full-matrix least-squares (SHELXL-2014; G. M. Sheldrick, SHELXTL Version 2014/7. http://shelx.uni-ac.gwdg.de/SHELX/index.php). All hydrogen atoms were placed using a riding model. Their positions were constrained relative to their parent atom using the appropriate HFIX command in SHELXL-2014. Crystallographic data are summarized in Table E. Atomic coordinates, bond lengths, bond angles, and displacement parameters are listed in Tables F-K.

TABLE E

Crystal data and structure refinement for C26.

| | |
|---|---|
| Empirical formula | $C_{14}H_{18}FNO_2$ |
| Formula weight | 251.29 |
| Temperature | 100.0 K |
| Wavelength | 0.71073 Å |
| Crystal system | Monoclinic |
| Space group | P 1 $2_1$/c 1 |
| Unit cell dimensions | a = 21.238(2) Å    α = 90° |
| | b = 4.8573(5) Å    β = 97.271(5)° |
| | c = 12.8319(13) Å  γ = 90° |
| Volume | 1313.1(2) Å$^3$ |
| Z | 4 |
| Density (calculated) | 1.271 Mg/m$^3$ |
| Absorption coefficient | 0.094 mm$^{-1}$ |
| F(000) | 536 |
| Crystal size | 0.313 × 0.155 × 0.117 mm$^3$ |
| Theta range for data collection | 2.901 to 25.387° |
| Index ranges | −21 <= h <= 25, −5 <= k <= 5, −15 <= l <= 13 |
| Reflections collected | 9647 |
| Independent reflections | 2400 [$R_{int}$ =0.0561] |
| Completeness to theta = 25.000° | 99.9% |
| Absorption correction | Semi-empirical from equivalents |
| Max. and min. transmission | 0.0916 and 0.0649 |
| Refinement method | Full-matrix least-squares on $F^2$ |
| Data/restraints/parameters | 2400/120/229 |
| Goodness-of-fit on $F^2$ | 1.081 |
| Final R indices [I > 2σ(I)] | R1 = 0.0655, wR2 = 0.1433 |
| R indices (all data) | R1 = 0.1181, wR2 = 0.1677 |
| Extinction coefficient | n/a |
| Largest diff. peak and hole | 0.199 and −0.206 e.Å$^{-3}$ |

TABLE F

Atomic coordinates (×10$^4$) and equivalent isotropic displacement parameters (Å$^2$ × 10$^3$) for C26. U(eq) is defined as one-third of the trace of the orthogonalized $U^{ij}$ tensor.

| | x | y | z | U(eq) |
|---|---|---|---|---|
| O(1) | 7454(1) | 1289(4) | 6754(2) | 44(1) |
| O(2) | 7039(1) | 5049(4) | 5898(1) | 29(1) |
| N(1) | 7846(1) | 5561(5) | 7148(2) | 42(1) |
| C(7) | 7455(1) | 3761(6) | 6618(2) | 29(1) |
| C(8) | 6549(1) | 3341(6) | 5343(2) | 33(1) |
| C(9) | 6224(1) | 5088(5) | 4470(2) | 26(1) |
| C(10) | 5705(1) | 6681(6) | 4620(2) | 33(1) |
| C(11) | 5423(2) | 8381(6) | 3827(2) | 37(1) |
| C(12) | 5665(2) | 8493(6) | 2874(2) | 34(1) |
| C(13) | 6178(2) | 6908(6) | 2722(2) | 35(1) |
| C(14) | 6459(2) | 5207(6) | 3512(2) | 32(1) |
| F(1) | 8476(2) | 8644(8) | 8816(3) | 53(1) |
| C(1) | 8433(5) | 4610(20) | 7822(7) | 37(2) |
| C(2) | 9098(5) | 5300(20) | 7506(7) | 50(2) |
| C(3) | 9531(4) | 4960(30) | 8517(7) | 74(3) |
| C(4) | 9117(5) | 4990(30) | 9444(7) | 42(2) |
| C(5) | 8476(4) | 5724(16) | 8928(5) | 34(1) |
| C(6) | 7938(4) | 4967(16) | 9490(6) | 46(2) |
| F(1B) | 8936(2) | 8411(8) | 7779(4) | 72(2) |
| C(1B) | 8246(4) | 4797(19) | 8080(7) | 45(2) |
| C(2B) | 8106(5) | 6190(20) | 9124(7) | 72(2) |
| C(3B) | 8737(6) | 5890(30) | 9817(8) | 125(4) |

TABLE F-continued

Atomic coordinates (×10$^4$) and equivalent isotropic displacement parameters (Å$^2$ × 10$^3$) for C26. U(eq) is defined as one-third of the trace of the orthogonalized $U^{ij}$ tensor.

| | x | y | z | U(eq) |
|---|---|---|---|---|
| C(4B) | 9238(6) | 5150(30) | 9119(10) | 73(3) |
| C(5B) | 8919(4) | 5541(14) | 8036(8) | 56(2) |
| C(6B) | 9187(5) | 4170(20) | 7138(9) | 90(3) |

TABLE G

Bond lengths [Å] and angles [°] for C26.

| | |
|---|---|
| O(1)—C(7) | 1.213(3) |
| O(2)—C(7) | 1.349(3) |
| O(2)—C(8) | 1.446(3) |
| N(1)—H(1A) | 0.8800 |
| N(1)—H(1B) | 0.8800 |
| N(1)—C(7) | 1.331(4) |
| N(1)—C(1) | 1.497(10) |
| N(1)—C(1B) | 1.426(9) |
| C(8)—H(8A) | 0.9900 |
| C(8)—H(8B) | 0.9900 |
| C(8)—C(9) | 1.501(4) |
| C(9)—C(10) | 1.380(4) |
| C(9)—C(14) | 1.386(4) |
| C(10)—H(10) | 0.9500 |
| C(10)—C(11) | 1.387(4) |
| C(11)—H(11) | 0.9500 |
| C(11)—C(12) | 1.387(4) |
| C(12)—H(12) | 0.9500 |
| C(12)—C(13) | 1.367(4) |
| C(13)—H(13) | 0.9500 |
| C(13)—C(14) | 1.383(4) |
| C(14)—H(14) | 0.9500 |
| F(1)—C(5) | 1.426(8) |
| C(1)—H(1) | 1.0000 |
| C(1)—C(2) | 1.553(14) |
| C(1)—C(5) | 1.510(11) |
| C(2)—H(2A) | 0.9900 |
| C(2)—H(2B) | 0.9900 |
| C(2)—C(3) | 1.502(11) |
| C(3)—H(3A) | 0.9900 |
| C(3)—H(3B) | 0.9900 |
| C(3)—C(4) | 1.566(12) |
| C(4)—H(4A) | 0.9900 |
| C(4)—H(4B) | 0.9900 |
| C(4)—C(5) | 1.479(13) |
| C(5)—C(6) | 1.475(11) |
| C(6)—H(6A) | 0.9800 |
| C(6)—H(6B) | 0.9800 |
| C(6)—H(6C) | 0.9800 |
| F(1B)—C(5B) | 1.434(8) |
| C(1B)—H(1BA) | 1.0000 |
| C(1B)—C(2B) | 1.562(12) |
| C(1B)—C(5B) | 1.482(13) |
| C(2B)—H(2BA) | 0.9900 |
| C(2B)—H(2BB) | 0.9900 |
| C(2B)—C(3B) | 1.519(13) |
| C(3B)—H(3BA) | 0.9900 |
| C(3B)—H(3BB) | 0.9900 |
| C(3B)—C(4B) | 1.519(16) |
| C(4B)—H(4BA) | 0.9900 |
| C(4B)—H(4BB) | 0.9900 |
| C(4B)—C(5B) | 1.479(14) |
| C(5B)—C(6B) | 1.505(12) |
| C(6B)—H(6BA) | 0.9800 |
| C(6B)—H(6BB) | 0.9800 |
| C(6B)—H(6BC) | 0.9800 |
| C(7)—O(2)—C(8) | 116.1(2) |
| C(7)—N(1)—H(1A) | 119.6 |
| C(7)—N(1)—H(1B) | 119.2 |
| C(7)—N(1)—C(1) | 120.9(5) |
| C(7)—N(1)—C(1B) | 121.6(4) |
| C(1)—N(1)—H(1A) | 119.6 |
| C(1B)—N(1)—H(1B) | 119.2 |

TABLE G-continued

Bond lengths [Å] and angles [°] for C26.

| | |
|---|---|
| O(1)—C(7)—O(2) | 123.0(3) |
| O(1)—C(7)—N(1) | 126.1(3) |
| N(1)—C(7)—O(2) | 110.9(2) |
| O(2)—C(8)—H(8A) | 110.5 |
| O(2)—C(8)—H(8B) | 110.5 |
| O(2)—C(8)—C(9) | 106.1(2) |
| H(8A)—C(8)—H(8B) | 108.7 |
| C(9)—C(8)—H(8A) | 110.5 |
| C(9)—C(8)—H(8B) | 110.5 |
| C(10)—C(9)—C(8) | 120.9(2) |
| C(10)—C(9)—C(14) | 118.9(3) |
| C(14)—C(9)—C(8) | 120.2(3) |
| C(9)—C(10)—H(10) | 119.7 |
| C(9)—C(10)—C(11) | 120.7(3) |
| C(10)—C(11)—H(11) | 119.7 |
| C(10)—C(11)—C(12) | 119.8(3) |
| C(12)—C(11)—H(11) | 120.1 |
| C(11)—C(12)—H(12) | 120.2 |
| C(13)—C(12)—C(11) | 119.7(3) |
| C(13)—C(12)—H(12) | 120.2 |
| C(12)—C(13)—H(13) | 119.7 |
| C(12)—C(13)—C(14) | 120.6(3) |
| C(14)—C(13)—H(13) | 119.7 |
| C(9)—C(14)—H(14) | 119.8 |
| C(13)—C(14)—C(9) | 120.3(3) |
| C(13)—C(14)—H(14) | 119.8 |
| N(1)—C(1)—H(1) | 107.0 |
| N(1)—C(1)—C(2) | 120.1(7) |
| N(1)—C(1)—C(5) | 112.4(7) |
| C(2)—C(1)—H(1) | 107.0 |
| C(5)—C(1)—H(1) | 107.0 |
| C(5)—C(1)—C(2) | 102.7(8) |
| C(1)—C(2)—H(2A) | 111.1 |
| C(1)—C(2)—H(2B) | 111.1 |
| H(2A)—C(2)—H(2B) | 109.1 |
| C(3)—C(2)—C(1) | 103.2(7) |
| C(3)—C(2)—H(2A) | 111.1 |
| C(3)—C(2)—H(2B) | 111.1 |
| C(2)—C(3)—H(3A) | 110.0 |
| C(2)—C(3)—H(3B) | 110.0 |
| C(2)—C(3)—C(4) | 108.3(7) |
| H(3A)—C(3)—H(3B) | 108.4 |
| C(4)—C(3)—H(3A) | 110.0 |
| C(4)—C(3)—H(3B) | 110.0 |
| C(3)—C(4)—H(4A) | 111.0 |
| C(3)—C(4)—H(4B) | 111.0 |
| H(4A)—C(4)—H(4B) | 109.0 |
| C(5)—C(4)—C(3) | 103.6(7) |
| C(5)—C(4)—H(4A) | 111.0 |
| C(5)—C(4)—H(4B) | 111.0 |
| F(1)—C(5)—C(1) | 105.2(6) |
| F(1)—C(5)—C(4) | 105.8(7) |
| F(1)—C(5)—C(6) | 107.8(7) |
| C(4)—C(5)—C(1) | 106.2(7) |
| C(6)—C(5)—C(1) | 114.4(7) |
| C(6)—C(5)—C(4) | 116.6(6) |
| C(5)—C(6)—H(6A) | 109.5 |
| C(5)—C(6)—H(6B) | 109.5 |
| C(5)—C(6)—H(6C) | 109.5 |
| H(6A)—C(6)—H(6B) | 109.5 |
| H(6A)—C(6)—H(6C) | 109.5 |
| H(6B)—C(6)—H(6C) | 109.5 |
| N(1)—C(1B)—H(1BA) | 108.3 |
| N(1)—C(1B)—C(2B) | 116.7(7) |
| N(1)—C(1B)—C(5B) | 112.3(7) |
| C(2B)—C(1B)—H(1BA) | 108.3 |
| C(5B)—C(1B)—H(1BA) | 108.3 |
| C(5B)—C(1B)—C(2B) | 102.5(8) |
| C(1B)—C(2B)—H(2BA) | 111.3 |
| C(1B)—C(2B)—H(2BB) | 111.3 |
| H(2BA)—C(2B)—H(2BB) | 109.2 |
| C(3B)—C(2B)—C(1B) | 102.2(9) |
| C(3B)—C(26)—H(2BA) | 111.3 |
| C(3B)—C(2B)—H(2BB) | 111.3 |
| C(2B)—C(3B)—H(3BA) | 110.1 |
| C(2B)—C(3B)—H(3BB) | 110.1 |
| H(3BA)—C(3B)—H(3BB) | 108.4 |
| C(4B)—C(3B)—C(2B) | 108.0(8) |
| C(4B)—C(3B)—H(3BA) | 110.1 |
| C(4B)—C(3B)—H(3BB) | 110.1 |
| C(3B)—C(4B)—H(4BA) | 110.8 |
| C(3B)—C(4B)—H(4BB) | 110.8 |
| H(4BA)—C(4B)—H(4BB) | 108.9 |
| C(5B)—C(4B)—C(3B) | 104.6(9) |
| C(5B)—C(4B)—H(4BA) | 110.8 |
| C(5B)—C(4B)—H(4BB) | 110.8 |
| F(1B)—C(5B)—C(1B) | 107.3(6) |
| F(1B)—C(5B)—C(4B) | 108.7(8) |
| F(1B)—C(5B)—C(6B) | 103.5(8) |
| C(1B)—C(5B)—C(6B) | 112.4(8) |
| C(4B)—C(5B)—C(1B) | 105.2(9) |
| C(4B)—C(5B)—C(6B) | 119.3(8) |
| C(5B)—C(6B)—H(6BA) | 109.5 |
| C(5B)—C(6B)—H(6BB) | 109.5 |
| C(5B)—C(6B)—H(6BC) | 109.5 |
| H(6BA)—C(6B)—H(6BB) | 109.5 |
| H(6BA)—C(6B)—H(6BC) | 109.5 |
| H(6BB)—C(6B)—H(6BC) | 109.5 |

TABLE H

Anisotropic displacement parameters (Å$^2$ × 10$^3$) for C26.
The anisotropic displacement factor exponent takes the form: $-2\pi^2[h^2 a^{*2} U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| O(1) | 70(2) | 14(1) | 44(1) | 4(1) | −14(1) | −2(1) |
| O(2) | 44(1) | 15(1) | 27(1) | 1(1) | −5(1) | −1(1) |
| N(1) | 62(2) | 16(1) | 40(2) | 8(1) | −18(1) | −2(1) |
| C(7) | 46(2) | 15(2) | 24(2) | −1(1) | 1(1) | 0(1) |
| C(8) | 44(2) | 23(2) | 30(2) | 4(1) | −3(1) | −8(2) |
| C(9) | 38(2) | 18(1) | 23(2) | 1(1) | −1(1) | −7(1) |
| C(10) | 45(2) | 30(2) | 23(2) | −4(1) | 5(1) | −6(2) |
| C(11) | 44(2) | 32(2) | 32(2) | −5(1) | −1(1) | 5(2) |
| C(12) | 48(2) | 24(2) | 26(2) | 2(1) | −6(1) | 0(2) |
| C(13) | 51(2) | 28(2) | 24(2) | 2(1) | 4(1) | −5(2) |
| C(14) | 38(2) | 25(2) | 34(2) | 0(1) | 4(1) | 0(1) |
| F(1) | 76(3) | 25(2) | 52(3) | 0(2) | −13(2) | −2(2) |
| C(1) | 54(3) | 21(3) | 32(3) | 3(2) | −10(2) | 3(3) |
| C(2) | 61(3) | 58(6) | 28(3) | −3(3) | −6(2) | −7(3) |
| C(3) | 49(3) | 136(10) | 34(3) | 6(4) | −3(3) | 5(3) |
| C(4) | 46(3) | 51(5) | 28(3) | 6(3) | −4(2) | 0(3) |
| C(5) | 48(3) | 20(3) | 30(3) | 2(2) | −7(2) | −1(2) |
| C(6) | 62(4) | 28(4) | 49(4) | 5(3) | 7(3) | 2(3) |
| F(1B) | 64(3) | 29(2) | 118(6) | 8(2) | −9(2) | −3(2) |
| C(1B) | 61(3) | 21(3) | 45(3) | 10(2) | −22(2) | −4(3) |
| C(2B) | 83(5) | 72(6) | 54(3) | −3(3) | −16(3) | 1(4) |
| C(3B) | 99(5) | 189(12) | 75(4) | −23(4) | −34(3) | 24(5) |
| C(4B) | 77(5) | 47(5) | 85(4) | −1(4) | −29(3) | −3(4) |
| C(5B) | 60(3) | 21(3) | 79(4) | −1(3) | −18(2) | −1(2) |
| C(6B) | 95(6) | 61(5) | 112(5) | −14(4) | 10(4) | −1(4) |

TABLE J

Hydrogen coordinates (×10$^4$) and isotropic displacement parameters (Å$^2$ × 10$^3$) for C26.

| | x | y | z | U(eq) |
|---|---|---|---|---|
| H(1A) | 7758 | 7330 | 7101 | 50 |
| H(1B) | 7858 | 7263 | 6917 | 50 |
| H(8A) | 6243 | 2747 | 5820 | 40 |
| H(8B) | 6737 | 1685 | 5055 | 40 |
| H(10) | 5539 | 6611 | 5273 | 39 |
| H(11) | 5064 | 9465 | 3936 | 44 |
| H(12) | 5476 | 9666 | 2329 | 41 |
| H(13) | 6342 | 6975 | 2067 | 41 |
| H(14) | 6815 | 4115 | 3397 | 39 |
| H(1) | 8406 | 2565 | 7872 | 44 |

TABLE J-continued

Hydrogen coordinates (×10⁴) and isotropic displacement parameters ($Å^2 \times 10^3$) for C26.

| | x | y | z | U(eq) |
|---|---|---|---|---|
| H(2A) | 9212 | 4006 | 6964 | 60 |
| H(2B) | 9112 | 7204 | 7237 | 60 |
| H(3A) | 9844 | 6481 | 8602 | 89 |
| H(3B) | 9765 | 3198 | 8513 | 89 |
| H(4A) | 9116 | 3163 | 9784 | 51 |
| H(4B) | 9275 | 6382 | 9979 | 51 |
| H(6A) | 7544 | 5716 | 9115 | 70 |
| H(6B) | 8005 | 5726 | 10203 | 70 |
| H(6C) | 7906 | 2958 | 9526 | 70 |
| H(1BA) | 8219 | 2756 | 8166 | 54 |
| H(2BA) | 7988 | 8146 | 9012 | 86 |
| H(2BB) | 7762 | 5217 | 9429 | 86 |
| H(3BA) | 8850 | 7645 | 10189 | 150 |
| H(3BB) | 8709 | 4434 | 10348 | 150 |
| H(4BA) | 9612 | 6371 | 9260 | 88 |
| H(4BB) | 9377 | 3216 | 9235 | 88 |
| H(6BA) | 9181 | 2164 | 7233 | 135 |
| H(6BB) | 9626 | 4780 | 7122 | 135 |
| H(6BC) | 8931 | 4655 | 6475 | 135 |

TABLE K

Hydrogen bonds for C26 [Å and °].

| D-H...A | d(D-H) | d(H...A) | d(D...A) | <(DHA) |
|---|---|---|---|---|
| N(1)-H(1A)...O(1)#1 | 0.88 | 2.06 | 2.930(3) | 170.0 |

Symmetry transformations used to generate equivalent atoms:
1 x,y+1,z

Step 3. Synthesis of rac-(1R,2S)-2-fluoro-2-methylcyclopentanamine, Hydrochloride Salt (C27)

A mixture of C26 (281 mg, 1.12 mmol), 20% palladium hydroxide on carbon (50 mg), and hydrogen chloride (2 M solution in methanol; 0.671 mL, 1.34 mmol) was stirred under a balloon of hydrogen overnight, whereupon it was filtered through diatomaceous earth. The filtrate was resubjected to the reaction conditions overnight, and again filtered through diatomaceous earth. Concentration of the filtrate provided C27 as a pale yellow solid (189 mg). By ¹H NMR analysis, this material was not entirely pure; a portion of it was progressed directly to the following step. ¹H NMR (400 MHz, DMSO-d₆), characteristic peaks: δ 2.12-1.55 (m, 6H), 1.50 (d, $J_{HF}$=22.0 Hz, 3H).

Step 4. Synthesis of rac-1-[4-{[(1R,2S)-2-fluoro-2-methylcyclopentyl]amino}-2-(methylthio)pyrimidin-5-yl]ethanone (C28)

A mixture of C27 (from the previous step; 122 mg, 0.723 mmol), 1-[4-chloro-2-(methylthio)pyrimidin-5-yl]ethanone (175 mg, 0.864 mmol), and triethylamine (0.401 mL, 2.88 mmol) in ethanol (12 mL) was stirred at room temperature for 1 hour. The reaction mixture was then diluted with water and extracted with ethyl acetate. The combined organic layers were dried over sodium sulfate, filtered, and concentrated in vacuo; silica gel chromatography (Gradient: 0% to 30% ethyl acetate in heptane) provided C28 as a white solid. Yield: 180 mg, 0.635 mmol, 57% over 2 steps. LCMS m/z 283.9 [M+H]⁺. ¹H NMR (400 MHz, chloroform-d), characteristic peaks: δ 9.55 (br s, 1H), 8.59 (s, 1H), 4.56-4.40 (m, 1H), 2.54 (s, 3H), 2.52 (s, 3H), 1.41 (d, $J_{HF}$=21.5 Hz, 3H).

Step 5. Synthesis of rac-8-[(1R,2S)-2-fluoro-2-methylcyclopentyl]-5-methyl-2-(methylthio)pyrido[2,3-d]pyrimidin-7(8H)-one (C29)

Ethyl (diethoxyphosphoryl)acetate (0.633 mL, 3.19 mmol) was slowly added to a 0° C. suspension of sodium hydride (60% suspension in mineral oil; 122 mg, 3.05 mmol) in tetrahydrofuran (4 mL); the cooling bath was then removed and a solution of C28 (180 mg, 0.635 mmol) in tetrahydrofuran (4 mL) was added. The reaction mixture was heated at 60° C. for 18 hours, whereupon it was cooled to room temperature, quenched by addition of water, and extracted twice with ethyl acetate. The combined organic layers were dried over magnesium sulfate, filtered, concentrated in vacuo, and purified using chromatography on silica gel (Gradient: 0% to 60% ethyl acetate in heptane), affording C29 as a pale yellow solid. Yield: 190 mg, 0.618 mmol, 97%. LCMS m/z 307.9 [M+H]⁺. ¹H NMR (400 MHz, chloroform-d) δ 8.68 (s, 1H), 6.44 (br s, 1H), 5.92-5.72 (m, 1H), 3.29-3.01 (m, 1H), 2.62 (s, 3H), 2.48-2.31 (m, 1H), 2.41 (d, J=1.2 Hz, 3H), 2.31-2.19 (m, 1H), 2.00-1.81 (m, 2H), 1.73-1.6 (m, 1H, assumed; partially obscured by water peak), 1.46 (d, $J_{HF}$=21.8 Hz, 3H).

Step 6. Synthesis of rac-6-bromo-8-[(1R,2S)-2-fluoro-2-methylcyclopentyl]-5-methyl-2-(methylthio)pyrido[2,3-c]pyrimidin-7(8H)-one (P10)

Bromine (32 μL, 0.62 mmol) was added to a solution of C29 (128 mg, 0.416 mmol) in dichloromethane (6.0 mL), and the mixture was stirred at room temperature for 15 minutes, whereupon 10% aqueous sodium thiosulfate solution was added. The resulting mixture was extracted with ethyl acetate, and the combined organic layers were dried over magnesium sulfate, filtered and concentrated in vacuo. Silica gel chromatography (Gradient: 0% to 100% ethyl acetate in heptane) afforded P10 as a white solid. Yield: 109 mg, 0.282 mmol, 68%. ¹H NMR (400 MHz, chloroform-d) δ 8.79 (s, 1H), 6.04-5.84 (m, 1H), 3.15-2.95 (m, 1H), 2.63 (s, 3H), 2.63 (s, 3H), 2.54-2.37 (m, 1H), 2.35-2.22 (m, 1H), 2.02-1.82 (m, 2H), 1.72-1.6 (m, 1H, assumed; partially obscured by water peak), 1.49 (d, $J_{HF}$=21.9 Hz, 3H).

Preparation P11 tert-Butyl (3S)-3-[6-bromo-5-methyl-2-(methylthio)-7-oxopyrido[2,3-c]pyrimidin-8(7H)-yl]pyrrolidine-1-carboxylate (P11)

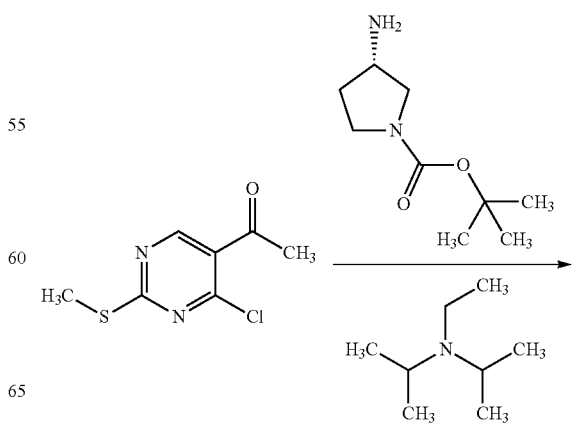

-continued

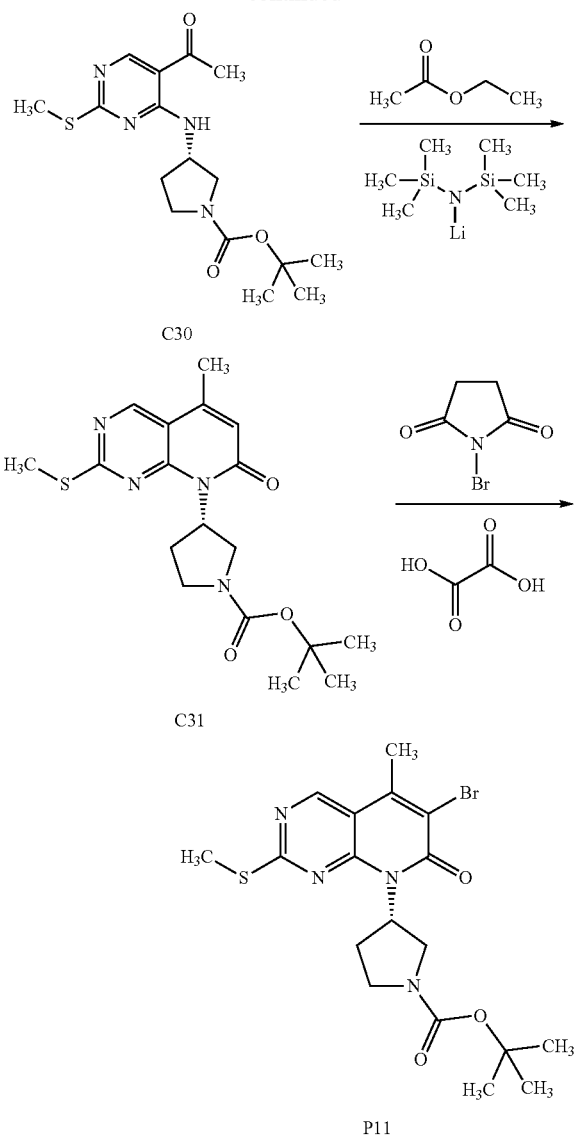

Step 1. Synthesis of tert-butyl (3S)-3-{[5-acetyl-2-(methylthio)pyrimidin-4-yl]amino}pyrrolidine-1-carboxylate (C30)

1-[4-Chloro-2-(methylthio)pyrimidin-5-yl]ethanone (4.50 g, 22.2 mmol) was added to a solution of tert-butyl (3S)-3-aminopyrrolidine-1-carboxylate (4.55 g, 24.4 mmol) and N,N-diisopropylethylamine (7.74 mL, 44.4 mmol) in acetonitrile (110 mL). The reaction mixture was stirred at room temperature (approximately 15° C.) for 2.5 days, whereupon it was concentrated in vacuo. The residue was purified via silica gel chromatography (Gradient: 0% to 40% ethyl acetate in petroleum ether) to afford C30 as a colorless gum. Yield: 7.50 g, 21.3 mmol, 96%. LCMS m/z 353.1 [M+H]+. $^1$H NMR (400 MHz, methanol-d$_4$) δ 8.66 (s, 1H), 4.80-4.71 (m, 1H), 3.81-3.71 (m, 1H), 3.56-3.43 (m, 2H), 3.37-3.31 (m, 1H, assumed; partially obscured by solvent peak), 2.56 (s, 3H), 2.53 (s, 3H), 2.37-2.25 (m, 1H), 2.10-1.97 (m, 1H), 1.47 (s, 9H).

Step 2. Synthesis of tert-butyl (3S)-3-[5-methyl-2-(methylthio)-7-oxopyrido[2,3-c]pyrimidin-8(7H)-yl]pyrrolidine-1-carboxylate (C31)

Lithium bis(trimethylsilyl)amide (1 M solution in tetrahydrofuran; 63.8 mL, 63.8 mmol) was added drop-wise to a 0° C. solution of C30 (7.50 g, 21.3 mmol) and ethyl acetate (6.56 g, 74.5 mmol) in tetrahydrofuran (200 mL). The reaction mixture was stirred in an ice bath for 30 minutes, whereupon it was heated to 40° C. for 1 hour. Aqueous ammonium chloride solution (100 mL) was added, followed by water (100 mL), and the resulting mixture was extracted with ethyl acetate (3×150 mL). The combined organic layers were washed with saturated aqueous sodium chloride solution (150 mL), concentrated in vacuo, and subjected to silica gel chromatography (Gradient: 10% to 50% ethyl acetate in dichloromethane), providing C31 as a yellowish solid. Yield: 6.27 g, 16.7 mmol, 78%. $^1$H NMR (400 MHz, chloroform-d) δ 8.71 (s, 1H), 6.47-6.42 (m, 1H), 6.26-6.14 (m, 1H), 3.99 (dd, J=10.2, 8.4 Hz, 1H), 3.88-3.75 (m, 1H), 3.72-3.57 (m, 1H), 3.52-3.40 (m, 1H), 2.97-2.81 (m, 1H), 2.58 (s, 3H), 2.43 (d, J=1.3 Hz, 3H), 2.18-2.06 (m, 1H), 1.52-1.43 (m, 9H).

Step 3. Synthesis of tert-butyl (3S)-3-[6-bromo-5-methyl-2-(methylthio)-7-oxopyrido[2,3-c]pyrimidin-8(7H)-yl]Pyrrolidine-1-carboxylate (P11)

N-Bromosuccinimide (3.26 g, 18.3 mmol) was added portion-wise to a 0° C. mixture of C31 (6.27 g, 16.7 mmol) and oxalic acid (150 mg, 1.67 mmol) in a mixture of acetonitrile (100 mL) and dichloromethane (50 mL). After the reaction mixture had been stirred for 45 minutes at 0° C., it was treated with saturated aqueous sodium sulfite solution (45 mL), diluted with water (80 mL), and extracted with dichloromethane (2×100 mL). The combined organic layers were concentrated in vacuo, and the residue was purified via silica gel chromatography (Gradient: 10% to 60% ethyl acetate in petroleum ether), affording P11 as a white solid. Yield: 5.30 g, 11.6 mmol, 69%. $^1$H NMR (400 MHz, chloroform-d) δ 8.82 (s, 1H), 6.37-6.26 (m, 1H), 3.99-3.78 (m, 2H), 3.78-3.61 (m, 1H), 3.56-3.45 (m, 1H), 2.90-2.71 (m, 1H), 2.64 (s, 3H), 2.60 (s, 3H), 2.24-2.08 (m, 1H), 1.52-1.43 (m, 9H).

Preparation P12

6-Acetyl-8-cyclopentyl-5-methyl-2-(methylsulfonyl)pyrido[2,3-d]pyrimidin-7(8H)-one (P12)

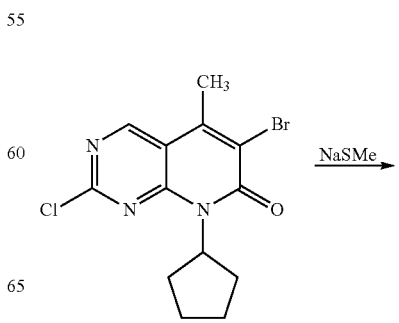

-continued

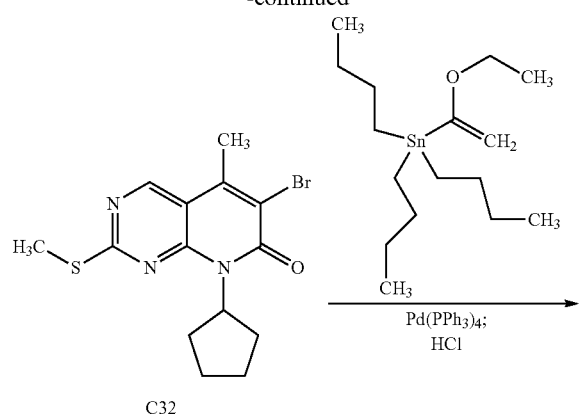

C32

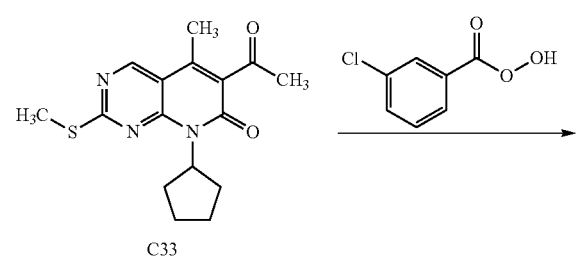

C33

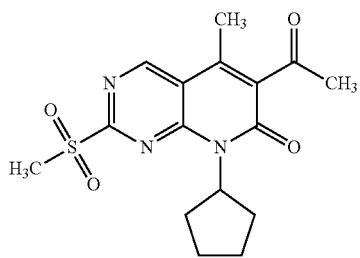

P12

Step 1. Synthesis of 6-bromo-8-cyclopentyl-5-methyl-2-(methylthio)pyrido[2,3-c]pyrimidin-7(8H)-one (C32)

To a 0° C. suspension of 6-bromo-2-chloro-8-cyclopentyl-5-methylpyrido[2,3-d]pyrimidin-7(8H)-one (9.70 g, 28.3 mmol) in a mixture of tetrahydrofuran (95 mL) and water (50 mL) was added sodium methanethiolate (3.97 g, 56.6 mmol). The reaction mixture was allowed to warm to room temperature and stir for 18 hours, whereupon the solid was collected via filtration and washed with water to provide C32 (4.30 g) as a white solid. The filtrate was extracted with ethyl acetate (3×150 mL), and the combined organic layers were washed with saturated aqueous sodium chloride solution, dried over sodium sulfate, filtered, and concentrated in vacuo to provide additional C32 (5.60 g) as a white solid. Combined yield: 9.90 g, 27.9 mmol, 99%. LCMS m/z 353.8 (bromine isotope pattern observed) [M+H]+. 1H NMR (400 MHz, chloroform-d) δ 8.79 (s, 1H), 6.12-5.99 (m, 1H), 2.63 (s, 6H), 2.36-2.22 (m, 2H), 2.17-2.04 (m, 2H), 1.95-1.83 (m, 2H), 1.74-1.62 (m, 2H).

Step 2. Synthesis of 6-acetyl-8-cyclopentyl-5-methyl-2-(methylthio)pyrido[2,3-d]pyrimidin-7(8H)-one (C33)

A suspension of C32 (18.0 g, 50.8 mmol), tributyl(1-ethoxyethenyl)stannane (83.07 g, 230.0 mmol), and tetrakis(triphenylphosphine)palladium(0) (2.94 g, 2.54 mmol) in toluene (250 mL) was stirred at 110° C. for 16 hours, whereupon it was cooled and treated with hydrochloric acid (6 M; 20 mL). After the resulting mixture had been stirred for 20 minutes, it was filtered; the filtrate was adjusted to a pH of 7 by addition of 2 M aqueous sodium hydroxide solution, and then extracted with ethyl acetate (3×50 mL). The combined organic layers were washed with saturated aqueous sodium chloride solution (2×50 mL), dried over sodium sulfate, filtered, and concentrated in vacuo. Purification via silica gel chromatography (Gradient: 0% to 20% ethyl acetate in petroleum ether) afforded C33 as a yellow solid. Yield: 14.0 g, 44.1 mmol, 87%. LCMS m/z 317.9 [M+H]+. 1H NMR (400 MHz, chloroform-d) δ 8.80 (s, 1H), 5.98-5.88 (m, 1H), 2.63 (s, 3H), 2.55 (s, 3H), 2.38 (s, 3H), 2.37-2.28 (m, 2H), 2.13-2.01 (m, 2H), 1.94-1.84 (m, 2H), 1.75-1.64 (m, 2H).

Step 3. Synthesis of 6-acetyl-8-cyclopentyl-5-methyl-2-(methylsulfonyl)pyrido[2,3-d]pyrimidin-7(8H)-one (P12)

A solution of 3-chloroperoxybenzoic acid (16.7 g, 96.8 mmol) in dichloromethane (300 mL) was added over 30 minutes, in a drop-wise manner, to a −5° C. solution of C33 (14.0 g, 44.1 mmol) in dichloromethane (300 mL). After the reaction mixture had been stirred at 15° C. for 16 hours, it was diluted with saturated aqueous sodium sulfite solution (6 mL), followed by saturated aqueous sodium carbonate solution (35 mL). The resulting mixture was extracted with dichloromethane (2×50 mL), and the combined organic layers were dried over sodium sulfate, filtered, and concentrated in vacuo. By 1H NMR analysis, the reaction was incomplete, so this material was dissolved in dichloromethane (150 mL), cooled to −5° C., and again treated drop-wise with a solution of 3-chloroperoxybenzoic acid (3.0 g, 17 mmol) in dichloromethane (10 mL). This reaction mixture was stirred at 15° C. for 3 hours, whereupon it was treated with saturated aqueous sodium sulfite solution (2 mL), diluted with saturated aqueous sodium carbonate solution (20 mL), and extracted with dichloromethane (2×30 mL). The combined organic layers were dried over sodium sulfate, filtered, and concentrated in vacuo to give P12 as a yellow solid (15 g). This material was combined with the product from a similar reaction carried out using C33 (1.47 g, 4.63 mmol), mixed with dichloromethane (60 mL) and petroleum ether (400 mL), and stirred for 40 minutes. Filtration provided P12 as a yellow solid. Combined yield: 14.3 g, 40.9 mmol, 84%. LCMS m/z 350.3 [M+H]+. 1H NMR (400 MHz, chloroform-d) δ 9.10 (s, 1H), 5.96-5.85 (m, 1H), 3.39 (s, 3H), 2.57 (s, 3H), 2.46 (s, 3H), 2.33-2.21 (m, 2H), 2.21-2.10 (m, 2H), 2.01-1.90 (m, 2H), 1.77-1.65 (m, 2H).

Alternate Preparation of P12

6-Acetyl-8-cyclopentyl-5-methyl-2-(methylsulfonyl)pyrido[2,3-d]pyrimidin-7(8H)-one (P12)

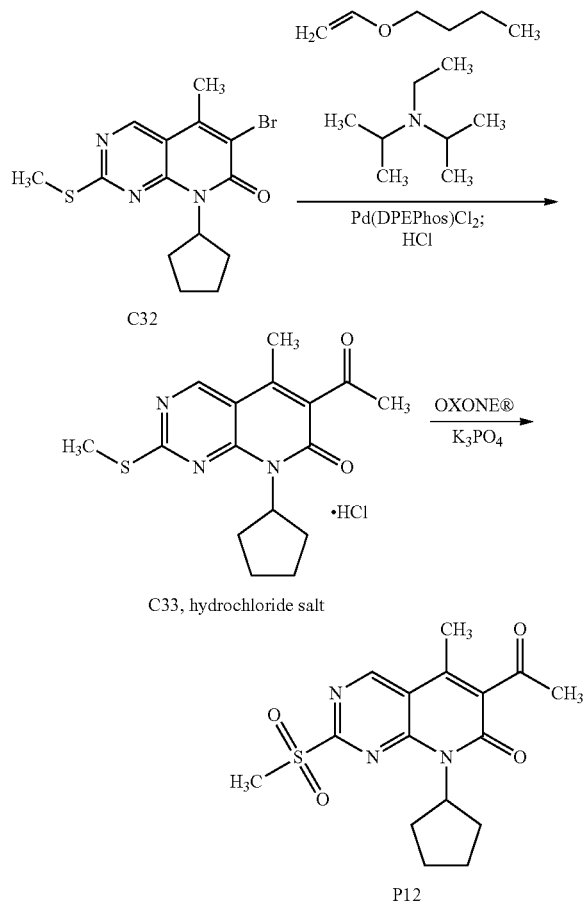

Step 1. Synthesis of 6-acetyl-8-cyclopentyl-5-methyl-2-(methylsulfanyl)pyrido[2,3-d]pyrimidin-7(8H)-one, hydrochloride salt (C33, Hydrochloride Salt)

A mixture of C32 (172.7 g, 487.5 mmol), butyl ethenyl ether (146.0 g, 1.458 mol), N,N-diisopropylethylamine (121 mL, 695 mmol), and {bis[2-(diphenylphosphino)phenyl]ether}palladium(II) dichloride [Pd(DPEPhos)Cl$_2$; 6.98 g, 9.75 mmol] in n-butanol (1 L) was degassed for 15 minutes with nitrogen, and then heated to an internal temperature of 89° C. The reaction mixture was stirred overnight, using a mechanical stirrer, whereupon aqueous sodium carbonate solution (5%; 1 L) was added. The organic layer was concentrated under reduced pressure, using a water bath at 50° C., to remove the n-butanol, and the resulting solid was dissolved in ethyl acetate (1 L). Activated charcoal (60 g) was added, and the mixture was stirred for 10 minutes before being filtered through a pad of diatomaceous earth. The filter pad was washed with ethyl acetate, and the combined filtrates were treated with SiliCycle SiliaMetS® thiol metal scavenger (45.0 g), stirred at room temperature for 30 minutes at room temperature, and filtered. The filter pad was washed with ethyl acetate, and the combined filtrates were again treated with SiliCycle SiliaMetS® thiol metal scavenger (22.5 g), stirred at room temperature for 30 minutes, and filtered. The filter pad was washed with ethyl acetate, and the combined filtrates were concentrated in vacuo to afford a solid, which was dissolved in ethyl acetate (1 L) and treated with hydrochloric acid (6 M; 90 mL). After this reaction mixture had been stirred at room temperature for 2 hours, it was filtered, and the collected solids were washed with a 1:1 mixture of tert-butyl methyl ether and ethyl acetate to provide C33, hydrochloride salt as a solid (132 g). The filtrate was concentrated to dryness under reduced pressure; the residue was dissolved in a mixture of tert-butyl methyl ether and ethyl acetate (1:1, 300 mL), and slurried for 30 minutes. This mixture was then filtered, and the collected solids were washed with a 1:1 mixture of tert-butyl methyl ether and ethyl acetate, providing additional C33, hydrochloride salt (31 g) as an off-white solid. Combined yield: 163 g, 460 mmol, 94%. LCMS m/z 318.2 [M+H]$^+$. $^1$H NMR (400 MHz, CDCl$_3$) 8.95 (s, 1H), 8.33 (br s, 1H), 5.94-5.83 (m, 1H), 2.79 (s, 3H), 2.55 (s, 3H), 2.41 (s, 3H), 2.34-2.23 (m, 2H), 2.14-2.02 (m, 2H), 1.99-1.88 (m, 2H), 1.78-1.66 (m, 2H).

Step 2. Synthesis of 6-acetyl-8-cyclopentyl-5-methyl-2-(methylsulfonyl)pyrido[2,3-c]pyrimidin-7(8H)-one (P12)

A solution of C33, hydrochloride salt (154 g, 435 mmol) in tetrahydrofuran (1.8 L) was diluted with water (500 mL), treated with potassium phosphate (40.2 g, 189 mmol), and cooled to 15° C. under mechanical stirring. Potassium peroxymonosulfate (Oxone®; 402.0 g, 654 mmol) was then slowly added into the stirring solution over several minutes. The ice bath was sporadically applied thereafter to maintain the internal temperature below 25° C., and stirring was continued for 2 additional hours. LCMS analysis at this point indicated conversion to the product: LCMS m/z 350.1 [M+H]$^+$. The reaction mixture was then filtered, and the collected solid was washed with ethyl acetate. The aqueous layer of the combined filtrates was extracted with ethyl acetate, and the combined organic layers were washed twice with saturated aqueous sodium chloride solution, dried over magnesium sulfate, filtered, and concentrated in vacuo. The residue was slurried in a mixture of ethyl acetate in heptane (5%; 1 L) for 1 hour; the solid was collected via filtration and washed with 5% ethyl acetate in heptane, providing P12 (135 g) as a pale yellow solid. Concentration of the filtrate under reduced pressure provided a residue, which was slurried for 4 hours in a mixture of ethyl acetate in heptane (5%; 250 mL), whereupon the solid was collected via filtration and washed with 5% ethyl acetate in heptane to afford additional P12 (4.0 g) as a white solid. Combined yield: 139 g, 398 mmol, 91%. $^1$H NMR (400 MHz, CDCl$_3$) 9.11 (s, 1H), 5.96-5.85 (m, 1H), 3.39 (s, 3H), 2.57 (s, 3H), 2.46 (s, 3H), 2.33-2.22 (m, 2H), 2.22-2.10 (m, 2H), 2.01-1.91 (m, 2H), 1.78-1.65 (m, 2H).

Preparation P13

6-Acetyl-2-(decylthio)-5-methylpyrido[2,3-c]pyrimi-din-7(8H)-one (P13)

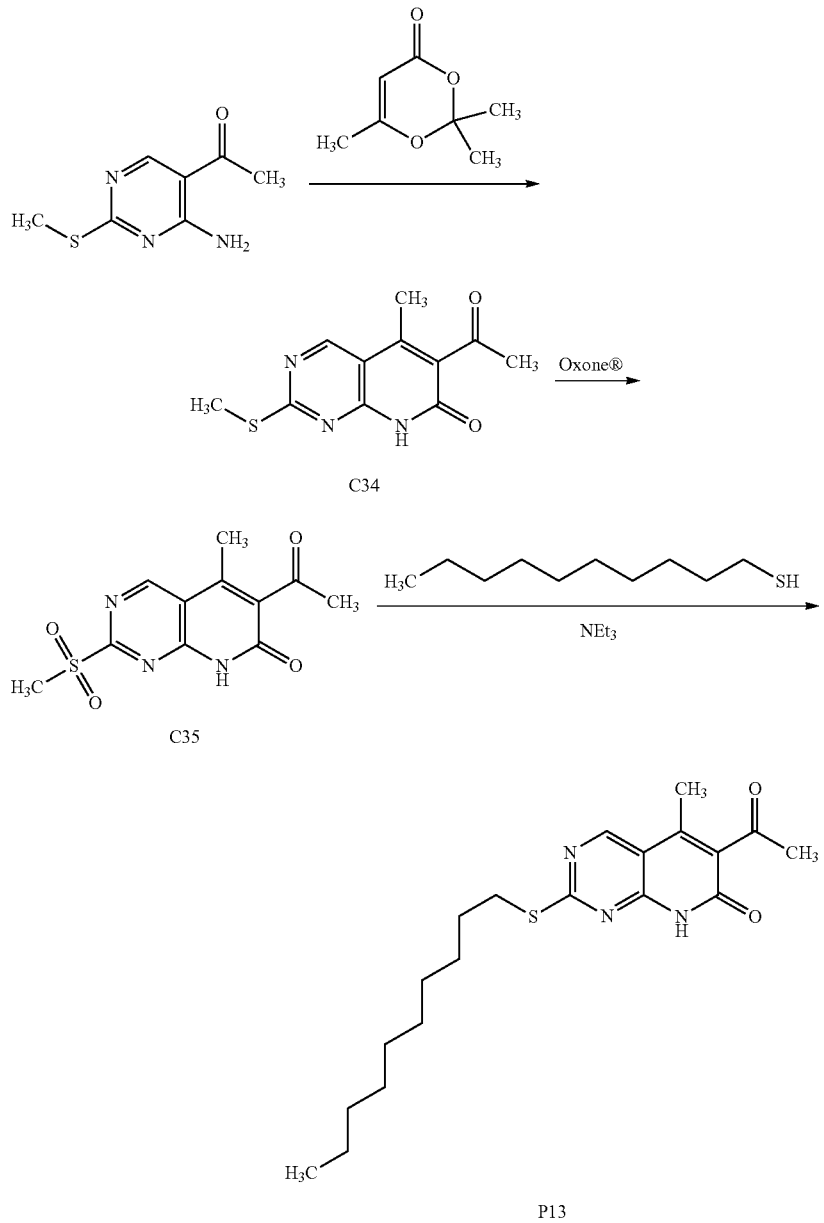

Step 1. Synthesis of 6-acetyl-5-methyl-2-(methyl-thio)pyrido[2,3-c]pyrimidin-7(8H)-one (C34)

A mixture of 1-[4-amino-2-(methylthio)pyrimidin-5-yl]ethanone (17.2 g, 93.9 mmol) and 2,2,6-trimethyl-4H-1,3-dioxin-4-one (53.4 g, 376 mmol) in toluene (375 mL) was heated at 100° C. overnight, and subsequently left standing at room temperature (15° C. to 25° C.) for 2 days. The reaction mixture was then diluted with ethyl acetate (300 mL); the solids were collected via filtration and rinsed with ethyl acetate (200 mL), affording C34 as a brownish solid. Yield: 19.2 g, 77.0 mmol, 82%. $^1$H NMR (400 MHz, DMSO-$d_6$) δ 12.59 (br s, 1H), 9.01 (s, 1H), 2.57 (s, 3H), 2.44 (s, 3H), 2.34 (s, 3H).

Step 2. Synthesis of 6-acetyl-5-methyl-2-(methyl-sulfonyl)pyrido[2,3-d]pyrimidin-7(8H)-one (C35)

Potassium peroxymonosulfate (Oxone®; 128 g, 208 mmol) was added to a suspension of C34 (17.2 g, 69.0 mmol) in a mixture of tetrahydrofuran (800 mL) and water (160 mL) at room temperature (20° C.). The reaction mixture was stirred at 25° C. for 27 hours, whereupon it was diluted with water (800 mL), stirred at room temperature (15° C.) for 2 hours, and filtered. The collected solid was washed sequentially with water (300 mL) and tert-butyl methyl ether (100 mL), then mixed with water (300 mL), stirred at room temperature (20° C.) for 1 hour, and filtered.

The filter cake was washed with water (100 mL) and combined with the product of a similar reaction carried out using C34 (2.10 g, 8.42 mmol). This material was again mixed with water (150 mL), stirred at room temperature (20° C.) for 1 hour, and filtered. This filter cake was washed with water (80 mL) to provide C35 as a white solid. Combined yield: 9.0 g, 32.0 mmol, 41%. LCMS m/z 282.1 [M+H]$^+$. $^1$H NMR (400 MHz, DMSO-$d_6$) δ 13.31 (br s, 1H), 9.39 (s, 1H), 3.43 (s, 3H), 2.46 (s, 3H), 2.41 (s, 3H).

Step 3. Synthesis of 6-acetyl-2-(decylthio)-5-methylpyrido[2,3-c]pyrimidin-7(8H)-one (P13)

To a solution of C35 (1.12 g, 3.98 mmol) in tetrahydrofuran (19 mL) was added triethylamine (1.66 mL, 11.9 mmol), followed by decane-1-thiol (96%, 1.08 g, 5.95 mmol), and the reaction mixture was placed in a heating block at 62° C. After 3 hours, LCMS analysis indicated conversion to the product P13: LCMS m/z 376.3 [M+H]$^+$; the reaction mixture was allowed to cool to room temperature and stir for 15 hours. It was then concentrated in vacuo and the residue was purified using silica gel chromatography (Gradient: 0% to 100% ethyl acetate in heptane), providing P13 as a white solid. (It was noted that the product precipitated during the chromatographic purification.) Yield: 1.37 g, 3.65 mmol, 92%. $^1$H NMR (400 MHz, chloroform-d) δ 9.95 (br s, 1H), 8.82 (s, 1H), 3.18 (t, J=7.3 Hz, 2H), 2.59 (s, 3H), 2.44 (s, 3H), 1.74 (pentet, J=7.4 Hz, 2H), 1.50-1.39 (m, 2H), 1.37-1.19 (m, 12H), 0.87 (t, J=6.7 Hz, 3H).

Example 1

6-Acetyl-8-cyclobutyl-2-{[(3S,4R)-3-hydroxytetrahydro-2H-pyran-4-yl]amino}-5-methylpyrido[2,3-d]pyrimidin-7(8H)-one (1)

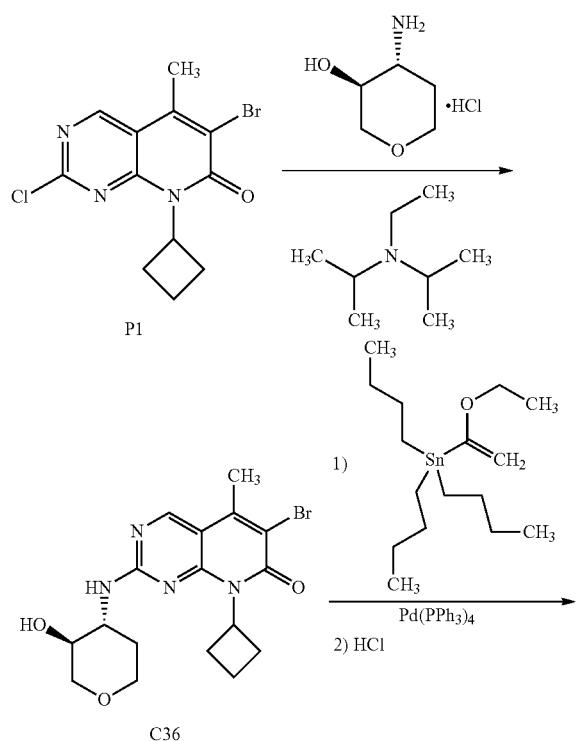

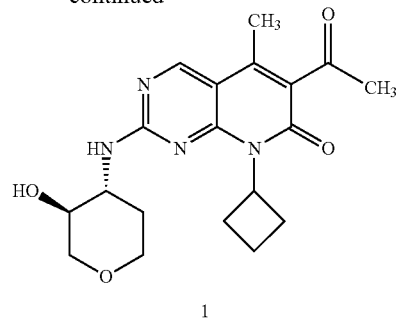

Step 1. Synthesis of 6-bromo-8-cyclobutyl-2-{[(3S, 4R)-3-hydroxytetrahydro-2H-pyran-4-yl]amino}-5-methylpyrido[2,3-d]pyrimidin-7(8H)-one (C36)

A solution of P1 (150 mg, 0.456 mmol), (3S,4R)-4-aminotetrahydro-2H-pyran-3-ol hydrochloride (77.1 mg, 0.502 mmol), and N,N-diisopropylethylamine (0.40 mL, 2.3 mmol) in dimethyl sulfoxide (1.8 mL) was heated at 60° C. for 5 hours. The reaction mixture was then cooled to room temperature and diluted with water (15 mL); the resulting solid was collected via filtration to provide C36 as a light red solid. Yield: 168 mg, 0.410 mmol, 90%. LCMS m/z 411.1 (bromine isotope pattern observed) [M+H]$^+$. $^1$H NMR (400 MHz, chloroform-d), characteristic peaks: 8.58 (s, 1H), 5.89-5.67 (m, 1H), 5.54-5.24 (br s, 1H), 4.09 (dd, J=11.4, 4.9 Hz, 1H), 4.04-3.97 (m, 1H), 3.65 (ddd, J=9.3, 9.1, 4.8 Hz, 1H), 3.50 (br dd, J=11.8, 11.5 Hz, 1H), 3.32-3.18 (m, 1H), 2.54 (s, 3H), 2.41-2.28 (m, 2H), 2.16-1.96 (m, 2H), 1.91-1.78 (m, 1H), 1.78-1.66 (m, 2H, assumed; partially obscured by water peak).

Step 2. Synthesis of 6-acetyl-8-cyclobutyl-2-{[(3S, 4R)-3-hydroxytetrahydro-2H-pyran-4-yl]amino}-5-methylpyrido[2,3-d]pyrimidin-7(8H)-one (1)

A mixture of C36 (165 mg, 0.403 mmol), tetrakis(triphenylphosphine)palladium(0) (23.5 mg, 20.3 μmol), and tributyl(1-ethoxyethenyl)stannane (204 mg, 0.565 mmol) in toluene (4 mL) was sparged with nitrogen for 5 minutes and then heated at 110° C. for 12 hours. The reaction mixture was then concentrated in vacuo, and the residue was dissolved in 2-methyltetrahydrofuran (8 mL). Water (150 μL) and hydrogen chloride (4 M solution in 1,4-dioxane; 0.20 mL, 0.80 mmol) were added, and this reaction mixture was stirred at room temperature. After 2 hours, LCMS analysis indicated conversion to 1: LCMS m/z 373.2 [M+H]$^+$. After 5 hours, the reaction mixture was concentrated under reduced pressure, and the residue was diluted with saturated aqueous sodium bicarbonate solution, and extracted three times with ethyl acetate. The combined organic layers were concentrated in vacuo, and purified via supercritical fluid chromatography (Column: Nacalai USA Cosmosil 3-hydroxyphenyl; Mobile phase A: carbon dioxide; Mobile phase B: methanol; Gradient: 12% B for 0.2 minutes, then ramp to 28% B at 4% per minute; Back pressure: 100 bar) to provide 1. Yield: 83.5 mg, 0.224 mmol, 56%. $^1$H NMR (400 MHz, 80° C., DMSO-$d_6$) δ 8.75 (s, 1H), 7.49 (br s, 1H), 5.80-5.65 (m, 1H), 4.70 (br s, 1H), 4.05-3.93 (m, 1H), 3.93-3.81 (m, 2H), 3.65-3.53 (m, 1H), 3.38 (dd, J=11.8, 11.0 Hz, 1H), 3.27-3.05 (m, 3H), 2.41 (s, 3H), 2.36-2.21 (m, 2H), 2.28 (s, 3H), 2.07-1.91 (m, 2H), 1.91-1.75 (m, 1H), 1.69-1.53 (m, 1H).

Example 2

6-Acetyl-8-cyclopentyl-2-{[(3S,4R)-3-hydroxytetrahydro-2H-pyran-4-yl]amino}-5-methylpyrido[2,3-d]pyrimidin-7(8H)-one (2)

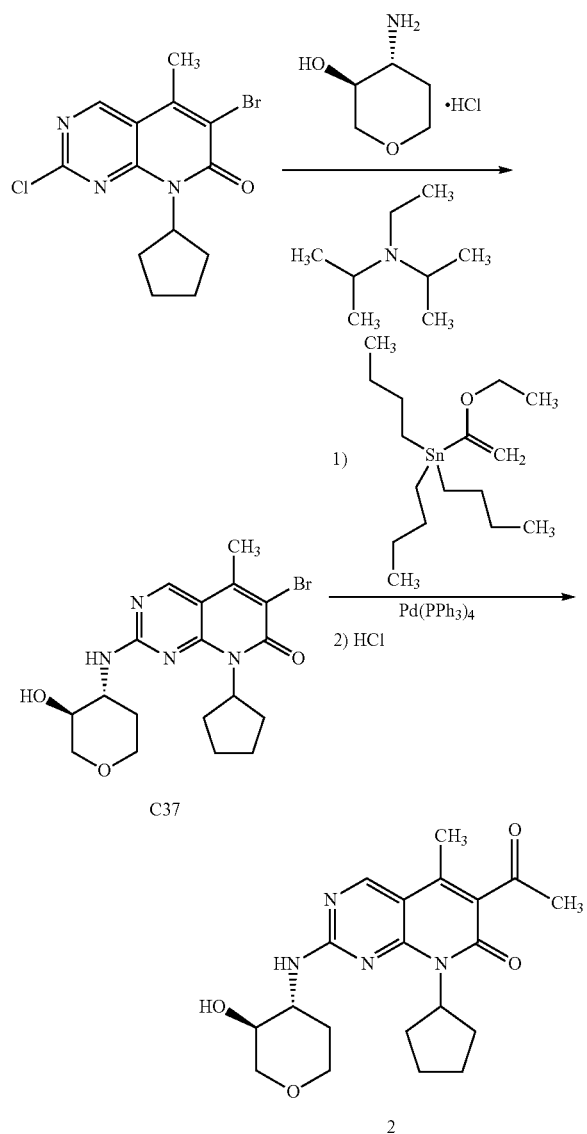

Step 1. Synthesis of 6-bromo-8-cyclopentyl-2-{[(3S,4R)-3-hydroxytetrahydro-2H-pyran-4-yl]amino}-5-methylpyrido[2,3-d]pyrimidin-7(8H)-one (C37)

To a suspension of 6-bromo-2-chloro-8-cyclopentyl-5-methylpyrido[2,3-d]pyrimidin-7(8H)-one (12.0 g, 35.0 mmol) and (3S,4R)-4-aminotetrahydro-2H-pyran-3-ol hydrochloride (5.92 g, 38.5 mmol) in dimethyl sulfoxide (100 mL) was added N,N-diisopropylethylamine (23.3 mL, 134 mmol). The reaction mixture was heated at 60° C. for 21 hours, whereupon it was cooled to ambient temperature and poured into ice water (1.5 L). The resulting solid was collected via filtration to provide C37 as a pink solid. $^1$H NMR analysis indicated that this compound exists as a mixture of rotamers. Yield: 13.1 g, 30.9 mmol, 88%. LCMS m/z 423.1 (bromine isotope pattern observed) [M+H]$^+$. $^1$H NMR (400 MHz, DMSO-d$_6$) δ 8.79 (br s, 1H), [7.91-7.77 (m) and 7.74-7.61 (m), total 1H], [6.10-5.91 (m) and 5.90-5.74 (m), total 1H], 4.95 (d, J=5.2 Hz, 1H), 4.07-3.74 (m, 3H), 3.53 (br s, 1H), 3.40-3.24 (m, 1H, assumed; partially obscured by water peak), 3.03 (dd, J=11.1, 9.7 Hz, 1H), 2.52 (s, 3H), 2.43-2.24 (m, 1H), 2.23-2.07 (m, 1H), 2.06-1.83 (m, 3H), 1.83-1.69 (m, 2H), 1.69-1.46 (m, 3H).

Step 2. Synthesis of 6-acetyl-8-cyclopentyl-2-{[(3S,4R)-3-hydroxytetrahydro-2H-pyran-4-yl]amino}-5-methylpyrido[2,3-d]pyrimidin-7(8H)-one (2)

A solution of C37 (450 mg, 1.06 mmol), tetrakis(triphenylphosphine)palladium(0) (62.0 mg, 53.6 µmol), and tributyl(1-ethoxyethenyl)stannane (537 mg, 1.49 mmol) in toluene (11 mL) was sparged with nitrogen for 5 minutes and then heated at 110° C. for 18 hours. Volatiles were removed in vacuo and the residue was dissolved in 2-methyltetrahydrofuran (10 mL), treated with water (0.15 mL) and hydrogen chloride (4 M solution in 1,4-dioxane; 0.30 mL, 1.2 mmol), and stirred at room temperature for 6 hours. The reaction mixture was then concentrated, and the residue was purified via silica gel chromatography [Gradient: 15% to 100% (9:1 ethyl acetate/ethanol) in heptane]. The purified material (approximately 500 mg) was mixed with ethyl acetate (8 mL) and heptane (15 mL) and heated at 75° C. Additional heptane (6 mL) was added, and the mixture was allowed to cool to room temperature. The resulting material was collected via filtration to afford 2 as a solid. Yield: 310 mg, 0.802 mmol, 76%. LCMS m/z 387.2 [M+H]$^+$. $^1$H NMR (400 MHz, 80° C., DMSO-d$_6$) 8.76 (s, 1H), 7.44 (br s, 1H), 5.81 (quintet, J=9.0 Hz, 1H), 4.68 (br s, 1H), 3.99-3.80 (m, 3H), 3.64-3.53 (m, 1H), 3.36 (ddd, J=11.7, 11.6, 2.1 Hz, 1H), 3.08 (dd, J=11.2, 9.5 Hz, 1H), 2.45-2.29 (m, 2H), 2.41 (s, 3H), 2.28 (s, 3H), 2.08-1.92 (m, 3H), 1.86-1.71 (m, 2H), 1.71-1.52 (m, 3H).

Example 3

6-Acetyl-8-(2-azaspiro[3.3]heptan-6-yl)-2-{[(3S,4R)-3-hydroxytetrahydro-2H-pyran-4-yl]amino}-5-methylpyrido[2,3-d]pyrimidin-7(8H)-one (3)

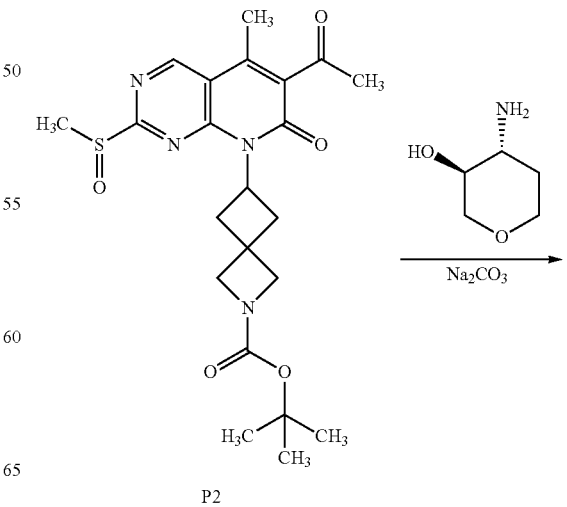

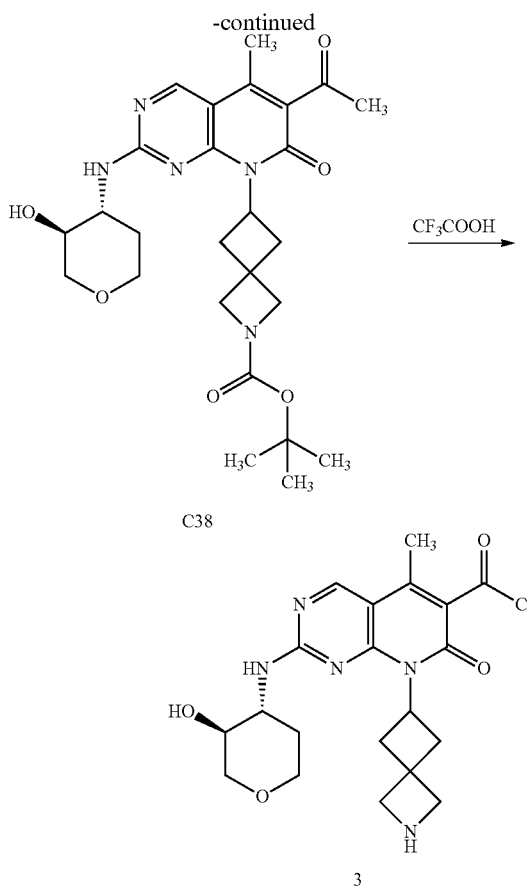

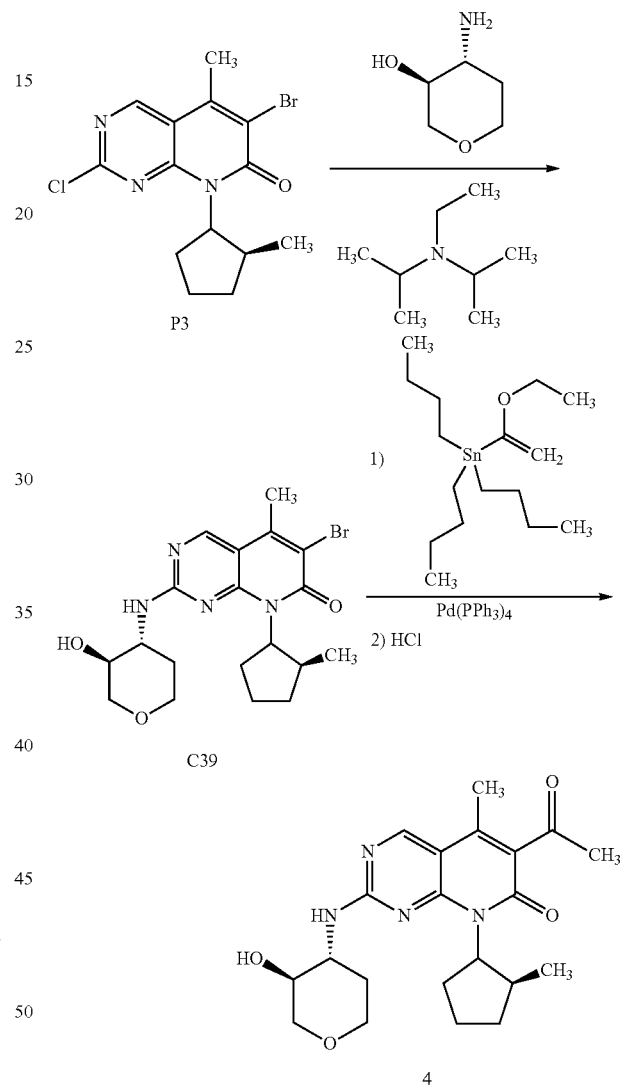

Step 1. Synthesis of tert-butyl 6-[6-acetyl-2-{[(3S,4R)-3-hydroxytetrahydro-2H-pyran-4-yl]amino}-5-methyl-7-oxopyrido[2,3-c]pyrimidin-8(7H)-yl]-2-azaspiro[3.3]heptane-2-carboxylate (C38)

A mixture of P2 (from Preparation P2, step 5; 120 mg, ≤0.225 mmol), (3S,4R)-4-aminotetrahydro-2H-pyran-3-ol (36.6 mg, 0.312 mmol), and sodium carbonate (55.2 mg, 0.521 mmol) in tetrahydrofuran (8 mL) was stirred at 60° C. for 18 hours. The reaction mixture was purified using silica gel chromatography (Gradient: 0% to 25% methanol in dichloromethane) to provide C38 as a light yellow glass. Yield: 100 mg, 0.195 mmol, 87% over 2 steps. LCMS m/z 535.9 [M+Na⁺].

Step 2. Synthesis of 6-acetyl-8-(2-azaspiro[3.3]heptan-6-yl)-2-{[(3S,4R)-3-hydroxytetrahydro-2H-pyran-4-yl]amino}-5-methylpyrido[2,3-d]pyrimidin-7(8H)-one (3)

A solution of C38 (100 mg, 0.195 mmol) in a mixture of trifluoroacetic acid (2 mL) and dichloromethane (5 mL) was stirred at room temperature (10° C.) for approximately 1 hour. The reaction mixture was then concentrated in vacuo and purified via reversed-phase HPLC (Column: YMC-Triart C18, 7 μm; Mobile phase A: water containing 0.05% ammonium hydroxide; Mobile phase B: acetonitrile; Gradient: 9% to 49% B) to afford 3 as a white solid. Yield: 49.1 mg, 0.119 mmol, 61%. LCMS m/z 414.3 [M+H]⁺. ¹H NMR (400 MHz, chloroform-d) δ 8.59 (s, 1H), 6.06-5.30 (m, 2H), 4.06 (dd, J=11.4, 4.8 Hz, 1H), 4.02-3.87 (m, 2H), 3.79 (br s, 2H), 3.75 (br s, 2H), 3.69-3.58 (m, 1H), 3.56-3.43 (m, 1H), 3.31-3.07 (m, 4H), 2.66-2.54 (m, 2H), 2.50 (s, 3H), 2.29 (s, 3H), 2.20-2.05 (m, 1H), 1.76-1.61 (m, 1H).

Example 4

6-Acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one (4)

Step 1. Synthesis of 6-bromo-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one (C39)

A solution of P3 (150 mg, 0.421 mmol) (3S,4R)-4-aminotetrahydro-2H-pyran-3-ol (73.9 mg, 0.631 mmol), and N,N-diisopropylethylamine (272 mg, 0.366 mL, 2.10 mmol) in dimethyl sulfoxide (2 mL) was heated at 70° C. for 18 hours. The reaction mixture was then diluted with dichloromethane (30 mL), washed sequentially with water (3×10 mL) and saturated aqueous sodium chloride solution (10 mL), dried over sodium sulfate, filtered, and concentrated in vacuo; silica gel chromatography (Gradient: 0% to 100% ethyl acetate in dichloromethane) provided C39 as a white glass. Yield: 130 mg, 0.297 mmol, 71%. LCMS m/z 437.1 (bromine isotope pattern observed) [M+H]⁺.

Step 2. Synthesis of 6-acetyl-2{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one (4)

Nitrogen was bubbled through a solution of C39 (130 mg, 0.297 mmol) in toluene (10 mL), and then tributyl(1-ethoxyethenyl)stannane (429 mg, 1.19 mmol) and tetrakis(triphenylphosphine)palladium(0) (34.3 mg, 29.7 μmol) were added. The reaction vessel was sealed and heated at 110° C. for 18 hours, whereupon the reaction mixture was cooled to room temperature and filtered. After the filtrate had been concentrated in vacuo, the residue was dissolved in ethyl acetate (20 mL), acidified to a pH of approximately 5 by addition of 6 M hydrochloric acid, and stirred for about 10 minutes. The resulting biphasic mixture was basified to a pH of approximately 8 by addition of aqueous sodium bicarbonate solution, and the aqueous layer was extracted with ethyl acetate (2×10 mL). The combined organic layers were dried over sodium sulfate, filtered, and concentrated under reduced pressure; the residue was purified using chromatography on silica gel (Gradient: 0% to 100% ethyl acetate in dichloromethane) to afford 4 as a white solid. Yield: 58.8 mg, 0.147 mmol, 49%. LCMS m/z 401.0 [M+H]⁺. ¹H NMR (400 MHz, methanol-d₄) δ 8.76 (s, 1H), 6.22-6.05 (m, 1H), 4.14-3.89 (m, 3H), 3.73-3.57 (br m, 1H), 3.54-3.45 (m, 1H), 3.22 (br dd, J=10.4, 10.1 Hz, 1H), 2.82-2.56 (br m, 1H), 2.46 (s, 3H), 2.43-2.31 (m, 1H), 2.34 (s, 3H), 2.16-1.98 (m, 2H), 1.98-1.80 (m, 3H), 1.72-1.52 (m, 2H), 0.79 (d, J=7.1 Hz, 3H).

Example 5

3-Acetyl-1-cyclopentyl-7-{[(3S,4R)-3-hydroxytetrahydro-2H-pyran-4-yl]amino}-4-methyl-1,6-naphthyridin-2(1H)-one (5)

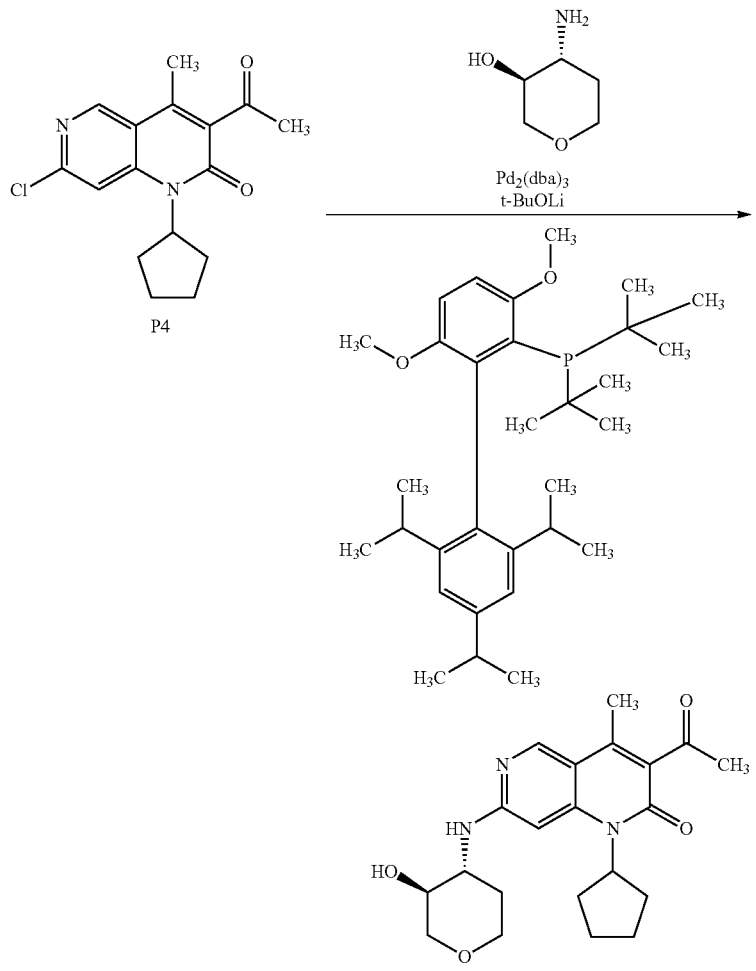

A freshly opened bottle of N,N-dimethylformamide was sparged with nitrogen for approximately 15 minutes. A mixture of P4 (63.0 g, 207 mmol), (3S,4R)-4-aminotetrahydro-2H-pyran-3-ol (29.1 g, 248 mmol) and lithium tert-butoxide (19.9 g, 249 mmol) was dissolved in the sparged N,N-dimethylformamide (300 mL), and the flask was purged under gentle nitrogen pressure for approximately 15 minutes.

In a separate flask, a mixture of di-tert-butyl[3,6-dimethoxy-2',4',6'-tri(propan-2-yl)[biphenyl]-2-yl]phosphane (tBuBrettPhos; 2.00 g, 4.13 mmol) and tris(dibenzylideneacetone)dipalladium(0) (1.89 g, 2.06 mmol) was purged under gentle nitrogen pressure for approximately 15 minutes. N,N-Dimethylformamide (100 mL; previously sparged with nitrogen) was added, and the resulting solution was heated in a 70° C. oil bath for approximately 7 minutes, whereupon it was cooled to room temperature. This catalyst mixture was then poured into the flask containing P4, and the reaction mixture was stirred at 40° C. for 1 hour. After it had cooled to room temperature, the reaction mixture was poured into water (700 mL), and adjusted to pH 5 to 6 by addition of 1 M hydrochloric acid. Ethyl acetate (500 mL) was then added, and the resulting mixture was stirred to facilitate dissolution of a tarry solid. The aqueous layer was extracted with ethyl acetate (4×400 mL), and the combined organic layers were washed sequentially with an aqueous solution of lithium chloride (7% by weight; 2×400 mL) and saturated aqueous sodium chloride solution (250 mL), dried over magnesium sulfate, and filtered using a fritted funnel (about 12.7 cm wide) that had been layered with diatomaceous earth (about 3.8 cm), silica gel (approximately 3.8 cm) and sand. The filter pad was rinsed with ethyl acetate (3.5 L), and the combined filtrates were concentrated in vacuo; the residue was slurried with heptane and concentrated under reduced pressure, affording a light orange solid (79.0 g). After this material had been combined with products from a number of reactions run in a similar manner using P4 (total of 160 g, 525 mmol), it was purified via supercritical fluid chromatography (Column: Chiral Technologies DCpak P4VP, 5 µm; Mobile phase: 4:1 carbon dioxide/methanol; Back pressure: 100 bar). Combined yield: 193.7 g, 502.5 mmol, 69%. LCMS m/z 386.1 [M+H]$^+$. $^1$H NMR (400 MHz, chloroform-d) δ 8.49 (s, 1H), 6.32 (s, 1H), 5.66 (br s, 1H), 5.34 (pentet, J=9.0 Hz, 1H), 4.64 (d, J=5.5 Hz, 1H), 4.10 (dd, J=11.4, 4.9 Hz, 1H), 4.01 (br dd, J=11.7, 4.5 Hz, 1H), 3.88-3.77 (m, 1H), 3.57 (ddd, J=9.4, 9.2, 4.9 Hz, 1H), 3.47 (ddd, J=11.9, 11.8, 2.1 Hz, 1H), 3.20 (dd, J=11.4, 9.9 Hz, 1H), 2.53 (s, 3H), 2.34 (s, 3H), 2.29-2.16 (m, 2H), 2.12-1.99 (m, 3H), 1.99-1.87 (m, 2H), 1.81-1.66 (m, 3H).

Further purification was carried out as follows. A solution of 5 (185 g, 480 mmol) in dichloromethane (approximately 750 mL) was prepared via application of minimal heat until 5 was in solution. SiliaMetS Thiol (SH) (Silicycle; 18.3 g) was added, and the resulting mixture was stirred at a gentle reflux for 30 minutes, whereupon it was cooled in an ice bath for 5 minutes, and filtered through a 1 cm pad of diatomaceous earth, followed by a dichloromethane (approximately 250 mL) rinse of the filter pad. The combined filtrates were distilled at atmospheric pressure to remove dichloromethane (approximately 250 mL). tert-Butyl methyl ether (500 mL) and seed crystals of 5 (approximately 100 mg; see the origin of these crystals below) were added, and additional solvent (approximately 250 mL, boiling point approximately 45° C.) was removed by distillation. tert-Butyl methyl ether (500 mL) was again added, and the mixture was stirred, resulting in precipitation of solid; distillation was continued until a total of approximately 1.3 L had been collected, and the boiling point of the distillate was 50.6° C. At this point, the mixture was allowed to cool to room temperature with stirring, whereupon the solid was collected by filtration and rinsed with tert-butyl methyl ether (2×100 mL), affording 5 as a yellow solid (163 g, 423 mmol, 88% for the purification).

Alternative reaction conditions to obtain 5 from P4 and (3S,4R)-4-aminotetrahydro-2H-pyran-3-ol include using Pd(OAc)$_2$ of (AllylPdCl)$_2$ and t-BuBrettPhos as the catalyst/ligand; using solvents including isopropyl acetate, methyl ethyl ketone, toluene, THF, and 2-methyltetrhydrofuran that preferably contains THF [up to approximately 20% of THF]; and using another base including NaOt-Bu, KOt-Bu, KOt-Amyl, K$_3$PO$_4$, and Cs$_2$CO$_3$. Alternative workup conditions include quenching the reaction with aqueous ammonium chloride and washing the aqueous layer with organic solvent consistent with the reaction solvent. Purification of 5 can be accomplished with an acid/base workup followed by a thiol-silica gel plug. Water is added to the combined organic layers, and the pH is adjusted to about 6 by addition of 1 M hydrochloric acid. tert-Butyl methyl ether is used as a wash. The pH can be adjusted to about 5 with NaOH and K$_3$PO$_4$. Example 5 is extracted with an organic solvent like dichloromethane and purified similarly as discussed above. A short chain alcohol, e.g., C$_{1-3}$ alcohol, can be included in the organic layer to elute 5 from the thiol-silica gel plug. Any color present could be removed by standard procedures before crystallization from a short chain alcohol.

Generation of Seed Crystals of 5

A slurry of 5 (40 g) in ethanol (235 mL) was heated at reflux until a solution was obtained. Water (600 mL) was added to the hot solution in a drop-wise manner over 35 minutes, and solvent (an ethanol/water azeotrope) was collected using a short-path distillation head while a vacuum of approximately 450 mbar was maintained. Heating was continued for 45 minutes after completion of the water addition; during this time, approximately 125 mL of solvent were collected. The heat was then turned off, and the mixture was allowed to stir and cool to room temperature overnight. Filtration, followed by washing of the filter cake with water, provided 5 (37.5 g) as a light beige solid, which was shown to be crystalline via powder X-ray diffraction analysis; a portion of this material was used as the seed crystals employed above.

Generation of a Crystal of 5 for X-Ray Structural Determination

A sample of 5 (150 mg, 0.389 mmol) was dissolved in methanol (2 mL) and heated to reflux, providing a solution. Water (4 mL) was added and heating was continued to remove methanol. The resulting solid was collected via filtration, and provided a crystal of 5 suitable for X-ray structural determination (see below). Crystalline 5 is anhydrous based on the lack of presence of solvent, including water, in the crystalline lattice. Yield: 139 mg, 0.361 mmol, 93%. $^1$H NMR (400 MHz, DMSO-d$_6$) δ 8.57 (s, 1H), 7.13 (d, J=7.4 Hz, 1H), 6.44 (s, 1H), 5.34 (pentet, J=9.0 Hz, 1H), 5.12 (d, J=5.2 Hz, 1H), 3.91-3.75 (m, 3H), 3.47-3.3 (m, 2H, assumed; partially obscured by water peak), 3.07 (dd, J=11.1, 9.5 Hz, 1H), 2.39 (s, 3H), 2.26 (s, 3H), 2.21-2.08 (m, 2H), 2.08-1.94 (m, 3H), 1.91-1.77 (m, 2H), 1.73-1.59 (m, 2H), 1.51-1.38 (m, 1H).

Single-Crystal X-Ray Structural Determination of 5

Single Crystal X-Ray Analysis

Data collection was performed on a Bruker D8 Venture diffractometer at room temperature. Data collection consisted of omega and phi scans.

The structure was solved by intrinsic phasing using SHELX software suite in the monoclinic space group P2$_1$. The structure was subsequently refined by the full-matrix least squares method. All non-hydrogen atoms were found and refined using anisotropic displacement parameters.

The disordered positions at C17-C15 were noted but not treated with a disorder model. The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). An attempt was made to determine the absolute configuration directly from the X-ray diffraction data by the method of Hooft and also with the Parsons method. The final refined Hooft parameter and Parsons parameter were both given as 0.12 with an esd of 0.06. This value indicates that the stereochemistry of 5 depicted in the scheme above represents the absolute configuration.

The final R-index was 4.2%. A final difference Fourier revealed no missing or misplaced electron density.

Pertinent crystal, data collection and refinement information is summarized in Table L. Atomic coordinates, bond lengths, bond angles, and displacement parameters are listed in Tables M-P.

Software and References

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Strayer, and A. L. Spek, *J. Appl. Cryst.* 2008, 41, 96-103.

H. D. Flack, *Acta Cryst.* 1983, A39, 867-881.

TABLE L

Crystal data and structure refinement for 5.

| | |
|---|---|
| Empirical formula | $C_{21}H_{27}N_3O_4$ |
| Formula weight | 385.45 |
| Temperature | 293(2) K |
| Wavelength | 1.54178 Å |
| Crystal system | Monoclinic |
| Space group | $P2_1$ |
| Unit cell dimensions | a = 9.6343(3) Å   α = 90° |
| | b = 9.2601(3) Å   β = 97.547(2)° |
| | c = 11.1908(4) Å   γ = 90° |
| Volume | 989.73(6) Å$^3$ |
| Z | 2 |
| Density (calculated) | 1.293 Mg/m$^3$ |
| Absorption coefficient | 0.736 mm$^{-1}$ |
| F(000) | 412 |
| Crystal size | 0.220 × 0.080 × 0.060 mm$^3$ |
| Theta range for data collection | 4.630 to 72.311° |
| Index ranges | −11 <= h <= 11, −11 <= k <= 11, −13 <= l <= 13 |
| Reflections collected | 31769 |
| Independent reflections | 3863 [$R_{int}$ = 0.0363] |
| Completeness to theta = 67.679° | 99.3% |
| Absorption correction | Empirical |
| Refinement method | Full-matrix least-squares on $F^2$ |
| Data/restraints/parameters | 3863/3/261 |
| Goodness-of-fit on F2 | 1.050 |
| Final R indices [I >2σ(I)] | R1 = 0.0415, wR2 = 0.1137 |
| R indices (all data) | R1 = 0.0442, wR2 = 0.1171 |
| Absolute structure parameter | 0.11(6) |
| Extinction coefficient | n/a |
| Largest diff. peak and hole | 0.302 and −0.236 e.Å$^{-3}$ |

TABLE M

Atomic coordinates (×10$^4$) and equivalent isotropic displacement parameters (Å$^2$ × 10$^3$) for 5. U(eq) is defined as one-third of the trace of the orthogonalized U$^{ij}$ tensor.

| | x | y | z | U(eq) |
|---|---|---|---|---|
| N(1) | 9697(2) | 4394(3) | 4774(2) | 53(1) |
| N(2) | 9158(2) | 4372(3) | 6695(2) | 46(1) |
| N(3) | 4911(2) | 5202(2) | 5519(2) | 36(1) |
| O(1) | 8944(2) | 6876(3) | 3237(2) | 64(1) |
| O(2) | 10612(3) | 4542(4) | 1214(2) | 93(1) |
| O(3) | 3389(4) | 6836(4) | 8920(4) | 115(1) |
| O(4) | 2691(2) | 5473(3) | 6001(2) | 68(1) |
| C(1) | 9889(3) | 5800(3) | 2945(3) | 51(1) |
| C(2) | 9793(4) | 5677(5) | 1581(3) | 74(1) |
| C(3) | 10188(5) | 3206(6) | 1636(4) | 92(1) |
| C(4) | 10309(4) | 3151(5) | 2992(4) | 72(1) |
| C(5) | 9482(3) | 4379(3) | 3471(2) | 45(1) |
| C(6) | 8697(2) | 4556(3) | 5507(2) | 40(1) |
| C(7) | 7301(2) | 4863(3) | 5087(2) | 39(1) |
| C(8) | 6338(2) | 4995(2) | 5896(2) | 34(1) |
| C(9) | 6823(2) | 4904(3) | 7148(2) | 37(1) |
| C(10) | 8236(3) | 4569(3) | 7462(2) | 44(1) |
| C(11) | 5869(3) | 5132(3) | 8017(2) | 41(1) |
| C(12) | 6412(3) | 5109(5) | 9343(2) | 65(1) |
| C(13) | 4512(3) | 5366(3) | 7620(2) | 43(1) |
| C(14) | 3436(3) | 5668(4) | 8465(2) | 55(1) |
| C(15) | 2508(4) | 4508(6) | 8742(3) | 84(1) |
| C(16) | 3955(3) | 5346(3) | 6343(2) | 44(1) |
| C(17) | 4324(3) | 5237(3) | 4226(2) | 41(1) |
| C(18) | 4829(4) | 6495(3) | 3493(2) | 56(1) |
| C(19) | 4950(7) | 5850(5) | 2262(3) | 105(2) |
| C(20) | 4370(5) | 4405(5) | 2216(3) | 80(1) |
| C(21) | 4515(3) | 3862(3) | 3503(3) | 49(1) |

TABLE N

Bond lengths [Å] and angles [°] for 5.

| | |
|---|---|
| N(1)—C(6) | 1.353(3) |
| N(1)—C(5) | 1.446(3) |
| N(1)—H(1X) | 0.93(2) |
| N(2)—C(10) | 1.326(3) |
| N(2)—C(6) | 1.357(3) |
| N(3)—C(16) | 1.393(3) |
| N(3)—C(8) | 1.397(3) |
| N(3)—C(17) | 1.483(3) |
| O(1)—C(1) | 1.416(4) |
| O(1)—H(1Y) | 0.98(2) |
| O(2)—C(3) | 1.404(6) |
| O(2)—C(2) | 1.408(5) |
| O(3)—C(14) | 1.199(4) |
| O(4)—C(16) | 1.233(3) |
| C(1)—C(5) | 1.514(4) |
| C(1)—C(2) | 1.522(4) |
| C(1)—H(1A) | 0.9800 |
| C(2)—H(2A) | 0.9700 |
| C(2)—H(2B) | 0.9700 |
| C(3)—C(4) | 1.507(6) |
| C(3)—H(3A) | 0.9700 |
| C(3)—H(3B) | 0.9700 |
| C(4)—C(5) | 1.526(4) |
| C(4)—H(4A) | 0.9700 |
| C(4)—H(4B) | 0.9700 |
| C(5)—H(5) | 0.9800 |
| C(6)—C(7) | 1.395(3) |
| C(7)—C(8) | 1.384(3) |
| C(7)—H(7) | 0.9300 |
| C(8)—C(9) | 1.420(3) |
| C(9)—C(10) | 1.396(3) |
| C(9)—C(11) | 1.439(3) |
| C(10)—H(10) | 0.9300 |
| C(11)—C(13) | 1.342(4) |
| C(11)—C(12) | 1.507(3) |
| C(12)—H(12A) | 0.9600 |
| C(12)—H(12B) | 0.9600 |
| C(12)—H(12C) | 0.9600 |

TABLE N-continued

Bond lengths [Å] and angles [°] for 5.

| | |
|---|---|
| C(13)—C(16) | 1.459(3) |
| C(13)—C(14) | 1.518(3) |
| C(14)—C(15) | 1.456(5) |
| C(15)—H(15A) | 0.9600 |
| C(15)—H(15B) | 0.9600 |
| C(15)—H(15C) | 0.9600 |
| C(17)—C(21) | 1.533(4) |
| C(17)—C(18) | 1.540(4) |
| C(17)—H(17) | 0.9800 |
| C(18)—C(19) | 1.519(5) |
| C(18)—H(18A) | 0.9700 |
| C(18)—H(18B) | 0.9700 |
| C(19)—C(20) | 1.449(6) |
| C(19)—H(19A) | 0.9700 |
| C(19)—H(19B) | 0.9700 |
| C(20)—C(21) | 1.514(5) |
| C(20)—H(20A) | 0.9700 |
| C(20)—H(20B) | 0.9700 |
| C(21)—H(21A) | 0.9700 |
| C(21)—H(21B) | 0.9700 |
| C(6)—N(1)—C(5) | 126.3(2) |
| C(6)—N(1)—H(1X) | 114(2) |
| C(5)—N(1)—H(1X) | 118(2) |
| C(10)—N(2)—C(6) | 117.2(2) |
| C(16)—N(3)—C(8) | 121.58(18) |
| C(16)—N(3)—C(17) | 116.28(19) |
| C(8)—N(3)—C(17) | 122.12(18) |
| C(1)—O(1)—H(1Y) | 103(2) |
| C(3)—O(2)—C(2) | 111.1(3) |
| O(1)—C(1)—C(5) | 108.4(2) |
| O(1)—C(1)—C(2) | 109.2(3) |
| C(5)—C(1)—C(2) | 109.9(3) |
| O(1)—C(1)—H(1A) | 109.8 |
| C(5)—C(1)—H(1A) | 109.8 |
| C(2)—C(1)—H(1A) | 109.8 |
| O(2)—C(2)—C(1) | 112.8(3) |
| O(2)—C(2)—H(2A) | 109.0 |
| C(1)—C(2)—H(2A) | 109.0 |
| O(2)—C(2)—H(2B) | 109.0 |
| C(1)—C(2)—H(2B) | 109.0 |
| H(2A)—C(2)—H(2B) | 107.8 |
| O(2)—C(3)—C(4) | 112.4(4) |
| O(2)—C(3)—H(3A) | 109.1 |
| C(4)—C(3)—H(3A) | 109.1 |
| O(2)—C(3)—H(3B) | 109.1 |
| C(4)—C(3)—H(3B) | 109.1 |
| H(3A)—C(3)—H(3B) | 107.9 |
| C(3)—C(4)—C(5) | 110.7(3) |
| C(3)—C(4)—H(4A) | 109.5 |
| C(5)—C(4)—H(4A) | 109.5 |
| C(3)—C(4)—H(4B) | 109.5 |
| C(5)—C(4)—H(4B) | 109.5 |
| H(4A)—C(4)—H(4B) | 108.1 |
| N(1)—C(5)—C(1) | 111.9(2) |
| N(1)—C(5)—C(4) | 110.5(3) |
| C(1)—C(5)—C(4) | 109.7(2) |
| N(1)—C(5)—H(5) | 108.2 |
| C(1)—C(5)—H(5) | 108.2 |
| C(4)—C(5)—H(5) | 108.2 |
| N(1)—C(6)—N(2) | 114.4(2) |
| N(1)—C(6)—C(7) | 123.5(2) |
| N(2)—C(6)—C(7) | 122.2(2) |
| C(8)—C(7)—C(6) | 119.9(2) |
| C(8)—C(7)—H(7) | 120.1 |
| C(6)—C(7)—H(7) | 120.1 |
| C(7)—C(8)—N(3) | 122.15(19) |
| C(7)—C(8)—C(9) | 118.55(19) |
| N(3)—C(8)—C(9) | 119.30(19) |
| C(10)—C(9)—C(8) | 116.5(2) |
| C(10)—C(9)—C(11) | 123.4(2) |
| C(8)—C(9)—C(11) | 120.1(2) |
| N(2)—C(10)—C(9) | 125.6(2) |
| N(2)—C(10)—H(10) | 117.2 |
| C(9)—C(10)—H(10) | 117.2 |
| C(13)—C(11)—C(9) | 118.7(2) |
| C(13)—C(11)—C(12) | 121.7(2) |
| C(9)—C(11)—C(12) | 119.6(2) |
| C(11)—C(12)—H(12A) | 109.5 |
| C(11)—C(12)—H(12B) | 109.5 |
| H(12A)—C(12)—H(12B) | 109.5 |
| C(11)—C(12)—H(12C) | 109.5 |
| H(12A)—C(12)—H(12C) | 109.5 |
| H(12B)—C(12)—H(12C) | 109.5 |
| C(11)—C(13)—C(16) | 122.7(2) |
| C(11)—C(13)—C(14) | 122.6(2) |
| C(16)—C(13)—C(14) | 114.8(2) |
| O(3)—C(14)—C(15) | 121.1(3) |
| O(3)—C(14)—C(13) | 119.8(3) |
| C(15)—C(14)—C(13) | 119.0(3) |
| C(14)—C(15)—H(15A) | 109.5 |
| C(14)—C(15)—H(15B) | 109.5 |
| H(15A)—C(15)—H(15B) | 109.5 |
| C(14)—C(15)—H(15C) | 109.5 |
| H(15A)—C(15)—H(15C) | 109.5 |
| H(15B)—C(15)—H(15C) | 109.5 |
| O(4)—C(16)—N(3) | 121.1(2) |
| O(4)—C(16)—C(13) | 121.6(2) |
| N(3)—C(16)—C(13) | 117.3(2) |
| N(3)—C(17)—C(21) | 116.1(2) |
| N(3)—C(17)—C(18) | 115.5(2) |
| C(21)—C(17)—C(18) | 106.2(2) |
| N(3)—C(17)—H(17) | 106.1 |
| C(21)—C(17)—H(17) | 106.1 |
| C(18)—C(17)—H(17) | 106.1 |
| C(19)—C(18)—C(17) | 104.7(3) |
| C(19)—C(18)—H(18A) | 110.8 |
| C(17)—C(18)—H(18A) | 110.8 |
| C(19)—C(18)—H(18B) | 110.8 |
| C(17)—C(18)—H(18B) | 110.8 |
| H(18A)—C(18)—H(18B) | 108.9 |
| C(20)—C(19)—C(18) | 108.7(3) |
| C(20)—C(19)—H(19A) | 110.0 |
| C(18)—C(19)—H(19A) | 110.0 |
| C(20)—C(19)—H(19B) | 110.0 |
| C(18)—C(19)—H(19B) | 110.0 |
| H(19A)—C(19)—H(19B) | 108.3 |
| C(19)—C(20)—C(21) | 106.6(3) |
| C(19)—C(20)—H(20A) | 110.4 |
| C(21)—C(20)—H(20A) | 110.4 |
| C(19)—C(20)—H(20B) | 110.4 |
| C(21)—C(20)—H(20B) | 110.4 |
| H(20A)—C(20)—H(20B) | 108.6 |
| C(20)—C(21)—C(17) | 102.9(2) |
| C(20)—C(21)—H(21A) | 111.2 |
| C(17)—C(21)—H(21A) | 111.2 |
| C(20)—C(21)—H(21B) | 111.2 |
| C(17)—C(21)—H(21B) | 111.2 |
| H(21A)—C(21)—H(21B) | 109.1 |

Symmetry transformations used to generate equivalent atoms.

TABLE P

Anisotropic displacement parameters (Å$^2$ × 10$^3$) for 5. The anisotropic displacement factor exponent takes the form: $-2\pi^2[h^2 a^{*2}U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| N(1) | 32(1) | 79(2) | 48(1) | 11(1) | 7(1) | 9(1) |
| N(2) | 35(1) | 58(1) | 44(1) | 8(1) | 0(1) | 3(1) |

TABLE P-continued

Anisotropic displacement parameters (Å$^2$ × 10$^3$) for 5. The anisotropic displacement factor exponent takes the form: $-2\pi^2[h^2 a^{*2}U^{11} + \ldots + 2 h k a^* b^* U^{12}]$.

|       | $U^{11}$ | $U^{22}$ | $U^{33}$ | $U^{23}$ | $U^{13}$ | $U^{12}$ |
|-------|------|------|------|------|------|------|
| N(3)  | 35(1) | 42(1) | 32(1) | 1(1) | 4(1) | 4(1) |
| O(1)  | 57(1) | 53(1) | 81(2) | 1(1) | 2(1) | 2(1) |
| O(2)  | 91(2) | 128(3) | 69(2) | −6(2) | 43(1) | −10(2) |
| O(3)  | 127(3) | 86(2) | 151(3) | −48(2) | 92(2) | −17(2) |
| O(4)  | 38(1) | 118(2) | 49(1) | 0(1) | 9(1) | 10(1) |
| C(1)  | 41(1) | 59(2) | 53(2) | 3(1) | 4(1) | −4(1) |
| C(2)  | 77(2) | 93(3) | 51(2) | 12(2) | 9(2) | −12(2) |
| C(3)  | 101(3) | 96(3) | 87(3) | −22(2) | 45(2) | 8(3) |
| C(4)  | 68(2) | 70(2) | 82(2) | 2(2) | 29(2) | 20(2) |
| C(5)  | 34(1) | 54(2) | 49(1) | 2(1) | 10(1) | 1(1) |
| C(6)  | 33(1) | 44(1) | 44(1) | 5(1) | 6(1) | 0(1) |
| C(7)  | 35(1) | 47(1) | 34(1) | 3(1) | 2(1) | 1(1) |
| C(8)  | 34(1) | 32(1) | 36(1) | 1(1) | 3(1) | −3(1) |
| C(9)  | 38(1) | 39(1) | 33(1) | 1(1) | 2(1) | −2(1) |
| C(10) | 42(1) | 50(1) | 37(1) | 5(1) | −1(1) | −2(1) |
| C(11) | 46(1) | 45(1) | 34(1) | −1(1) | 6(1) | −7(1) |
| C(12) | 62(2) | 99(2) | 33(1) | −4(2) | 5(1) | −2(2) |
| C(13) | 47(1) | 47(2) | 37(1) | −2(1) | 13(1) | −2(1) |
| C(14) | 56(2) | 70(2) | 43(1) | −10(1) | 16(1) | −2(1) |
| C(15) | 81(2) | 113(3) | 67(2) | −19(2) | 38(2) | −36(2) |
| C(16) | 42(1) | 53(2) | 39(1) | 0(1) | 10(1) | 1(1) |
| C(17) | 36(1) | 52(1) | 35(1) | −3(1) | 0(1) | 7(1) |
| C(18) | 82(2) | 44(1) | 40(1) | 4(1) | 2(1) | 14(1) |
| C(19) | 200(6) | 76(3) | 40(2) | 0(2) | 24(2) | −20(3) |
| C(20) | 119(3) | 78(2) | 41(2) | −14(2) | 6(2) | 11(2) |
| C(21) | 52(1) | 48(1) | 46(1) | −6(1) | −1(1) | −5(1) |

Thus, one embodiment of the invention provides 3-acetyl-1-cyclopentyl-7-{[(3S,4R)-3-hydroxytetrahydro-2H-pyran-4-yl]amino}-4-methyl-1,6-naphthyridin-2(1H)-one as a crystalline solid. In another further embodiment, the crystalline solid is anhydrous.

Acquisition of Powder X-ray Diffraction (PXRD) Data for Crystal 5

A sample the crystal 5 (anhydrous) was submitted for PXRD analysis and found to be a crystalline material (designated as Form I). Powder X-ray diffraction analysis was conducted using a Bruker D8 Advance diffractometer equipped with a Cu radiation source. The divergence slit was set at 10 mm continuous illumination. Diffracted radiation was detected by a LYNXEYE_EX detector with motorized slits. The X-ray tube voltage and amperage were set to 40 kV and 40 mA respectively. Data was collected at the Cu wavelength (CuK$_\alpha$=1.5418λ) in the Theta-Theta goniometer from 3.0 to 40.0 degrees 2-Theta using a step size of 0.01 degrees and a step time of 1.0 second with an antiscatter screen in place. Samples were rotated during data collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +1-0.2° 2-Theta (USP-941). One diffraction pattern was consistently observed and is provided in FIG. 1. A list of diffraction peaks expressed in terms of the degree 2θ and relative intensities with a relative intensity of 3.0% of a PXRD from a sample of crystal 5 (obtained by the methods provided herein) are shown in Table X1 below.

TABLE X1

| Angle (2-Theta) | Relative Intensity (%) |
|---|---|
| 8.0 | 100.0 |
| 14.9 | 3.7 |
| 16.0 | 45.3 |
| 16.2 | 34.9 |
| 17.4 | 3.5 |
| 18.6 | 50.5 |
| 19.1 | 71.8 |
| 19.9 | 7.3 |
| 20.8 | 18.2 |
| 20.9 | 17.7 |
| 21.3 | 19.8 |
| 21.5 | 9.3 |
| 21.8 | 4.1 |
| 22.3 | 6.1 |
| 23.3 | 68.9 |
| 26.0 | 9.2 |
| 26.2 | 12.7 |
| 26.5 | 7.7 |
| 28.1 | 9.5 |
| 30.0 | 13.7 |
| 30.4 | 3.3 |
| 31.1 | 7.3 |
| 32.3 | 4.1 |
| 33.2 | 4.2 |
| 33.9 | 7.8 |
| 36.2 | 5.3 |

Examples 6 and 7
6-Acetyl-8-[(1S,2S)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one and 6-Acetyl-8-[(1R,2R)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one [6 (DIAST-1) and 7 (DIAST-2)]
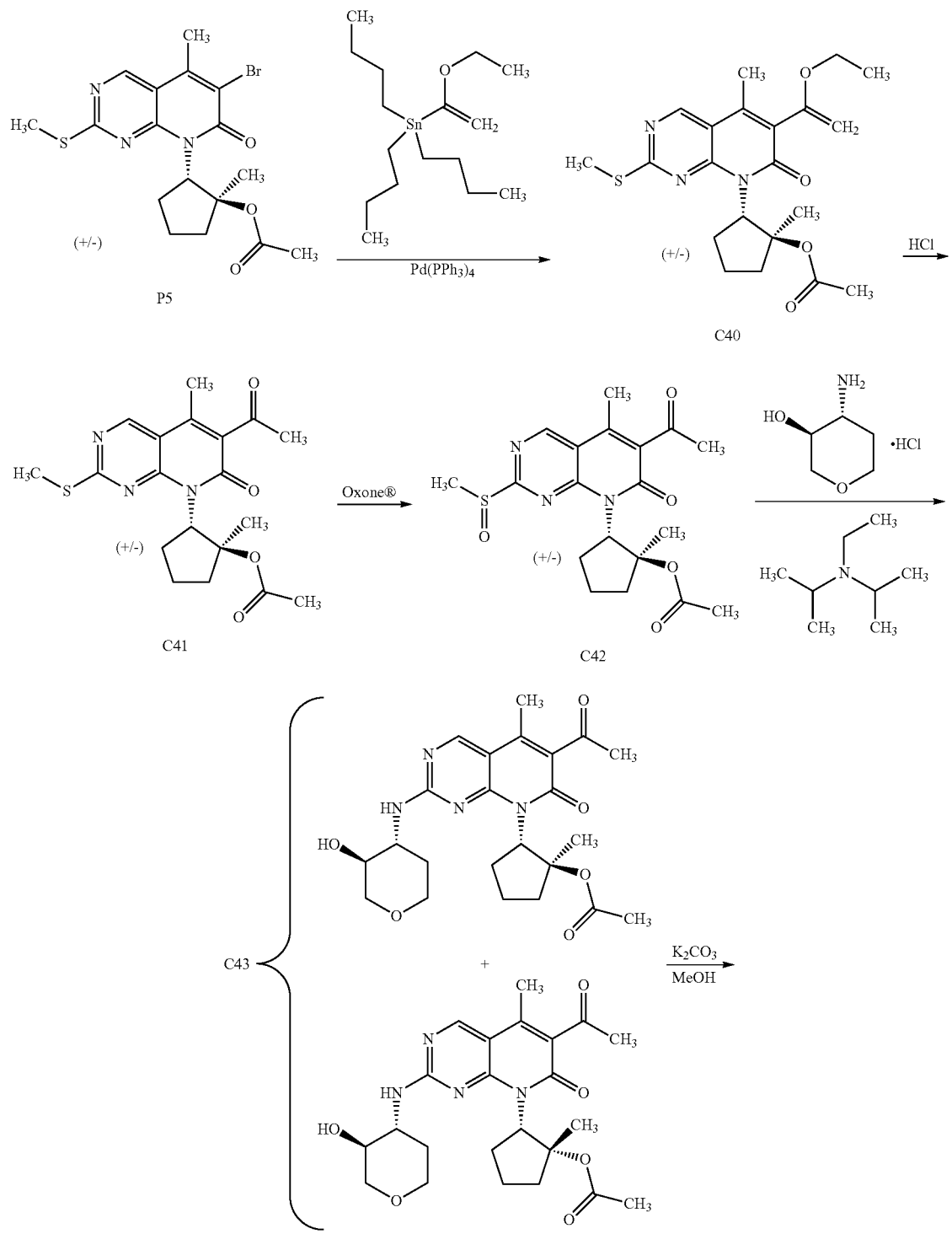

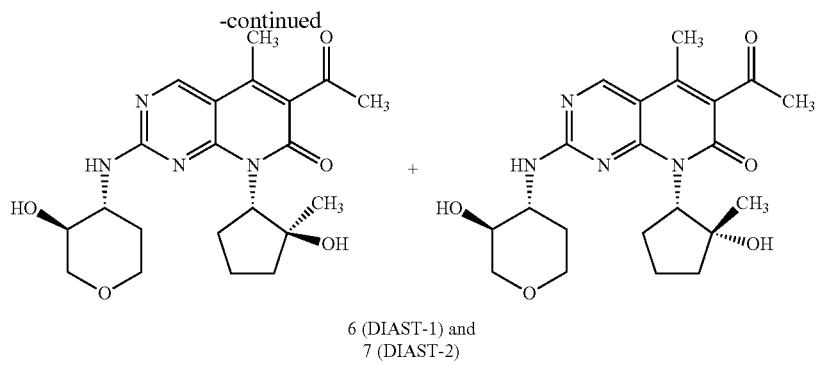

6 (DIAST-1) and
7 (DIAST-2)

Step 1. Synthesis of rac-(1S,2S)-2-[6-(1-ethoxyethenyl)-5-methyl-2-(methylthio)-7-oxopyrido[2,3-d]pyrimidin-8(7H)-yl]-1-methylcyclopentyl acetate (C40)

A mixture of P5 (447 mg, 1.05 mmol), tributyl(1-ethoxyethenyl)stannane (568 mg, 1.57 mmol), and tetrakis(triphenylphosphine)palladium(0) (72.7 mg, 62.9 μmol) in toluene (10 mL) was heated at reflux for 5 hours. LCMS analysis of the reaction mixture at this point indicated the presence of product C40: LCMS m/z 418.1 [M+H]$^+$. After the reaction mixture had been filtered through diatomaceous earth, the filtrate was concentrated in vacuo, and the residue was purified using silica gel chromatography (Gradient: 20% to 60% ethyl acetate in heptane) to afford C40 as a pale yellow foam. Yield: 380 mg, 0.91 mmol, 87%. $^1$H NMR (400 MHz, chloroform-d), characteristic peaks: δ 8.76 (s, 1H), 6.48-6.23 (m, 1H), 4.54 (d, J=2.5 Hz, 1H), 4.17 (d, J=2.5 Hz, 1H), 3.93 (q, J=7.0 Hz, 2H), 2.62 (s, 3H), 2.62-2.52 (m, 1H), 2.45 (s, 3H), 1.99 (s, 3H), 1.85-1.71 (m, 1H), 1.44 (br s, 3H), 1.35 (t, J=7.0 Hz, 3H).

Step 2. Synthesis of rac-(1S,2S)-2-[6-acetyl-5-methyl-2-(methylthio)-7-oxopyrido[2,3-d]pyrimidin-8(7H)-yl]-1-methylcyclopentyl acetate (C41)

Hydrochloric acid (1.0 M; 3.46 mL, 3.46 mmol) was added to a solution of C40 (361 mg, 0.865 mmol) in tetrahydrofuran (27 mL), and the reaction mixture was stirred at room temperature for 40 minutes. LCMS analysis of the reaction mixture at this point indicated the presence of product C41: LCMS m/z 390.1 [M+H]$^+$. Saturated aqueous sodium bicarbonate solution was added, and the resulting mixture was extracted with ethyl acetate. The combined organic layers were dried over magnesium sulfate, filtered, concentrated in vacuo, and subjected to chromatography on silica gel, providing C41 as a solid. Yield: 315 mg, 0.809 mmol, 94%. $^1$H NMR (400 MHz, chloroform-d), characteristic peaks: δ 8.80 (s, 1H), 6.48-6.24 (br s, 1H), 2.61 (s, 3H), 2.51 (s, 3H), 2.38 (s, 3H), 2.36-2.24 (m, 1H), 2.10-1.97 (m, 2H), 1.99 (s, 3H), 1.87-1.73 (m, 1H), 1.45 (br s, 3H).

Step 3. Synthesis of rac-(1S,2S)-2-[6-acetyl-5-methyl-2-(methylsulfinyl)-7-oxopyrido[2,3-d]pyrimidin-8(7H)-yl]-1-methylcyclopentyl acetate (C42)

A solution of potassium peroxymonosulfate (Oxone®; 1.05 g, 1.71 mmol) in water (5 mL) was added to a solution of C41 (315 mg, 0.809 mmol) in tetrahydrofuran (20 mL), and the reaction mixture was stirred at room temperature for 16 hours. LCMS analysis of the reaction mixture at this point indicated that C42 had been formed: LCMS m/z 346.0 [(M-acetic acid)+H]$^+$. Water was added, and the resulting mixture was extracted twice with ethyl acetate. The combined organic layers were dried over sodium sulfate, filtered, and concentrated in vacuo to provide C42 as a pale yellow solid. Yield: 299 mg, 0.737 mmol, 91%. $^1$H NMR (400 MHz, chloroform-d), characteristic peaks: δ 9.13 (s, 1H), 6.46-6.02 (br s, 1H), 3.36 (s, 3H), 2.53 (s, 3H), 2.46 (s, 3H), 2.36-2.20 (m, 2H), 2.16-2.02 (m, 2H), 1.98 (s, 3H), 1.44 (br s, 3H).

Step 4. Synthesis of (1S,2S)-2-[6-acetyl-2-{[(3S,4R)-3-hydroxytetrahydro-2H-pyran-4-yl]amino}-5-methyl-7-oxopyrido[2,3-d]pyrimidin-8(7H)-yl]-1-methylcyclopentyl acetate and (1R,2R)-2-[6-acetyl-2-{[(3S,4R)-3-hydroxytetrahydro-2H-pyran-4-yl]amino}-5-methyl-7-oxopyrido[2,3-d]pyrimidin-8(7H)-yl]-1-methylcyclopentyl acetate (C43)

A mixture of C42 (170 mg, 0.419 mmol), (3S,4R)-4-aminotetrahydro-2H-pyran-3-ol hydrochloride (129 mg, 0.840 mmol), and N,N-diisopropylethylamine (0.348 mL, 2.00 mmol) in dimethyl sulfoxide (3 mL) was stirred at 50° C. for 1 hour. LCMS analysis of the reaction mixture at this point indicated the presence of C43, as two peaks of equal size for the two component diastereomers: LCMS m/z 399.2 [(M-acetic acid)+H]$^+$. After the reaction mixture had been diluted with water and extracted with dichloromethane, the combined organic layers were dried over magnesium sulfate, filtered, and concentrated in vacuo. Silica gel chromatography (Gradient: 0% to 10% ethyl acetate in heptane) provided C43 as an off-white solid. The $^1$H NMR spectrum of C43 was consistent with the presence of 2 diastereomers. Yield: 170 mg, 0.371 mmol, 88%. $^1$H NMR (400 MHz, chloroform-d), characteristic peaks: δ [8.63 (s) and 8.62 (s), total 1H], 6.35-6.07 (m, 1H), 4.13-4.04 (m, 1H), 4.04-3.91 (m, 2H), 3.71-3.42 (m, 2H), 3.21 (ddd, J=11.3, 9.6, 6.2 Hz, 1H), [2.49 (s) and 2.49 (s), total 3H], [2.34 (s) and 2.33 (s), total 3H], [2.04 (s) and 2.02 (s), total 3H], 1.47 (br s, 3H).

Step 5. Synthesis of 6-acetyl-8-[(1S,2S)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one and 6-acetyl-8-[(1R,2R)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one [6 (DIAST-1) and 7 (DIAST-2)]

Potassium carbonate (512 mg, 3.70 mmol) was added to a solution of C43 (170 mg, 0.371 mmol) in methanol (12 mL). The reaction mixture was stirred at room temperature for 24 hours, whereupon it was diluted with water and extracted with dichloromethane. The combined organic layers were dried over sodium sulfate, filtered, concentrated in vacuo, and purified via chromatography on silica gel (Gradient: 0% to 10% ethyl acetate in heptane) to provide a mixture of 6 and 7 as a pale yellow solid. Yield: 115 mg, 0.276 mmol, 74%. Separation of the two diastereomers was carried out using supercritical fluid chromatography (Column: Chiral Technologies Chiralcel OJ-H, 5 μm; Mobile phase: 4:1 carbon dioxide/methanol; Back pressure: 100 bar). The first-eluting diastereomer was designated as 6, and the second-eluting diastereomer as 7; both were isolated as solids.

6 (DIAST-1)—Yield: 23.1 mg, 55.5 μmol, 20% for the separation. LCMS m/z 416.9 [M+H]$^+$. $^1$H NMR (400 MHz, 80° C., DMSO-d$_6$), characteristic peaks: δ 8.77 (s, 1H), 7.45 (br s, 1H), 5.91-5.82 (m, 1H), 4.11 (s, 1H), 4.03-3.93 (m, 1H), 3.90-3.81 (m, 2H), 3.58-3.47 (m, 1H), 3.38 (ddd, J=11.7, 11.6, 2.3 Hz, 1H), 3.08 (dd, J=11.2, 9.6 Hz, 1H), 2.66-2.55 (m, 1H), 2.39 (s, 3H), 2.29 (s, 3H), 2.20-2.10 (m, 1H), 2.05-1.81 (m, 4H), 1.78-1.69 (m, 1H), 1.69-1.56 (m, 1H), 1.03 (s, 3H). Retention time: 0.54 minutes (Column: Chiral Technologies Chiralcel OJ-3, 4.6×100 mm, 3 μm; Mobile phase: 4:1 carbon dioxide/methanol; Flow rate: 4 mL/minute; Back pressure: 120 bar).

7 (DIAST-2)—Yield: 23.4 mg, 56.2 μmol, 20% for the separation. LCMS m/z 416.9 [M+H]$^+$. $^1$H NMR (400 MHz, 80° C., DMSO-d$_6$), characteristic peaks: δ 8.77 (s, 1H), 7.41 (br d, J=7.6 Hz, 1H), 5.88 (dd, J=9.4, 7.5 Hz, 1H), 3.99 (s, 1H), 3.97-3.87 (m, 1H), 3.87 (dd, J=11.1, 4.8, 1H), 3.84-3.77 (m, 1H), 3.64-3.54 (m, 1H), 3.37 (ddd, J=11.8, 11.5, 2.4 Hz, 1H), 3.09 (dd, J=11.0, 9.6 Hz, 1H), 2.39 (s, 3H), 2.29 (s, 3H), 2.27-2.17 (m, 1H), 2.15-2.06 (m, 1H), 2.04-1.93 (m, 1H), 1.93-1.82 (m, 2H), 1.76-1.67 (m, 1H), 1.58-1.44 (m, 1H), 1.04 (s, 3H). Retention time: 0.79 minutes (Analytical conditions identical to those used for 6).

Examples 8 and 9

6-Acetyl-8-cyclopentyl-2-{[(3S,4R)-3-hydroxy-2,2-dimethyltetrahydro-2H-pyran-4-yl]amino}-5-methylpyrido[2,3-d]pyrimidin-7(8H)-one and 6-Acetyl-8-cyclopentyl-2-{[(3R,4S)-3-hydroxy-2,2-dimethyltetrahydro-2H-pyran-4-yl]amino}-5-methylpyrido[2,3-d]pyrimidin-7(8H)-one [8 (ENT-1) and 9 (ENT-2)]

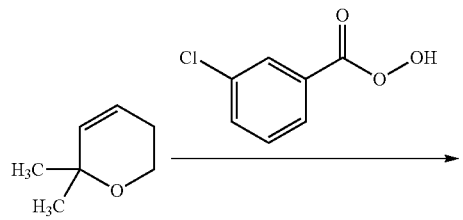

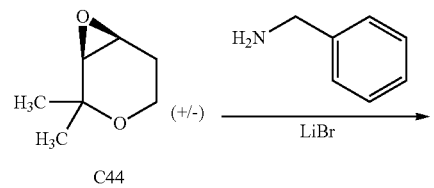

C44

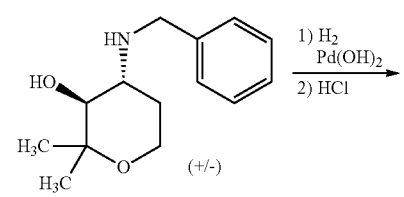

C45

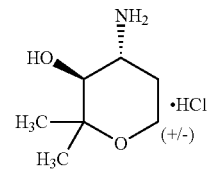

C46

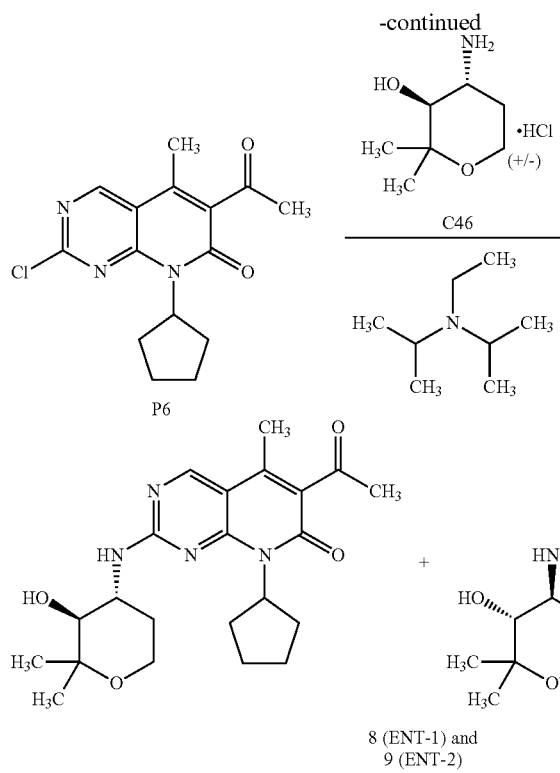
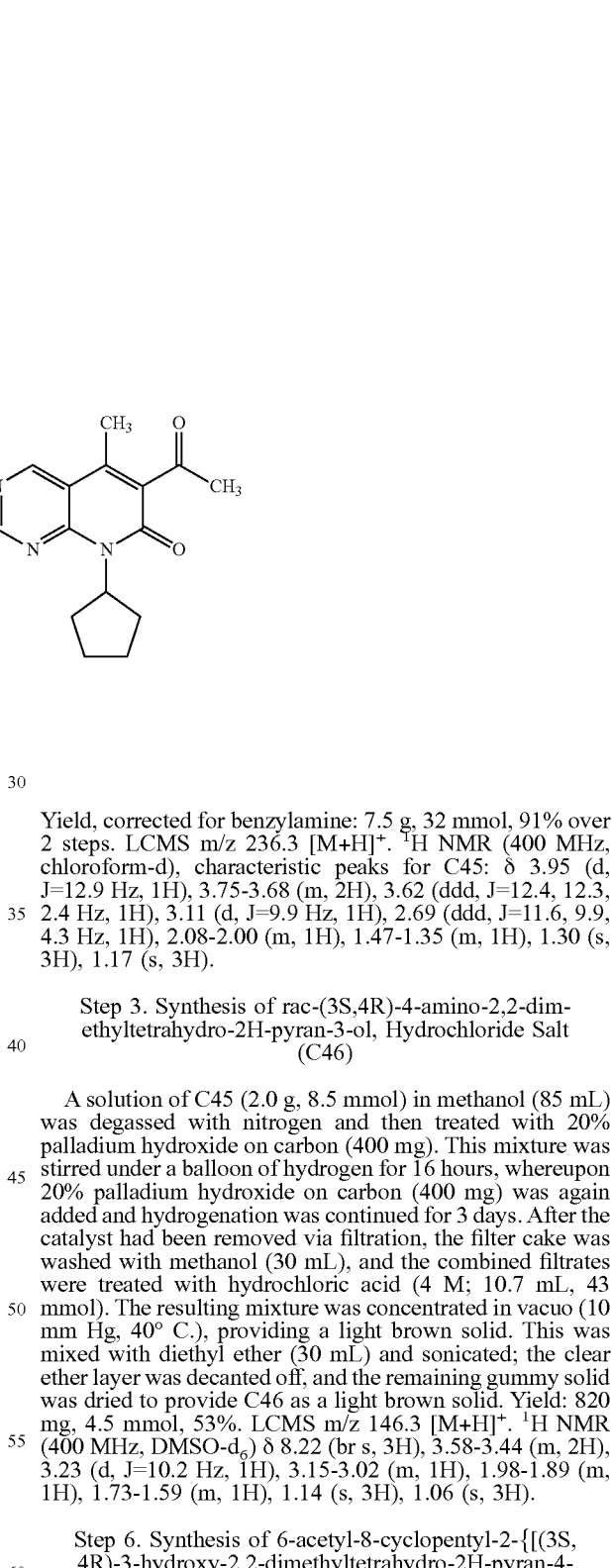

8 (ENT-1) and
9 (ENT-2)

Step 1. Synthesis of rac-(1S,6S)-2,2-dimethyl-3,7-dioxabicyclo[4.1.0]heptane (C44)

3-Chloroperoxybenzoic acid (70%, 11.2 g, 45.4 mmol) was added to a solution of 6,6-dimethyl-3,6-dihydro-2H-pyran (see L-I. Olsson and A. Claesson, *Synthesis* 1979, 743-745) (3.9 g, 35 mmol) in chloroform (35 mL), which was stirring in a water bath to maintain the reaction mixture at room temperature. After 16 hours, the reaction mixture, still in the water bath, was carefully treated with a solution of sodium sulfite (4.4 g, 35 mmol) in water (20 mL). Saturated aqueous sodium bicarbonate solution (20 mL) was added, and the aqueous layer was extracted with dichloromethane (2×80 mL). The combined organic layers were dried over sodium sulfate, filtered, and gently evaporated (10 mm Hg, <20° C.) to provide C44 (4.49 g), which was taken directly to the following step. By $^1$H NMR analysis, this material contained 3-chlorobenzoic acid-derived impurities. $^1$H NMR (400 MHz, chloroform-d), C44 peaks only: δ 3.58 (ddd, J=11.8, 8.6, 4.7 Hz, 1H), 3.44 (ddd, J=11.8, 5.2, 4.2 Hz, 1H), 3.40-3.36 (m, 1H), 2.91 (d, J=4.3 Hz, 1H), 2.00-1.86 (m, 2H), 1.32 (s, 3H), 1.29 (s, 3H).

Step 2. Synthesis of rac-(3S,4R)-4-(benzylamino)-2,2-dimethyltetrahydro-2H-pyran-3-ol (C45)

A mixture of C44 (from the previous step; 4.49 g, 35 mmol), benzylamine (11.5 mL, 105 mmol), and lithium bromide (30.4 g, 350 mmol) in toluene (35 mL) was heated at 60° C. for 16 hours. The reaction mixture was then concentrated in vacuo, mixed with methanol, and concentrated again, whereupon the residue was partitioned between saturated aqueous sodium bicarbonate solution (100 mL) and ethyl acetate (500 mL). Water (400 mL) was added to assist in solubilization, and the aqueous layer was extracted with ethyl acetate (2×400 mL). The combined organic layers were dried over sodium sulfate, filtered, and concentrated under reduced pressure to provide C45 (14.2 g). By $^1$H NMR analysis, this sample contained substantial benzylamine. Yield, corrected for benzylamine: 7.5 g, 32 mmol, 91% over 2 steps. LCMS m/z 236.3 [M+H]$^+$. $^1$H NMR (400 MHz, chloroform-d), characteristic peaks for C45: δ 3.95 (d, J=12.9 Hz, 1H), 3.75-3.68 (m, 2H), 3.62 (ddd, J=12.4, 12.3, 2.4 Hz, 1H), 3.11 (d, J=9.9 Hz, 1H), 2.69 (ddd, J=11.6, 9.9, 4.3 Hz, 1H), 2.08-2.00 (m, 1H), 1.47-1.35 (m, 1H), 1.30 (s, 3H), 1.17 (s, 3H).

Step 3. Synthesis of rac-(3S,4R)-4-amino-2,2-dimethyltetrahydro-2H-pyran-3-ol, Hydrochloride Salt (C46)

A solution of C45 (2.0 g, 8.5 mmol) in methanol (85 mL) was degassed with nitrogen and then treated with 20% palladium hydroxide on carbon (400 mg). This mixture was stirred under a balloon of hydrogen for 16 hours, whereupon 20% palladium hydroxide on carbon (400 mg) was again added and hydrogenation was continued for 3 days. After the catalyst had been removed via filtration, the filter cake was washed with methanol (30 mL), and the combined filtrates were treated with hydrochloric acid (4 M; 10.7 mL, 43 mmol). The resulting mixture was concentrated in vacuo (10 mm Hg, 40° C.), providing a light brown solid. This was mixed with diethyl ether (30 mL) and sonicated; the clear ether layer was decanted off, and the remaining gummy solid was dried to provide C46 as a light brown solid. Yield: 820 mg, 4.5 mmol, 53%. LCMS m/z 146.3 [M+H]$^+$. $^1$H NMR (400 MHz, DMSO-d$_6$) δ 8.22 (br s, 3H), 3.58-3.44 (m, 2H), 3.23 (d, J=10.2 Hz, 1H), 3.15-3.02 (m, 1H), 1.98-1.89 (m, 1H), 1.73-1.59 (m, 1H), 1.14 (s, 3H), 1.06 (s, 3H).

Step 6. Synthesis of 6-acetyl-8-cyclopentyl-2-{[(3S,4R)-3-hydroxy-2,2-dimethyltetrahydro-2H-pyran-4-yl]amino}-5-methylpyrido[2,3-d]pyrimidin-7(8H)-one and 6-acetyl-8-cyclopentyl-2-{[(3R,4S)-3-hydroxy-2,2-dimethyltetrahydro-2H-pyran-4-yl]amino}-5-methylpyrido[2,3-d]pyrimidin-7(8H)-one [8 (ENT-1) and 9 (ENT-2)]

A vial containing a solution of P6 (317 mg, 1.04 mmol), C46 (290 mg, 1.6 mmol), and N,N-diisopropylethylamine (0.90 mL, 5.2 mmol) in dimethyl sulfoxide (4 mL) was capped and heated to 80° C. (block temperature) with stirring for 16 hours. The reaction mixture was then partitioned between dichloromethane (100 mL) and saturated aqueous sodium bicarbonate solution (20 mL), and the aqueous layer was extracted with dichloromethane (30 mL). The combined organic layers were dried over sodium sulfate, filtered, and concentrated in vacuo. Separation of the component enantiomers was carried out using supercritical fluid chromatography (Column: Chiral Technologies Chiralpak AD-H, 5 μm; Mobile phase: 3:2 carbon dioxide/methanol; Back pressure: 100 bar); the first-eluting enantiomer, which exhibited a negative (−) rotation, was designated as 8, and the second-eluting enantiomer, which exhibited a positive (+) rotation, was designated as 9. From examination of the ¹H NMR spectra, both of these materials were assumed to exist as a mixture of rotamers.

8 (ENT-1)—Yield: 162 mg, 0.391 mmol, 38%. LCMS m/z 415.0 [M+H]⁺. ¹H NMR (700 MHz, DMSO-d₆) δ [8.78 (s) and 8.73 (s), total 1H], [7.72-7.65 (m) and 7.56-7.50 (m), total 1H], [5.91-5.81 (m) and 5.74-5.62 (m), total 1H], 5.08-4.99 (m, 1H), [4.14 (br s) and 4.04 (br s), total 1H], [3.6-3.49 (m) and 3.31-3.19 (m), total 1H, assumed; downfield signal partially obscured by water peak], 2.38 (s, 3H), 2.36-2.28 (m, 1H), 2.23 (s, 3H), 2.16 (br s, 1H), 2.01-1.49 (m, 10H), 1.16 (s, 3H), 1.12 (s, 3H). Retention time: 1.27 minutes (Column: Chiral Technologies Chiralpak AD-3, 4.6×100 mm, 3 μm; Mobile phase: 3:2 carbon dioxide/methanol; Flow rate: 4 mL/minute; Back pressure: 120 bar).

9 (ENT-2)—Yield: 151 mg, 0.364 mmol, 35%. LCMS m/z 415.0 [M+H]⁺. ¹H NMR (700 MHz, DMSO-d₆) δ [8.78 (s) and 8.73 (s), total 1H], [7.69 (br s) and 7.53 (br s), total 1H], [5.86 (br s) and 5.68 (br s), total 1H], 5.08-4.98 (m, 1H), [4.14 (br s) and 4.04 (br s), total 1H], [3.6-3.49 (m) and 3.30-3.18 (m), total 1H, assumed; downfield signal partially obscured by water peak], 2.38 (s, 3H), 2.36-2.29 (m, 1H), 2.23 (s, 3H), 2.20-2.12 (m, 1H), 2.01-1.49 (m, 10H), 1.16 (s, 3H), 1.12 (s, 3H). Retention time: 2.24 minutes (Analytical conditions identical to those used for 8).

Example 10

6-Acetyl-8-[(1R,2S)-2-ethylcyclopentyl]-2-{[(3S,4R)-3-hydroxytetrahydro-2H-pyran-4-yl]amino}-5-methylpyrido[2,3-d]pyrimidin-7(8H)-one (10)

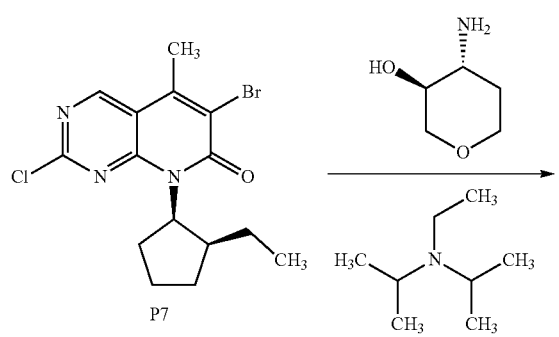

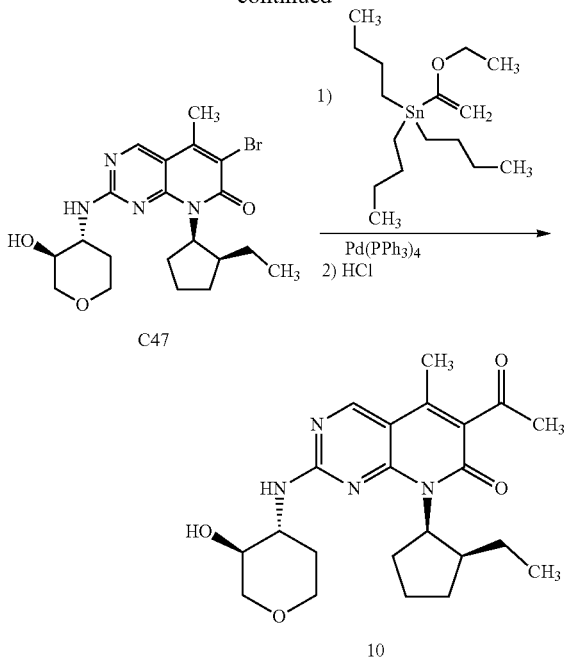

Step 1. Synthesis of 6-bromo-8-[(1R,2S)-2-ethylcyclopentyl]-2-{[(3S,4R)-3-hydroxytetrahydro-2H-pyran-4-yl]amino}-5-methylpyrido[2,3-d]pyrimidin-7(8H)-one (C47)

A solution of P7 (80 mg, 0.22 mmol), (3S,4R)-4-aminotetrahydro-2H-pyran-3-ol (75.8 mg, 0.647 mmol), and N,N-diisopropylethylamine (0.239 mL, 1.37 mmol) in dimethyl sulfoxide (1.5 mL) was stirred at 60° C. for 16 hours. (3S,4R)-4-Aminotetrahydro-2H-pyran-3-ol (75.8 mg, 0.647 mmol) and N,N-diisopropylethylamine (0.239 mL, 1.37 mmol) were again added, and the reaction mixture was stirred at 65° C. for 3 hours, whereupon it was diluted with water. The resulting solids were collected via filtration and washed with water, then dissolved in ethyl acetate and dried over sodium sulfate, filtered, and concentrated in vacuo. The residue was purified using silica gel chromatography (Gradient: 0% to 100% ethyl acetate in heptane); the resulting material was dissolved in a mixture of water and acetonitrile, and then lyophilized, affording C47 as a light yellow solid. Yield: 60 mg, 0.13 mmol, 59%. LCMS m/z 452.8 (bromine isotope pattern observed) [M+H]⁺. ¹H NMR (400 MHz, DMSO-d₆) δ 8.76 (s, 1H), 7.39 (br s, 1H), 6.15-6.05 (m, 1H), 4.71-4.65 (m, 1H), 3.95-3.79 (m, 3H), 3.64-3.54 (m, 1H), 3.37 (ddd, J=11.7, 11.5, 2.2 Hz, 1H), 3.10 (dd, J=11.1, 9.5 Hz, 1H), 2.54 (s, 3H), 2.14-2.04 (m, 1H), 2.04-1.94 (m, 2H), 1.94-1.82 (m, 3H), 1.62-1.42 (m, 3H), 1.15-1.03 (m, 2H), 0.74 (t, J=7.4 Hz, 3H).

Step 2. Synthesis of 6-acetyl-8-[(1R,2S)-2-ethylcyclopentyl]-2-{[(3S,4R)-3-hydroxytetrahydro-2H-pyran-4-yl]amino}-5-methylpyrido[2,3-d]pyrimidin-7(8H)-one (10)

A solution of C47 (60 mg, 0.13 mmol), tributyl(1-ethoxyethenyl)stannane (84.0 mg, 0.233 mmol), and tetrakis(triphenylphosphine)palladium(0) (7.8 mg, 6.8 μmol) in toluene (8 mL) was purged with nitrogen and then heated to 110° C. for 20 hours. After the reaction mixture had been filtered through a syringe filter, the filtrate was concentrated in vacuo, and the residue was diluted with tetrahydrofuran. Hydrogen chloride (4 M solution in 1,4-dioxane; 0.332 mL, 1.33 mmol) and water (0.5 mL) were added, and the reaction mixture was stirred for 1.5 hours at room temperature, whereupon it was concentrated under reduced pressure. Purification via supercritical fluid chromatography (Column: Nacalai Cosmosil 3-Hydroxyphenyl; Mobile phase: 88:12 carbon dioxide/methanol) afforded 10. From $^1$H NMR analysis, this material was presumed to exist as a mixture of rotamers. Yield: 30 mg, 72 μmol, 55%. LCMS m/z 415.2 [M+H]$^+$. $^1$H NMR (700 MHz, DMSO-d$_6$), characteristic peaks: δ [8.80 (s) and 8.77 (s), total 1H], [7.91 (br s) and 7.75 (br s), total 1H], [6.12 (br s) and 6.00 (br s), total 1H], [5.00 (s) and 4.98 (s), total 1H], 4.03-3.75 (m, 3H), 3.62-3.48 (m, 1H), 3.11-2.99 (m, 1H), 2.38 (s, 3H), 2.26 (s, 3H), 2.07-1.78 (m, 5H), 1.57-1.40 (m, 2H), 1.15-0.99 (m, 2H), [0.75 (br s) and 0.71 (br s), total 3H].

Example 11

3-Acetyl-7-{[(3S,4R)-3-hydroxytetrahydro-2H-pyran-4-yl]amino}-4-methyl-1-[(3S)-tetrahydrofuran-3-yl]-1,6-naphthyridin-2(1H)-one (11)

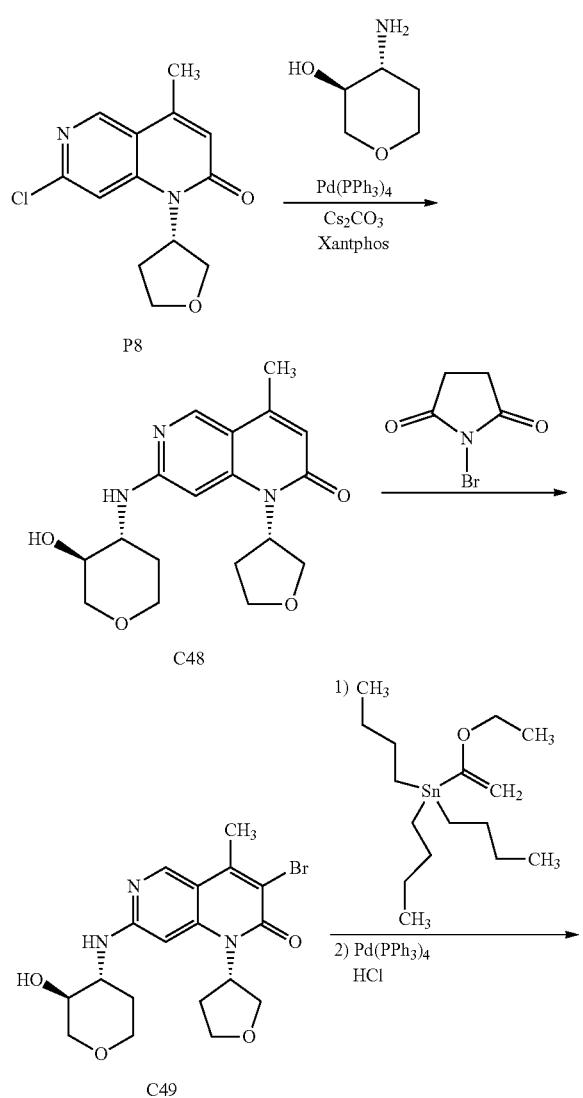

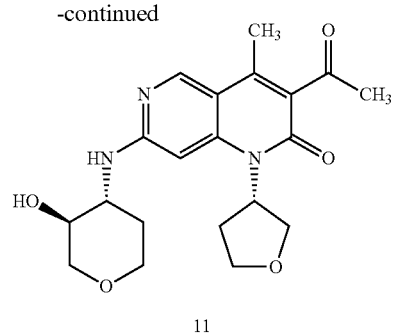

11

Step 1. Synthesis of 7-{[(3S,4R)-3-hydroxytetrahydro-2H-pyran-4-yl]amino}-4-methyl-1-[(3S)-tetrahydrofuran-3-yl]-1,6-naphthyridin-2(1H)-one (C48)

To a mixture of P8 (150 mg, 0.567 mmol), (3S,4R)-4-aminotetrahydro-2H-pyran-3-ol (79.7 mg, 0.680 mmol), cesium carbonate (554 mg, 1.70 mmol), tetrakis(triphenylphosphine)palladium(0) (65.5 mg, 56.7 μmol), and 4,5-bis(diphenylphosphino)-9,9-dimethylxanthene (Xantphos; 65.6 mg, 0.113 mmol) was added toluene (6 mL). Nitrogen was bubbled through the resulting suspension, which was then stirred at 110° C. for 16 hours. After another addition of 4,5-bis(diphenylphosphino)-9,9-dimethylxanthene (32.8 mg, 56.7 μmol) and tetrakis(triphenylphosphine)palladium (0) (32.8 mg, 28.4 μmol), nitrogen was again bubbled through the reaction mixture, and it was subsequently heated at 110° C. for 4 hours, then filtered. The filtrate was concentrated in vacuo; LCMS analysis at this point indicated the presence of C48: LCMS m/z 346.0 [M+H]$^+$. Upon preparative thin-layer chromatography on silica gel (Eluent: 10:1 dichloromethane/methanol), C48 was isolated as a yellow oil. Yield: 80 mg, 0.23 mmol, 41%. $^1$H NMR (400 MHz, chloroform-d) δ 8.39 (s, 1H), 6.80 (s, 1H), 6.45-6.34 (m, 1H), 6.24 (d, J=1.3 Hz, 1H), 4.76 (br d, J=5.7 Hz, 1H), 4.50-4.42 (m, 1H), 4.14 (dd, J=10.3, 4.0 Hz, 1H), 4.09 (dd, J=11.4, 4.9 Hz, 1H), 4.03-3.97 (m, 1H), 3.92 (dd, J=10.1, 10.0 Hz, 1H), 3.82-3.69 (m, 2H), 3.56 (ddd, J=9.4, 9.2, 4.8 Hz, 1H), 3.47 (ddd, J=11.8, 11.7, 2.1 Hz, 1H), 3.22 (dd, J=11.3, 9.7 Hz, 1H), 2.37 (br s, 3H), 2.33-2.23 (m, 2H), 2.08-1.98 (m, 1H), 1.78-1.66 (m, 1H).

Step 2. Synthesis of 3-bromo-7-{[(3S,4R)-3-hydroxytetrahydro-2H-pyran-4-yl]amino}-4-methyl-1-[(3S)-tetrahydrofuran-3-yl]-1,6-naphthyridin-2(1H)-one (C49)

To a 0° C. solution of C48 (80 mg, 0.23 mmol) in a mixture of acetonitrile (5 mL) and dichloromethane (2.5 mL) was added a solution of N-bromosuccinimide (45.3 mg, 0.255 mmol) in acetonitrile (5 mL). The reaction mixture was stirred at 0° C. for 10 minutes; LCMS analysis of the reaction mixture at this point indicated conversion to C49: LCMS m/z 425.9 (bromine isotope pattern observed) [M+H]$^+$. After the reaction mixture had been diluted with dichloromethane (50 mL), it was washed sequentially with saturated aqueous sodium sulfite solution (10 mL) and saturated aqueous sodium chloride solution (30 mL), dried over sodium sulfate, filtered, and concentrated in vacuo. Preparative thin-layer chromatography on silica gel (Eluent: 15:1 dichloromethane/methanol) provided C49 as a white solid. Yield: 60 mg, 0.14 mmol, 61%. $^1$H NMR (400 MHz, chloroform-d) δ 8.51 (s, 1H), 6.81 (s, 1H), 6.45-6.31 (m, 1H), 4.86-4.76 (m, 1H), 4.52-4.41 (m, 1H), 4.21-4.04 (m, 2H), 4.04-3.89 (m, 2H), 3.86-3.70 (m, 2H), 3.62-3.53 (m, 1H), 3.53-3.43 (m, 1H), 3.27-3.18 (m, 1H), 2.60 (s, 3H), 2.35-2.24 (m, 2H), 2.09-2.00 (m, 1H), 1.78-1.64 (m, 1H).

Step 3. Synthesis of 3-acetyl-7-{[(3S,4R)-3-hydroxytetrahydro-2H-pyran-4-yl]amino}-4-methyl-1-[(3S)-tetrahydrofuran-3-yl]-1,6-naphthyridin-2(1H)-one (11)

To a suspension of C49 (60 mg, 0.14 mmol) in toluene (10 mL) were added tributyl(1-ethoxyethenyl)stannane (255 mg, 0.706 mmol) and tetrakis(triphenylphosphine)palladium(0) (16.3 mg, 14.1 µmol). After the reaction mixture had been degassed three times with nitrogen, it was stirred at 110° C. for 16 hours, and cooled to room temperature. Concentrated hydrochloric acid (0.333 mL) was added, and the reaction mixture was stirred at 10° C. for 15 minutes, whereupon it was diluted with dichloromethane (30 mL) and washed sequentially with water (15 mL), aqueous sodium hydroxide solution (2 M; 10 mL), and saturated aqueous sodium chloride solution (2×15 mL). The organic layer was then dried over sodium sulfate, filtered, and concentrated in vacuo. After preparative thin-layer chromatography on silica gel (Eluent: 10:1 dichloromethane/methanol), the product was combined with the product from a similar reaction carried out using C49 (23 mg, 54 µmol) and purified by reversed-phase HPLC (Column: Agela Durashell C-18, 5 µm; Mobile phase A: 0.05% ammonium hydroxide in water; Mobile phase B: acetonitrile; Gradient: 14% to 34% B) to afford 11 as a solid. Combined yield: 28.5 mg, 73.6 µmol, 38%. LCMS m/z 388.3 [M+H]$^+$. $^1$H NMR (400 MHz, methanol-d$_4$) δ 8.57 (s, 1H), 6.89 (s, 1H), 6.27-6.16 (m, 1H), 4.54-4.46 (m, 1H), 4.13 (dd, J=10.1, 4.2 Hz, 1H), 4.01-3.89 (m, 3H), 3.84-3.69 (m, 2H), 3.57 (ddd, J=9.5, 9.3, 4.8 Hz, 1H), 3.50 (ddd, J=11.8, 11.8, 2.2 Hz, 1H), 3.22 (dd, J=11.1, 9.7 Hz, 1H), 2.47 (s, 3H), 2.43-2.33 (m, 1H), 2.35 (s, 3H), 2.32-2.22 (m, 1H), 2.12-2.05 (m, 1H), 1.66-1.55 (m, 1H).

Examples 12 and 13

6-Acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one and 6-Acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one [12 (DIAST-1) and 13 (DIAST-2)]

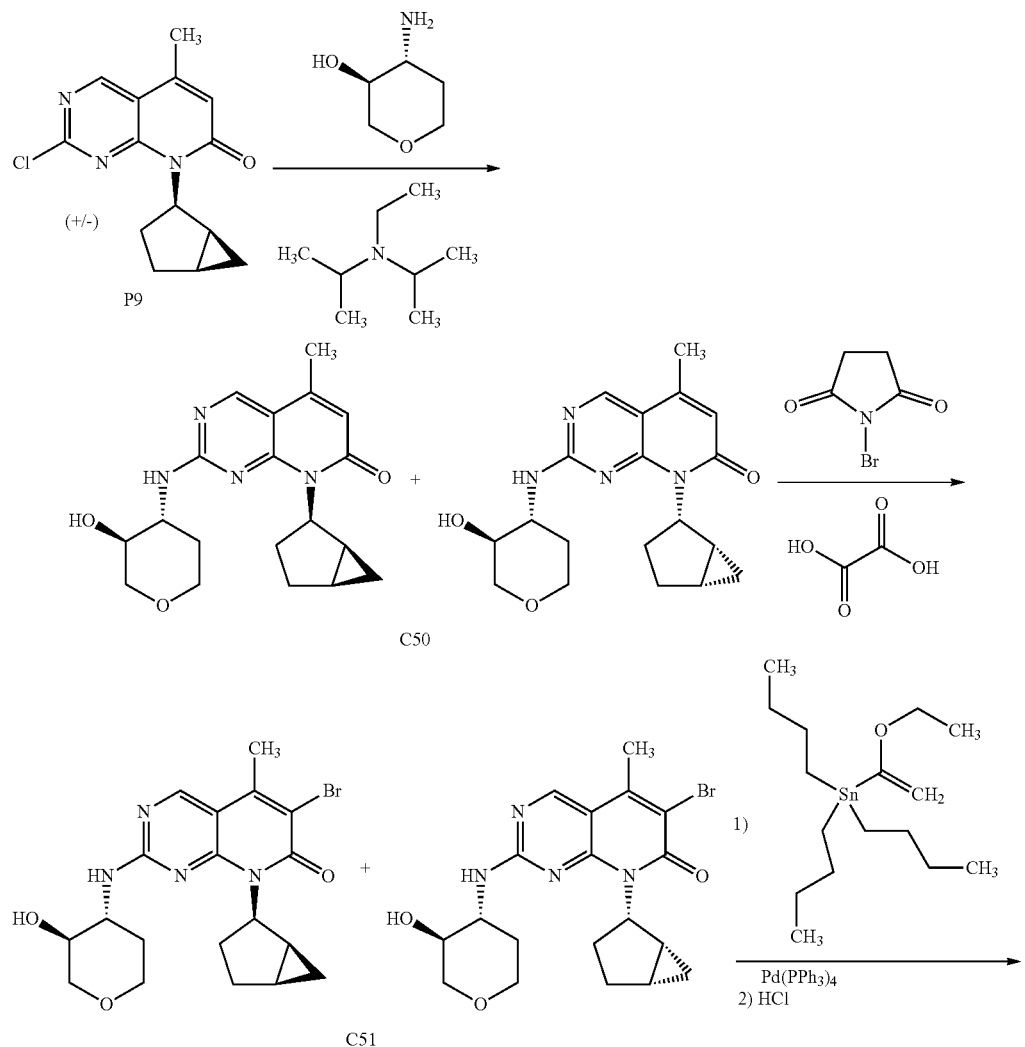

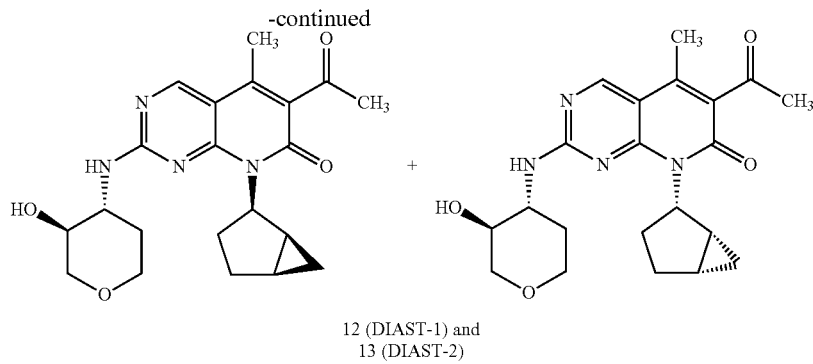

12 (DIAST-1) and
13 (DIAST-2)

Step 1. Synthesis of 8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one and 8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one (C50)

A mixture of P9 (260 mg, 0.897 mmol), (3S,4R)-4-aminotetrahydro-2H-pyran-3-ol (158 mg, 1.35 mmol), and N,N-diisopropylethylamine (348 mg, 2.69 mmol) in dimethyl sulfoxide (3 mL) was stirred at 70° C. for three hours, whereupon the reaction mixture was poured into water (50 mL) and extracted with ethyl acetate (2×50 mL). The combined organic layers were dried over sodium sulfate, filtered, and concentrated in vacuo. After the residue had been combined with the product from a similar reaction carried out using P9 (30 mg, 0.10 mmol), it was purified using silica gel chromatography (Gradient: 0% to 5% methanol in dichloromethane) to afford C50, which consisted of the indicated mixture of 2 diastereomers, as a white solid. Combined yield: 150 mg, 0.421 mmol, 42%.

Step 2. Synthesis of 8-[(1S,2R,5R)-bicyclo[3.1.0]hexan-2-yl]-6-bromo-2-{[(3S,4R)-3-hydroxytetrahydro-2H-pyran-4-yl]amino}-5-methylpyrido[2,3-d]pyrimidin-7(8H)-one and 8-[(1R,2S,5S)-bicyclo[3.1.0]hexan-2-yl]-6-bromo-2-{[(3S,4R)-3-hydroxytetrahydro-2H-pyran-4-yl]amino}-5-methylpyrido[2,3-d]pyrimidin-7(8H)-one (C51)

A solution of C50 (120 mg, 0.337 mmol), N-bromosuccinimide (65.9 mg, 0.370 mmol), and oxalic acid (3.0 mg, 33 μmol) in acetonitrile (10 mL) was stirred in a sealed tube for 5 hours at 25° C. Aqueous sodium bisulfite solution (10 mL) was added; after the resulting mixture had been stirred at room temperature for a few minutes, it was partitioned between ethyl acetate (50 mL) and water (50 mL), and the aqueous layer was extracted with ethyl acetate (2×50 mL). The combined organic layers were dried over sodium sulfate, filtered, and concentrated in vacuo, providing C51 (150 mg) as a gum. This material was progressed to the following step.

Step 3. Synthesis of 6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one and 6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one [12 (DIAST-1) and 13 (DIAST-2)]

Argon was bubbled through a solution of C51 (from the previous step; ≤0.337 mmol) and tributyl(1-ethoxyethenyl)stannane (531 mg, 1.47 mmol) in toluene (10 mL) for a few minutes, whereupon tetrakis(triphenylphosphine)palladium (0) (42.5 mg, 36.8 μmol) was added. The reaction mixture was stirred in a sealed tube at 110° C. for 18 hours, cooled to room temperature, and treated with hydrochloric acid (1.0 M, 5 mL, 5 mmol). This reaction mixture was allowed to stir at 25° C. for 4 hours, and then basified to pH 8 to 9 by addition of aqueous sodium carbonate solution. The resulting mixture was partitioned between ethyl acetate (30 mL) and water (30 mL), and the aqueous layer was extracted with ethyl acetate (2×30 mL). After the combined organic layers had been dried, filtered, and concentrated in vacuo, the residue was purified by reversed-phase HPLC to provide the crude product (140 mg) as an oil; the component diastereomers of this mixture were then separated via supercritical fluid chromatography [Column: Regis Technologies, (S,S)-Whelk-01, 5 μm; Mobile phase: 3:2 carbon dioxide/(ethanol containing 0.05% diethylamine)]. The first-eluting diastereomer was designated as 12, and the second-eluting diastereomer as 13; both compounds were obtained as solids. 12 (DIAST-1)—Yield: 22 mg, 55 μmol, 16% over 2 steps. LCMS m/z 398.9 [M+H]$^+$. $^1$H NMR (400 MHz, chloroform-d) δ 8.59 (s, 1H), 6.00 (br s, 1H), 5.52-5.23 (br m, 1H), 4.08 (dd, J=11.4, 4.8 Hz, 1H), 4.05-3.90 (m, 2H), 3.71-3.59 (m, 1H), 3.55-3.44 (m, 1H), 3.28-3.17 (m, 1H), 2.52 (s, 3H), 2.50-2.37 (m, 1H), 2.30 (s, 3H), 2.15-2.04 (m, 1H), 1.97-1.83 (m, 2H), 1.81-1.68 (m, 1H, assumed; partially obscured by water peak), 1.53-1.43 (m, 1H), 1.42-1.27 (m, 3H), 0.65-0.56 (m, 1H). Retention time: 4.36 minutes [Column: Regis Technologies, (S,S)-Whelk-01, 4.6×250 mm; 5 μm; Mobile phase: 3:2 carbon dioxide/(ethanol containing 0.05% diethylamine); Flow rate: 2.5 mL/minute]. This compound exhibited a negative (−) rotation.

13 (DIAST-2)—Yield: 18 mg, 45 μmol, 13% over 2 steps. LCMS m/z 398.9 [M+H]$^+$. $^1$H NMR (400 MHz, chloroform-d) δ 8.59 (s, 1H), 6.01 (br s, 1H), 5.51-5.22 (br m, 1H), 4.09 (dd, J=11.4, 5.0 Hz, 1H), 4.05-3.90 (m, 2H), 3.70-3.60 (m, 1H), 3.55-3.44 (m, 1H), 3.28-3.17 (m, 1H), 2.52 (s, 3H), 2.48-2.35 (m, 1H), 2.31 (s, 3H), 2.15-2.03 (m, 1H), 1.96-

1.84 (m, 2H), 1.80-1.67 (m, 1H), 1.54-1.44 (m, 1H), 1.41-1.24 (m, 3H), 0.66-0.57 (m, 1H). Retention time: 4.90 minutes (Analytical conditions identical to those used for 12). This compound exhibited a positive (+) rotation.

Examples 14 and 15

3-Acetyl-1-(3-hydroxycyclopentyl)-7-{[(3S,4R)-3-hydroxytetrahydro-2H-pyran-4-yl]amino}-4-methyl-1,6-naphthyridin-2(1H)-one, DIAST-1 [14 (DIAST-1)] and 3-Acetyl-1-(3-hydroxycyclopentyl)-7-{[(3S,4R)-3-hydroxytetrahydro-2H-pyran-4-yl]amino}-4-methyl-1,6-naphthyridin-2(1H)-one, DIAST-2 [15 (DIAST-2)]

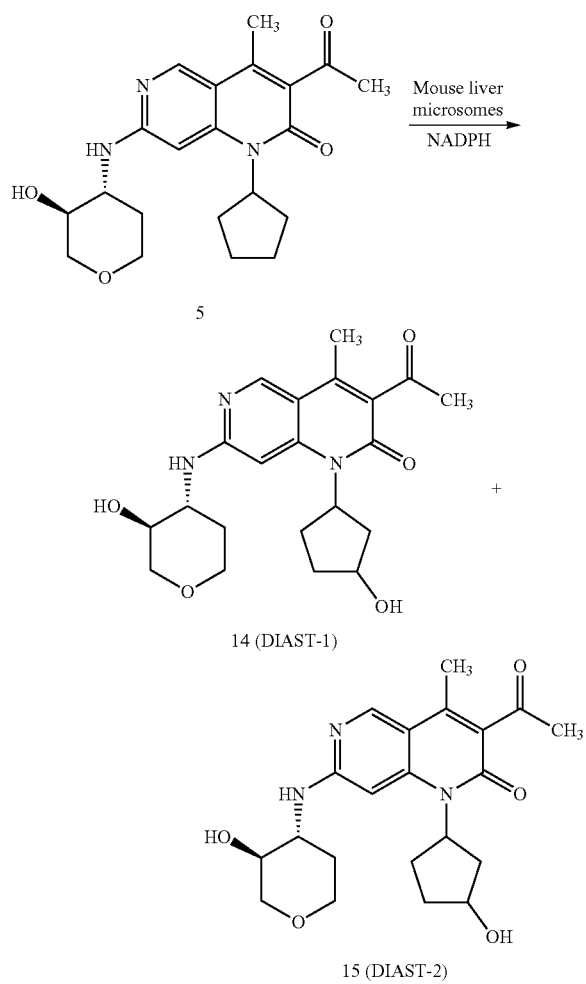

A 500 mL Erlenmeyer flask was charged with deionized water (27.0 mL), to which was added potassium phosphate buffer solution (pH 7.5, 1.0 M; 4.0 mL), aqueous magnesium chloride solution (0.165 M; 0.8 mL, 132 µmol) and a solution of 5 in acetonitrile (0.005 M; 0.16 mL, 0.8 µmol). The mixture was treated with female mouse liver microsomes (4.0 mL, Corning Gentest 452702), followed by the addition of a freshly prepared aqueous solution of NADPH (dihydronicotinamide adenine dinucleotide phosphate; 0.013 M; 4.0 mL, 52 µmol). The uncapped Erlenmeyer flask was shaken using a Thermo Scientific Precision shaker with a 1" throw at 37° C. for 1 hour. The reaction mixture was divided into equal portions (20 mL each) and poured into two 50 mL Falcon conical centrifuge tubes. The solutions were quenched by adding acetonitrile (20 mL) to each Falcon tube. The Falcon tubes were vortexed and centrifuged at 3000 rpm for 5 minutes. The supernatant was decanted and transferred in equal portions (20 mL each) to two 50 mL Falcon conical centrifuge tubes and the solvent was evaporated using a EZ-2 Plus Genevac (1 hour HPLC setting, 34° C./238 mbar to 41° C./7 mbar). The remaining aqueous solutions were combined (~20 mL) into a 50 mL Falcon conical centrifuge tube and treated with acetonitrile (0.5 mL) and neat formic acid (0.5 mL), then charged with deionized water to a final volume of 50 mL. The solution was divided into equal portions (25 mL each), poured into two high speed centrifuge tubes, and centrifuged at 40,000G for 30 minutes. The supernatant was decanted into a 50 mL glass conical tube and the solution was adsorbed onto a C18 HPLC column (Zorbax Polaris C18-A, 250×4.6 mm, 5 µm) using a JASCO PU-1580 HPLC pump at a flow rate of 0.8 mL/min over ~60 minutes. The HPLC column was transferred to a Thermo LTQ Velos mass spectrometer in line with a Waters Acquity UHPLC instrument comprised of a quaternary pump, autosampler and photodiode array UV/vis detector. A gradient (0.1% formic acid in water (A) and acetonitrile (B)) was applied to separate products of interest. After passing through the photodiode array detector, the eluent was split at a ratio of approximately 15:1, with the larger portion going to a fraction collector, and the smaller portion to the mass spectrometer (fractions were collected every 20 seconds). Fractions containing peaks of interest were analyzed by UHPLC-UV-HRMS using an AB Sciex TripleTOF 5600-1 mass spectrometer in line with a Waters Acquity UPLC System-1. Samples were injected (2 µL) onto a C18 UHPLC column (Phenomenex Kinetex C18, 2.1×50 mm, 1.7 µm) and a 0.1% formic acid in water (A) and acetonitrile (B) gradient was applied at a flow rate of 0.4 mL/min, maintained at 40° C. After UHPLC-UV-HRMS analysis, fractions were pooled and the solvent was removed using an EZ-2 Plus Genevac (3 hour HPLC setting, 34° C./238 mbar to 41° C./7 mbar). The dried samples were analyzed by NMR spectroscopy and quantified by external calibration against the $^1$H NMR spectrum of a 5.0 mM benzoic acid standard solution in DMSO-$d_6$ using the ERETIC2 function within Topspin V3.2. The first-eluting diastereomer collected was designated as 14 (DIAST-1). Yield: 18 µg, 45 nmol. $^1$H NMR (600 MHz, DMSO-$d_6$) δ 8.57 (s, 1H), 7.26 (d, J=7.5 Hz, 1H), 6.44 (s, 1H), 5.58-5.44 (m, 1H), 4.49-4.41 (m, 1H), 3.90-3.76 (m, 3H), 3.45-3.33 (m, 2H), 3.08 (t, J=10.3 Hz, 1H), 2.39 (s, 3H), 2.38-2.32 (m, 1H), 2.30-2.23 (m, 4H), 2.12-1.97 (m, 3H), 1.74 (t, J=10.8 Hz, 1H), 1.70-1.63 (m, 1H), 1.50-1.38 (m, 1H). HRMS (TOF, m/z): [M+H]$^+$ calcd for $C_{21}H_{28}N_3O_5$, 402.2029; found, 402.2031 (0.5 ppm). UHPLC retention time 2.605 minutes; Phenomenex Kinetex C18 column (2.1×50 mm, 1.7 µm); column temperature 40° C.; flow rate 0.1 mL/minute; detection range UV 220-400 nm; mobile phase: solvent A=formic acid (0.1%), solvent B=acetonitrile (100%); gradient elution: 0-0.5 minutes solvent A (95%) and solvent B (5%), 0.5-6.5 minutes solvent A (50%) and solvent B (50%), 6.5-7.9 minutes solvent A (20%) and solvent B (80%), 7.9-8.0 minutes solvent A (5%) and solvent B (95%), 8.0-9.1 minutes solvent A (95%) and solvent B (5%), 9.1-10.0 minutes solvent A (100%) and solvent B (0%); total run time 10.0 minutes.

The second-eluting diastereomer that was collected was designated as 15 (DIAST-2). Yield: 3 µg, 7.5 nmol. $^1$H NMR (600 MHz, DMSO-$d_6$) δ 8.58 (s, 1H), 7.00 (d, J=7.8 Hz, 1H), 6.76 (s, 1H), 5.57-5.35 (m, 1H), 4.27-4.20 (m, 1H), 3.85-3.77 (m, 3H), 3.47-3.35 (m, 2H), 3.08 (t, J=10.4 Hz, 1H), 2.40 (s, 3H), 2.27 (s, 3H), 2.18-2.08 (m, 2H), 2.02-1.96 (m, 1H), 1.96-1.90 (m, 1H), 1.82-1.74 (m, 2H), 1.51-1.38

(m, 2H). HRMS (TOF, m/z): [M+H]+ calcd for $C_{21}H_{28}N_3O_5$, 402.2029; found, 402.2028 (−0.2 ppm). UHPLC retention time 2.796 minutes; Phenomenex Kinetex C18 column, conditions identical to those used for 14 (DIAST-1) above. The relative and absolute stereochemistries of 14 and 15 around the cyclopentane were not determined; these compounds represent 2 of the 4 possible diastereomers. The 4 diastereomers related to 14 and 15 may be individually synthesized by one skilled in the art, from the commercially available starting materials (1S,3R)-3-aminocyclopentanol (A1), (1R,3R)-3-aminocyclopentanol (A2), (1S,3S)-3-aminocyclopentanol (A3), and (1R,3S)-3-aminocyclopentanol (A4). Using A1 as an example, reaction with 1-(4,6-dichloropyridin-3-yl)ethanone, using the method described in Preparation P4, may be followed by hydroxy group protection using tert-butyl(dimethyl)silyl chloride and 1H-imidazole to afford 1-(4-{[(1R,3S)-3-{[tert-butyl(dimethyl)silyl]oxy}cyclopentyl]amino}-6-chloropyridin-3-yl)ethanone. Reaction with 2,2,6-trimethyl-4H-1,3-dioxin-4-one, again using the method described in Preparation P4, provides 3-acetyl-1-[(1R,3S)-3-{[tert-butyl(dimethyl)silyl]oxy}cyclopentyl]-7-chloro-4-methyl-1,6-naphthyridin-2(1H)-one (B1). Reaction of B1 with (3S,4R)-4-aminotetrahydro-2H-pyran-3-ol, using the method of Example 5, followed by silyl group removal with an acid such as acetic acid or trifluoroacetic acid, or alternatively a source of fluoride ion, such as tetrabutylammonium fluoride, will then afford 3-acetyl-1-[(1R,3S)-3-hydroxycyclopentyl]-7-{[(3S,4R)-3-hydroxytetrahydro-2H-pyran-4-yl]amino}-4-methyl-1,6-naphthyridin-2(1H)-one (D1), one of the diastereomers represented by structures 14 and 15.

In a similar manner, starting materials A2, A3, and A4 may be respectively converted to the diastereomers 3-acetyl-1-[(1R,3R)-3-hydroxycyclopentyl]-7-{[(3S,4R)-3-hydroxytetrahydro-2H-pyran-4-yl]amino}-4-methyl-1,6-naphthyridin-2(1H)-one (D2), 3-acetyl-1-[(1S,3S)-3-hydroxycyclopentyl]-7-{[(3S,4R)-3-hydroxytetrahydro-2H-pyran-4-yl]amino}-4-methyl-1,6-naphthyridin-2(1H)-one (D3), and 3-acetyl-1-[(1S,3R)-3-hydroxycyclopentyl]-7-{[(3S,4R)-3-hydroxytetrahydro-2H-pyran-4-yl]amino}-4-methyl-1,6-naphthyridin-2(1H)-one (D4).

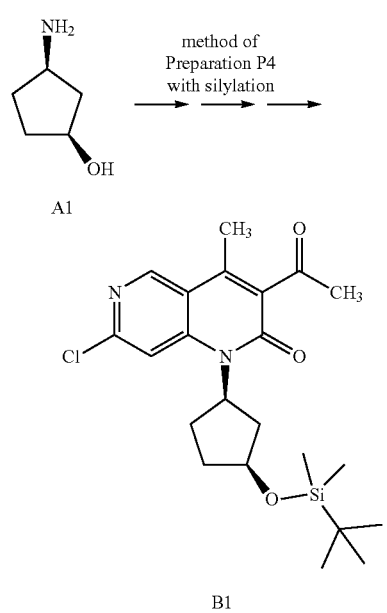

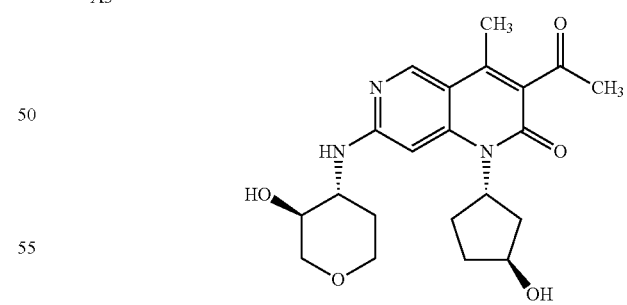

B1

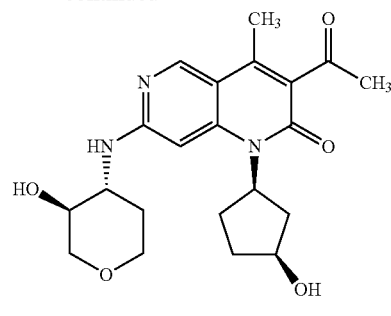

D1

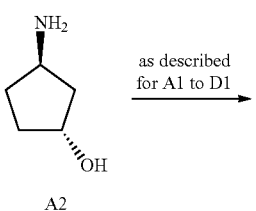

A2

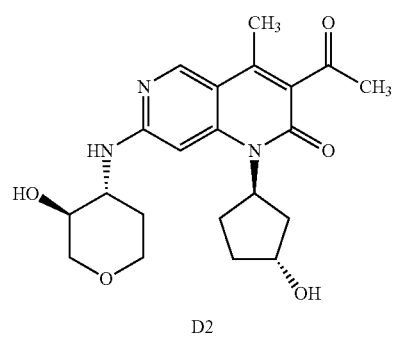

D2

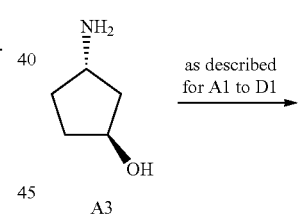

A3

D3

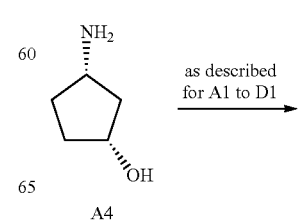

A4

-continued
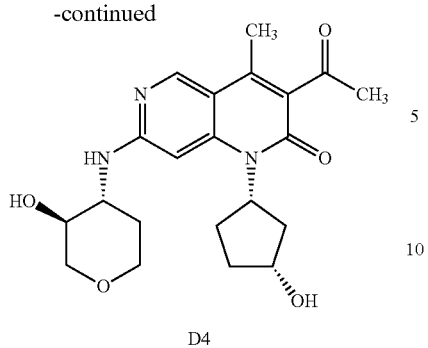
D4
Examples 16 and 17
6-Acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one and 6-Acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one [16 (DIAST-1) and 17 (DIAST-2)]
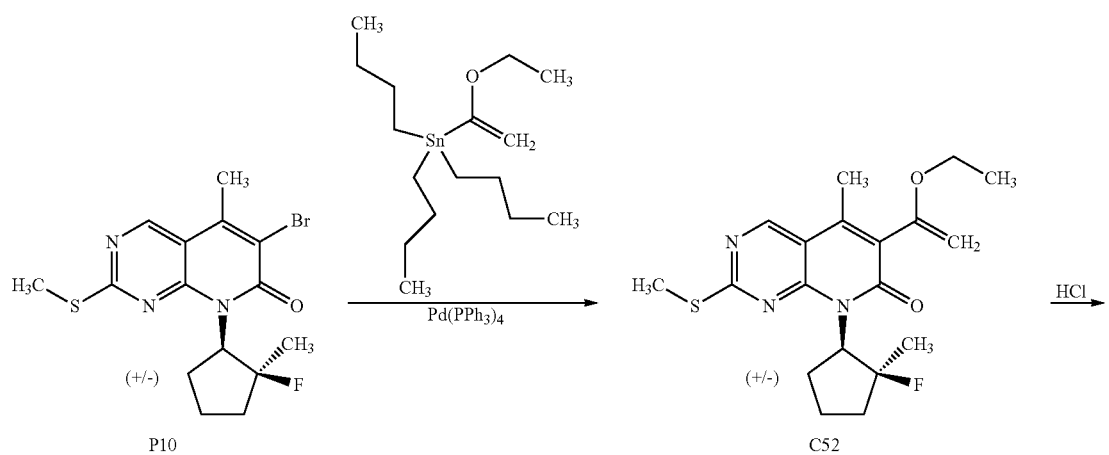
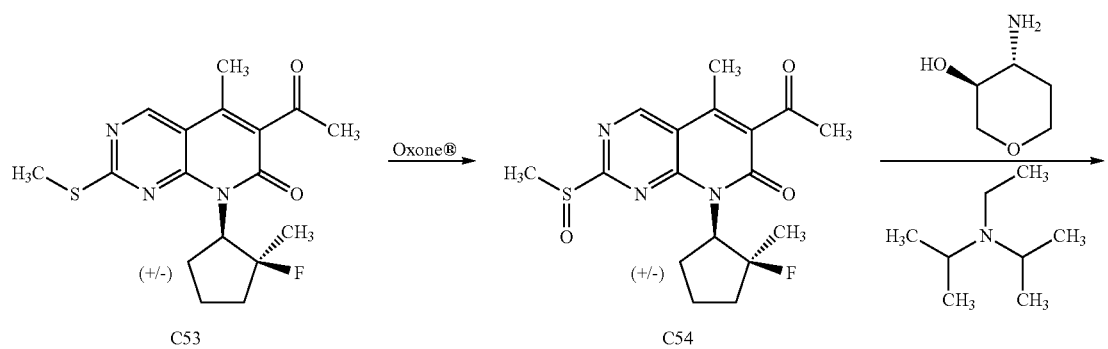
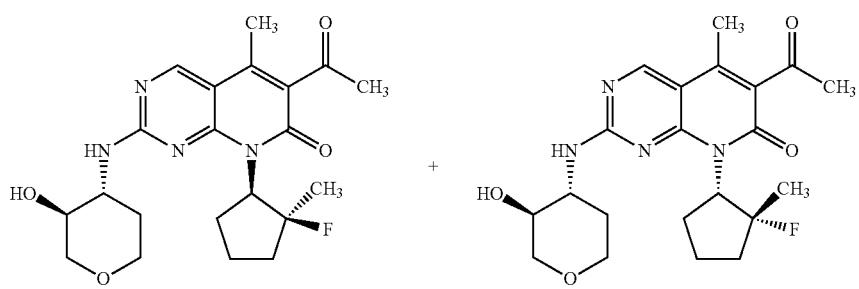
16 (DIAST-1) and 17 (DIAST-2)

Step 1. Synthesis of rac-6-(1-ethoxyethenyl)-8-[(1R, 2S)-2-fluoro-2-methylcyclopentyl]-5-methyl-2-(methylthio)pyrido[2,3-d]pyrimidin-7(8H)-one (C52)

A mixture of P10 (108 mg, 0.280 mmol), tributyl(1-ethoxyethenyl)stannane (151 mg, 0.418 mmol), and tetrakis(triphenylphosphine)palladium(0) (19.4 mg, 16.8 µmol) in toluene (3.0 mL) was heated at 110° C. for 2 hours. LCMS analysis of the reaction mixture at this point indicated the presence of the product C52: LCMS m/z 377.9 [M+H]$^+$. The reaction mixture was filtered through diatomaceous earth and the filtrate was concentrated in vacuo. Purification via silica gel chromatography (Gradient: 20% to 60% ethyl acetate in heptane) afforded C52 as a pale yellow foam. Yield: 91 mg, 0.24 mmol, 86%. $^1$H NMR (400 MHz, chloroform-d) δ 8.74 (s, 1H), 5.94-5.72 (m, 1H), 4.54 (d, J=2.5 Hz, 1H), 4.20 (d, J=2.5 Hz, 1H), 3.94 (q, J=7.0 Hz, 2H), 2.62 (s, 3H), 2.51-2.33 (m, 1H), 2.44 (s, 3H), 2.31-2.19 (m, 1H), 1.98-1.81 (m, 3H), 1.71-1.57 (m, 1H), 1.48 (d, $J_{HF}$=21.8 Hz, 3H), 1.36 (t, J=7.0 Hz, 3H).

Step 2. Synthesis of rac-6-acetyl-8-[(1R,2S)-2-fluoro-2-methylcyclopentyl]-5-methyl-2-(methylthio)pyrido[2,3-d]pyrimidin-7(8H)-one (C53)

Hydrogen chloride (4.0 M solution in 1,4-dioxane; 0.181 mL, 0.724 mmol) was added to a solution of C52 (91 mg, 0.24 mmol) in dichloromethane (2 mL), and the reaction mixture was stirred at room temperature for 1 hour. LCMS analysis of the reaction mixture at this point indicated the presence of the product C53: LCMS m/z 350.2 [M+H]$^+$. Concentration in vacuo provided C53 as a solid, which was taken directly to the following step.

Step 3. Synthesis of rac-6-acetyl-8-[(1R,2S)-2-fluoro-2-methylcyclopentyl]-5-methyl-2-(methylsulfinyl)pyrido[2,3-d]pyrimidin-7(8H)-one (C54)

A solution of potassium peroxymonosulfate (Oxone®; 326 mg, 0.530 mmol) in water (1 mL) was added to a solution of C53 (from the previous step; 88 mg, 0.24 mmol) in tetrahydrofuran (4 mL), and the reaction mixture was stirred at room temperature for 16 hours. LCMS analysis of the reaction mixture at this point indicated the presence of the product C54: LCMS m/z 345.9 [(M−HF)+H]$^+$. Water was added, and the resulting mixture was extracted twice with ethyl acetate. The combined organic layers were dried over sodium sulfate, filtered, and concentrated in vacuo to afford C54 as a pale yellow solid. Yield: 89.0 mg, 0.24 mmol, quantitative over 2 steps.

Step 4. Synthesis of 6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one and 6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one [16 (DIAST-1) and 17 (DIAST-2)]

A mixture of C54 (43 mg, 0.12 mmol), (3S,4R)-4-aminotetrahydro-2H-pyran-3-ol (24.1 mg, 0.206 mmol), and N,N-diisopropylethylamine (86 µL, 0.49 mmol) in dimethyl sulfoxide (2 mL) was stirred at room temperature for 3 hours. Separation of the component diastereomers was carried out using supercritical fluid chromatography [Column: Chiral Technologies Chiralpak IC, 5 µm; Mobile phase: 3:2 carbon dioxide/(2-propanol containing 10 mM ammonium hydroxide)]. The first-eluting diastereomer was designated as 16, and the second-eluting diastereomer as 17; both were obtained as solids.

16 (DIAST-1)—Yield: 17 mg, 41 µmol, 34%. LCMS m/z 418.9 [M+H]$^+$. $^1$H NMR (400 MHz, 80° C., DMSO-d$_6$), characteristic peaks: δ 8.75 (s, 1H), 7.50-7.37 (m, 1H), 5.87-5.73 (m, 1H), 4.72-4.59 (m, 1H), 3.99-3.80 (m, 3H), 3.63-3.54 (m, 1H), 3.35 (ddd, J=11.7, 11.6, 2.3 Hz, 1H), 3.10 (dd, J=11.1, 9.5 Hz, 1H), 2.39 (s, 3H), 2.29 (s, 3H), 2.18-2.06 (m, 1H), 2.00-1.84 (m, 3H), 1.69-1.54 (m, 2H), 1.44 (d, $J_{HF}$=21.9 Hz, 3H). Retention time: 1.22 minutes [Column: Chiral Technologies Chiralpak IC-3, 4.6×100 mm, 3 µm; Mobile phase: 3:2 carbon dioxide/(2-propanol containing 10 mM ammonium hydroxide); Flow rate: 4 mL/minute; Back pressure: 120 bar]. This compound exhibited a negative (−) rotation.

17 (DIAST-2)—Yield: 14 mg, 33 µmol, 28%. LCMS m/z 419.0 [M+H]$^+$. $^1$H NMR (400 MHz, 80° C., DMSO-d$_6$), characteristic peaks: δ 8.75 (s, 1H), 7.50-7.38 (m, 1H), 5.87-5.73 (m, 1H), 4.66 (br s, 1H), 4.00-3.79 (m, 3H), 3.64-3.54 (m, 1H), 3.36 (ddd, J=11.7, 11.5, 2.4 Hz, 1H), 3.10 (dd, J=11.1, 9.5 Hz, 1H), 2.39 (s, 3H), 2.29 (s, 3H), 2.19-2.06 (m, 1H), 2.01-1.81 (m, 3H), 1.70-1.51 (m, 2H), 1.44 (d, $J_{HF}$=21.9 Hz, 3H). Retention time: 1.51 minutes (Analytical conditions identical to those used for 16). This compound exhibited a positive (+) rotation.

Example 18

6-Acetyl-2-{[(3S,4R)-3-hydroxytetrahydro-2H-pyran-4-yl]amino}-5-methyl-8-[(3S)-pyrrolidin-3-yl]pyrido[2,3-d]pyrimidin-7(8H)-one (18)

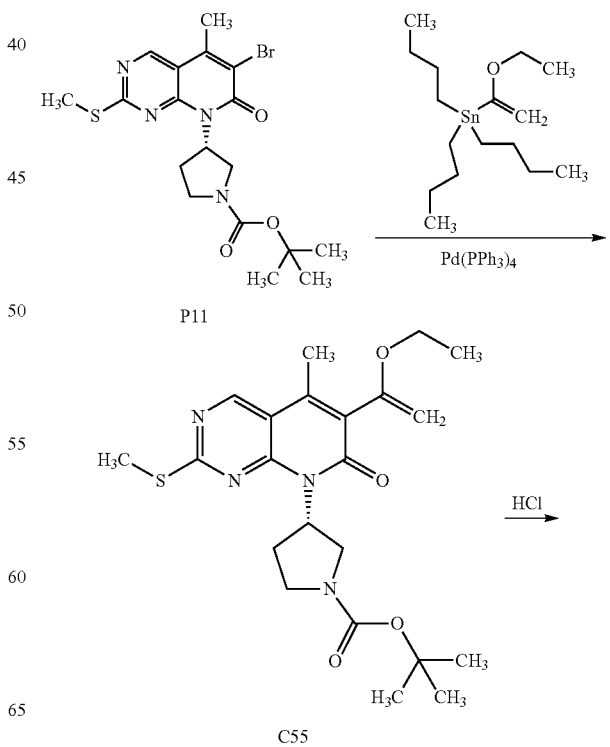

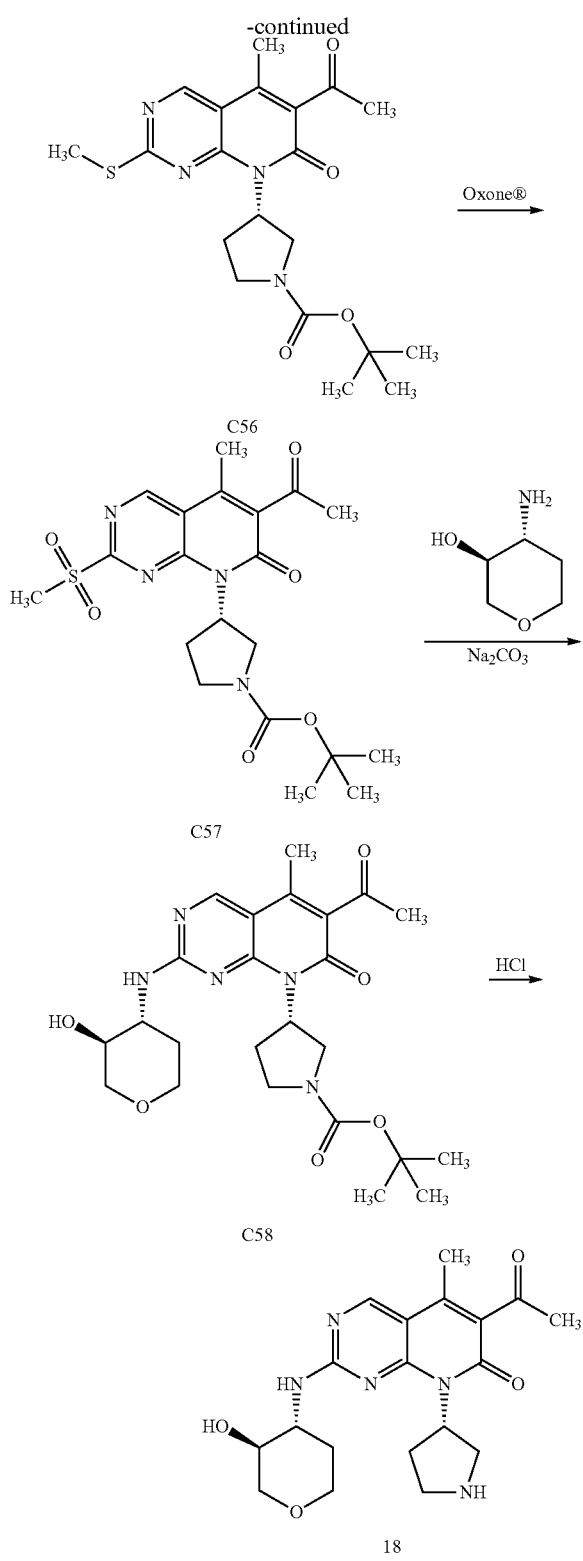

mmol) were added to a solution of P11 (5.30 g, 11.6 mmol) in a mixture of toluene (80 mL) and 1,4-dioxane (40 mL). The reaction mixture was stirred at 110° C. for 5 hours, whereupon it was concentrated in vacuo and purified via chromatography on silica gel (Gradient: 10% to 60% ethyl acetate in petroleum ether), affording C55 as a yellow oil. Yield: 4.48 g, 10.0 mmol, 86%. LCMS m/z 447.2 [M+H]$^+$.

Step 2. Synthesis of tert-butyl (3S)-3-[6-acetyl-5-methyl-2-(methylthio)-7-oxopyrido[2,3-d]pyrimidin-8(7H)-yl]pyrrolidine-1-carboxylate (C56)

Hydrochloric acid (1 M; 40.1 mL, 40.1 mmol) was added to a 20° C. solution of C55 (4.48 g, 10.0 mmol) in tetrahydrofuran (150 mL), and the reaction mixture was stirred for 2 hours. After it had been basified by addition of saturated aqueous sodium bicarbonate solution, the reaction mixture was extracted with ethyl acetate (2×100 mL); the combined organic layers were dried over sodium sulfate, filtered, and concentrated in vacuo. Chromatography on silica gel (Gradient: 10% to 60% ethyl acetate in petroleum ether) provided C56 as a white gum. Yield: 2.64 g, 6.31 mmol, 63%. LCMS m/z 441.1 [M+Na$^+$]. $^1$H NMR (400 MHz, chloroform-d) δ 8.81 (s, 1H), 6.27-6.12 (m, 1H), 3.97 (dd, J=10.2, 8.3 Hz, 1H), 3.88-3.74 (m, 1H), 3.74-3.57 (m, 1H), 3.52-3.40 (m, 1H), 2.94-2.75 (m, 1H), 2.58 (s, 3H), 2.53 (s, 3H), 2.38 (s, 3H), 2.20-2.05 (m, 1H), 1.52-1.41 (m, 9H).

Step 3. Synthesis of tert-butyl (3S)-3-[6-acetyl-5-methyl-2-(methylsulfonyl)-7-oxopyrido[2,3-c]pyrimidin-8(7H)-yl]pyrrolidine-1-carboxylate (C57)

To a solution of C56 (1.00 g, 2.39 mmol) in a mixture of tetrahydrofuran (40 mL) and water (20 mL) was added potassium peroxymonosulfate (Oxone®; 2.64 g, 4.29 mmol). The reaction mixture was stirred at room temperature (17° C.) for 3 hours, whereupon it was diluted with water (40 mL) and extracted with ethyl acetate (2×40 mL). The combined organic layers were washed with saturated aqueous sodium chloride solution (50 mL), dried over sodium sulfate, filtered, and concentrated in vacuo to afford C57 as a yellow gum, which was used without additional purification. Yield: 1.08 g, quantitative. LCMS m/z 473.1 [M+Na$^+$].

Step 4. Synthesis of tert-butyl (3S)-3-[6-acetyl-2-{[(3S,4R)-3-hydroxytetrahydro-2H-pyran-4-yl]amino}-5-methyl-7-oxopyrido[2,3-d]pyrimidin-8(7H)-yl]pyrrolidine-1-carboxylate (C58)

A suspension of (3S,4R)-4-aminotetrahydro-2H-pyran-3-ol (226 mg, 1.93 mmol), C57 (700 mg, 1.55 mmol), and sodium carbonate (341 mg, 3.22 mmol) in tetrahydrofuran (15 mL) was stirred at room temperature (20° C.) for approximately 20 hours. The reaction mixture was then partitioned between water (35 mL) and ethyl acetate (35 mL), and the organic layer was washed with saturated aqueous sodium chloride solution (20 mL), dried over sodium sulfate, filtered, and concentrated in vacuo. The residue was purified using chromatography on silica gel (Gradient: 0% to 10% methanol in dichloromethane) to provide C58 as a yellow gum. Yield: 700 mg, 1.44 mmol, 93%. LCMS m/z 510.2 [M+Na$^+$].

Step 5. Synthesis of 6-acetyl-2-{[(3S,4R)-3-hydroxytetrahydro-2H-pyran-4-yl]amino}-5-methyl-8-[(3S)-pyrrolidin-3-yl]pyrido[2,3-d]pyrimidin-7(8H)-one (18)

Step 1. Synthesis of tert-butyl (3S)-3-[6-(1-ethoxyethenyl)-5-methyl-2-(methylthio)-7-oxopyrido[2,3-d]pyrimidin-8(7H)-yl]pyrrolidine-1-carboxylate (C55)

Tributyl(1-ethoxyethenyl)stannane (10.1 g, 28.0 mmol) and tetrakis(triphenylphosphine)palladium(0) (1.34 g, 1.16

A solution of C58 (700 mg, 1.44 mmol) in methanol (10 mL) was treated with hydrogen chloride (4 M solution in methanol; 8 mL) and stirred at room temperature (20° C.) for approximately 20 hours. The reaction mixture was then concentrated under reduced pressure and purified via normal-phase HPLC (Column: Agela Durashell NH₂, 5 µm; Mobile phase A: 4:1 petroleum ether/dichloromethane; Mobile phase B: methanol; Gradient: 5% to 95% B) to afford 18 as a white solid. Yield: 350 mg, 0.903 mmol, 63%. LCMS m/z 388.2 [M+H]⁺. ¹H NMR (400 MHz, chloroform-d), characteristic peaks: δ 8.64 (s, 1H), 6.18-5.97 (m, 1H), 4.15-3.85 (m, 3H), 3.77-3.16 (m, 5H), 3.15 (dd, J=11.0, 10.5 Hz, 1H), 2.92 (ddd, J=10.8, 10.6, 6.6 Hz, 1H), 2.53 (s, 3H), 2.33 (s, 3H), 1.81-1.61 (m, 1H).

Example 19

6-Acetyl-8-(3,3-dimethylcyclobutyl)-2-{[(3S,4R)-3-hydroxytetrahydro-2H-pyran-4-yl]amino}-5-methylpyrido[2,3-d]pyrimidin-7(8H)-one (19)

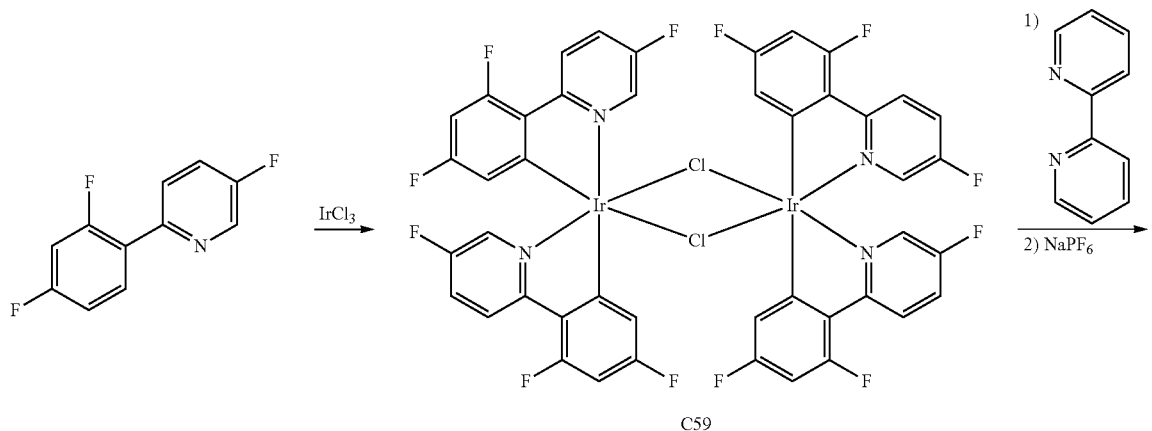

C59

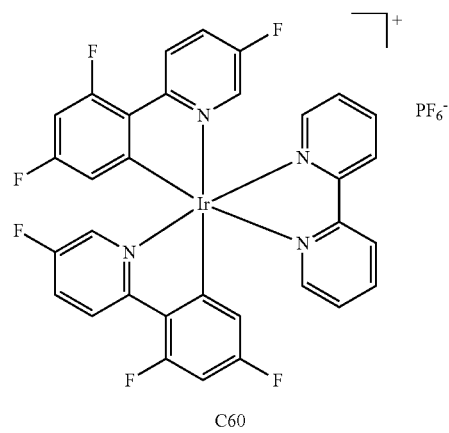

C60

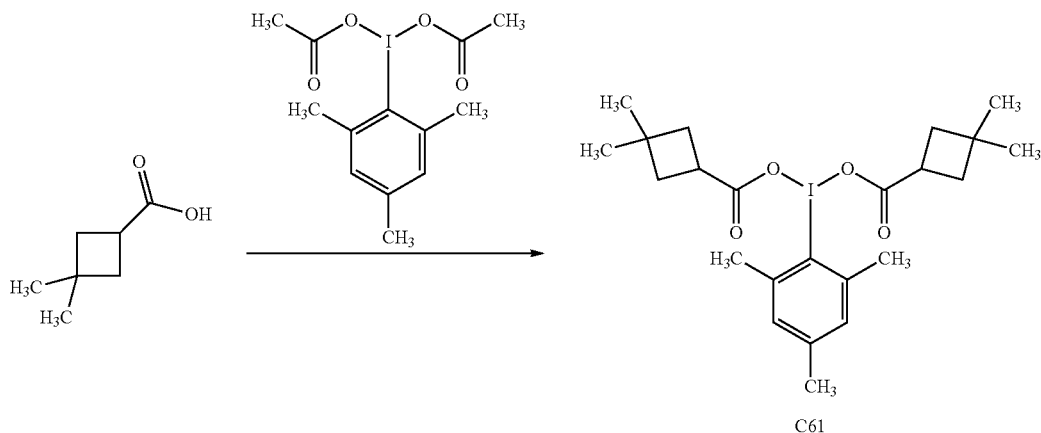

C61

-continued
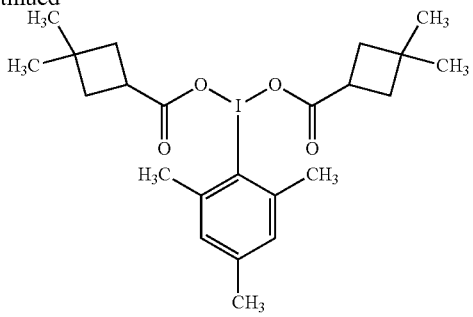
C61
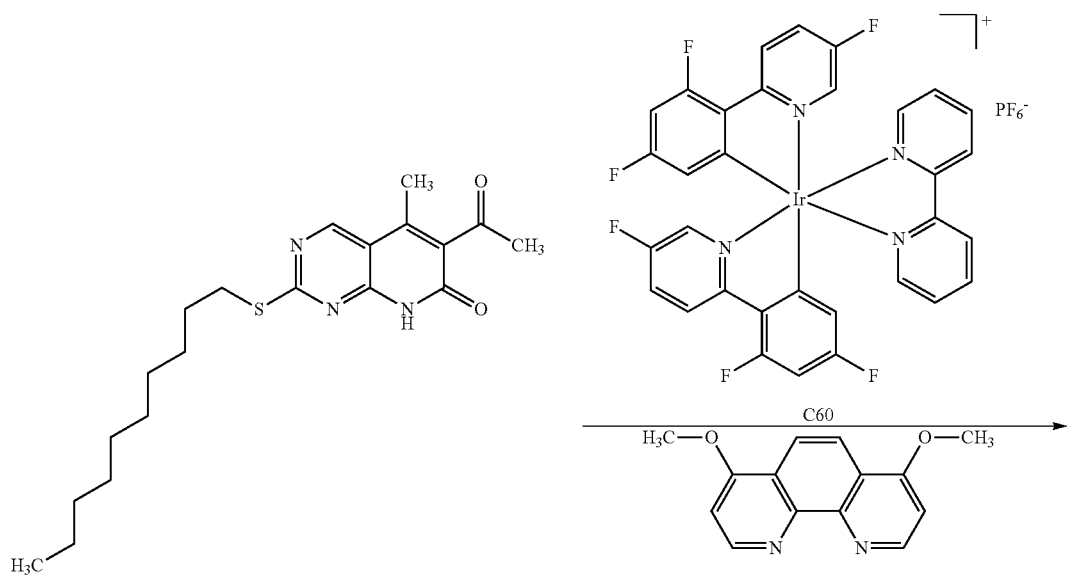
P13
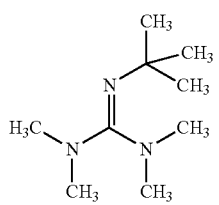
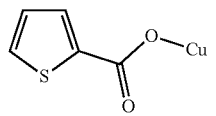

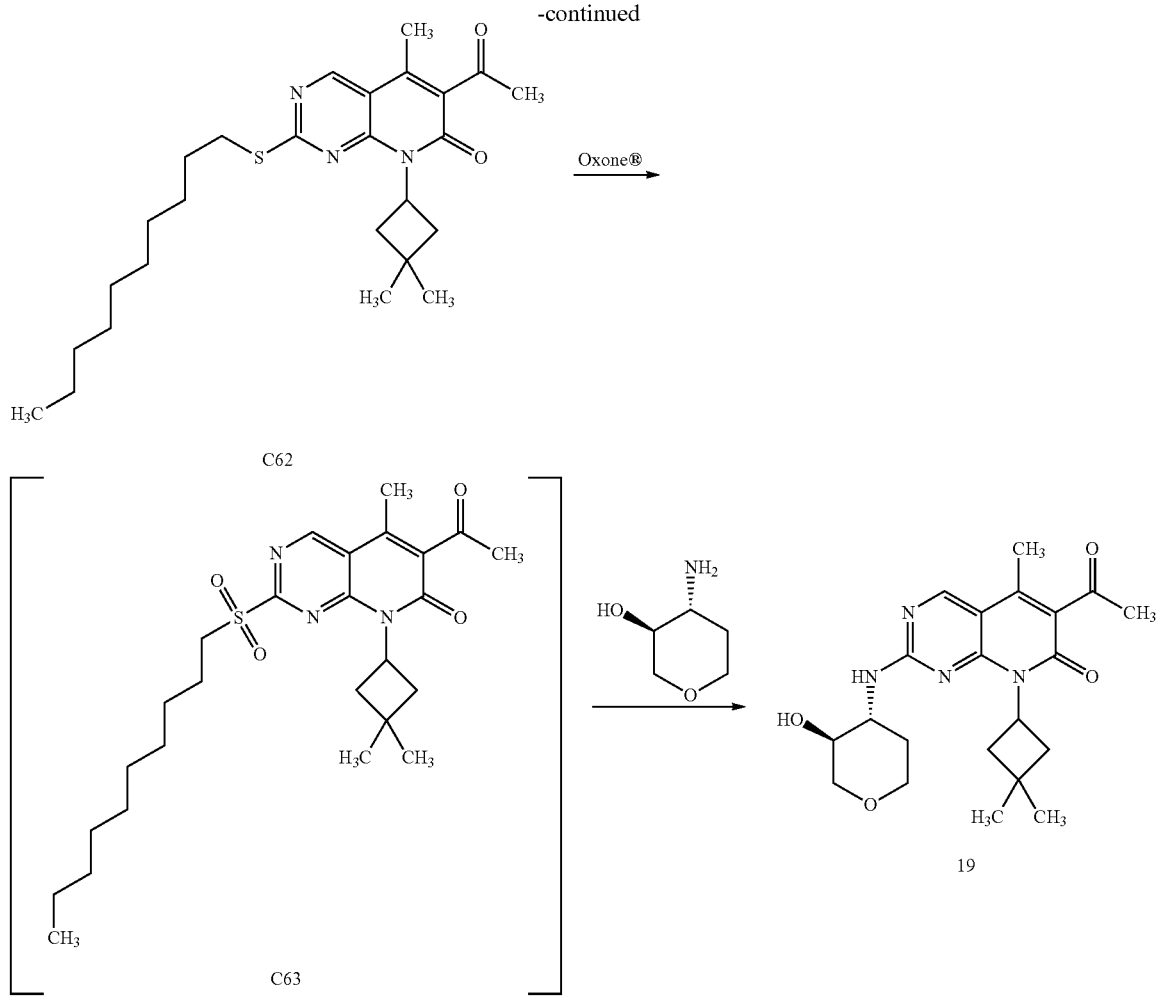

Step 1. Synthesis of di-ρ-chloro{tetrakis[3,5-difluoro-2-(5-fluoropyridin-2-yl-κN)phenyl-κC¹]}diiridium (C59)

A mixture of 2-(2,4-difluorophenyl)-5-fluoropyridine (2.46 g, 11.8 mmol) and iridium(III) chloride (1.56 g, 5.23 mmol) in 2-ethoxyethanol (24 mL) and water (10 mL) was degassed under vacuum and the reaction vessel was then charged with nitrogen. This evacuation cycle was repeated twice, whereupon the reaction mixture was heated to 120° C. for 18 hours. It was then cooled to room temperature (28° C.) and solids were collected via filtration; the filter cake was washed with water (150 mL) to provide C59 as a yellow solid. Yield: 3.11 g, 2.41 mmol, 92%.

Step 2. Synthesis of (2,2'-bipyridine-κ²N¹,N¹){bis[3,5-difluoro-2-(5-fluoropyridin-2-yl)phenyl]}iridium hexafluorophosphate (C60)

A mixture of C59 (3.11 g, 2.41 mmol) and 2,2'-bipyridine (901 mg, 5.77 mmol) in ethane-1,2-diol (120 mL) was degassed under vacuum and purged with nitrogen; this evacuation cycle was repeated, and then the reaction mixture was stirred for 19 hours at 145° C. After cooling to room temperature (20° C.), the reaction mixture was poured into deionized water (900 mL), and the resulting mixture was extracted with n-hexane (6×300 mL). The aqueous layer was concentrated in vacuo to remove residual n-hexane. To this solution was added an aqueous solution of sodium hexafluorophosphate (0.1 g/mL in deionized water; 460 mL); the resulting solid was collected via filtration and washed with water (50 mL) followed by n-hexane (50 mL). This solid (3.7 g) was dissolved in acetone (30 mL) and refluxed for 20 minutes, whereupon n-heptane (20 mL) was added. The resulting mixture was filtered; the filter cake was washed with n-hexane (50 mL) and subsequently purified by silica gel chromatography (Gradient: 0% to 10% acetone in dichloromethane). This material (1.5 g) was recrystallized from acetone to afford C60 as a bright yellow solid. Yield: 1.0 g, 1.1 mmol, 46%. LCMS m/z 765.3 [M⁺]. ¹H NMR (400 MHz, DMSO-d₆) δ 8.88 (d, J=8.1 Hz, 2H), 8.37-8.27 (m, 4H), 8.11-8.02 (m, 2H), 7.88 (br d, J=5.8 Hz, 2H), 7.74-7.67 (m, 2H), 7.65 (br dd, J=2.7, 2.6 Hz, 2H), 7.00 (ddd, J=12.2, 9.4, 2.4 Hz, 2H), 5.73 (dd, J=8.4, 2.4 Hz, 2H).

Step 3. Synthesis of bis{[(3,3-dimethylcyclobutyl)carbonyl]oxy}(2,4,6-trimethylphenyl)-λ³-iodane (C61)

3,3-Dimethylcyclobutanecarboxylic acid (38.4 mg, 0.300 mmol) was treated with a solution of bis(acetyloxy)(2,4,6-trimethylphenyl)-λ³-iodane (56 mg, 0.15 mmol) in dichloromethane (1 mL). Toluene (2 mL) was added, the reaction vial was capped, and the reaction mixture was heated to 55°

C. overnight, whereupon it was concentrated using a Genevac evaporator. The residue was mixed with toluene (1 mL) and stirred for 30 minutes at 55° C. After the mixture had been evaporated again, the residue (C61) was stored in the refrigerator, for use in the following step. $^1$H NMR (400 MHz, chloroform-d) δ 7.06 (s, 2H), 2.93 (pentet, J=8.8 Hz, 2H), 2.69 (s, 6H), 2.34 (s, 3H), 1.99-1.80 (m, 8H), 1.07 (s, 6H), 1.01 (s, 6H).

Step 4. Synthesis of 6-acetyl-2-(decylthio)-8-(3,3-dimethylcyclobutyl)-5-methylpyrido[2,3-c]pyrimidin-7(8H)-one (C62)

A reaction vial containing a mixture of C60 (0.7 mg, 0.8 μmol) and copper(I) thiophene-2-carboxylate (3 mg, 16 μmol) was purged with nitrogen. A solution of 4,7-dimethoxy-1,10-phenanthroline (5.5 mg, 22 μmol) and 2-tert-butyl-1,1,3,3-tetramethylguanidine (26 mg, 0.15 mmol) in 1,4-dioxane (0.25 mL) was added, and the vial was vortexed and again purged with nitrogen. A solution of P13 (28 mg, 75 μmol) in 1,4-dioxane (0.5 mL) was added, followed by a solution of C61 (from the previous step; ≤0.15 mmol) in 1,4-dioxane (1 mL); the C61 container was rinsed with additional 1,4-dioxane (0.5 mL), which was added to the reaction mixture. After the reaction vial had been sealed, it was irradiated with a Kessil LED lamp at 440 nm for 3 hours. The reaction mixture was then partitioned between 10% aqueous citric acid solution and ethyl acetate (2 mL) with vortexing. The organic layer was separated, and the extraction was repeated; the combined organic layers were eluted through a SiliCycle silica solid-phase extraction cartridge with ethyl acetate. The solvent was removed in vacuo, and purification was carried out via reversed-phase HPLC (Column: Waters XBridge C18, 5 μm; Mobile phase A: water containing 0.03% ammonium hydroxide; Mobile phase B: acetonitrile containing 0.03% ammonium hydroxide; Gradient: 80% to 95% B) to provide C62. Yield: 6.1 mg, 13 μmol, 17%. LCMS m/z 458.6 [M+H]$^+$. $^1$H NMR (400 MHz, methanol-d$_4$) δ 8.92 (s, 1H), 5.93 (pentet, J=9.2 Hz, 1H), 3.27-3.20 (m, 2H), 3.01-2.92 (m, 2H), 2.49 (s, 3H), 2.38 (s, 3H), 2.16-2.09 (m, 2H), 1.86-1.75 (m, 2H), 1.57-1.47 (m, 2H), 1.44-1.21 (m, 18H), 0.88 (t, J=7 Hz, 3H).

Step 5. Synthesis of 6-acetyl-8-(3,3-dimethylcyclobutyl)-2-{[(3S,4R)-3-hydroxytetrahydro-2H-pyran-4-yl]amino}-5-methylpyrido[2,3-c]pyrimidin-7(8H)-one (19)

A mixture of C62 (6.1 mg, 13 μmol) and potassium peroxymonosulfate (Oxone®; 15 mg, 24 μmol) in a mixture of tetrahydrofuran and water (4:1, 0.75 mL) was stirred at room temperature for 66 hours. The reaction mixture was then partitioned between water (0.75 mL) and ethyl acetate (2 mL), and the organic layer was eluted through a solid-phase extraction cartridge loaded with sodium sulfate; this extraction process was repeated, and solvent was removed in vacuo to provide intermediate C63 [6-acetyl-2-(decylsulfonyl)-8-(3,3-dimethylcyclobutyl)-5-methylpyrido[2,3-d]pyrimidin-7(8H)-one]. This material was dissolved in methanol (1 mL), and half of it was concentrated under reduced pressure and then treated with a solution of (3S,4R)-4-aminotetrahydro-2H-pyran-3-ol (1.2 mg, 10 μmol) in tetrahydrofuran (0.25 mL). The reaction vial was shaken at 65° C. overnight, whereupon the reaction mixture was partitioned between ethyl acetate (1.2 mL) and water (0.60 mL) with vortexing. The organic layer was eluted through a solid-phase extraction cartridge loaded with sodium sulfate; the extraction process was repeated using ethyl acetate (0.60 mL), and solvent was removed from the combined organic layers in vacuo. Purification was carried out via reversed-phase HPLC (Column: Waters Sunfire C18, 5 μm; Mobile phase A: 0.05% trifluoroacetic acid in water; Mobile phase B: 0.05% trifluoroacetic acid in acetonitrile; Gradient: 5% to 60% B) to provide 19. Yield: 1.6 mg, 4.0 μmol, 62%. LCMS m/z 401.4 [M+H]$^+$. Retention time: 0.922 minutes (Column: Phenomenex Kinetex C18, 2.1×30 mm, 2.6 μm; Mobile phase A: 0.05% trifluoroacetic acid in water; Mobile phase B: 0.05% trifluoroacetic acid in acetonitrile; Gradient: 5% to 95% B over 2.0 minutes, then hold at 95% B for 0.7 minutes; Flow rate: 1.0 mL/minute).

TABLE 1

Method of synthesis, structure, and physiochemical data for Examples 20-34.

| Ex. No. | Method of Preparation; Non-commercial starting materials | Structure | $^1$H NMR; Mass spectrum, observed ion m/z [M + H]$^+$ or HPLC retention time; Mass spectrum m/z [M + H]$^+$ |
|---|---|---|---|
| 20 | Example 2[1] | 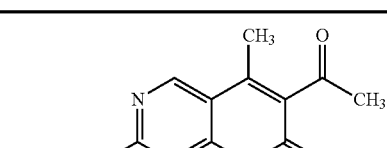 | $^1$H NMR (700 MHz, DMSO-d$_6$), mixture of rotamers, characteristic peaks: δ [8.78 (s) and 8.75 (s), total 1H], [7.82 (br s), and 7.69 (br s), total 1H], 2.40 (s, 3H), 2.25 (s, 3H), 1.96-1.75 (m, 3H), 1.57-1.43 (m, 3H), 1.31-1.21 (m, 2H); 416.9 |

TABLE 1-continued

Method of synthesis, structure, and physiochemical data for Examples 20-34.

| Ex. No. | Method of Preparation; Non-commercial starting materials | Structure | ¹H NMR; Mass spectrum, observed ion m/z [M + H]⁺ or HPLC retention time; Mass spectrum m/z [M + H]⁺ |
|---|---|---|---|
| 21 | Examples 16 and 17[2] | 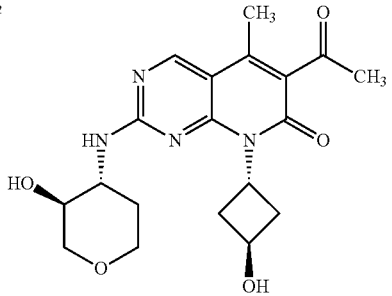 | ¹H NMR (400 MHz, 80° C., DMSO-$d_6$) δ 8.75 (s, 1H), 7.47 (d, J = 8.0 Hz, 1H), 6.10 (pentet, J = 8.9 Hz, 1H), 4.73 (d, J = 4.3 Hz, 1H), 4.69 (d, J = 5.2 Hz, 1H), 4.63-4.52 (m, 1H), 4.01-3.81 (m, 3H), 3.63-3.53 (m, 1H), 3.38 (ddd, J = 11.7, 11.5, 2.4 Hz, 1H), 3.33-3.19 (m, 2H), 3.10 (dd, J = 11.1, 9.5 Hz, 1H), 2.41 (s, 3H), 2.28 (s, 3H), 2.27-2.16 (m, 2H), 2.05-1.96 (m, 1H), 1.67-1.52 (m, 1H); 389.1 |
| 22 | Examples 16 and 17[3,4] | 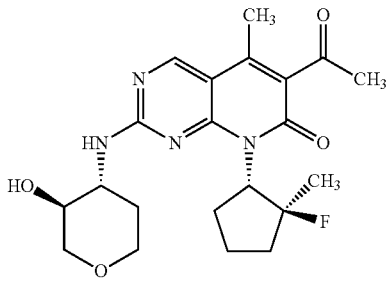 | First-eluting diastereomer (see footnote 4); ¹H NMR (400 MHz, DMSO-$d_6$) δ 8.81 (s, 1H), 7.63-7.53 (m, 1H), 6.25-6.08 (m, $J_{HF}$ = 32.2 Hz, 1H), 4.71 (br s, 1H), 3.96-3.77 (m, 3H), 3.67-3.55 (m, 1H), 3.34 (ddd, J = 11.7, 11.6, 2.1 Hz, 1H), or 3.08 (dd, J = 11.1, 9.7 Hz, 1H), 2.40 (s, 3H), 2.32 (s, 3H), 2.10-1.91 (m, 4H), 1.89-1.75 (m, 1H), 1.60-1.48 (m, 1H), 1.36-1.23 (m, 2H), 1.24 (d, $J_{HF}$ = 22.8 Hz, 3H); 419.0 |
| 23 | Examples 16 and 17[3,4] | 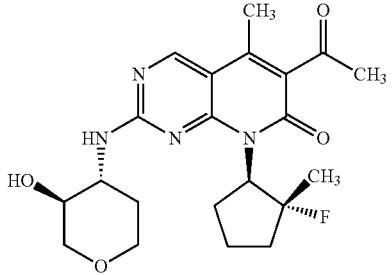 [SMILES: CC(=O)c1c(C)c2cnc(N[C@@H]3CCOC[C@H]3O)nc2n([C@@H]2CCC[C@@]2(C)F)c1=O] | Second-eluting diastereomer (see footnote 4); ¹H NMR (400 MHz, DMSO-$d_6$) δ 8.81 (s, 1H), 7.62-7.49 (m, 1H), 6.23-6.03 (m, $J_{HF}$ = 32.3 Hz, 1H), 4.64 (d, J = 5.3 Hz, 1H), 3.96-3.80 (m, 3H), 3.65-3.53 (m, 1H), 3.34 (ddd, J = 11.6, 11.6, 2.1 Hz, 1H), or 3.06 (dd, J = 11.1, 9.6 Hz, 1H), 2.40 (s, 3H), 2.31 (s, 3H), 2.08-1.93 (m, 4H), 1.88-1.75 (m, 1H), 1.68-1.55 (m, 1H), 1.32-1.19 (m, 2H), 1.26 (d, $J_{HF}$ = 22.7 Hz, 3H); 419.0 |

TABLE 1-continued

Method of synthesis, structure, and physiochemical data for Examples 20-34.

| Ex. No. | Method of Preparation; Non-commercial starting materials | Structure | $^1$H NMR; Mass spectrum, observed ion m/z [M + H]$^+$ or HPLC retention time; Mass spectrum m/z [M + H]$^+$ |
|---|---|---|---|
| 24 | Examples 16 and 17[5] | 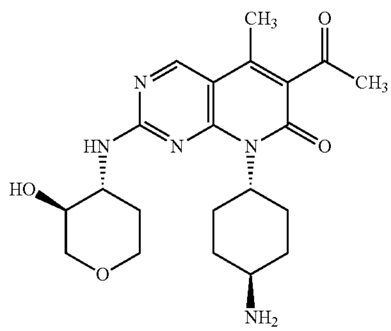 [SMILES: CC(=O)c1c(C)c2cnc(N[C@@H]3CCOC[C@H]3O)nc2n([C@H]2CC[C@H](N)CC2)c1=O] | $^1$H NMR (400 MHz, 80° C., DMSO-d$_6$) δ 8.75 (s, 1H), 7.59-7.47 (m, 1H), 5.34-5.20 (m, 1H), 4.82-4.70 (m, 1H), 3.97-3.81 (m, 3H), 3.67-3.54 (m, 1H), 3.37 (ddd, J = 11.7, 11.6, 2.1 Hz, 1H), 2.81-2.68 (m, 3H), 2.40 (s, 3H), 2.27 (s, 3H), 2.06-1.96 (m, 1H), 1.96-1.87 (m, 2H), 1.66-1.49 (m, 3H), 1.30-1.12 (m, 2H); 416.4 |
| 25 | Example 24[6] | 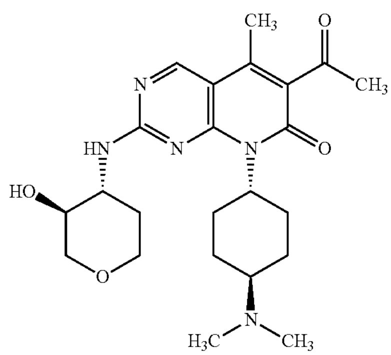 [SMILES: CC(=O)c1c(C)c2cnc(N[C@@H]3CCOC[C@H]3O)nc2n([C@H]2CC[C@H](N(C)C)CC2)c1=O] | $^1$H NMR (400 MHz, DMSO-d$_6$), mixture of rotamers, characteristic peaks: δ [8.79 (s) and 8.77 (s), total 1H], [7.98 (d, J = 8.0 Hz) and 7.81-7.73 (m), total 1H], 5.4-4.94 (m, 2H), 4.03-3.76 (m, 3H), 3.03 (dd, J = 10.5, 10.4 Hz, 1H), 2.39 (s, 3H), 2.27-2.23 (m, 3H), 2.21 (s, 6H), 2.00-1.84 (m, 3H), 1.70-1.47 (m, 3H), 1.40-1.21 (m, 2H); 444.3 |
| 26 | Example 18[7] | 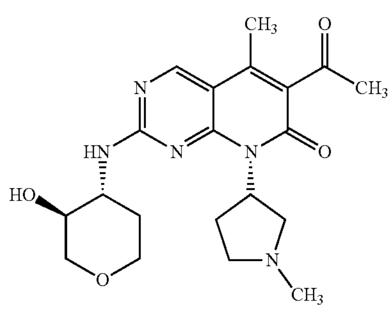 | $^1$H NMR (400 MHz, chloroform-d), characteristic peaks: δ 8.62 (s, 1H), 6.13-6.00 (m, 1H), 4.15-3.14 (m, 7H), 3.13-3.01 (m, 1H), 2.82-2.23 (m, 2H), 2.53 (s, 3H), 2.44 (s, 3H), 2.33 (s, 3H), 2.21-1.99 (m, 2H), 1.8-1.57 (m, 1H, assumed; partially obscured by water peak); 402.3 |
| 27 | Example 18[8] | 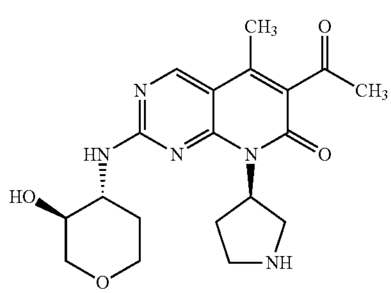 [SMILES: CC(=O)c1c(C)c2cnc(N[C@@H]3CCOC[C@H]3O)nc2n([C@@H]2CCNC2)c1=O] | $^1$H NMR (400 MHz, chloroform-d), characteristic peaks: δ 8.63 (s, 1H), 6.14-6.03 (m, 1H), 4.10-3.89 (m, 3H), 2.52 (s, 3H), 2.33 (s, 3H), 2.17-2.04 (m, 2H), 1.80-1.61 (m, 1H); 388.4 |

TABLE 1-continued

Method of synthesis, structure, and physiochemical data for Examples 20-34.

| Ex. No. | Method of Preparation; Non-commercial starting materials | Structure | $^1$H NMR; Mass spectrum, observed ion m/z [M + H]$^+$ or HPLC retention time; Mass spectrum m/z [M + H]$^+$ |
|---|---|---|---|
| 28 | Example 3[9] | 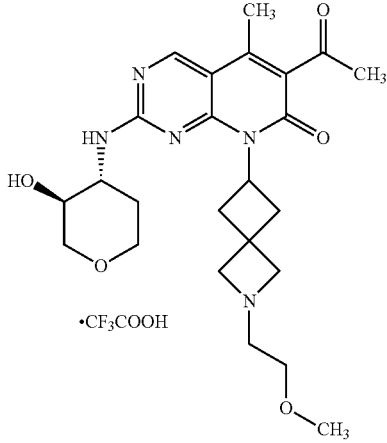 [SMILES: "·CF3COOH" ; COCCN1CC2(CC(n3c(=O)c(C(C)=O)c(C)c4cnc(N[C@@H]5CCOC[C@H]5O)nc43)C2)C1] | 1.33 minutes[10]; 472.6 |
| 29 | Example 3[11] | 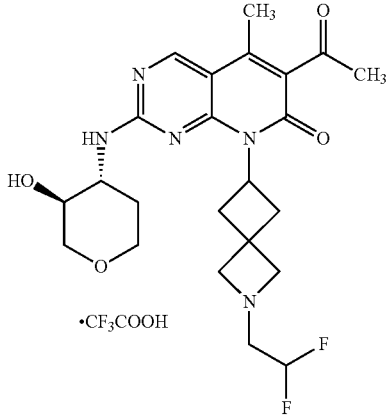 [SMILES: "·CF3COOH" ; CC(=O)c1c(C)c2cnc(N[C@@H]3CCOC[C@H]3O)nc2n(C2CC3(C2)CN(CC(F)F)C3)c1=O] | 1.43 minutes[10]; 478.6 |
| 30 | P12[12] | 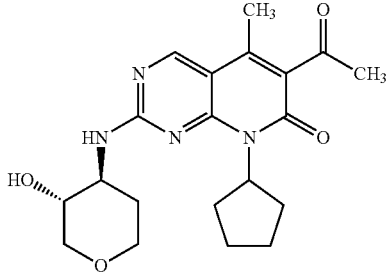 [SMILES: CC(=O)c1c(C)c2cnc(N[C@H]3CCOC[C@@H]3O)nc2n(C2CCCC2)c1=O] | $^1$H NMR (400 MHz, DMSO-d$_6$), mixture of rotamers, characteristic peaks: δ 8.79 (br s, 1H), [7.91 (br d, J = 8 Hz) and 7.81-7.67 (m), total 1H], 5.98-5.64 (m, 1H), 5.05-4.90 (m, 1H), 4.03-3.62 (m, 3H), 3.61-3.47 (m, 1H), 3.03 (dd, J = 11.2, 9.8 Hz, 1H), 2.40 (s, 3H), 2.26 (s, 3H), 2.05-1.84 (m, 3H), 1.70-1.46 (m, 3H); 386.9 |

TABLE 1-continued

Method of synthesis, structure, and physiochemical data for Examples 20-34.

| Ex. No. | Method of Preparation; Non-commercial starting materials | Structure | ¹H NMR; Mass spectrum, observed ion m/z [M + H]⁺ or HPLC retention time; Mass spectrum m/z [M + H]⁺ |
|---|---|---|---|
| 31 | Preparation P1, Example 1[13] | 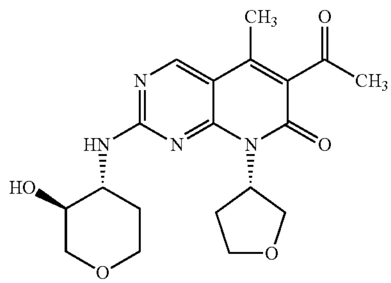 [SMILES: CC(=O)c1c(C)c2cnc(N[C@@H]3CCOC[C@H]3O)nc2n([C@H]2CCOC2)c1=O] | 1.54 minutes[10]; 389.2 |
| 32 | Example 18[14] | 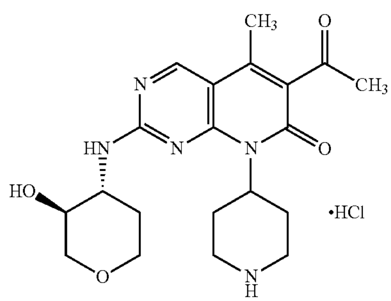 [SMILES: CC(=O)c1c(C)c2cnc(N[C@@H]3CCOC[C@H]3O)nc2n(C2CCNCC2)c1=O ; Cl] | ¹H NMR (400 MHz, deuterium oxide) δ 8.79 (s, 1H), 5.74-5.57 (m, 1H), 4.19-4.0 (m, 1H), 4.06 (dd, J = 11.4, 4.7 Hz, 1H), 4.00 (dt, J = 12, 4 Hz, 1H), 3.92-3.76 (m, 1H), 3.69-3.56 (m, 3H), 3.45-3.33 (m, 1H), 3.25-3.09 (m, 2H), 3.10-2.88 (m, 2H), 2.54 (s, 3H), 2.32 (s, 3H), 2.22-2.11 (m, 1H), 2.09- 1.94 (m, 2H), 1.87- 1.72 (m, 1H); 402.3 |
| 33 | P4[15] | 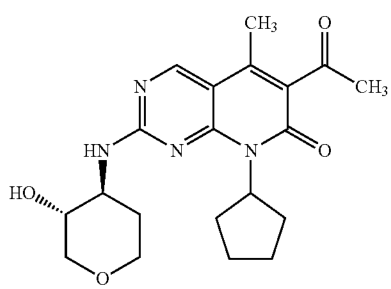 [SMILES: CC(=O)c1c(C)c2cnc(N[C@H]3CCOC[C@@H]3O)nc2n(C2CCCC2)c1=O] | ¹H NMR (400 MHz, methanol-d₄), characteristic peaks: δ 8.56 (s, 1H), 6.56 (s, 1H), 5.40 (pentet, J = 9 Hz, 1H), 4.02-3.82 (m, 3H), 3.60-3.45 (m, 2H), 2.46 (s, 3H), 2.34 (s, 3H), 2.31-2.19 (m, 2H), 2.17-2.04 (m, 3H), 2.00-1.88 (m, 2H), 1.82-1.69 (m, 2H), 1.68-1.56 (m, 1H); 386.3 |

TABLE 1-continued

Method of synthesis, structure, and physiochemical data for Examples 20-34.

| Ex. No. | Method of Preparation; Non-commercial starting materials | Structure | $^1$H NMR; Mass spectrum, observed ion m/z [M + H]$^+$ or HPLC retention time; Mass spectrum m/z [M + H]$^+$ |
|---|---|---|---|
| 34 | Example 19; P13 | (structure shown) | 0.567 minutes[16]; 359.3 |

1. The requisite 6-bromo-2-chloro-8-(cis-4-hydroxycyclohexyl)-5-methylpyrido[2,3-d]pyrimidin-7(8H)-one was synthesized using the method described in Preparation P1, by using cis-4-aminocyclohexanol in place of cyclobutanamine. The hydroxy group of intermediate cis-4-[(5-bromo-2-chloropyrimidin-4-yl)amino]cyclohexanol was protected as its tert-butyldimethylsilyl ether; this protecting group came off during the bromination step (in this case, carried out with bromine in dichloromethane).
2. Reaction of 1-[4-chloro-2-(methylthio)pyrimidin-5-yl]ethanone with trans-3-aminocyclobutanol and triethylamine, followed by hydroxy protection with tert-butyl(diphenyl)silyl chloride and 1H-imidazole, provided 1-{4-[(trans-3-{[tert-butyl(diphenyl)silyl]oxy}cyclobutyl)amino]-2-(methylthio)pyrimidin-5-yl}ethanone. This material was converted to the requisite 6-bromo-8-(trans-3-{[tert-butyl(diphenyl)silyl]oxy}cyclobutyl)-5-methyl-2-(methylthio)pyrido[2,3-d]pyrimidin-7(8H)-one using the chemistry described for synthesis of P10 from C28 in Preparation P10. The silyl protecting group was removed from intermediate 8-(trans-3-{[tert-butyl(diphenyl)silyl]oxy}cyclobutyl)-6-(1-ethoxyethenyl)-5-methyl-2-(methylthio)pyrido[2,3-d]pyrimidin-7(8H)-one during its acid-mediated conversion to 6-acetyl-8-(trans-3-hydroxycyclobutyl)-5-methyl-2-(methylthio)pyrido[2,3-d]pyrimidin-7(8H)-one.
3. Reaction of methymagnesium bromide with 2-(dibenzylamino)cyclopentanone provided rac-(1S,2R)-2-(dibenzylamino)-1-methylcyclopentanol, which was hydrogenated over palladium hydroxide to provide rac-(1S,2R)-2-amino-1-methylcyclopentanol. Protection of the amino group with benzyl chloroformate afforded rac-benzyl [(1R,2S)-2-hydroxy-2-methylcyclopentyl]carbamate, which was converted to rac-6-bromo-8-[(1R,2R)-2-fluoro-2-methylcyclopentyl]-5-methyl-2-(methylthio)pyrido[2,3-d]pyrimidin-7(8H)-one using the chemistry described in Preparation P10. Confirmation that the compounds in this series were diastereomeric to those of Preparation P10 was obtained by comparison of the physicochemical data for intermediate rac-8-[(1R,2R)-2-fluoro-2-methylcyclopentyl]-5-methyl-2-(methylthio)pyrido[2,3-d]pyrimidin-7(8H)-one {$^1$H NMR (400 MHz, chloroform-d δ 8.72 (s, 1H), 6.45-6.18 (m, 2H), 2.65 (s, 3H), 2.43 (d, J = 1.3 Hz, 3H), [2.60-2.28 (m) and 2.14-1.83 (m), total 6H], 1.28 (d, $J_{HF}$ = 22.9 Hz, 3H). LCMS m/s 308.1 [M + H]$^+$}with that of the rac-(1R,2S) isomer C29 in Preparation P10.
4. Separation of diastereomeric Examples 22 and 23 was carried out using supercritical fluid chromatography (Column: Phenomenex Lux Cellulose-4, 3 μm; Mobile phase: 18% methanol in carbon dioxide; Back pressure: 100 bar). The first-eluting diastereomer was designated as Example 22, and the second-eluting diastereomer as Example 23. Retention time for Example 22: 2.56 minutes (Column: Chiral Technologies Chiralpak IC, 4.6 × 100 mm, 5 μm; Mobile phase A: carbon dioxide; Mobile phase B: methanol; Gradient: 12% to 70% B over 10 minutes; Flow rate: 4.0 mL/minute; Back pressure: 100 bar). Retention time for Example 23: 1.83 minutes (Analytical conditions identical to those used for Example 22). 5. Reaction of 1-[4-chloro-2-(methylthio)pyrimidin-5-yl]ethanone with tert-butyl (trans-4-aminocyclohexyl)carbamate and N, N-diisopropylethylamine afforded ter-butyl (trans-4-{[5-acetyl-2-(methylthio)pyrimidin-4-yl]amino}cyclohexyhcarbamate, which was converted to tert-butyl {trans-4-[6-bromo-5-methyl-2-(methylthio)-7-oxopyrido[2,3 d]pyrimidin-8(7H)-yl]cyclohexyl}carbamate according to the method described in Preparation P10 for synthesis of P10 from C28 (except that N-bromosuccinimide and catalytic oxalic acid were used in place of bromine). The tert-butoxycarbonyl group was removed in the final step, using hydrogen chloride in methanol, to provide Example 24.
6. Reaction of the hydrochloride salt of Example 24 with formaldehyde and sodium triacetoxyborohydride provided Example 25.
7. Reaction of Example 18 with formaldehyde, N,N-diisopropylethylamine, and sodium triacetoxyborohydride provided Example 26.
8. The requisite tert-butyl (3R)-3-[6-bromo-5-methyl-2-(methylthio)-7-oxopyrido[2,3-d]pyrimidin-8(7H)-yl]pyrrolidine-1-carboxylate was synthesized using the method described in Preparation P10, but employing tert-butyl (3R)-3-aminopyrrolidine-1-carboxylate in place of C27. The bromination reaction was carried out using N-bromosuccinimide and catalytic oxalic acid, rather than bromine.
9. Alkylation of Example 3 with 1-bromo-2-methoxyethane and N,N-diisopropylethylamine provided Example 28.
10. Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.
11. Alkylation of Example 3 with 2,2-difluoroethyl trifluoromethanesulfonate and N,N-diisopropylethylamine provided Example 29.
12. A sample of trans-4-aminotetrahydro-2H-pyran-3-ol, largely composed of (3S,4R)-4-aminotetrahydro-2H-pyran-3-ol, but containing a small amount of (3R,4S)-4-aminotetrahydro-2H-pyran-3-ol, was reacted with P12 and N,N-diisopropylethylamine. Separation of the resulting enantiomers was carried out using supercritical fluid chromatography (Column: Chiral Technologies Chiralpak AS-H, 5 pm; Mobile phase: 4:1 carbon dioxide/methanol). The first-eluting enantiomer, which exhibited a positive (+) rotation, was the minor component, and was designated as Example 30. The second-eluting enantiomer was 2, which exhibited a negative (-) rotation. Retention time for Example 30: 0.86 minutes (Column: Chiral Technologies Chiralpak AS-3, 4.6 × 100 mm, 3 μm; Mobile phase: 4:1 carbon dioxide/methanol; Flow rate: 4 mL/minute; Back pressure: 120 bar). Retention time for 2: 1.03 minutes (Analytical conditions identical to those used for Example 30).
13. In this case, intermediate 6-bromo-2-{[(3S,4R)-3-hydroxytetrahydro-2H-pyran-4-yl]amino}-5-methyl-8-[(3S)-tetrahydrofuran-3-yl]pyrido[2,3-d]pyrimidin-7(8H)-one was converted to Example 31 by reaction with 1-(ethenyloxy)butane and N,N-diisopropylethylamine in the presence of dichloro[bis(2-(diphenylphosphino)phenyhether]palladium(II) [see M. T. Maloney et al., *Organic Process Research & Development* 2016, 20, 1203-1216], followed by enol ether cleavage with hydrochloric acid.
14. Synthesis of the requisite tert-butyl 4-[6-bromo-5-methyl-2-(methylthio)-7-oxopyrido[2,3-d]pyrimidin-8(7H)-yl]piperidine-1-carboxylate was carried out using the method described in Preparation P2, through the use of ter-butyl 4-aminopiperidine-1-carboxylate in place of tert-butyl 6-amino-2-azaspiro [3.3]heptane-2-carboxylate.
15. Reaction of P4 with (3R,4S)-4-aminotetrahydro-2H-pyran-3-ol, in the presence of [(2-dicyclohexylphosphino-3,6-dimethoxy-2',4',6'-triisopropyl-1,1'-biphenyl)-2-(2-amino-1,1'-biphenyl)]palladium(II) methanesulfonate methanesulfonate (BrettPhos Pd G3) and cesium carbonate, at 100° C. in toluene, afforded Example 33.
16. Conditions for analytical HPLC. Column: Phenomenex Kinetex C18, 2.1 × 30 mm, 2.6 μm; Mobile phase A: 0.05% trifluoroacetic acid in water; Mobile phase B: 0.05% trifluoroacetic acid in acetonitrile; Gradient: 5% to 50% B over 2.0 minutes, then hold at 95% B for 0.7 minutes; Flow rate: 1.0 mL/minute.

In Vitro Purified Enzyme Assays to Determine Potency for CDKs

CDK4/Cyclin D1 and CDK6/Cylcin D3 CHEF Assay

The Chelation-Enhanced Fluorescence (CHEF) monitors the phosphorylation state in real time where the level of fluorescence is directly proportional to the amount of phosphorylated substrate. CHEF exploits a synthetic α-amino acid with a side chain bearing an 8-hydroxyquinoline derivative (sulfonamido-oxine, Sox), which, upon coordination to Mg(II), relays information on the phosphorylation state of a proximal serine, threonine or tyrosine residue in peptide-based kinase substrates. Phosphorylation of a specific peptide (Catalog # AQT0258) from AssayQuant Technologies results in an increase in fluorescence at the excitation and emission wavelengths of 360 nm Ex/485 nm Em.

Examples along with DMSO (negative) and Palbociclib (positive) controls were added to 384-well plates at 100-fold their final concentrations followed by the addition of 10 nM CDK4/Cyclin D1 (LJIC-2007F1) or 10 nM CDK6/Cyclin D3 (LJIC-2009H2) for a 20 minute pre-incubation in assay buffer containing 40 mM HEPES, 1 mM Dithiothreito (DTT, 10 mM MgCl2, 1% Glycerol, 0.1% BSA. Enzyme reactions were initiated by the addition of AssayQuant Technologies peptide and ATP substrates (10 µM CHEF peptide (Catalog # AQT0258), 2 mM ATP) and allowed to proceed for 2 hours followed by fluorescence read of the reaction. $K_i$ determinations were made from a plot of the fractional velocity as a function of inhibitor concentration fit to the Morrison equation with the enzyme concentration as a variable.

CDK4/Cyclin D1 Mobility Shift Assay (MSA)

The purpose CDK4/Cyclin D1 assay is to evaluate the inhibition (% inhibition, $K_{iapp}$ and $K_i$ values) in the presence of small molecule inhibitors by using a fluorescence based microfluidic mobility shift assay. CDK4/Cyclin D1 catalyzes the production of ADP from ATP that accompanies the phosphoryl transfer to the substrate peptide 5-FAM-Dyrktide. The mobility shift assay electrophoretically separates the fluorescently labeled peptides (substrate and phosphorylated product) following the kinase reaction. Both substrate and product are measured and the ratio of these values is used to generate % Conversion of substrate to product by the LabChip EZ Reader. Typical reaction solutions contained 2% DMSO (±inhibitor), 10 mM MgCl$_2$, 1 mM DTT, 3.5 mM ATP, 0.005% Tween-20, 3 µM 5-FAM-Dyrktide, 3 nM activated CDK4/Cyclin D1 in 40 mM HEPES buffer at pH 7.5.

Inhibitor $K_i$ determinations for activated CDK4/Cyclin D1 (2007 E1/2008+PO4) were initiated with the addition of ATP (50 µL final reaction volume), following a eighteen minute pre-incubation of enzyme and inhibitor at 22° C. in the reaction mix. The reaction was stopped after 195 minutes by the addition of 50 µL of 30 mM EDTA. $K_i$ determinations were made from a plot of the fractional velocity as a function of inhibitor concentration fit to the Morrison equation with the enzyme concentration as a variable.

CDK6/Cyclin D3 Mobility Shift Assay

The purpose of the CDK6/Cyclin D3 assay is to evaluate the inhibition (% inhibition, $K_{iapp}$ and $K_i$ values) in the presence of small molecule inhibitors by using a fluorescence based microfluidic mobility shift assay. CDK6/Cyclin D3 catalyzes the production of ADP from ATP that accompanies the phosphoryl transfer to the substrate peptide 5-FAM-Dyrktide The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Typical reaction solutions contained 2% DMSO (±inhibitor), 2% glycerol, 10 mM MgCl$_2$, 1 mM DTT, 3.5 mM ATP, 0.005% Tween 20 (TW-20), 3 µM 5-FAM-Dyrktide, 4 nM activated CDK6/Cyclin D3 in 40 mM HEPES buffer at pH 7.5.

Inhibitor $K_i$ determinations for activated CDK6/Cyclin D3 (LJIC-2009G1/2010+PO4) were initiated with the addition of ATP (50 µL final reaction volume), following a eighteen minute pre-incubation of enzyme and inhibitor at 22° C. in the reaction mix. The reaction was stopped after 95 minutes by the addition of 50 µL of 30 mM EDTA. $K_i$ determinations were made from a plot of the fractional velocity as a function of inhibitor concentration fit to the Morrison equation with the enzyme concentration as a variable.

CDK6/Cyclin D1 Mobility Shift Assay (MSA)

The purpose of the CDK6/Cyclin D1 assay is to evaluate the inhibition (% inhibition, $K_{iapp}$ and $K_i$ values) in the presence of small molecule inhibitors by using a fluorescence based microfluidic mobility shift assay. CDK6/Cyclin D1 catalyzes the production of ADP from ATP that accompanies the phosphoryl transfer to the substrate peptide 5-FAM-Dyrktide The mobility shift assay electrophoretically separates the fluorescently labeled peptides (substrate and phosphorylated product) following the kinase reaction. Both substrate and product are measured and the ratio of these values is used to generate % conversion of substrate to product by the LabChip EZ Reader. Typical reaction solutions contained 2% DMSO (±inhibitor), 2% glycerol, 10 mM MgCl$_2$, 1 mM DTT, 3.5 mM ATP, 0.005% Tween 20 (TW-20), 3 µM 5-FAM-Dyrktide, 4 nM activated CDK6/Cyclin D1 in 40 mM HEPES buffer at pH 7.5.

Inhibitor $K_i$ determinations for activated CDK6/Cyclin D1 (LJIC-2003 A2/1865) were initiated with the addition of ATP (50 µL final reaction volume), following a fifteen minute pre-incubation of enzyme and inhibitor at 22° C. in the reaction mix. The reaction was stopped after 35 minutes by the addition of 50 µL of 30 mM EDTA. $K_i$ determinations were made from a plot of the fractional velocity as a function of inhibitor concentration fit to the Morrison equation with the enzyme concentration as a variable.

$K_i$ Calculation

For all the CDK4 and CDK6 assays the $K_i$ constant for compounds were calculated for each enzyme using the Morrison equation. Fractional activity was measured at different compound concentrations, [I] and the data fit to the Morrison equation where [E] is the enzyme concentration, [S] is the ATP concentration, and $Km^{App}$ is the apparent Km for ATP for each enzyme under each assay format. With the $K_i$ calculations dependent on the assay conditions for each assay format the resulting $K_i$ becomes assay independent with a strong one to one correlation of $K_i$ values for compounds tested in both assay formats.

$$\frac{Vi}{Vo} = 1 - \frac{\left([E]+[I]+\left(Ki\left(1+\frac{S}{Km^{App}}\right)\right)\right) - \sqrt{\left([E]+[I]+\left(Ki*\left(1+\frac{S}{Km^{App}}\right)\right)\right)^2 - 4[E][I]}}{2[E]},$$

For Ki Calculations, see also Morrison, J. F. (1969) Kinetics of the reversible inhibition of enzyme-catalysed reactions by tight-binding inhibitors, *Biochimica et biophysica acta* 185, 269-286; and Murphy, D. J. (2004) Determination of accurate KI values for tight-binding enzyme inhibitors: an in silico study of experimental error and assay design, *Analytical biochemistry* 327, 61-67.

In Table 2, assay data are presented to two (2) significant figures as the geometric mean ($K_i$) based on the number of replicates listed (Number). A cell having NA means there was no data for that Example in the indicated assay.

TABLE 2

Biological activity and Compound name for Examples 1-34.

| Example Number | CDK4/ Cyclin D1 GMean $K_i$ (nM) (CI) | CDK4/ Cyclin/ D1 Number | CDK6/ Cyclin D3: GMean $K_i$ (nM) (CI) | CDK6/ Cyclin D3: Number | Compound Name |
|---|---|---|---|---|---|
| 1 | $1.8^a$ (0.8, 2.9) | 3 | $2.0^a$ (1.1, 2.9) | 3 | 6-acetyl-8-cyclobutyl-2-{[(3S,4R)-3-hydroxytetrahydro-2H-pyran-4-yl]amino}-5-methylpyrido[2,3-d]pyrimidin-7(8H)-one |
| 2 | $0.8^b$ (0.6, 1.0) | 7 | $1.2^b$ (0.9, 1.4) | 7 | 6-acetyl-8-cyclopentyl-2-{[(3S,4R)-3-hydroxytetrahydro-2H-pyran-4-yl]amino}-5-methylpyrido[2,3-d]pyrimidin-7(8H)-one |
| 3 | $1.1^a$ (0.8, 1.5) | 6 | $2.1^a$ (1.3, 2.0) | 6 | 6-acetyl-8-(2-azaspiro[3.3]heptan-6-yl)-2-{[(3S,4R)-3-hydroxytetrahydro-2H-pyran-4-yl]amino}-5-methylpyrido[2,3-d]pyrimidin-7(8H)-one |
| 4 | $1.6^a$ (0.6, 2.6) | 4 | $2.1^a$ (1.3, 3.0) | 5 | 6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one |
| 5 | $0.4^b$ (0.2, 0.5) | 14 | $1.3^b$ (1.1, 1.4) | 19 | 3-acetyl-1-cyclopentyl-7-{[(3S,4R)-3-hydroxytetrahydro-2H-pyran-4-yl]amino}-4-methyl-1,6-naphthyridin-2(1H)-one |
| 6 | $113^a$ (51, 175) | 3 | $190^a$ (116, 263) | 3 | First-eluting diastereomer (DISAT-1, see Examples 6 and 7); 6-acetyl-8-[(1S,2S)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one, or or 6-acetyl-8-[(1R,2R)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one |
| 7 | $7.2^a$ (4.5, 10.0) | 3 | $7.7^a$ (5.2, 10.2) | 3 | Second-eluting diastereomer (DISAT-2, see Examples 6 and 7); 6-acetyl-8-[(1S,2S)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one or 6-acetyl-8-[(1R,2R)-2-hydroxy-2-methylcyclopentyl]-2-{[(3S,4R)-3-hydroxytetrahydro-2H-pyran-4-yl]amino}-5-methylpyrido[2,3-d]pyrimidin-7(8H)-one |
| 8 | $>1200^a$ (NA) | 3 | $>560^a$ (NA) | 3 | First-eluting enantiomer (ENT-1) see Examples 8 and 9); 6-acetyl-8-cyclopentyl-2-{[(3S,4R)-3-hydroxy-2,2-dimethyltetrahydro-2H-pyran-4-yl]amino}-5-methylpyrido[2,3-d]pyrimidin-7(8H)-one or 6-acetyl-8-cyclopentyl-2-{[(3R,4S)-3-hydroxy-2,2-dimethyltetrahydro-2H-pyran-4-yl]amino}-5-methylpyrido[2,3-d]pyrimidin-7(8H)-one |

TABLE 2-continued

Biological activity and Compound name for Examples 1-34.

| Example Number | CDK4/ Cyclin D1 GMean $K_i$ (nM) (CI) | CDK4/ Cyclin/ D1 Number | CDK6/ Cyclin D3: GMean $K_i$ (nM) (CI) | CDK6/ Cyclin D3: Number | Compound Name |
|---|---|---|---|---|---|
| 9 | 2.7[a] (1.6, 3.9) | 2 | 6.7[a] (2.8, 10.7) | 3 | Second-eluting enantiomer (ENT-2) see Examples 8 and 9); 6-acetyl-8-cyclopentyl-2-{[(3S,4R)-3-hydroxy-2,2-dimethyltetrahydro-2H-pyran-4-yl]amino}-5-methylpyrido[2,3-d]pyrimidin-7(8H)-one or 6-acetyl-8-cyclopentyl-2-{[(3R,4S)-3-hydroxy-2,2-dimethyltetrahydro-2H-pyran-4-yl]amino}-5-methylpyrido[2,3-d]pyrimidin-7(8H)-one |
| 10 | 2.7[a] (1.1, 4.3) | 3 | 5.0[a] (2.8, 7.3) | 3 | 6-acetyl-8-[(1R,2S)-2-ethylcyclopentyl]-2-{[(3S,4R)-3-hydroxytetrahydro-2H-pyran-4-yl]amino}-5-methylpyrido[2,3-d]pyrimidin-7(8H)-one |
| 11 | 34[a] (NA) | 1 | 16[a] (NA) | 1 | 3-acetyl-7-{[(3S,4R)-3-hydroxytetrahydro-2H-pyran-4-yl]amino}-4-methyl-1-[(3S)-tetrahydrofuran-3-yl]-1,6-naphthyridin-2(1H)-one |
| 12 | 8.5[a] (4.5, 12.6) | 3 | 9.7[a] (6.2, 13.1) | 3 | First-eluting diastereomer (DIAST-1, see Examples 12 and 13); 6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one or 6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one |
| 13 | 2.1[a] (1.1, 3.0) | 3 | 3.3[a] (2.8, 3.8) | 3 | Second-eluting diastereomer (DIAST-2, see Examples 12 and 13); 6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one or 6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one |
| 14 | 0.9[a] (0.5, 1.2) | 2 | 2.6[a] (0, 5.5) | 2 | 3-acetyl-1-(3-hydroxycyclopentyl)-7-{[(3S,4R)-3-hydroxytetrahydro-2H-pyran-4-yl]amino}-4-methyl-1,6-naphthyridin-2(1H-one, DIAST-1 (see Examples 14 and 15) |
| 15 | 3.8[a] (3.1, 4.5) | 2 | 7.7[a] (NA) | 1 | 3-acetyl-1-(3-hydroxycyclopentyl)-7-{[(3S,4R)-3-hydroxytetrahydro-2H-pyran-4-yl]amino}-4-methyl-1,6-naphthyridin-2(1H-one, DIAST-2 (see Examples 14 and 15) |

TABLE 2-continued

Biological activity and Compound name for Examples 1-34.

| Example Number | CDK4/ Cyclin D1 GMean $K_i$ (nM) (CI) | CDK4/ Cyclin/ D1 Number | CDK6/ Cyclin D3: GMean $K_i$ (nM) (CI) | CDK6/ Cyclin D3: Number | Compound Name |
|---|---|---|---|---|---|
| 16 | 2.6[a] (1.1, 4.1) | 3 | 5.0[a] (4.5, 5.5) | 3 | First-eluting diastereomer (DIAST-1, see Examples 16 and 17); 6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one or 6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one |
| 17 | N/A | N/A | 10.5[c] (9.5, 11.5) | 2 | Second-eluting diastereomer (DIAST-2, see Examples 16 and 17); 6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one or 6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one |
| 18 | 9.6[a] (7.7, 11.5) | 3 | 34[a] (19, 49) | 3 | 6-acetyl-2-{[(3S,4R)-3-hydroxytetrahydro-2H-pyran-4-yl]amino}-5-methyl-8-[(3S)-pyrrolidin-3-yl]pyrido[2,3-d]pyrimidin-7(8H)-one |
| 19 | 4.5[a] (1.0, 8.0) | 4 | 4.2[a] (0, 9.9) | 2 | 6-acetyl-8-(3,3-dimethylcyclobutyl)-2-{[(3S,4R)-3-hydroxytetrahydro-2H-pyran-4-yl]amino}-5-methylpyrido[2,3-d]pyrimidin-7(8H)-one |
| 20 | 54[a] (18, 90) | 3 | 58[a] (40, 75) | 3 | 6-acetyl-8-(cis-4-hydroxycyclohexyl)-2-{[(3S,4R)-3-hydroxytetrahydro-2H-pyran-4-yl]amino}-5-methylpyrido[2,3-d]pyrimidin-7(8H)-one |
| 21 | 13[a] (7, 20) | 3 | 13[a] (11, 16) | 3 | 6-acetyl-8-(trans-3-hydroxycyclobutyl)-2-{[(3S,4R)-3-hydroxytetrahydro-2H-pyran-4-yl]amino}-5-methylpyrido[2,3-d]pyrimidin-7(8H)-one |
| 22 | N/A | N/A | 2.8[c] (2.2, 3.4) | 2 | First-eluting diastereomer (see footnote 4 in Table 1); 6-acetyl-8-[(1S,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one or 6-acetyl-8-[(1R,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one |

TABLE 2-continued

Biological activity and Compound name for Examples 1-34.

| Example Number | CDK4/ Cyclin D1 GMean $K_i$ (nM) (CI) | CDK4/ Cyclin/ D1 Number | CDK6/ Cyclin D3: GMean $K_i$ (nM) (CI) | CDK6/ Cyclin D3: Number | Compound Name |
|---|---|---|---|---|---|
| 23 | >1100$^a$ (N/A) | 3 | >560$^a$ (N/A) | 3 | Second-eluting diastereomer (see footnote 4 in Table 1); 6-acetyl-8-[(1S,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one or 6-acetyl-8-[(1R,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one |
| 24 | 13$^a$ (11, 14) | 2 | 24$^a$ (8, 39) | 3 | 6-acetyl-8-(trans-4-aminocyclohexyl)-2-{[(3S,4R)-3-hydroxytetrahydro-2H-pyran-4-yl]amino}-5-methylpyrido[2,3-d]pyrimidin-7(8H)-one |
| 25 | 36$^a$ (5, 67) | 2 | 110$^a$ (8, 216) | 3 | 6-acetyl-8-[trans-4-(dimethylamino)cyclohexyl]-2-{[(3S,4R)-3-hydroxytetrahydro-2H-pyran-4-yl]amino}-5-methylpyrido[2,3-d]pyrimidin-7(8H)-one |
| 26 | 13$^a$ (11, 15) | 3 | 39$^a$ (16, 63) | 3 | 6-acetyl-2-{[(3S,4R)-3-hydroxytetrahydro-2H-pyran-4-yl]amino}-5-methyl-8-[(3S)-1-methylpyrrolidin-3-yl]pyrido[2,3-d]pyrimidin-7(8H)-one |
| 27 | 9.9$^a$ (6, 14) | 3 | 25$^a$ (4, 46) | 3 | 6-acetyl-2-{[(3S,4R)-3-hydroxytetrahydro-2H-pyran-4-yl]amino}-5-methyl-8-[(3R)-pyrrolidin-3-yl]pyrido[2,3-d]pyrimidin-7(8H)-one |
| 28 | 10$^a$ (7, 14) | 3 | 36$^a$ (29, 44) | 4 | 6-acetyl-2-{[(3S,4R)-3-hydroxytetrahydro-2H-pyran-4-yl]amino}-8-[2-(2-methoxyethyl)-2-azaspiro[3.3]heptan-6-yl]-5-methylpyrido[2,3-d]pyrimidin-7(8H)-one, trifluoroacetate salt |
| 29 | 1.9$^a$ (1.6, 2.1) | 3 | 4.9$^a$ (3.0, 6.9) | 3 | 6-acetyl-8-[2-(2,2-difluoroethyl)-2-azaspiro[3.3]heptan-6-yl]-2-{[(3S,4R)-3-hydroxytetrahydro-2H-pyran-4-yl]amino}-5-methylpyrido[2,3-d]pyrimidin-7(8H)-one, trifluoroacetate salt |
| 30 | 430$^a$ (320, 540) | 4 | >570$^a$ (N/A) | 5 | 6-acetyl-8-cyclopentyl-2-{[(3R,4S)-3-hydroxytetrahydro-2H-pyran-4-yl]amino}-5-methylpyrido[2,3-d]pyrimidin-7(8H)-one |
| 31 | 27$^a$ (N/A) | 1 | 29$^a$ (N/A) | 1 | 6-acetyl-2-{[(3S,4R)-3-hydroxytetrahydro-2H-pyran-4-yl]amino}-5-methyl-8-[(3S)-tetrahydrofuran-3-yl]pyrido[2,3-d]pyrimidin-7(8H)-one |
| 32 | 16$^a$ (11, 21) | 5 | 27$^a$ (21, 33) | 5 | 6-acetyl-2-{[(3S,4R)-3-hydroxytetrahydro-2H-pyran-4-yl]amino}-5-methyl-8-(piperidin-4-yl)pyrido[2,3-d]pyrimidin-7(8H)-one, hydrochloride salt |
| 33 | 62$^a$ (39, 85) | 4 | 130$^a$ (60, 200) | 4 | 3-acetyl-1-cyclopentyl-7-{[(3R,4S)-3-hydroxytetrahydro-2H-pyran-4-yl]amino}-4-methyl-1,6-naphthyridin-2(1H)-one |

TABLE 2-continued

Biological activity and Compound name for Examples 1-34.

| Example Number | CDK4/ Cyclin D1 GMean $K_i$ (nM) (CI) | CDK4/ Cyclin/ D1 Number | CDK6/ Cyclin D3: GMean $K_i$ (nM) (CI) | CDK6/ Cyclin D3: Number | Compound Name |
|---|---|---|---|---|---|
| 34 | 52[a] (44, 59) | 2 | 85[a] (56, 115) | 3 | 6-acetyl-8-cyclopropyl-2-{[(3S,4R)-3-hydroxytetrahydro-2H-pyran-4-yl]amino}-5-methylpyrido[2,3-d]pyrimidin-7(8H)-one |

[a]Tested in CHEF Assay
[b]Tested in both CHEF and MSA
[c]Tested in CDK6/D1 $K_i$ assay using MSA
CI - 95% Confidence Interval Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula I:

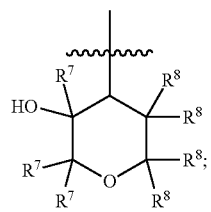

I or a pharmaceutically acceptable salt thereof, wherein:
A is CH or N;
$R^1$ is $C_1$-$C_2$ alkyl or $C_1$-$C_2$ fluoroalkyl;
$R^2$ is $C_1$-$C_4$ alkyl optionally substituted with 1, 2, or 3 substituents each independently selected from the group consisting of —OH, $C_1$-$C_2$ alkoxy, and F;
$R^3$ is 4- to 8-membered heterocyclyl, $C_3$-$C_8$ cycloalkyl, (4- to 8-membered heterocyclyl)-$C_1$-$C_4$ alkyl-, or ($C_3$-$C_8$ cycloalkyl)-$C_1$-$C_4$ alkyl-,
  wherein each of the 4- to 8-membered heterocyclyl and the 4- to 8-membered heterocyclyl moiety in (4- to 8-membered heterocyclyl)-$C_1$-$C_4$ alkyl- is optionally substituted with 1 or 2 $R^5$,
  wherein each of the $C_3$-$C_8$ cycloalkyl and the $C_3$-$C_8$ cycloalkyl moiety in ($C_3$-$C_8$ cycloalkyl)-$C_1$-$C_4$ alkyl- is optionally substituted with 1 or 2 $R^5$ and further optionally substituted with 1 —N($R^6$)$_2$, and
  wherein each of the $C_1$-$C_4$ alkyl moieties in (4- to 8-membered heterocyclyl)-$C_1$-$C_4$ alkyl- and ($C_3$-$C_8$ cycloalkyl)-$C_1$-$C_4$ alkyl- is optionally substituted with 1, 2, or 3 $R^5$;

$R^4$ is a moiety having the structure of

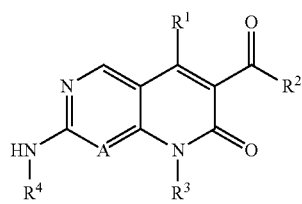

each $R^5$ is independently selected from the group consisting of —F, —OH, —CN, $C_1$-$C_4$ alkyl, $C_1$-$C_4$ fluoroalkyl, $C_1$-$C_4$ alkoxy, $C_1$-$C_4$ fluoroalkoxy, $C_1$-$C_4$ alkoxy-$C_1$-$C_4$ alkyl-, $C_1$-$C_4$ fluoroalkoxy-$C_1$-$C_4$ alkyl-, $C_1$-$C_4$ alkoxy-$C_1$-$C_4$ fluoroalkyl, and $C_1$-$C_4$ fluoroalkoxy-$C_1$-$C_4$ fluoroalkyl-;

each $R^6$ is independently selected from the group consisting of H and $C_1$-$C_2$ alkyl;

each $R^7$ is independently H or $C_1$-$C_2$ alkyl; and each $R^8$ is independently H, F, or $C_1$-$C_2$ alkyl.

2. The compound of claim 1, or a pharmaceutically acceptable salt thereof, wherein:
A is CH or N;
$R^1$ is CH$_3$ or $C_1$ fluoroalkyl;
$R^2$ is CH$_3$;
$R^3$ is 5- to 7-membered heterocyclyl, $C_3$-$C_6$ cycloalkyl, (5- to 7-membered heterocyclyl)-$C_1$-$C_4$ alkyl-, or ($C_3$-$C_6$ cycloalkyl)-$C_1$-$C_4$ alkyl-,
  wherein each of the 5- to 7-membered heterocyclyl and the 5- to 7-membered heterocyclyl moiety in (5- to 7-membered heterocyclyl)-$C_1$-$C_4$ alkyl- is optionally substituted with 1 $R^5$,
  wherein each of the $C_3$-$C_6$ cycloalkyl and the $C_3$-$C_6$ cycloalkyl moiety in ($C_3$-$C_6$ cycloalkyl)-$C_1$-$C_4$ alkyl- is optionally substituted with 1 or 2 $R^5$ and further optionally substituted with 1 —N($R^6$)$_2$, and
  wherein each of the $C_1$-$C_4$ alkyl moieties in (5- to 7-membered heterocyclyl)-$C_1$-$C_4$ alkyl- and ($C_3$-$C_6$ cycloalkyl)-$C_1$-$C_4$ alkyl- is optionally substituted with 1, 2, or 3 $R^5$;

R⁴ is a moiety having the structure of

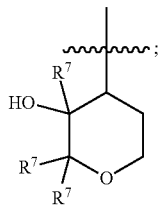

each R⁵ is independently selected from the group consisting of —F, —OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-;

each R⁶ is independently selected from the group consisting of H and $C_1$-$C_2$ alkyl; and each R⁷ is independently H or CH₃, provided that no more than two R⁷ are CH₃.

3. The compound of claim 1, wherein the compound is a compound of Formula II:

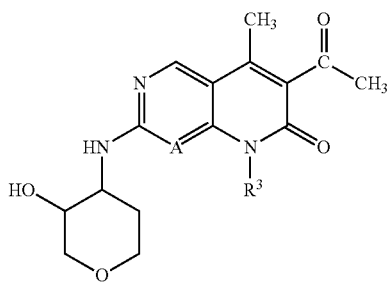

or a pharmaceutically acceptable salt thereof.

4. The compound of claim 3, or a pharmaceutically acceptable salt thereof, wherein the compound is a compound of Formula III:

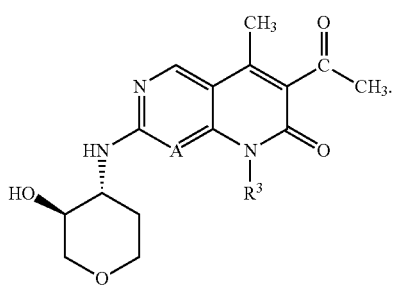

5. The compound of claim 4, or a pharmaceutically acceptable salt thereof, wherein:

A is CH or N;

R³ is 5- to 7-membered heterocyclyl optionally substituted with 1 R⁵; and

R⁵ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-.

6. The compound of claim 5, or a pharmaceutically acceptable salt thereof, wherein R³ is selected from the group consisting of 2-azaspiro[3.3]heptanyl, tetrahydrofuranyl, pyrrolidinyl, and piperidinyl, wherein each of the heterocyclyl selections is optionally substituted with 1 R⁵; and R⁵ is selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl-, and $C_1$-$C_2$ fluoroalkoxy-$C_1$-$C_2$ fluoroalkyl-.

7. The compound of claim 5, or a pharmaceutically acceptable salt thereof, wherein R³ is 2-azaspiro[3.3]heptan-6-yl optionally substituted with 1 R⁵ that is selected from the group consisting of $C_1$-$C_2$ alkyl, $C_1$-$C_2$ fluoroalkyl, $C_1$-$C_2$ alkoxy-$C_1$-$C_2$ alkyl-, and $C_1$-$C_2$ fluoroalkoxy-$C_1$-$C_2$ alkyl-.

8. The compound of claim 4, or a pharmaceutically acceptable salt thereof, wherein:

A is CH or N;

R³ is $C_3$-$C_6$ cycloalkyl optionally substituted with 1 or 2 R⁵ and further optionally substituted with 1 —N(R⁶)₂;

each R⁵ is independently selected from the group consisting of F, OH, —CN, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-; and each R⁶ is independently selected from the group consisting of H and $C_1$-$C_2$ alkyl.

9. The compound of claim 8, or a pharmaceutically acceptable salt thereof, wherein R³ is selected from the group consisting of cyclopropyl, cyclobutyl, cyclopentyl, cyclohexyl, and bicyclo[3.1.0]hexanyl, wherein each of the selections is optionally substituted with 1 or 2 R⁵ and further optionally substituted with 1 —N(R⁶)₂.

10. The compound of claim 8, or a pharmaceutically acceptable salt thereof, wherein R³ is cyclobutyl optionally substituted with 1 or 2 R⁵; and each R⁵ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-.

11. The compound of claim 8, or a pharmaceutically acceptable salt thereof, wherein R³ is cyclopentyl optionally substituted with 1 or 2 R⁵; and each R⁵ is independently selected from the group consisting of F, OH, $C_1$-$C_2$ alkyl, $C_1$-$C_2$ fluoroalkyl, $C_1$-$C_2$ alkoxy, $C_1$-$C_2$ fluoroalkoxy, $C_1$-$C_2$ alkoxy-$C_1$-$C_2$ alkyl-, $C_1$-$C_2$ fluoroalkoxy-$C_1$-$C_2$ alkyl-, $C_1$-$C_2$ alkoxy-$C_1$-$C_2$ fluoroalkyl, and $C_1$-$C_2$ fluoroalkoxy-$C_1$-$C_2$ fluoroalkyl-.

12. The compound of claim 8, or a pharmaceutically acceptable salt thereof, wherein R³ is cyclopentyl.

13. The compound of claim 1, or a pharmaceutically acceptable salt thereof, wherein A is CH.

14. The compound of any claim 1, or a pharmaceutically acceptable salt thereof, wherein A is N.

15. A compound selected from the group consisting of:

6-acetyl-8-cyclobutyl-2-{[(3S,4R)-3-hydroxytetrahydro-2H-pyran-4-yl]amino}-5-methylpyrido[2,3-d]pyrimidin-7(8H)-one;

6-acetyl-8-cyclopentyl-2-{[(3S,4R)-3-hydroxytetrahydro-2H-pyran-4-yl]amino}-5-methylpyrido[2,3-d]pyrimidin-7(8H)-one;

6-acetyl-8-(2-azaspiro[3.3]heptan-6-yl)-2-{[(3S,4R)-3-hydroxytetrahydro-2H-pyran-4-yl]amino}-5-methylpyrido[2,3-d]pyrimidin-7(8H)-one;

6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one;

3-acetyl-1-cyclopentyl-7-{[(3S,4R)-3-hydroxytetrahydro-2H-pyran-4-yl]amino}-4-methyl-1,6-naphthyridin-2(1H)-one;

6-acetyl-8-[(1S,2R,5R)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one;

6-acetyl-8-[(1R,2S,5S)-bicyclo[3.1.0]hexan-2-yl]-2-{[(3S,4R)-3-hydroxytetrahydro-2H-pyran-4-yl]amino}-5-methylpyrido[2,3-d]pyrimidin-7(8H)-one;

6-acetyl-8-[(1R,2S)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one;

6-acetyl-8-[(1S,2R)-2-fluoro-2-methylcyclopentyl]-2-{[(3S,4R)-3-hydroxytetrahydro-2H-pyran-4-yl]amino}-5-methylpyrido[2,3-d]pyrimidin-7(8H)-one; and 6-acetyl-8-[2-(2,2-difluoroethyl)-2-azaspiro[3.3]heptan-6-yl]-2-{[(3S,4R)-3-hydroxytetrahydro-2H-pyran-4-yl]amino}-5-methylpyrido[2,3-d]pyrimidin-7(8H)-one, or a pharmaceutically acceptable salt thereof.

16. A compound of claim 1 that is selected from the group consisting of:

6-acetyl-8-cyclobutyl-2-{[(3S,4R)-3-hydroxytetrahydro-2H-pyran-4-yl]amino}-5-methylpyrido[2,3-d]pyrimidin-7(8H)-one;

6-acetyl-8-cyclopentyl-2-{[(3S,4R)-3-hydroxytetrahydro-2H-pyran-4-yl]amino}-5-methylpyrido[2,3-d]pyrimidin-7(8H)-one;

6-acetyl-2-{[(3S,4R)-3-hydroxytetrahydro-2H-pyran-4-yl]amino}-5-methyl-8-[(1R,2S)-2-methylcyclopentyl]pyrido[2,3-d]pyrimidin-7(8H)-one;

3-acetyl-1-cyclopentyl-7-{[(3S,4R)-3-hydroxytetrahydro-2H-pyran-4-yl]amino}-4-methyl-1,6-naphthyridin-2(1H)-one; and 6-acetyl-8-[2-(2,2-difluoroethyl)-2-azaspiro[3.3]heptan-6-yl]-2-{[(3S,4R)-3-hydroxytetrahydro-2H-pyran-4-yl]amino}-5-methylpyrido[2,3-d]pyrimidin-7(8H)-one, or a pharmaceutically acceptable salt thereof.

17. A pharmaceutical composition comprising a compound of claim 1 or a pharmaceutically acceptable salt thereof, and a pharmaceutically acceptable carrier.

18. A pharmaceutical composition comprising a compound of claim 15 or a pharmaceutically acceptable salt thereof, and a pharmaceutically acceptable carrier.

19. A method for treating a disease or disorder in a subject, which method comprises administering to the subject in need thereof a therapeutically effective amount of a compound of claim 1 or a pharmaceutically acceptable salt thereof, wherein the disease or disorder is selected from the group consisting of pulmonary hypertension, pulmonary arterial hypertension, pulmonary hypertension with left heart disease, pulmonary hypertension with lung disease and/or hypoxemia, pulmonary hypertension due to chronic thrombotic and/or embolic disease, and diseases associated with pulmonary hypertension including sarcoidosis, histiocytosis X, lymphangiomatosis and compression of pulmonary vessels.

20. The method of claim 19, wherein the disease or disorder is pulmonary arterial hypertension.

21. A compound that is 3-acetyl-1-cyclopentyl-7-{[(3S,4R)-3-hydroxytetrahydro-2H-pyran-4-yl]amino}-4-methyl-1,6-naphthyridin-2(1H)-one, or a pharmaceutically acceptable salt thereof.

22. A compound that is 3-acetyl-1-cyclopentyl-7-{[(3S,4R)-3-hydroxytetrahydro-2H-pyran-4-yl]amino}-4-methyl-1,6-naphthyridin-2(1H)-one.

23. A crystalline form of 3-acetyl-1-cyclopentyl-7-{[(3S,4R)-3-hydroxytetrahydro-2H-pyran-4-yl]amino}-4-methyl-1,6-naphthyridin-2(1H)-one.

24. The crystalline form of claim 23, wherein the crystalline form is anhydrous.

25. The crystalline form of claim 24, wherein the crystalline form (designated as Form I) has a powder X-ray diffraction pattern (CuKα radiation) comprising at least two characteristic peaks, in terms of 2θ, selected from at 8.0±0.2°; 18.6±0.2°; 19.1±0.2°; and 21.3±0.2°.

26. The crystalline form of claim 25, having a powder X-ray diffraction pattern (CuKα radiation) comprising at least three characteristic peaks, in terms of 2θ, selected from at 8.0±0.2°; 18.6±0.2°; 19.1±0.2°; and 21.3±0.2°.

27. The crystalline form of claim 26, having a powder X-ray diffraction pattern (CuKα radiation) comprising four characteristic peaks, in terms of 2θ, selected from at 8.0±0.2°; 18.6±0.2°; 19.1±0.2°; and 21.3±0.2°.

28. A pharmaceutical composition comprising a compound of claim 21 or a pharmaceutically acceptable salt thereof, and a pharmaceutically acceptable carrier.

29. A pharmaceutical composition comprising a compound of claim 24 or a pharmaceutically acceptable salt thereof, and a pharmaceutically acceptable carrier.

30. A method for treating a disease or disorder in a subject, which method comprises administering to the subject in need thereof a therapeutically effective amount of a compound of claim 21 or a pharmaceutically acceptable salt thereof, wherein the disease or disorder is selected from the group consisting of pulmonary hypertension, pulmonary arterial hypertension, pulmonary hypertension with left heart disease, pulmonary hypertension with lung disease and/or hypoxemia, pulmonary hypertension due to chronic thrombotic and/or embolic disease, and diseases associated with pulmonary hypertension including sarcoidosis, histiocytosis X, lymphangiomatosis and compression of pulmonary vessels.

* * * * *